United States Patent [19]

Martinez et al.

[11] Patent Number: 5,719,280
[45] Date of Patent: Feb. 17, 1998

[54] BENZOCYCLOALKYLAZOLETHIONE DERIVATIVES AND PROCESSES FOR PREPARING THE SAME

[75] Inventors: Gregory Ricardo Martinez, Mountain View; Owen Will Gooding, Los Gatos; David Bruce Repke, Milpitas; Philip Jay Teitelbaum, Boulder Creek; Keith Adrian Murray Walker, Los Altos Hills; Roger Lewis Whiting, Los Altos, all of Calif.

[73] Assignee: Syntex (U.S.A.) Inc., Palo Alto, Calif.

[21] Appl. No.: 833,560

[22] Filed: Apr. 7, 1997

Related U.S. Application Data

[60] Continuation of Ser. No. 639,387, Apr. 29, 1996, abandoned, which is a division of Ser. No. 403,209, Mar. 17, 1995, Pat. No. 5,538,988, which is a continuation-in-part of Ser. No. 233,655, Apr. 26, 1994, Pat. No. 5,438,150.

[51] Int. Cl.$^6$ .................. C07D 403/04; C07D 233/60
[52] U.S. Cl. .................. 544/132; 544/139; 544/360; 544/370; 546/210; 548/263.2; 548/263.8; 548/314.7; 548/324.7; 548/324.5; 564/428; 564/460; 564/462
[58] Field of Search .................. 544/132, 139, 544/360, 370; 546/210; 548/263.2, 263.8, 314.7, 324.5; 564/428, 460, 462

[56] References Cited

U.S. PATENT DOCUMENTS 3,547,942 12/1970 Godefroi et al. .................. 260/309
4,994,103 2/1991 De Bruyn et al. .

FOREIGN PATENT DOCUMENTS 0 207 563 A2 1/1987 European Pat. Off. .
0371730 6/1990 European Pat. Off. .
0371732 6/1990 European Pat. Off. .
0371733 6/1990 European Pat. Off. .

OTHER PUBLICATIONS

Schubert, et al., 76683u "Synthesis and ring closure reactions of imidazole 4,5-dialdehydes", *Chemical Abstracts* 75:457 (1971).

De Bruyn et al., 38996g "Preparation of 1H-imidazole-5-carboxylic acid derivatives as herbicides", *Chemical Abstracts* 110:546 (1989).

Kruse et al., "Multisubstrate Inhibitors of Dopamine β-Hydroxylase. 1. Some 1-Phenyl and 1-Phenyl-Bridged Derivatives of Imidazole-2-thione", *J. Med. Chem.*, 29:2465–2472 (1986).

Kruse et al., "Multisubstrate Inhibitors of Dopamine β-Hydroxylase. 2. [1] Structure–Activity Relationships at the Phenethylamine Binding Site", *J. Med. Chem.* 30:486–494 (1987).

Bjork et al., "Resolved N,N-Dialkylated 2-Amino-8-hydroxytetralins: Stereoselective Interactions with 5-HT$_{1A}$ Receptors in the Brain", *J. Med. Chem.* 32:779–784 (1989).

Hillver et al., "(S)-5-Fluoro 8-hydroxy-2-(dipropylamino)tetralin: A Putative 5-HT$_{1A}$-Receptor Antagonist", *J. Med. Chem.* 33:1541–1544 (1990).

Wyrick et al., "Synthesis and Pharmacological Evaluation of 1-Phenyl-3-amino-1,2,3,4-tetrahydronaphthalenes as Ligands for a Novel Receptor with σ-like Neuromodulatory Activity" *J. Med. Chem.* 36:2542–2551 (1993).

Kawasaki et al., "Asymmetric Reduction of Prochiral Cyclic Ketones with Lithium Aluminum Hydride Partially Decomposed by (1R,2S)-(-)-N-Methylephedrine and 2-Alkylaminopyridine" *Chem. Letters* pp. 239–242 (1984).

Kruse, L.I.; Kaiser, C.; DeWolf, W.E.; Finkelstein, J.A.; Frazee, J.S.; Hilbert, E.L.; Ross, S.T.; Flaim, K.E.; Sawyer, J.L. Some Benzyl-Substituted Imidazoles, Tirazoles, Tetrazoles, Pyridinethiones, and Structural Relatives as Multisubstrate Inhibitors of Dopamine β-Hydroxylase. 4. Structural-Activity Relationships at the Copper Binding Site, *J. Med. Chem.* 1990, 33, 781–789.

Kruse, L.I; Kaiser, C.; DeWolf, W.E.; Frazee, J.S.; Erickson, R.W.; Ezekiel M.; Ohlstein, E.H.; Ruffolo, R.R.; Berkowitz, B.A. Substituted 1-Benzylimidazole-2-thiols as Potent and Orally Active Inhibitors of Dopamine β-Hydroxylase. *J. Med. Chem.* 1986, 29, 887–889.

*Primary Examiner*—Joseph McKane
*Attorney, Agent, or Firm*—Heller Ehrman White & McAuliffe

[57] ABSTRACT

The present invention relates to novel benzocycloalkylazolethione compounds which are dopamine β-hydroxylase inhibitors in which the benzocycloalkyl portion of the compound is selected from indanyl, 1,2,3,4-tetrahydronaphthalenyl and 6,7,8,9-tetrahydro-5H-benzocycloheptenyl (in which the benzo is optionally substituted with one to three substituents) and the azolethione portion of the compound is selected from 2-thioxo-2,3-dihydro-1H-imidazol-3-yl, 5-thioxo-4,5-dihydro-1H-[1,2,4]triazol-4-yl and 5-thioxo-4,5-dihydro-1H-[1,2,4]triazol-1-yl (each optionally substituted with one to three substituents); and the prodrugs, pharmaceutically acceptable salts, individual isomers and mixtures of isomers and the methods of using and preparing such benzocycloalkylazolethione compounds.

18 Claims, No Drawings

BENZOCYCLOALKYLAZOLETHIONE DERIVATIVES AND PROCESSES FOR PREPARING THE SAME

CROSS-REFERENCE TO RELATED APPLICATIONS

This application is a continuation of Ser. No. 08/639,387 filed Apr. 29, 1996, now abandoned which is a division of U.S. Ser. No. 08/403,209, filed Mar. 17, 1995, now U.S. Pat. No. 5,538,988; which is a CIP of Ser. No. 08/233,655, entitled "Process for Making 5-Aminomethyl-1-benzocycloalkyl-1,3-dihydroimidazolethione Derivatives", filed Apr. 26, 1994 now U.S. Pat. No. 5,458,150 and incorporated herein by reference.

BACKGROUND OF THE INVENTION

1. Field of the Invention

This invention relates to novel benzocycloalkylazolethione dopamine β-hydroxylase inhibitors and the methods of using and preparing such inhibitors.

2. Description of the Field

Dopamine is a catecholamine neurotransmitter found predominately, along with specific dopaminergic receptors, in the central nervous system. Norepinephrine is a circulating catecholamine, which acts at discrete adrenergic receptors in peripheral systems. Dopamine β-hydroxylase (DBH) catalyzes the conversion of dopemine to norepinephrine and is found in both central and peripheral sympathetic neurons. Inhibition of DBH concurrently elevates dopamine levels by blocking its metabolism and reduces norepinephrine levels by blocking its synthesis. Thus, drugs which inhibit DBH are useful for treating diseases associated with reduced dopamine levels (e.g., Parkinson's disease) and for treating diseases associated with elevated norepinephrine levels (e.g., hypertension, congestive heart failure, etc.). Fusaric acid, a DBH inhibitor, decreases the tremors and other abnormalities associated with Parkinson's disease. Fusaric acid also reduces blood pressure in hypertensive patients; however, release of norepinephrine from the adrenal gland and a resultant tachycardia is also observed. Other more selective DBH inhibitors are known but often possess disadvantageous effects.

SUMMARY OF THE INVENTION

The present invention relates to a compound of Formula I:

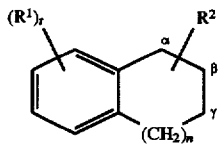

in which:

n is 0, 1 or 2;

t is 0, 1, 2 or 3;

$R^1$ is independently halo, hydroxy or $(C_{1-4})$alkyloxy; and $R^2$ is attached at the α-, β- or γ-position and is a group selected from Formulae (a), (b) and (c):

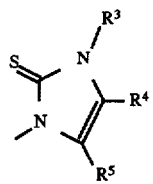

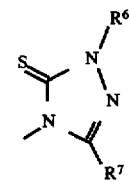

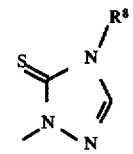

in which:

$R^4$ is hydro, $R^3$ is hydro or —$(CH_2)_qR^9$ {in which q is 0, 1, 2, 3 or 4 and $R^9$ is carboxy, $(C_{1-4})$alkyloxycarbonyl, carbamoyl or a group selected from aryl and heteroaryl (which group is optionally further substituted with one to two substituents independently selected from hydroxy, $(C_{1-4})$alkyloxy, cyano, 1H-tetrazo-5-yl, carboxy and $(C_{1-4})$alkyloxycarbonyl)} and $R^5$ is hydro or —$NHR^{10}$ {in which $R^{10}$ is hydro, $(C_{1-4})$alkanoyl, trifluoro$(C_{1-4})$alkanoyl, carbamoyl, $(C_{1-4})$alkyloxycarbonyl, $(C_{1-4})$alkylcarbamoyl, di$(C_{1-4})$alkylcarbamoyl, amino$(C_{1-4})$alkanoyl, $(C_{1-4})$alkylamino$(C_{1-4})$alkanoyl, di$(C_{1-4})$alkylamino$(C_{1-4})$alkanoyl, a group selected from aroyl and heteroaroyl (which aroyl and heteroaroyl are optionally further substituted with one to two substituents independently selected from hydroxy, $(C_{1-4})$alkyloxy, cyano, 1H-tetrazol-5-yl, carboxy and $(C_{1-4})$alkyloxycarbonyl) or —$C(NR^{11})NHR^{12}$ (in which $R^{11}$ and $R^{12}$ are independently hydro, acetyl or tert-butoxycarbonyl)}; or $R^4$ and $R^5$ are each hydro and $R^3$ is —$NHR^{10}$ (in which $R^{10}$ is as defined above); or $R^5$ is hydro, $R^3$ is hydro or —$(CH_2)_qR^9$ (in which q and $R^9$ are as defined above) and $R^4$ is $(C_{1-4})$alkyl, di$(C_{1-4})$alkylaminomethyl, piperidin-1-ylmethyl, morpholin-4-ylmethyl, formyl, 1-hydroxy$(C_{1-4})$alkyl or —$CH_2NHR^{13}$ {in which $R^{13}$ is hydro, $(C_{1-4})$alkyl, $(C_{1-4})$alkanoyl, trifluoro$(C_{1-4})$alkanoyl, carbamoyl, $(C_{1-4})$alkyloxycarbonyl, $(C_{1-4})$alkylcarbamoyl, di$(C_{1-4})$alkylcarbamoyl, amino$(C_{1-4})$alkanoyl, $(C_{1-4})$alkylamino$(C_{1-4})$alkanoyl, di$(C_{1-4})$alkylamino$(C_{1-4})$alkanoyl, carboxy$(C_{1-4})$alkyl, $(C_{1-4})$alkyloxycarbonyl$(C_{1-4})$alkyl, carbamoyl$(C_{1-4})$alkyl, a group selected from aroyl, heteroaroyl, aryl$(C_{1-4})$alkyl and heteroaryl$(C_{1-4})$alkyl (which aroyl, heteroaroyl, aryl and heteroaryl are optionally further substituted with one to two substituents independently selected from hydroxy, $(C_{1-4})$alkyloxy, cyano, 1H-tetrazol-5-yl, carboxy and $(C_{1-4})$alkyloxycarbonyl) or —$C(NR^{11})NHR^{12}$ (in which $R^{11}$ and $R^{12}$ are as defined above)}; or $R^3$ is hydro or —$(CH_2)_qR^9$ (in which q and $R^9$ are as defined above), $R^4$ is hydro, $(C_{1-4})$alkyl or —$C(O)R^{14}$ (in which $R^{14}$ is amino, hydroxy $(C_{1-4})$alkyloxy, 2-(dimethylamino)ethylamino, 4-methylpiperazin-1-yl, 2-(dimethylamino)ethylmercapto, 4-(methylsulfonylamino)anilino or 1H-tetrazol-5-ylamino) and $R^5$ is cyano, hydroxymethyl, 1H-tetrazol-5-yl, 4,5-dihydroimidazol-2-yl, pyrrolidin-1-ylmethyl, piperidin-1-ylmethyl, morpholin-4-ylmethyl, piperazin-1-ylmethyl, 4-($C_{1-4}$)alkylpiperazin-1-ylmethyl, —C(O)$R^{14}$ (in which $R^{14}$ are as defined above), —C(NH)N$R^{15}R^{16}$ (in which $R^{15}$ and $R^{16}$ are independently hydro, ($C_{1-4}$)alkyl or trifluoro($C_{1-4}$)alkyl) or —$CH_2R^{10}R^{17}$ (in which $R^{10}$ is as defined above and $R^{17}$ is hydro or $C_{1-4}$)alkyl); or $R^3$ is hydro or —$(CH_2)_qR^9$ (in which q and $R^9$ are as defined above) and $R^4$ and $R^5$ are dependently di($C_{1-4}$) alkylaminomethyl, piperidin-1-ylmethyl, morpholin-4-ylmethyl or hydroxymethyl;

$R^6$ is hydro, 2-carboxyethyl, 2-carbamoylethyl or 2-($C_{1-4}$) alkyloxycarbonylethyl;

$R^7$ is hydro, pyrrolidin-1-ylmethyl, piperidin-1-ylmethyl, morpholin-4-ylmethyl, piperazin-1-ylmethyl, 4-($C_{1-4}$) alkylpiperazin-1-ylmethyl or —$CH_2NR^{10}R^{17}$ (in which $R^{10}$ and $R^{17}$ are as defined above); and $R^8$ is hydro, 2-carboxyethyl, 2-carbamoylethyl, 2-($C_{1-4}$) alkyloxycarbonylethyl or —NH$R^{10}$ (in which $R^{10}$ are as defined above); and the pharmaceutically acceptable salts, individual isomers, and mixtures of isomers thereof.

Another aspect of this invention is a pharmaceutical composition comprising a therapeutically effective amount of a compound of Formula I or an individual isomer, a mixture of isomers, or the pharmaceutically acceptable salt or salts thereof, in combination with one or more pharmaceutically acceptable excipients.

Another aspect of this invention is a method for treating a condition capable of amelioration by inhibition of dopamine β-hydroxylase in an animal in need thereof, which method comprises administering to such animal a therapeutically effective amount of a compound of Formula I, or of an individual isomer, mixture of isomers, or the pharmaceutically acceptable salt or salts thereof.

Another aspect of this invention is the processes for preparing compounds of Formula I and is set forth in "Detailed Description of the Invention".

Another aspect of this invention relates to a compound of Formula II:

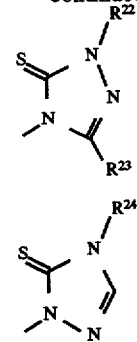

in which:

n is 0, 1 or 2;

t is 0, 1, 2 or 3;

$R^1$ is independently halo, hydroxy or ($C_{1-4}$)alkyloxy; and $R^{18}$ is attached at the α-, β- or γ-position and is a group selected from Formulae (d), (e) and (f):

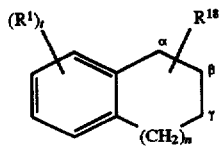

-continued

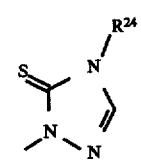

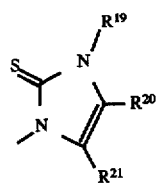

in which:

$R^{20}$ is hydro, $R^{19}$ is hydro or —$(CH_2)_qR^9$ {in which q is 0, 1, 2, 3 or 4 and $R^9$ is carboxy, ($C_{1-4}$) alkyloxycarbonyl, carbamoyl or a group selected from aryl and heteroaryl (which group is optionally further substituted with one to two substituents independently selected from hydroxy, ($C_{1-4}$)alkyloxy, cyano, 1H-tetrazo-5-yl, carboxy and ($C_{1-4}$)alkyloxycarbonyl)} and $R^{21}$ is —N$R^{25}R^{26}$ (in which $R^{25}$ is hydro or ($C_{1-4}$)alkyl and $R^{26}$ is L-alanyl, L-arginyl, L-asparaginyl, L-α-aspartyl, L-β-aspartyl, L-cysteinyl, L-glutaminyl, L-α-glutamyl, L-γ-glutamyl, N-($C_{1-4}$) alkanoyl-L-α-glutamyl, N-($C_{1-4}$)alkanoyl-L-γ-glutamyl, glycyl, L-histidyl, L-isoleucyl, L-leucyl, L-lysyl, L-methionyl, L-ornithinyl, L-phenylalanyl, L-prolyl, L-seryl, L-threonyl, L-tryptophyl, L-tyrosyl, L-valyl, 1-amino-cyclopropylcarbonyl, 1-aminocyclobutylcarbonyl, 1-aminocyclopentylcarbonyl or 1-aminocyclohexylcarbonyl); or $R^{20}$ and $R^{21}$ are each hydro and $R^{19}$ is —N$R^{25}R^{26}$ (in which $R^{25}$ and $R^{26}$ are as defined above); or $R^{21}$ is hydro, $R^{19}$ is hydro or —$(CH_2)_qR^9$ (in which q and $R^9$ are as defined above) and $R^{20}$ is —$CH_2NR^{25}R^{26}$ (in which $R^{25}$ and $R^{26}$ are as defined above); or $R^{19}$ is hydro or —$(CH_2)_qR^9$ (in which q and $R^9$ are as defined above), $R^{20}$ is hydro, ($C_{1-4}$)alkyl or —C(O)$R^{14}$ (in which $R^{14}$ is amino, hydroxy ($C_{1-4}$)alkyloxy, 2-(dimethylamino) ethylamino, 4-methylpiperazin-1-yl, 2-(dimethylamino)ethylmercapto, 4-(methylsulfonylamino)anilino or 1H-tetrazol-5-ylamino) and $R^{21}$ is —$CH_2NR^{25}R^{26}$ (in which $R^{25}$ and $R^{26}$ is as defined above); and $R^{22}$ is hydro, 2-carboxyethyl, 2-carbamoylethyl or 2-($C_{1-4}$)alkyloxycarbonylethyl;

$R^{23}$ is —$CH_2NR^{25}R^{26}$ (in which $R^{25}$ and $R^{26}$ are as defined above); and $R^{24}$ is —N$R^{25}R^{26}$ (in which $R^{25}$ and $R^{26}$ are as defined above); and the pharmaceutically acceptable salts, individual isomers, and mixtures of isomers thereof.

Another aspect of this invention is a pharmaceutical composition comprising a therapeutically effective amount of a compound of Formula II, or of an individual isomer, a mixture of isomers, or the pharmaceutically acceptable salt or salts thereof, in combination with one or more pharmaceutically acceptable excipients.

Another aspect of this invention is a method for treating a condition capable of amelioration by inhibition of dopamine β-hydroxylase in an animal in need thereof, which method comprises administering to such animal a therapeutically effective amount of a compound of Formula II, or of an individual isomer, mixture of isomers, or the pharmaceutically acceptable salt or salts thereof.

Another aspect of this invention is the processes for preparing compounds of Formula II and is set forth in "Detailed Description of the Invention".

Another aspect of this invention relates to a compound of Formula III:

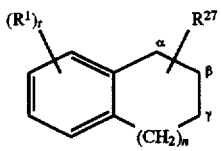

in which:

n is 0, 1 or 2;

t is 0, 1, 2 or 3;

$R^1$ is independently halo, hydroxy or $(C_{1-4})$alkyloxy; and $R^{27}$ is attached at the α-, β- or γ-position and is a group selected from Formulae (g), (h) and (i):

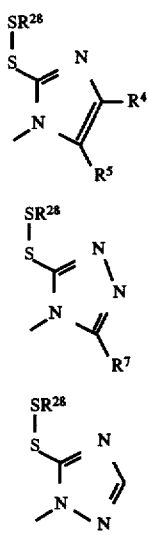

in which:

$R^4$ is hydro and $R^5$ is hydro or —$NHR^{10}$ {in which $R^{10}$ is hydro, $(C_{1-4})$alkanoyl, trifluoro$(C_{1-4})$alkanoyl, carbamoyl, $(C_{1-4})$alkyloxycarbonyl, $(C_{1-4})$alkylcarbamoyl, di$(C_{1-4})$alkylcarbamoyl, amino$(C_{1-4})$alkanoyl, $(C_{1-4})$alkylamino$(C_{1-4})$alkanoyl, di$(C_{1-4})$alkylamino$(C_{1-4})$alkanoyl, a group selected from aroyl and heteroaroyl (which aroyl and heteroaroyl are optionally further substituted with one to two substituents independently selected from hydroxy, $(C_{1-4})$alkyloxy, cyano, 1H-tetrazol-5-yl, carboxy and $(C_{1-4})$alkyloxycarbonyl) or —$C(NR^{11})NHR^{12}$ (in which $R^{11}$ and $R^{12}$ are independently hydro, acetyl or tert-butoxycarbonyl)}; or $R^5$ is hydro and $R^4$ is $(C_{1-4})$alkyl, di$(C_{1-4})$alkylaminomethyl, piperidin-1-ylmethyl, morpholin-4-ylmethyl, 1-hydroxy$(C_{1-4})$alkyl or —$CH_2NHR^{13}$ {in which $R^{13}$ is hydro, $(C_{1-4})$alkyl, $(C_{1-4})$alkanoyl, trifluoro$(C_{1-4})$alkanoyl, carbamoyl, $(C_{1-4})$alkyloxycarbonyl, $(C_{1-4})$alkylcarbamoyl, di$(C_{1-4})$alkylcarbamoyl, amino$(C_{1-4})$alkanoyl, $(C_{1-4})$alkylamino$(C_{1-4})$alkanoyl, di$(C_{1-4})$alkylamino$(C_{1-4})$alkanoyl, carboxy$(C_{1-4})$alkyl, $(C_{1-4})$alkyloxycarbonyl$(C_{1-4})$alkyl, carbamoyl$(C_{1-4})$alkyl, a group selected from aroyl, heteroaroyl, aryl$(C_{1-4})$alkyl and heteroaryl $(C_{1-4})$alkyl (which aroyl, heteroaroyl, aryl and heteroaryl are optionally further substituted with one to two substituents independently selected from hydroxy, $(C_{1-4})$alkyloxy, cyano, 1H-tetrazol-5-yl, carboxy and $(C_{1-4})$alkyloxycarbonyl) or —$C(NR^{11})NHR^{12}$ (in which $R^{11}$ and $R^{12}$ are as defined above)}; or $R^4$ is hydro, $(C_{1-4})$alkyl or —$C(O)R^{14}$ (in which $R^{14}$ is amino, hydroxy $(C_{1-4})$alkyloxy, 2-(dimethylamino) ethylamino, 4-methylpiperazin-1-yl, 2-(dimethylamino)ethylmercapto, 4-(methylsulfonylamino)anilino or 1H-tetrazol-5-ylamino) and $R^5$ is hydroxymethyl, 1H-tetrazol-5-yl, 4,5-dihydroimidazol-2-yl, pyrrolidin-1-ylmethyl, piperidin-1-ylmethyl, morpholin-4-ylmethyl, piperazin-1-ylmethyl, 4-$(C_{1-4})$alkylpiperazin-1-ylmethyl, —$C(O)R^{14}$ (in which $R^{14}$ are as defined above), —$C(NH)NR^{15}R^{16}$ (in which $R^{15}$ and $R^{16}$ are independently hydro, $(C_{1-4})$alkyl or trifluoro$(C_{1-4})$alkyl) or —$CH_2NR^{10}R^{17}$ (in which $R^{10}$ is as defined above and $R^{17}$ is hydro or $C_{1-4})$alkyl); or $R^4$ and $R^5$ are dependently di$(C_{1-4})$alkylaminomethyl, piperidin-1-ylmethyl, morpholin-4-ylmethyl or hydroxymethyl;

$R^6$ is hydro, 2-carboxyethyl, 2-carbamoylethyl or 2-$(C_{1-4})$alkyloxycarbonylethyl;

$R^7$ is hydro, pyrrolidin-1-ylmethyl, piperidin-1-ylmethyl, morpholin-4-ylmethyl, piperazin-1-ylmethyl, 4-$(C_{1-4})$alkylpiperazin-1-ylmethyl or —$CH_2NR^{10}R^{17}$ (in which $R^{10}$ and $R^{17}$ are as defined above); and $R^{28}$ is $(C_{2-6})$alkyl {which alkyl is further substituted by one to two substituents independently selected from —$N(R^{29})_2$, —$C(O)OR^{30}$, —$PO(OR^{30})_2$, —$SO_3R^{30}$, —$SO_2NHR^{30}$ and —$OR^{30}$ (in which each $R^{29}$ is independently hydro, acetyl or trifluoroacetyl and each $R^{30}$ is independently hydro or $(C_{1-5})$alkyl)}; and the pharmaceutically acceptable salts, individual isomers, and mixtures of isomers thereof.

Another aspect of this invention is a pharmaceutical composition comprising a therapeutically effective amount of a compound of Formula III, or of an individual isomer, a mixture of isomers, or the pharmaceutically acceptable salt or salts thereof, in combination with one or more pharmaceutically acceptable excipients.

Another aspect of this invention is a method for treating a condition capable of amelioration by inhibition of dopamine β-hydroxylase in an animal in need thereof, which method comprises administering to such animal a therapeutically effective amount of a compound of Formula III, or of an individual isomer, mixture of isomers, or the pharmaceutically acceptable salt or salts thereof.

Another aspect of this invention is the processes for preparing compounds of Formula III and is set forth in "Detailed Description of the Invention".

Another aspect of this invention is a compound of the formula:

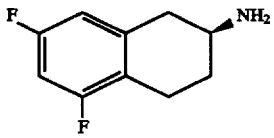

namely (S)-5,7-difluoro-1,2,3,4-tetrahydronaphthalen-2-ylamine.

Another aspect of this invention is the processes for preparing (S)-5,7-difluoro-1,2,3,4-tetrahydronaphthalen-2-ylamine and is set forth in "Detailed Description of the Invention".

DETAILED DESCRIPTION OF THE INVENTION

Definitions:

As used herein:

"Alkyl" means a straight or branched saturated hydrocarbon radical having from one to the number of carbon atoms designated (e.g., $(C_{1-4})$alkyl includes the radicals methyl, ethyl, prop-1-yl, prop-2-yl, but-1-yl, but-2-yl, 2-methylpropyl and 1,1-dimethylethyl).

"Trifluoroalkyl" means a radical alkyl as defined above having from one to the number of carbon atoms designated wherein is contained a trifluoromethyl group (e.g., trifluoro $(C_{1-4})$alkyl includes trifluoromethyl, 2,2,2-trifluoroethyl, 3,3,3-trifluoroprop-1-yl, 1,1,1-trifluoroprop-2-yl, etc.).

"Alkyloxy" means the radical —OR, wherein R is alkyl having from one to the number of carbon atoms designated (e.g., $(C_{1-4})$alkyloxy includes the radicals methoxy, ethoxy, prop-1-yloxy, prop-2-yloxy, but-1-yloxy, but-2-yloxy, 2-methylprop-1-yloxy and 2-methylprop-2-yloxy).

"Aryl", as in aryl or aryl$(C_{1-4})$alkyl, means an organic radical derived from an aromatic hydrocarbon containing 6 to 14 carbon atoms and includes monocyclic or condensed carbocyclic aromatic rings (e.g., phenyl, naphthyl, anthracenyl, phenanthrenyl, etc.) optionally further substituted with one to two substituents independently selected from halo and cyano.

"Aroyl" means the radical —C(O)R, wherein R is aryl as defined above (e.g., benzoyl, etc.).

"Heteroaryl", as in heteroaryl or heteroaryl$(C_{1-4})$alkyl, means an organic radical derived from an aromatic hydrocarbon containing 5 to 14 atoms, 1 to 5 of which are hetero atoms chosen from N, O, or S, and includes monocyclic, condensed heterocyclic and condensed carbocyclic and heterocyclic aromatic rings (e.g., thienyl, furyl, pyrrolyl, pyrimidinyl, isoxazolyl, oxazolyl, indolyl, benzo[b]thienyl, isobenzofuranyl, purinyl, isoquinolyl, pterdinyl, perimidinyl, imidazolyl, pyridyl, pyrazolyl, pyrazinyl, etc.) optionally further substituted with one to two substituents independently selected from halo and cyano.

"Heteroaroyl" means the radical —C(O)R, wherein R is heteroaryl as defined above (e.g., nicotinoyl, 2-furanoyl, picolinoyl, etc.).

"Carbamoyl", as in carbamoyl, $(C_{1-4})$alkylcarbamoyl, di$(C_{1-4})$alkylcarbamoyl or carbamoyl$(C_{1-4})$alkyl, means aminocarbonyl.

"Alkanoyl" means the radical —C(O)R having from one to the number of carbon atoms designated (e.g., formyl, acetyl, propionyl, butyryl, etc.)

"Halo" means fluoro, chloro or bromo.

"Leaving group" has the meaning conventionally associated with it in synthetic organic chemistry, i.e., an atom or group displaceable under alkylating conditions, and includes halo and alkane- or arenesulfonyloxy, such as mesyloxy, ethanesulfonyloxy, benzenesulfonyloxy, trifluoromethanesufonyloxy and tosyloxy, and the like.

"Animal" includes humans, non-human mammals, e.g., dogs, cats, rabbits, cattle, horses, sheep, goats, swine, and deer, and non-mammals, e.g., birds and the like.

"Disease" specifically includes any unhealthy condition of an animal or part thereof and includes an unhealthy condition which may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as formic acid, acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Therapeutically effective amount" means that amount which, when administered to an animal for treating a disease, is sufficient to effect such treatment for the disease.

"Treating" or "treatment" of a disease includes:

(1) preventing the disease from occurring in an animal which may be predisposed to the disease but does not yet experience or display symptoms of the disease, (2) inhibiting the disease, i.e., arresting its development, or (3) relieving the disease, i.e., causing regression of the disease.

Compounds of Formula I in which $R^3$, $R^5$ or $R^8$ is amino or in which $R^4$, $R^5$ or $R^7$ is aminomethyl can react with amino acids to give compounds of Formula II. Suitable amino acids include L-alanine, L-arginine, L-asparagine, L-aspartic acid, L-cysteine, L-glutamine, L-glutamic acid, glycine, L-histidine, L-isoleucine, L-leucine, L-lysine, L-methionine, L-ornithine, L-phenylalanine, L-proline, L-serine, L-threonine, L-tryptophan, L-tyrosine or L-valine and achiral cyclo amino acids such as 1-amino-1-cyclopropanecarboxylic acid, 1-amino-1-cyclobutanecarboxylic acid, 1-amino-1-cyclopentanecarboxylic (cycloleucine) or 1-amino-1-cyclohexanecarboxylic acid. The amino acid group imparts hydrophilic properties to the molecule. The hydrophilicity promotes the water solubility of the molecule. The amide bond is subsequently cleaved in vivo by proteolysis. Thus, compounds of Formula II are water soluble prodrugs for compounds of Formula I in which $R^3$, $R^5$ or $R^8$ is amino or in which $R^4$, $R^5$ or $R^7$ is aminomethyl.

Compounds of Formula I in which $R^3$, $R^6$ or $R^8$ is hydro can react to form a dithio linkage with a $(C_{2-6})$alkyl group which is substituted by one to two substituents independentyl selected from —N($R^{29}$)$_2$, —C(O)O$R^{30}$, —PO(O$R^{30}$)$_2$, —SO$_3R^{30}$, —SO$_2$NH$R^{30}$ and —O$R^{30}$, in which each $R^{29}$ is independently hydro, acetyl or trifluoroacetyl and each $R^{30}$ is independently hydro or $(C_{1-5})$alkyl. The substituted alkyl group imparts hydrophilic properties to the molecule. The hydrophilicity promotes the water solubility of the molecule. The dithio linkage is subsequently cleaved in vivo by chemical, enzymatic or metabolic transformation. Thus, compounds of Formula III are water soluble prodrugs for compounds of Formula I in which $R^3$, $R^6$ or $R^7$ is hydro.

The compounds of Formulae I, II and III are benzocycloalkylazolethione derivatives wherein the benzocycloalkyl portion of the molecule is of the general formula:

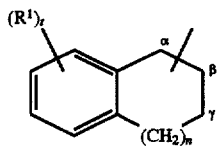

and are more specifically defined as follows:

(1) a group in which n is 0 and the monovalent carbon is at the 1- or 2-position (i.e., α- or β-position) having the formula:

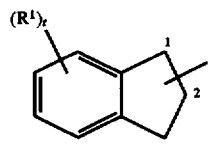

is referred to as optionally substituted indan-1-yl or indan-2-yl, respectively;

(2) a group in which n is 1 and the monovalent carbon is at the 1- or 2-position (i.e., α- or β-position) having the formula:

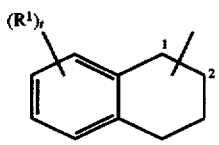

is referred to as optionally substituted 1,2,3,4-tetrahydronaphthalen-1-yl or 1,2,3,4-tetrahydronaphthalen-2-yl, respectively; and (3) a group in which n is 2 and the monovalent carbon is at the 5-, 6- or 7-position having the formula:

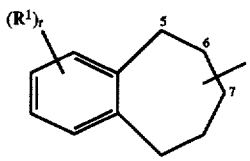

is referred to as optionally substituted 6,7,8,9-tetrahydro-5H-benzocyclohepten-5-yl, 6,7,8,9-tetrahydro-5H-benzocyclohepten-6-yl or 6,7,8,9-tetrahydro-5H-benzocyclohepten-7-yl, respectively.

The monovalent carbon of the benzocycloalkyl group may be a chiral center. Thus, compounds of Formula I and certain compounds used in the synthesis thereof may exist as either one of a pair of enantiomers of opposite chirality or as a mixture of such enantiomers. Compounds of Formulae II and III each contain one or two chiral centers. Compounds of Formulae II and III containing two chiral centers have two pairs of enantiomers (i.e., four diastereomers) and may exist as any one of the enantiomers or as a mixture thereof. The enantiomers are characterized by the absolute configuration of their chiral centers and described by the R- and S-sequencing rules of Cahn, Ingold and Prelog. When two chiral centers are present, the configuration of each chiral center is assigned an R or S descriptor as appropriate. Conventions for stereochemical nomenclature, methods for the determination of stereochemistry and the separation of stereoisomers are well-known in the art (e.g., see "Advanced Organic Chemistry", 3rd edition, March, Jerry, John Wiley & Sons, New York, 1985). Unless indicated otherwise, the illustration, description or naming of a particular chiral compound of Formulae I, II, III, 1–6, 8–32, 44–46 and 48 in the specification or in the claims is intended to include both individual enantiomers and the mixtures, racemic or otherwise, thereof.

The azolethione portion of the molecule (i.e., the $R^2$, $R^{18}$ and $R^{27}$ groups of compounds of Formulae I, II and III, respectively) is an imidazolethione or triazolethione group. For example, $R^2$ is specifically defined as follows:

(1) a group of Formula (a):

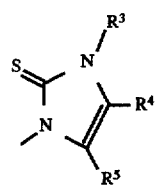

referred to as 1,3-dihydroimidazole-2-thione when forming the parent name or 2-thioxo-2,3-dihydro-1H-imidazolyl when forming a prefix to the parent name;

(2) a group of Formula (b):

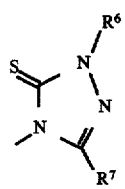

referred to as 2,4-dihydro[1,2,4]triazole-3-thione when forming the parent name or 5-thioxo-4,5-dihydro-1H-[1,2,4]triazolyl when forming a prefix to the parent name; or (3) a group of Formula (c):

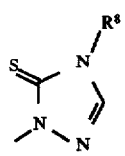

referred to as 2,4-dihydro[1,2,4]triazole-3-thione when forming the parent name or 5-thioxo-4,5-dihydro-1H-[1,2,4]triazolyl when forming a prefix to the parent name.

Certain $R^2$ and $R^{18}$ groups exist in tautomeric equilibrium between thioxo and mercapto tautomers (e.g., a group of Formula (a) in which $R^3$ is hydro). Compounds of Formula I or II which contain groups that can exist as either tautomer are named, illustrated or otherwise described in this application as thiones or thioxo substituted derivatives. However, it is to be understood that the mercapto tautomers are encompassed by such names, illustrations and descriptions as well.

The compounds of Formulae I, II and III are named by AUTONOM Version 1.0 by Beilstein-Institut and Springer-Verlag Berlin Heidelberg, a fully automatic computerized system for assigning IUPAC systematic nomenclature directly from the structural diagrams of organic compounds. For example, a compound of Formula I in which n is 1, t is 0 and $R^2$ is attached at the β-position and is a group of Formula (a), i.e., of the formula:

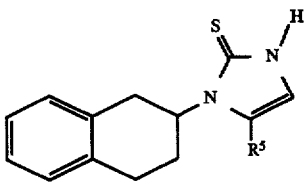

is named 5-aminomethyl-1-(1,2,3,4-tetrahydronaphthalen-2-yl)-1,3-dihydroimidazole-2-thione when $R^5$ is aminomethyl and is named 3-(1,2,3,4-tetrahydronaphthalen-2-yl)-2-thioxo-2,3-dihydro-1H-imidazole-4-carboxylic acid when $R^5$ is carboxy.

A compound of Formula I in which n is 1, t is 0 and $R^2$ is attached at the β-position and is a group of Formula (b) is named 5-aminomethyl-4-(1,2,3,4-tetrahydronaphthalen-1-yl)-2,4-dihydro[1,2,4]triazole-3-thione when $R^6$ is aminomethyl.

A compound of Formula I in which n is 1, t is 0 and $R^2$ is attached at the β-position and is a group of Formula (c) is named 4-amino-2-(1,2,3,4-tetrahydronaphthalen-2-yl)-2,4-dihydro[1,2,4]triazole-3-thione when $R^7$ is amino and is named N-[1-(1,2,3,4-tetrahydronaphthalen-2-yl)-5-thioxo-4,5-dihydro[1,2,4]triazol-4-yl]acetamide when $R^7$ is acetylamino.

A compound of Formula II in which n is 1, t is 0 and $R^{18}$ is attached at the β-position and is a group of Formula (d), wherein $R^{21}$ is L-α-aspartylaminomethyl, i.e., of the formula:

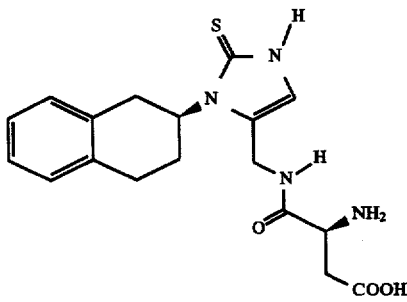

is named 3S -amino-N-[3-(1,2,3,4-tetrahydronaphthalen-2S-yl)-2-thioxo-2,3-dihydro-1H-imidazol-4-ylmethyl] succinamic acid.

A compound of Formula III in which n is 1, t is 0 and $R^{27}$ is attached at the β-position and is a group of Formula (g), wherein $R^5$ is aminomethyl and $R^{28}$ is 2-amino-2-carboxyethyl, i.e., of the formula:

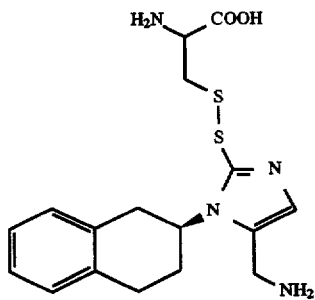

is named 2-amino-3-[5-aminomethyl-1-(1,2,3,4-tetrahydronaphthalen-2-yl)-1H-imidazol-2-yldisulfanyl] propionic acid.

Presently Preferred Embodiments:

While the breadth of compounds which are intended by the invention is as set forth in the Summary of the Invention, certain compounds of Formulae I, II and III are preferred. Preferred compounds of Formula I are those in which $R^2$ is a group of Formula (a) and are designated as compounds of Formula I(a). Preferred compounds of Formula I(a) are those in which $R^2$ is attached to the benzocycloalkyl portion of the molecule at the β-position, preferably wherein n is 0 or 1 and $R^5$ is di($C_{1-4}$)alkylaminomethyl, pyrrolidin-1-ylmethyl, piperidin-1-ylmethyl, morpholin-4-ylmethyl, piperazin-1-ylmethyl, 4-($C_{1-4}$)alkylpiperazin-1-ylmethyl or —$CH_2HR^{10}$. Most preferred compounds of Formula I(a) are those in which $R^2$ is attached at the β-position, n is 1, t is 2, each $R^1$ is fluoro, preferably at the 5- and 7-position, and $R^5$ is —$CH_2NHR^{10}$, in which $R^{10}$ is hydro, carbamoyl or ($C_{1-4}$)alkanoyl, preferably acetyl, particularly the S-enantiomer thereof.

Compounds of Formula I in which $R^2$ is a group of Formula (b) are designated as compounds of Formula I(b). Preferred compounds of Formula I(b) are those in which $R^2$ is attached at the β-position, preferably wherein n is 0 or 1 and $R^7$ is di($C_{1-4}$)alkylaminomethyl, pyrrolidin-1-ylmethyl, piperidin-1-ylmethyl, morpholin-4-ylmethyl, piperazin-1-ylmethyl, 4-($C_{1-4}$)alkylpiperazin-1-ylmethyl or —$CH_2NHR^{10}$. Most preferred compounds of Formula I(b) are those in which $R^2$ is attached at the β-position, n is 1, t is 2, each $R^1$ is fluoro, preferably at the 5- and 7-positions, and $R^6$ is di($C_{1-4}$)alkylaminomethyl, pyrrolidin-1-ylmethyl, piperidin-1-ylmethyl, morpholin-4-ylmethyl, piperazin-1-ylmethyl, 4-($C_{1-4}$)alkylpiperazin-1-ylmethyl or —$CH_2NHR^{10}$, particularly the S-enantiomer thereof.

Compounds of Formula I in which $R^2$ is a group of Formula (c) are designated compounds of Formula I(c). Preferred compounds of Formula I(c) are those in which $R^2$ is attached at the β-position, preferably wherein n is 0 or 1 and $R^8$ is —$NH_2$. Most preferred compounds of Formula I(c) are those in which $R^2$ is attached at the β-position, n is 1, t is 2, each $R^1$ is fluoro, preferably at the 5- and 7-position, and $R^8$ is —$NH_2$, particularly the S-enantiomer thereof.

Preferred compounds of Formula II are those in which $R^{18}$ is a group of Formula (d) and is attached at the β-position, preferably wherein n is 0 or 1 and $R^{21}$ is —$CH_2NHR^{26}$. Most preferred are compounds of Formula II in which $R^{18}$ is a group of Formula (d) and is attached at the β-position, n is 0 or 1, t is 2, each $R^1$ is fluoro, preferably at the 5- and 7-position, and $R^{21}$ is —$CH_2NHR^{26}$, preferably wherein $R^{26}$ is arginyl, α-aspartyl, β-aspartyl, histidyl or ornithinyl.

Preferred compounds of Formula III are those in which $R^{27}$ is a group of Formula (g) and is attached at the β-position, preferably wherein n is 0 or 1 and $R^5$ is di($C_{1-4}$) alkylaminomethyl, pyrrolidin-1-ylmethyl, piperidin-1-ylmethyl, morpholin-4-ylmethyl, piperazin-1-ylmethyl, 4-($C_{1-4}$)alkylpiperazin-1-ylmethyl or —$CH_2NHR^{10}$. Most preferred are compounds of Formula III in which $R^{27}$ is a group of Formula (g) and is attached at the β-position, n is 0 or 1, t is 2, each $R^1$ is fluoro, preferably at the 5- and 7-position, $R^5$ is di($C_{1-4}$)alkylaminomethyl, pyrrolidin-1-ylmethyl, piperidin-1-ylmethyl, morpholin-4-ylmethyl, piperazin-1-ylmethyl, 4-($C_{1-4}$)alkylpiperazin-1-ylmethyl or —$CH_2NHR^{10}$ and $R^{28}$ is a group selected from ethyl, 1,1-dimethylethyl and propyl (which group is further substituted with one to two substituents independently selected from carboxy, methoxycarbonyl, amino and trifluoroacetylamino, preferably wherein $R^{28}$ is (R)-2-amino-2-methoxycarbonylethyl, (R)-2-amino-2-carboxyethyl, (R)-2-trifluoroacetylamino-2-methoxycarbonylethyl, 2-aminoethyl, (S)-2-amino-2-carboxy-1,1-dimethylethyl or 3-amino-3-carboxyprop-1-yl.

Pharmacology and Utility:

The compounds of the invention are inhibitors of dopamine β-hydroxylase. Accordingly, the compounds of the invention are useful in treating diseases capable of amelioration by inhibition of dopamine β-hydroxylase. For example, in as much as the compounds of the invention block norepinephrine biosynthesis, they are useful in treating diseases caused or exacerbated by a hypersympathetic condition. In particular, because the compounds of the invention are peripheral vasodilators, they are useful as afterload reducing agents in treating congestive heart failure. Furthermore, because the compounds of the invention reduce norepinephrine levels, they alleviate the damaging effects to the myocardium that hypersympatheic activity produces in congestive heart failure. Thus, the compounds of the invention are particularly useful for treating congestive heart failure because they produce an initial improvement in cardiac output by reducing afterload and a sustained improvement in cardiac function by reducing norepinephrine levels in the myocardial tissue.

The dopamine β-hydroxylase inhibitor properties of test compounds can be determined by an art-recognized in vitro assay which relies upon the DBH-catalyzed conversion of tyramine to octopamine and the inhibition of DBH activity by test compounds and is described specifically in Example 53. Dopamine β-hydroxylase inhibitor properties of test compounds also can be determined by an art-recognized in vivo assay which relies upon dopamine and norepinephrine tissue concentrations and the effect of the test compounds thereon (e.g., see author: B. A. Berkowitz et al., 1988 *J. Pharm. Exp Ther.* 245, 850–857) and is described specifically in Example 54. The blood pressure lowering properties of test compounds can be determined by an in vivo assay utilizing spontaneously hypertensive rats which is described specifically in Example 55.

Administration and Pharmaceutical Composition:

In general, compounds of the invention will be administered in therapeutically effective amounts via any of the usual and acceptable modes known in the art, either singly or in combination with another compound of the invention or with another therapeutic agent. A therapeutically effective amount may vary widely depending on the severity of the disease, the age and relative health of the subject, the potency of the compound used and other factors. A therapeutically effective amount may range from approximately 0.1 milligram per Kg (mg/Kg) body weight per day to 30 mg/Kg body weight per day. Preferably the amount will be approximately 1.0 to 10 mg/Kg/day. Therefore, a therapeutically effective amount for a 70 Kg human may range from 7.0 to 2100 mg/day, preferably 70 to 700 mg/day.

One of ordinary skill in the art of treating such diseases will be able to ascertain a therapeutically effective amount of a compound of the invention for a given disease without undue experimentation and in reliance upon personal knowledge and the disclosure of this application. In general, compounds of the invention will be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of the invention in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the compound of the invention in aerosol form. Inert gases suitable for this purpose are nitrogen, carbon dioxide, nitrous oxide, etc. Other suitable pharmaceutical carriers and their formulations are described in A. R. Alfonso *Remington's Pharmaceutical Sciences* 1985, 17th ed. Easton, Pa.: Mack Publishing Company.

The amount of a compound of the invention in the composition may vary widely depending upon the type of formulation, size of a unit dosage, kind of excipients and other factors known to those of skill in the art of pharmaceutical sciences. In general, the final composition will comprise from 10% w to 90% w of the compound, preferably 25% w to 75% w, with the remainder being the excipient or excipients.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 56.

CHEMISTRY

Compounds of Formula I(a):

A method for making compounds of Formula I(a) in which $R^3$, $R^4$ and $R^5$ are each hydro is depicted by the following Reaction Scheme I:

Scheme I

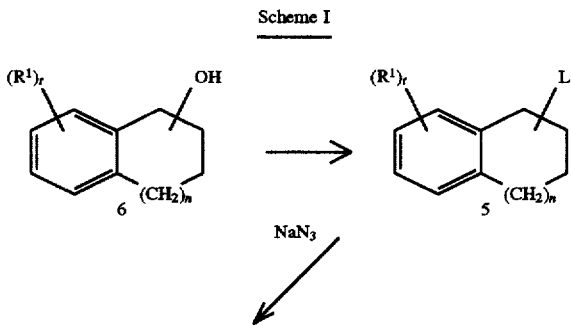

-continued
Scheme I

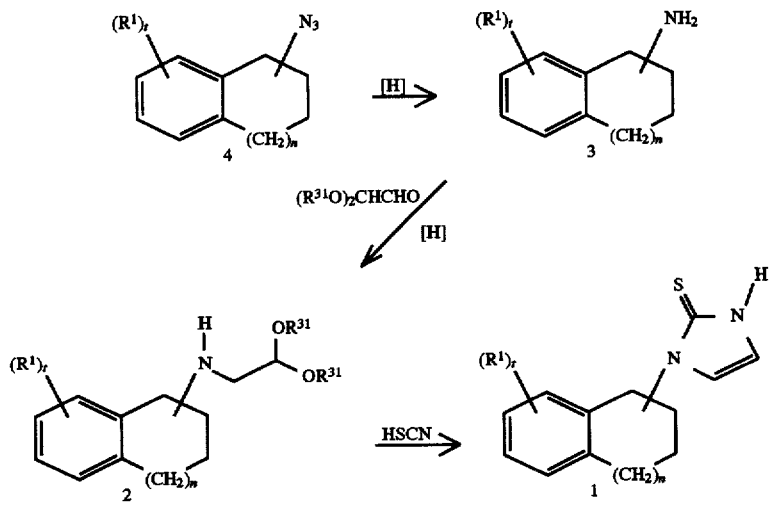

in which L is a leaving group, $R^{31}$ is alkyl, preferably methyl or ethyl, and each n, t and $R^1$ are as defined in the Summary of the Invention with respect to Formula I.

Compounds of Formula I(a) in which $R^3$, $R^4$ and $R^5$ are each hydro (Formula 1) can be prepared by reacting a compound of Formula 2 with thiocyanic acid in a suitable solvent, typically an alcohol (e.g., methanol, ethanol, any appropriate mixture of suitable alcohols, etc.) and preferably methanol. The reaction is carried out with potassium thiocyanate in the presence of aqueous acid (e.g., dilute hydrochloric acid, phosphoric acid or sulfuric acid, etc.) at 50° to 100° C., typically at 70° to 90° C. and preferably at approximately 80° C., and requires 1 to 5 hours.

Compounds of Formula 2 can be prepared by reductive amination of a dialkyloxyacetaldehyde, preferably dimethoxyacetaldehyde or diethoxyacetaldehyde, with a compound of Formula 3. The reductive amination is carried out in the presence of a chemical reducing agent (e.g., sodium cyanoborohydride, sodium borohydride, etc.) or catalytic hydrogenation (e.g., $H_2$, palladium on carbon, $H_2$, Raney® nickel, etc.) in a suitable solvent (e.g., methanol, ethanol, ethyl acetate, any appropriate mixture of suitable solvents, etc.). Optionally water is removed from the reaction mixture by standard methods (e.g., with drying agents such as molecular selves or by azeotroping). Further details of the reaction steps set forth in this and the preceding paragraph are provided in Example 9, infra. Alternatively, compounds of Formula 2 can be prepared by reductive amination of a compound of Formula 7:

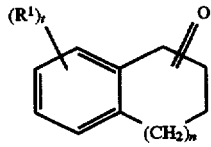

with a 2,2-dialkyloxyethylamine, preferably 2,2-dimethoxyethylamine or 2,2-diethoxyethylamine (for further details see Example 12, infra.).

Compounds of Formula 3 can be obtained commercially or can be prepared by reacting a compound of Formula 5 with an appropriate azide salt (e.g., sodium azide, lithium azide, etc.) in a suitable solvent (e.g., dimethyl sulfoxide (DMSO), N,N-dimethylformamide (DMF), etc.) to give an azide of Formula 4 and then reducing. The reaction with the azide salt is carried out at 50° to 90° C., typically at 50° to 60° C. and preferably at approximately 50° C., and requires 12 to 18 hours. Reduction of the compound of Formula 4 can be effected by catalytic hydrogenation (e.g., $H_2$, 10% palladium on carbon; or $H_2$, platinum on carbon, etc.) in a suitable solvent (e.g., ethyl acetate, ethanol, etc.). Further details of the reaction steps set forth in this paragraph are provided in Example 8, infra.

Compounds of Formula 5 are prepared by treating a compound of Formula 6 with an appropriate agent to create leaving group L. For example, compounds of Formula 5 in which L is mesyloxy can be prepared by reacting a compound of Formula 6 with methanesulfonyl chloride in a suitable solvent (e.g., diethyl ether, tetrahydrofuran (THF), methylene chloride, any appropriate mixture of suitable solvents, etc.). The reaction is carried out in the presence of triethylamine at −20° to 5° C., typically at −15° to −5° C. and preferably at approximately −10° C., and requires 3 to 15 hours (for further details see Example 7, infra.).

An alternative method for making compounds of Formula I(a) in which $R^3$, $R^4$ and $R^5$ are each hydro is depicted by the following Reaction Scheme II:

Scheme II

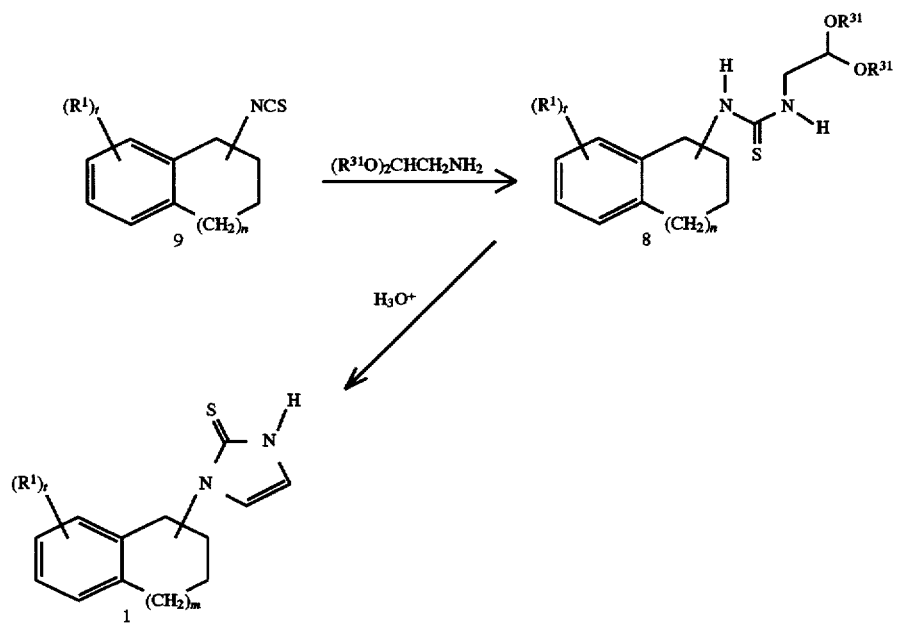

in which $R^{31}$ is alkyl, preferably methyl or ethyl, and each n, t and $R^1$ are as defined in the Summary of the Invention with respect to Formula I.

Compounds of Formula I(a) in which $R^3$, $R^4$ and $R^5$ are each hydro can be prepared by reacting a compound of Formula 9 with a 2,2-dialkyloxyethylamine, preferably 2,2-dimethoxyethylamine or 2,2-diethoxyethylamine, in a suitable solvent (e.g., DMF, DMSO, 1,3-dimethyl-3,4,5,6-tetrahydro-2(1H)-pyrimidinone (DMPU), etc.) to give a compound of Formula 8 and then treating the compound of Formula 8 with acid (e.g., hydrochloric acid) to effect ring closure. The reaction with the amine is carried out at 20° to 90° C., typically at 70° to 90° C. and preferably at approximately 85° C., and requires 1 to 2.5 hours. The treatment with acid and resultant ring closure is carried out at 20° to 90° C., typically at 70° to 85° C. and preferably at approximately 80° C., and requires 3 to 72 hours. Further details of the reaction steps set forth in this paragraph are provided in Example 11, infra.

Compounds of Formula 9 can be prepared by reacting a compound of Formula 3 with 1,1'-thiocarbonyldiimidazole in a suitable solvent (e.g., ethyl acetate, acetonitrile, acetone, methylene chloride, any appropriate mixture of suitable solvents, etc.). The reaction is carried out at 0° to 50° C., typically at 10° to 30° and preferably at approximately 20° C., and requires 3 to 18 hours (for further details see Example 10, infra.).

A method for making compounds of Formula I(a) in which $R^3$ is —$(CH_2)_q R^9$ is depicted by the following Reaction Scheme III:

Scheme III

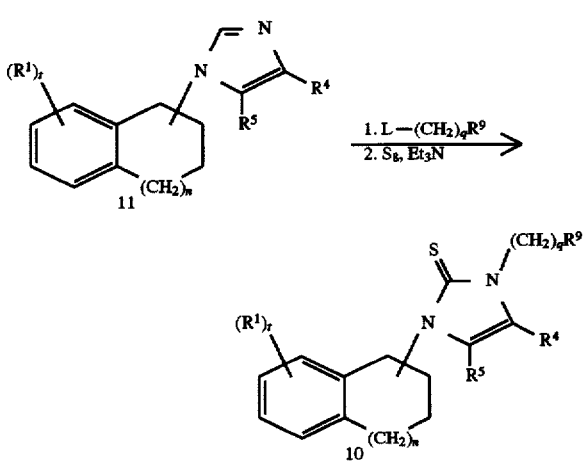

in which L is a leaving group and each n, t, $R^1$, $R^4$, $R^5$ and $R^9$ are as defined in the Summary of the Invention with respect to Formula I.

Compounds of Formula I(a) in which $R^3$ is —$(CH_2)_q R^9$ (Formula 10) can be prepared by alkylating a compound of Formula 11 with an alkylating agent of the formula L—$(CH_2)_q R^9$ to give the corresponding imidazolium salt and then sulfurizing. The alkylation is carried out in a suitable solvent (e.g., acetonitrile, DMF, THF, any appropriate mixture of suitable solvents), preferably acetonitrile or DMF, at 0° to 160° C., typically at approximately 25° C. to reflux, and requires 1 to 16 hours. The sulfurization is carried out with lac sulfur in a suitable mild base (e.g., triethylamine, pyridine, any appropriate mixture of mild bases, etc., preferably a mixture of triethylamine and pyridine) at 50° to 125° C., typically 80° to 100° C. and preferably at approximately 90° C., and requires 1 to 8 hours. In a similar fashion, compounds of Formula I(a) in which $R^3$ is amino can be prepared by reacting a compound of Formula 11 with an amino aryl or alkylsulfonate (e.g., O-mesitylenesulfonylhydroxylamine, O-methanesulfonylhydroxylamine or O-hydroxylaminesulfonic acid) to give the corresponding 3-aminoimidazolium salt and then sulfurizing. The reaction with the sulfonate is carried out in a suitable solvent (e.g., acetonitrile, methylene chloride, THF, any appropriate mixture of suitable solvents, etc., preferably acetonitrile) at 0° to 40° C., typically at 10° to 30° C. and preferably at approximately 20° C., and requires 0.5 to 18 hours. Further details of the reaction steps set forth in this paragraph are provided in Example 15, infra.

Compounds of Formula 11 can be prepared by reacting the corresponding compound of Formula 5 with an appropriately substituted imidazole in a suitable solvent (e.g., DMF, DMSO, acetonitrile, etc.). The reaction is carried out at 50° to 100° C., preferably at approximately 85° C., and requires 8 to 24 hours (for further details see Example 13, infra.). In a similar fashion, compounds of Formula 11 in which n is 1 and the imidazole portion of the molecule is attached at the β-position can be prepared by reacting an appropriately substituted 2-bromo-1,2,3,4-tetrahydronapththalen-1-one with an appropriately substituted imidazole and then reducing. The reduction can be carried out by catalytic hydrogenation (e.g., $H_2$, palladium hydroxide) in a suitable acidic solvent (e.g., sulfuric acid, acetic acid, any appropriate mixture of acids, etc.) at 15 to 100 psi, typically at 40 to 60 psi and preferably at approximately 50 psi, and requires 1 to 24 hours.

Alternatively, compounds of Formula 11 can be prepared by treating a corresponding of Formula I with Raney® nickel. The treatment with Raney® nickel is carried out in a suitable solvent (e.g., ethanol, methanol, acetic acid, water, any appropriate mixture of suitable solvents, etc. preferably ethanol) at 0° to 100° C., typically at 25° to 80° C. and preferably at approximately 80°, and requires 0.25 to 4 hours (for further details see Example 14, infra.).

Compounds of Formula I(a) in which $R^3$ and $R^4$ are hydro and $R^5$ is di($C_{1-4}$)alkylaminomethyl, piperidin-1-ylmethyl or morpholin-4-ylmethyl can be prepared by alkylating a compound of Formula 11 in which $R^4$ and $R^5$ are both hydro with an appropriately N,N-disubstituted methyleneammonium salt (e.g., a N,N-di($C_{1-4}$)alkylmethyleneammonium salt such as N,N-dimethylmethyleneammonium chloride, N,N-diethylmethyleneammonium chloride and the like, 1-methylenepiperidinium chloride, a 4-methylenemorpholinium chloride, etc.) and then sulfurizing. The alkylation is carried out in a suitable solvent (e.g., DMF, DMPU, acetonitrile, any appropriate mixture of suitable solvents, etc., preferably DMF) at 50° to 100° C., typically at 80° to 100° C. and preferably at approximately 95° C., and requires 4 to 18 hours.

Compounds of Formula I(a) in which $R^3$ is hydro can be prepared by reacting a compound of Formula 11 with a strong base (e.g., n-butyllithium, lithium diisopropylamide (LDA), etc.) in a suitable solvent (e.g., 1,2-dimethoxyethane, THF, 2-methoxyethyl ether, etc.) to give the corresponding 2-imidazolide and then sulfurizing. The reaction with the base is carried out by cooling a solution of a compound of Formula 12 to between 0° and −78° C., typically to between −50° and −78° and preferably to approximately −78° C., adding the base and then allowing the reaction to proceed for 0.25 to 3 hours. The sulfurization is carried out at 0° to −78° C., typically at −50° and −78° and preferably at approximately −78° C., and requires 2 to 18 hours. Further details of the reaction steps set forth in this paragraph are provided in Example 16, infra.

A method for making compounds of Formula I(a) in which $R^3$ and $R^4$ are hydro and $R^5$ is amino is depicted by the following Reaction Scheme IV:

Scheme IV

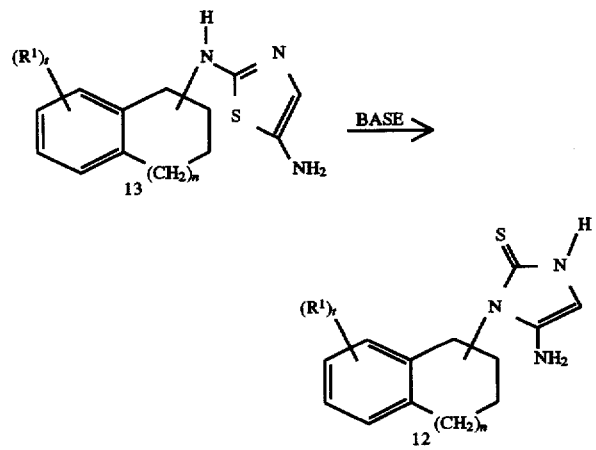

in which each n, t and $R^1$ are as defined in the Summary of the Invention with respect to Formula I.

Compounds of Formula I(a) in which $R^3$ and $R^4$ are hydro and $R^5$ is amino (Formula 12) can be prepared by treating a compound of Formula 13 with an alkali base (e.g., potassium hydroxide or sodium hydroxide) to effect rearrangement. The treatment with base and attendant rearrangement is carried out at 0° to 40° C., typically at 10° to 30° C. and preferably at approximately 20° C., and requires 0.1 to 2 hours.

Compounds of Formula 13 can be prepared by reacting a compound of Formula 9 with aminoacetonitrile hydrochloride in a suitable solvent (e.g., triethylemine, triethylamine in acetonitrile, dimethylformamide, or dimethylsulfoxide). The reaction is carried out at 20° to 100° C., typically at 10° to 30° C. and preferably at approximately 20° C., and requires 12 to 24 hours. Further details of the reaction steps set forth in this paragraph and the preceding paragraph are provided in Example 17, infra.

A method for making confounds of Formula I(a) in which $R^3$ is hydro, $R^4$ is hydro, ($C_{1-4}$)alkyl or ($C_{1-4}$)alkyloxycarbonyl and $R^5$ is cyano or ($C_{1-4}$)alkyloxycarbonyl is depicted by the following Reaction Scheme V:

Scheme V

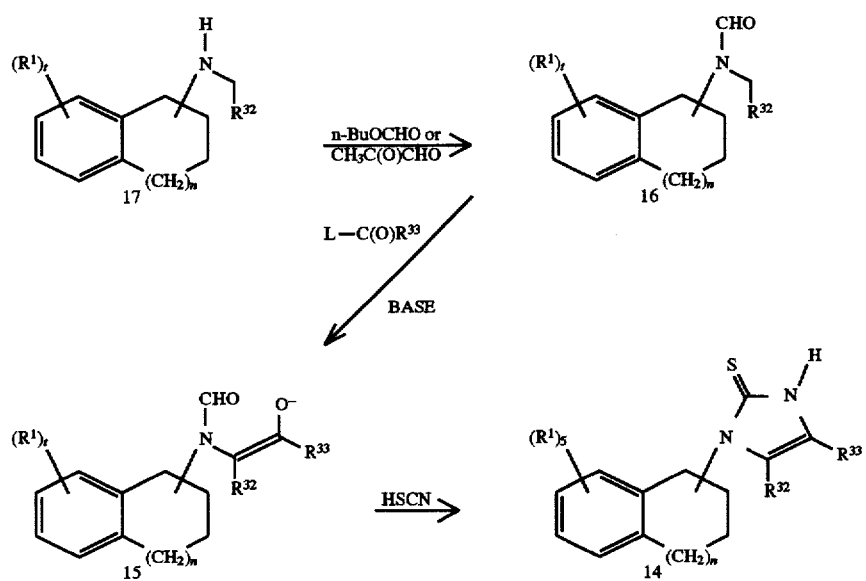

in which L is a leaving group (e.g., halo, alkyloxy, acyloxy, aryloxy, etc.), $R^{32}$ is cyano or $(C_{1-4})$alkyloxycarbonyl), $R^{33}$ is hydro, $(C_{1-4})$alkyl or $(C_{1-4})$alkyloxycarbonyl and each n, t and $R^1$ are as defined in the Summary of the Invention with respect to Formula I.

Compounds of Formula I(a) in which $R^3$ is hydro, $R^4$ is hydro, $(C_{1-4})$alkyl or $(C_{1-4})$alkyloxycarbonyl and $R^5$ is cyano or $(C_{1-4})$alkyloxycarbonyl (Formula 14) can be prepared by reacting a compound of Formula 16 with a compound of the formula $R^{33}C(O)L$ to give a compound of Formula 15 and then reacting the compound of Formula 15 with thiocyanic acid. The reaction with the compound of the formula $R^{33}C(O)L$ is carried out in the presence of base (e.g., potassium tert-butoxide, LDA, etc.) and in a suitable solvent (e.g., THF, 1,2-diethoxyethane, diethyl ether, any appropriate mixture of suitable solvents, etc.).

For example, a compound of Formula 15 in which $R^4$ is hydro can be prepared by reacting a compound of Formula 16 with an alkyl or arylformate (e.g., ethyl formate, phenyl formate, etc.) in the presence of potassium tert-butoxide. The reaction with the formate is carried out at −40° to 65° C., typically at −30° to 0° C. and preferably at approximately −15° C., and requires 3 to 24 hours (for further details see Example 24, infra.). A compound of Formula 15 in which $R^4$ is $(C_{1-4})$alkyl can be prepared by reacting a compound of Formula 16 with an $(C_{2-5})$alkanoic acid chloride or anhydride (e.g., acetyl chloride, propionyl chloride, acetic anhydride, etc.) in the presence of LDA. The reaction with the acid chloride or anhydride is carried out at −78° to −15° C., typically at −50° to −78° C. and preferably at approximately −78° C., and requires 1 to 24 hours (for further details see Example 25, infra.). The reaction with the thiocyanic acid is carried out with potassium thiocyanate in the presence of aqueous acid (e.g., aqueous hydrochloric acid, aqueous sulfuric acid, aqueous phosphoric acid, etc.) at 50° to 100° C., typically at 75° to 95° C. and preferably at approximately 85° C., and requires 1to 5 hours.

Compounds of Formula 16 can be prepared by heating a compound of Formula 17 in n-butyl formate at temperatures of 70° to 105° C., preferably at approximately 105° C., for 3 to 24 hours. Alternatively, compounds of Formula 16 can be prepared by reacting a compound of Formula 17 with acetic formic anhydride in a suitable solvent (e.g., methylene chloride, dichloromethane, THF, etc.). The reaction with acetic formic anhydride is carried out at −15° to 25° C., preferably at approximately 0° C., and requires 0.5 to 3 hours.

Compounds of Formula 17 in which $R^{32}$ is ethoxycarbonyl can be prepared by the reductive amination of ethyl glyoxalate with a compound of Formula 3. The reductive amination is carried out in the presence of a chemical reducing agent (e.g., sodium cyanoborohydride, sodium borohydride, etc.) or catalytic hydrogenation (e.g., $H_2$, palladium on carbon; $H_2$, nickel; etc.) in a suitable solvent (e.g., methanol, ethanol, ethyl acetate, any appropriate mixture of suitable solvents, etc.). Optionally water is removed from the reaction mixture by standard methods (e.g., with drying agents such as molecular seives or by azeotroping). For further details of the reaction steps set forth in this and the preceding paragraph see Example 23, infra.

Compounds of Formula 17 in which $R^{32}$ is cyano can be prepared by reacting a compound of Formula 3 with formaldehyde sodium bisulfite complex and potassium cyanide in a suitable solvent (e.g., water, aqueous ethanol, etc.). The reaction is carried out at 50° to 80° C., typically at 50° to 60° C. and preferably at approximately 50° C., and requires 0.5 to 2 hours (for further details see Example 19, infra.).

A method for making compounds of Formula I(a) in which $R^3$ and $R^5$ are hydro and $R^4$ is formyl is depicted by the following Reaction Scheme VI:

Scheme VI

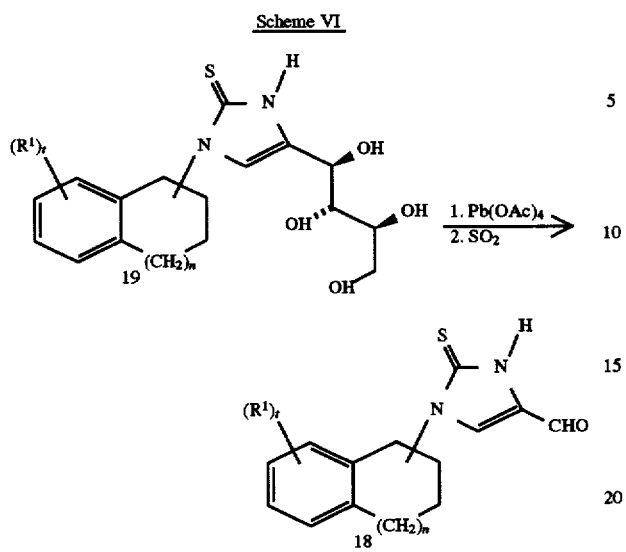

Scheme VII

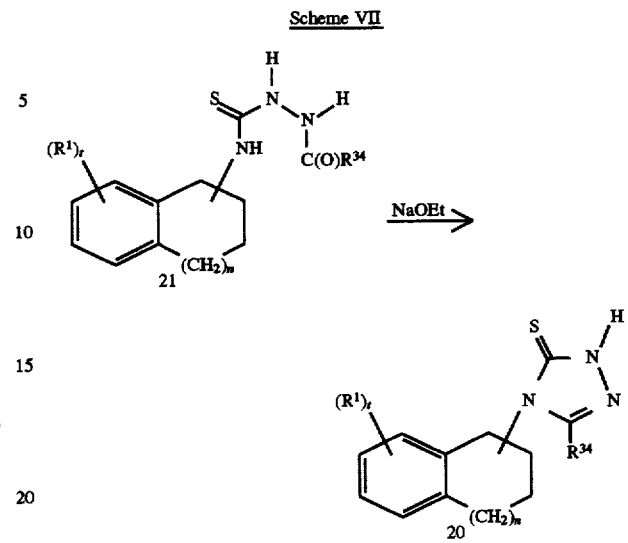

in which each n, t and $R^1$ are as defined in the Summary of the Invention with respect to Formula I.

Compounds of Formula I(a) in which $R^3$ and $R^5$ are hydro and $R^4$ is formyl (Formula 18) are prepared by oxidizing a compound of Formula 19. The oxidization is effected with an appropriate oxidizing agent (e.g., lead tetraacetate, periodic acid, etc.) in a suitable solvent (e.g., acetic acid-benzene, acetic acid-toluene, acetic acid, any appropriate mixture of suitable solvents, etc.) at 0° to 80° C., typically at 20° to 40° C. and preferably at approximately 25° C., and requires 0.25 to 4 hours.

Compounds of Formula 19 are prepared by reacting a compound of Formula 9 with D-(+)-glucosamine. The reaction is carried out in a suitable solvent, typically an alcohol (e.g., ethanol, methanol, any appropriate mixture of alcohols, etc.) and preferably ethanol, at 50° to 80° C., typically at 70° to 80° C. and preferably at approximately 80° C., and requires 1 to 2 hours. Further details of the reaction steps set forth in this and the preceding paragraph are provided in Example 22, infra.

Compounds of Formula I in which $R^3$ and $R^4$ are hydro and $R^5$ is hydroxymethyl can be prepared by reacting a compound of Formula 3, or the acid addition salt thereof, with thiocyanic acid and dihydroxyacetone in a suitable solvent (e.g., ethyl acetate, THF, dioxane, any appropriate mixture of suitable solvents, etc., preferably ethyl acetate) and then optionally treating the reaction mixture with sulfuric acid (treating with sulfuric acid enhances purity). The reaction is carried out with potassium thiocyanate in the presence of acid (e.g., glacial acetic acid, propionic acid, etc., preferably glacial acetic acid) under nitrogen at 20° to 50° C. for 0.5 to 3 hours (for further details see Example 18, infra.).

Compounds of Formula I(b):

A method for making compounds of Formula I(b) in which $R^7$ is hydro, aminomethyl, $(C_{1-4})$alkylaminomethyl, di$(C_{1-4})$alkylaminomethyl, pyrrolidin-1-ylmethyl, piperidin-1-ylmethyl, morpholin-4-ylmethyl, piperazin-1-ylmethyl or 4-$(C_{1-4})$alkylpiperazin-1-ylmethyl is depicted by the following Reaction Scheme VII:

in which $R^{34}$ is hydro, aminemethyl, $(C_{1-4})$ alkylaminomethyl, di$(C_{1-4})$alkylaminemethyl, pyrrolidin-1-ylmethyl, piperidin-1-ylmethyl, morpholin-4-ylmethyl, piperazin-1-ylmethyl or 4-$(C_{1-4})$alkylpiperazin-1-ylmethyl, or a protected derivative thereof, and each n, t and $R^1$ are as defined in the Summary of the Invention with respect to Formula I.

Compounds of Formula I(b) in which $R^7$ is hydro, aminemethyl, $(C_{1-4})$alkylaminemethyl, di$(C_{1-4})$ alkylaminomethyl, pyrrolidin-1-ylmethyl, piperidin-1-ylmethyl, morpholin-4-ylmethyl, piperazin-1-ylmethyl or 4-$(C_{1-4})$alkylpiperazin-1-ylmethyl (Formula 20) can be prepared by reacting a compound of Formula 21, or a protected derivative thereof, with a base (e.g., sodium ethoxide, potassium t-butoxide, etc.) in a suitable solvent, typically an alcohol (e.g., ethanol, t-butanol, isopropanol, any appropriate mixture of suitable alcohols, etc.) and preferably ethanol, to effect a ring closure and then removing any protective groups present. The reaction with the base and the resultant ring closure is carried out at 0° to 75° C., preferably approximately 20° C., and requires 1 to 24 hours. Deprotection can be effected by treating with acid in a suitable solvent (e.g., 15% anhydrous hydrogen chloride in ethyl acetate, trifluoroacetic acid in methylene chloride, etc.).

Compounds of Formula 21 are prepared by reacting a compound of Formula 9 with a hydrazide of the formula $H_2NHNC(O)R^{34}$, or a protected derivative thereof, in a suitable solvent (e.g., DMF, ethyl acetate, any appropriate mixture of suitable solvents, etc.). The reaction is carried out at 50° to 100° C., typically at 70° to 90° C. and preferably at approximately 80° C., and requires 1 to 4 hours.

Hydrazides of the formula $H_2NHNC(O)R^{34}$ can be prepared by reacting a corresponding methyl aminoacetate, or the protected derivative thereof, with hydrazine in suitable solvent (e.g., methanol, ethanol, DMF, any appropriate mixture of suitable solvents, etc.). The reaction is carried out at 20° to 80° C., typically at 50° to 70° C. and preferably at approximately 65° C., and requires 48 to 96 hours. Suitable methyl aminoacetates are commercially available or can be easily prepared by methods known in organic synthesis. For example, the protected derivative of methyl aminoacetate can be prepared by esterification of N-(tert-butoxycarbonyl) glycine. Other aminoacetates can be prepared by reacting a corresponding methyl chloroacetate with an amine of the formula NHR$^{36}$R$^{37}$ (in which R$^{36}$ and R$^{37}$ are independently ($C_{1-4}$)alkyl or together are —$(CH_2)_4$—, —$(CH_2)_5$—, —$(CH_2)_2O(CH_2)_2$— or —$(CH_2)_2NR^{38}(CH_2)_2$—, wherein $R^{38}$ is hydro or ($C_{1-4}$)alkyl) in a suitable solvent (e.g., acetonitrile, ethanol, DMF, any appropriate mixture of suitable solvents, etc.). The reaction is carried out at 0° to 100° C., typically at 65° to 95° C. and preferably at approximately 80° C., and requires 1 to 48 hours. Further details of the reaction steps set forth in this and the two preceding paragraphs are provided in Example 26.

Compounds of Formula I(c):

A method for making compounds of Formula I(c) in which $R^7$ is hydro is depicted by the following Reaction Scheme VIII:

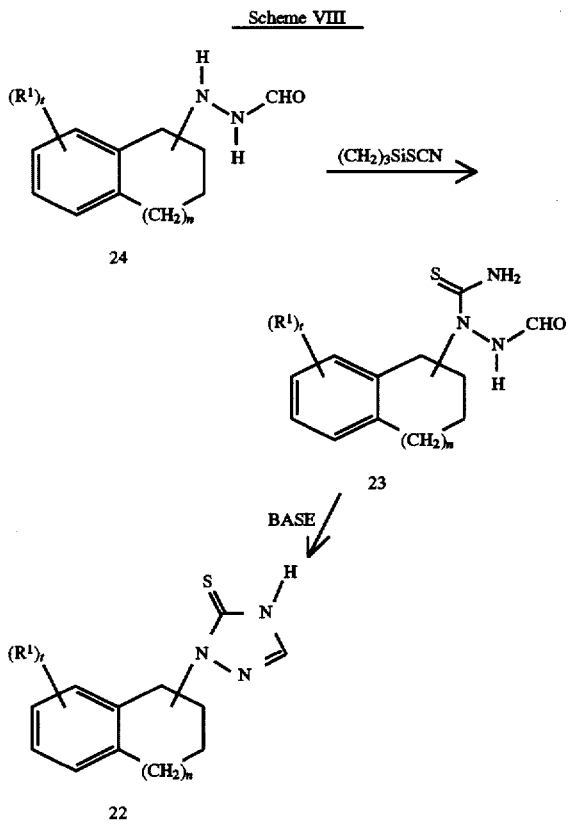

in which each n, t, and $R^1$ are as defined in the Summary of the Invention with respect to Formula I.

Compounds of Formula I(c) in which $R^7$ is hydro (Formula 22) can be prepared by reacting a compound of Formula 23 with a suitable base (e.g., 10% sodium hydroxide, potassium t-butoxide, etc.). The reaction with the base and resultant ring closure is carried out at 20° to 100° C., typically at 50° to 90° C. and preferably at approximately 70° C., and requires 1 to 24 hours.

Compounds of Formula 23 are prepared by reacting a compound of Formula 24 with an isothiocyanate (e.g., trimethylsilyl isothiocyanate, etc.) in a suitable solvent (e.g., toluene, 1,2-dimethoxyethane, any appropriate mixture of suitable solvents, etc.). The reaction is carried out at 20° to 110° C., typically at 50° to 90° C. and preferably at approximately 70° C., and requires 18 to 24 hours. Compounds of Formula 24 are prepared by reacting a compound of Formula 7 with formic hydrazide in a suitable solvent (e.g., ethanol, isopropanol, etc.) and then reducing. The reaction with the hydrazide is carried out in the presence of acid (e.g., hydrochloric acid, p-toluene sulfonic acid, boric acid, trifluoroacetic acid, etc.) at 20° to 100° C., typically at 60° to 90° C. and preferably at approximately 75° C., and requires 1 to 5 hours. The reduction can be effected with a chemical reducing agent (e.g., lithium borohydride, sodium borohydride, sodium cyanoborohydride, etc.) in a suitable solvent, typically an alcohol (e.g., ethanol, any appropriate mixture of alcohol etc.), preferably ethanol at 20° to 80° C. and requires 8 to 24 hours. Further details of the reaction steps set forth in this and the preceding paragraph are provided in Example 27, infra.

Compounds of Formula I(c) in which $R^7$ is amino can be prepared by reacting a compound of Formula 5 with 1,2,4-triazol-4-ylamino to give the corresponding 4-aminotriazolium salt and then sulfurizing. The reaction with the 4-amino[1,2,4]triazole is carried out at 50° to 100° C., typically at 80° to 90° C. and preferably at approximately 90° C., and requires 1 to 8 hours. The sulfurization is carried out with lac sulfur in the presence of a mild base (e.g., triethylamine, etc.) at 50° to 125° C., typically at 80° to 100° C. and preferably at approximately 90° C., and requires 1 to 8 hours (for further details see Example 28, infra.).

Additional Processes for Making Compounds of Formula I:

Compounds of Formula I in which $R^5$ is 1H-tetrazol-5-yl can be prepared by reacting a compound of Formula I in which $R^5$ is cyano with a hydrazoic acid derivative (e.g., tributyltin azide, triphenylsilyl azide, t-butyldiphenylsilyl azide, etc.). The reaction is carried out at 100° to 150° C., typically at 120° to 140° C. and preferably at approximately 130° C., and requires 2 to 18 hours (for further details see Example 21, infra.).

Compounds of Formula I in which $R^5$ is carbamoyl can be prepared by hydrolyzing compound of Formula I in which $R^5$ is cyano. The hydrolysis can be carried out with aqueous hydrochloric acid at 100° to 140° C., typically at 125° to 135° C. and preferably at approximately 130° C., and requires 2 to 18 hours. Proceeding as described above, 5,6-difluoroindan-2-yl-2-thioxo-2,3-dihydro-1H-imidazol-4-yl-carboxamide, m.p.>280° C., was prepared.

Compounds of Formula I in which $R^5$ is —C(NH)NR$^{15}$R$^{16}$ can be prepared by reacting a compound of Formula I in which $R^5$ is cyano with a reagent of the formula $(CH_3)_2AlNR^{15}R^{16}$, in a suitable solvent (e.g., toluene, benzene, methylene chloride, tetrachloroethane, any appropriate mixture of suitable solvents, etc.). The reaction is carried out at 20° to 130° C., typically at 60° to 100° C. and preferably at approximately 80° C., and requires 1 to 18 hours. The reagent of the formula $(CH_3)_2AlNR^{15}R^{16}$ is prepared by reacting an amine of the formula NHR$^{15}$R$^{16}$ with trimethylaluminum. Proceeding as described above 5-(aminoiminomethyl)-1-(5,6-difluoroindanyl-2-yl)-1,3-dihydroimidazole-2-thione and 1-(5,6-difluoroiindan-2-yl)-5-[imino-(2,2,2-trifluoroethylamino)methyl]-1,3-dihydroimidazole-2-thione, m.p. 199°-200° C., were prepared.

Compounds of Formula I in which $R^5$ is 4,5-dihydroimidazol-2-yl can be prepared by reacting compound of Formula I in which $R^5$ is cyano with ethylenediamine. The reaction can be carried out by heating the reactants in the presence p-toluenesulfonic acid at 100° to 250° C., typically at 180° to 220° C. and preferably at approximately 200° C., for 1 to 3 hours. Proceeding as described above, 1,2,3,4-tetrahydronaphthalen-2-yl-5-(4,5-dihydroimidazol-2-yl)-1,3-dihydroimidazole-2-thione, m.p. 130°-145° C., was prepared.

Compounds of Formula I in which $R^3$ and $R^4$ are hydro and $R^5$ is aminomethyl can be prepared by reducing compound of Formula I in which $R^5$ is cyano. The reduction can be effected with a chemical reducing agent (e.g., lithium aluminum hydride, borane in THF, aluminum hydride, etc.) in a suitable solvent (e.g., THF, 1,2-dimethoxyethane, 2,2-dimethoxyethyl ether, any appropriate mixture of suitable solvents, etc.) at 0° to 65° C., typically at 0° to 20° C. and preferably at approximately 0° C. and requires 1 to 5 hours (for further details see Example 20, infra.).

A preferred method for making compounds of Formula 1 in which $R^3$ and $R^4$ are hydro and $R^5$ is aminomethyl is depicted by the following Reaction Scheme IX:

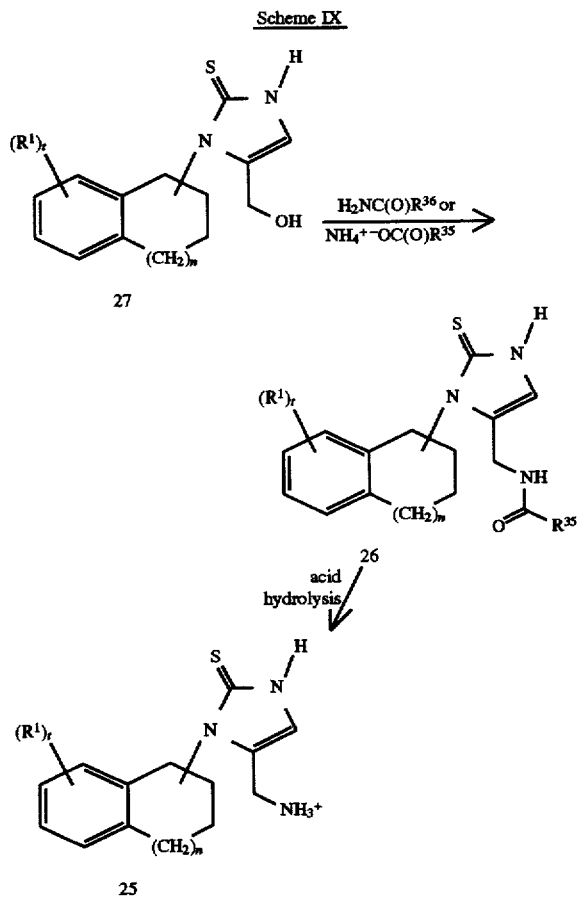

in which $R^{35}$ is hydro, $(C_{1-4})$alkyl or trifluoro$(C_{1-4})$alkyl and each n, t and $R^1$ are as defined in the Summary of the Invention with respect to Formula I.

The acid addition salt of a compound of Formula I in which $R^3$ and $R^4$ are each hydro and $R^5$ is aminomethyl (Formula 25) can be prepared by acid catalyzed hydrolysis of the corresponding compound of Formula I in which $R^5$ is formylaminomethyl, $(C_{1-4})$alkylcarbonylaminomethyl or trifluoro$(C_{1-4})$alkylcarbonylaminomethyl (Formula 26). The hydrolysis is carried out in a suitable solvent, typically an alcohol (e.g., isopropanol, ethanol, methanol, any appropriate mixture of alcohols, etc.) and preferably isopropanol, and under nitrogen at 65° to 82° C., preferably at reflux, and requires 0.5 to 4 hours.

Pharmaceutically acceptable acid addition salts of compounds of Formula I in which $R^3$ and $R^4$ are each hydro and $R^5$ is aminomethyl can be prepared by performing the hydrolysis with a pharmaceutically acceptable acid (e.g., 2 to 8 equivalents of concentrated hydrochloric acid, preferably approximately 5 equivalents). Alternatively, any acid addition salt form of a compound of Formula 25 can be converted to the corresponding free base form by reacting with an acceptable inorganic or organic base and then converted to a pharmaceutically acceptable acid addition salt by reacting with an appropriate pharmaceutically acceptable acid. Further details of the reaction steps set forth in this paragraph and the preceding paragraph are provided in Example 31, infra.

Compounds of Formula I in which $R^5$ is formylaminomethyl, $(C_{1-4})$alkylcarbonylaminomethyl or trifluoro$(C_{1-4})$alkylcarbonylaminomethyl can be prepared by reacting the corresponding compound of Formula I in which $R^5$ is hydroxymethyl (Formula 27) with a primary amide of the formula $H_2NC(O)R^{35}$ (e.g., formamide, acetamide, trifluoroacetamide, etc.). The reaction is carried out by adding the confound of Formula 27 to the amide and then heating the mixture under a stream of nitrogen for 0.5 to 2 hours at 150° to 190° C. Preferably the amide is formamide and the reaction is carried out by heating at 170° to 175° for approximately 1 hour. Proceeding similarly but substituting urea for the primary amide, compounds of Formula I in which $R^5$ is ureidomethyl can be prepared. Further details of the reaction steps set forth in this paragraph are provided in Example 29, infra.

A preferred process for preparing compounds of Formula 26 comprises reacting a compound of Formula 27 with an ammonium salt of the formula $NH_4^+ {}^-OC(O)R^{35}$ (e.g., ammonium formate, ammonium acetate, ammonium trifluoroacetate, etc., preferably ammonium formate). For example, a compound of Formula 27 can be reacted with ammonium formate to give a compound of Formula 24 wherein $R^{35}$ is hydro. The reaction is carried out neat or in formamide, preferably formamide at 100° to 180° C., preferably at 120° to 150° C., and requires 1 to 2 hours (for further details see Example 30, infra.).

Compounds of Formula I in which $R^3$ and $R^4$ are hydro and $R^5$ is aminomethyl, $(C_{1-4})$alkylaminomethyl, di$(C_{1-4})$ alkylaminomethyl, pyrrolidin-1-ylmethyl, piperidin-1-ylmethyl, morpholin-4-ylmethyl, piperazin-1-ylmethyl or 4-$(C_{1-4})$alkylpiperazin-1-ylmethyl can be prepared by converting a compound of Formula I in which $R^5$ is hydroxymethyl to a compound of Formula 28:

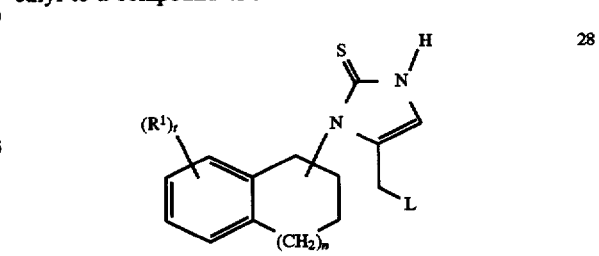

in which L is a leaving group and n, t and $R^1$ are as defined in the Summary of the Invention with respect to Formula I, and reacting the compound of Formula 28 with an amine of the formula $HNR^{36}R^{37}$, in which $R^{36}$ and $R^{37}$ are independently $(C_{1-4})$alkyl or together are $-(CH_2)_4-$, $-(CH_2)_5-$, $-(CH_2)_2O(CH_2)_2-$ or $-(CH_2)_2NR^{38}(CH_2)_2-$ (in which $R^{38}$ is hydro or $(C_{1-4})$alkyl). The conversion to the compound of Formula 28 is effected with an appropriate agent for forming a suitable leaving group (e.g., methanesulfonyl chloride, thionyl chloride, phosphorous pentachloride, phosphorous oxychloride, etc.) in a suitable solvent (e.g., methylene chloride, chloroform, THF, any appropriate mixture of suitable solvents, etc.). The reaction with the amine is carried out in a suitable solvent (e.g., THF, 1,2-dimethoxyethane, acetonitrile, any appropriate mixture of suitable solvents, etc.) at −10° to 20° C. and requires 1 to 4 hours. Further details of the reaction steps set forth in this paragraph are provide in Example 32, infra.

Compounds of Formula I in which $R^4$ is aminomethyl can be prepared by reacting a corresponding compound of Formula I in which $R^4$ is formyl with hydroxylamine hydrochloride to give the corresponding oxime and then reducing. The reaction with the hydroxylamine hydrochloride is carried out in the presence of a suitable base (e.g., sodium hydroxide, sodium acetate, etc.) and in a suitable solvent, typically an alcohol (e.g., ethanol, methanol, any appropriate mixture of alcohols, etc.) or a mixture of alcohol and water (e.g., ethanol/water (1:1), etc.) at 20° to 100° C., typically at 50° to 70° C. and preferably at approximately 60° C., and requires 1 to 8 hours. The reduction of the oxime can be effected with a chemical reducing agent (e.g., lithium aluminum hydride, etc.) in a suitable solvent (e.g., THF, any mixture of suitable solvents, etc.) at −50° to 50° C., typically at −20° to 20° C. and preferably at approximately 0° C. For further details of the reaction steps set forth in this paragraph see Example 47, infra.

Compounds of Formula I in which $R^4$ is —$CH_2NHR^{10}$, wherein $R^{10}$ is as defined in the Summary of the Invention with respect to Formula I, can be prepared by reductive amination of a compound of Formula I in which $R^4$ is formyl with an amine of the formula $NH_2R^{10}$ (e.g., glycine tert-butyl ester hydrochloride, glycinamide hydrochloride, phenethylamine, methyl 4-(2-amino-ethyl)benzoate, etc.). The reductive amination is carried out in the presence of a chemical reducing agent (e.g., sodium cyanoborohydride, sodium borohydrids, etc.) or catalytic hydrogenation (e.g., $H_2$, palladium on carbon, $H_2$, Raney® nickel, etc.) in a suitable solvent (e.g., THF, water, ethyl acetate, alcohol, any appropriate mixture of solvents, etc.), typically an alcohol (e.g., ethanol, methanol, any appropriate mixture of alcohols, etc.) at 20° to 100° C., preferably at approximately 50° C., and requires 1 to 8 hours (for further details see Example 48, infra.).

Compounds of Formula I in which $R^4$ is 1-hydroxy($C_{1-4}$)alkyl can be prepared by reacting a corresponding compound of Formula I in which $R^4$ is formyl with an appropriate alkylating agent (e.g., methylmagnesium chloride, ethylmagnesium chloride, n-propylmagnesium chloride, etc.). The alkylation is carried out neat at −20° to 60° C., typically at 0° to 25° C. and preferably at approximately 0° C. (for further details see Example 40, infra.).

Compounds of Formula I in which $R^3$, $R^5$ or $R^8$ is —$NHC(NR^{11})NHR^{12}$ or compounds of Formula I in which $R^4$, $R^5$ or $R^7$ is —$CH_2C(NR^{11})NHR^{12}$ in which $R^{11}$ is hydro, acetyl or tert-butoxycarbonyl and $R^{12}$ is acetyl or tert-butoxycarbonyl can be prepared by reacting a compound of Formula I in which $R^3$, $R^4$, $R^5$, $R^7$ or $R^8$ is amino or aminomethyl with an appropriately substituted amidine (e.g., $N^1$-(tert-butoxy-carbonyl)methylthioamidine, $N^1,N^2$-di(tert-butoxycarbonyl)methylthioamidine, $N^1,N^2$-di(acetyl)methylthioamidine, etc.). The reaction is carried out in a suitable solvent (e.g., THF, methanol, ethanol, DMF, water, any appropriate mixture of suitable solvents, etc., preferably THF) at 0° C. to reflux, typically at 20° C. to reflux and preferably at approximately 50° C., under an inert atmosphere, and requires 1 to 24 hours (for further details see Example 49, infra.).

Compounds of Formula I in which $R^3$, $R^5$ or $R^8$ is —$NHC(NR^{11})NHR^{12}$ or compounds of Formula I in which $R^4$, $R^5$ or $R^7$ is —$CH_2NHC(NR^{11})NHR^{12}$, wherein $R^{11}$ and $R^{12}$ are hydro, can be prepared by treating the corresponding compound of Formula I wherein $R^{11}$ and/or $R^{12}$ are acetyl or tert-butoxycarbonyl with a suitable acid (e.g., trifluoroacetic acid (TFA), hydrochloric acid, hydrobromic acid, sulfuric acid, etc., preferably TFA) and optionally with a suitable cosolvent (e.g., ethanol). The acid treatment is carried out at 0° to 120° C., typically at 0° to 80° C. and preferably at approximately 25° C., and requires 0.5 to 12 hours (for further details see Example 50, infra.).

Compounds of Formula I in which $R^3$ and $R^5$ are hydro and $R^4$ is di($C_{1-4}$)alkylaminomethyl, piperidin-1-ylmethyl or morpholin-4-ylmethyl can be prepared by alkylating a compound of Formula I in which $R^3$, $R^4$ and $R^5$ are each hydro with an appropriately N,N-disubstituted methyleneammonium salt. The alkylation is carried out in a suitable solvent (e.g., DMF, acetonitrile, any appropriate mixture of suitable solvents, etc., preferably DMF) at 50° to 130° C., typically at 80° to 110° C. and preferably at approximately 95° C., and requires 1 to 24 hours.

Compounds of Formula I in which $R^4$ is hydro, $R^5$ is di($C_{1-4}$)alkylaminomethyl, piperidin-1-ylmethyl or morpholin-4-ylmethyl and $R^3$ is other than hydro can be prepared by alkylating a corresponding compound of Formula I in which $R^5$ is hydro with about 1 molar equivalent of an appropriately N,N-disubstituted methyleneammonium salt. The alkylation is carried out in a suitable solvent (e.g., DMF, DMPU, acetonitrile, any appropriate mixture of suitable solvents, etc., preferably DMF) at 0° C. to reflux, typically at 25° to 100° C. and preferably at approximately 80° C., and requires 1 to 24 hours (for further details see Example 35, infra.).

Compounds of Formula I in which $R^3$ and $R^4$ are hydro and $R^5$ is di($C_{1-4}$)alkylaminomethyl, piperidin-1-ylmethyl or morpholin-4-ylmethyl can be prepared by alkylating a thio protected derivative of a corresponding compound of Formula I in which $R^5$ is hydro (e.g., the 3-(imidazol-2-ylthio)propionate derivative thereof) with about 1 molar equivalent of an appropriately N,N-disubstituted methyleneammonium salt and then deprotecting. The alkylation is carried out in a suitable solvent (e.g., DMF, DMPU, acetonitrile, any appropriate mixture of suitable solvents, etc., preferably DMF) at 50° to 130° C., preferably at 80° to 100° C., and requires 1 to 24 hours. The deprotection can be effected with a suitable base (e.g., a sodium alkoxide such as sodium ethoxide and the like, sodium hydroxide, potassium hydroxide, etc. preferably sodium ethoxide) at 0° to 50° C., preferably at approximately 25° C.

A suitable thio protected derivative can be prepared by reacting a compound of Formula I in which $R^3$ is hydro with ethyl acrylate to give a 3-(imidazol-2-ylthio)propionate derivative. The protection step is carried out in the presence of an acid (e.g., anhydrous hydrochloric acid) in a suitable solvent typically an alcohol (e.g., methanol, ethanol, any appropriate mixture of suitable alcohols, etc.) and preferably ethanol, at 0° C. to reflux, typically at 50° C. to reflux and preferably at approximately 80° C.

Compounds of Formula I in which $R^3$ is hydro and $R^4$ and $R^5$ are each di($C_{1-4}$)alkylaminomethyl, piperidin-1-ylmethyl or morpholin-4-ylmethyl can be prepared by alkylating a protected derivative of a corresponding compound of Formula I in which $R^4$ and $R^5$ are each hydro with 2 to 15 molar equivalents of an appropriately N,N-disubstituted methyleneammonium salt, typically 5 to 10 molar equivalents and preferably approximately 7 molar equivalents, and then deprotecting. The alkylation is carried out in a suitable solvent (e.g., DMF, DMPU, acetonitrile, any appropriate mixture of suitable solvents, etc., preferably DMF) at 50° to 130° C., typically at 90° to 110° C. and preferably at approximately 100° C., and requires 1 to 24 hours (for further details see Example 36, infra.).

Compounds of Formula I in which $R^4$ and/or $R^5$ are hydroxymethyl can be prepared by reducing a compound of Formula I in which $R^4$ and/or $R^5$ is ethoxycarbonyl. The reduction can be effected with a chemical reducing agent (e.g., sodium borohydride, calcium borohydride, lithium borohydride, lithium aluminum hydride, etc., preferably sodium borohydride in the presence of calcium chloride) in a suitable solvent (e.g., THF, diglyme, dioxane, any appropriate mixture of suitable solvents, etc., preferably THF) at −20° C. to reflux, typically at 0° to 80° C. and preferably at approximately 50° C., requiring 1 to 72 hours (for further details see Example 33, infra.).

Compounds of Formula I in which $R^3$, $R^4$, $R^5$, $R^6$, $R^7$, or $R^8$ is a group selected from aroyl, heteroaroyl, aryl($C_{1-4}$)alkyl and heteroaryl($C_{1-4}$)alkyl (which aroyl, heteroaroyl, aryl and heteroaryl are further substituted by a 1H-tetrazol-5-yl substituent can be prepared by reacting a corresponding of Formula I in which the aroyl, heteroaroyl, aryl and heteroaryl substituent which are further substituted by a cyano substituent with a hydrazoic acid derivative (e.g., tributyltin azide). The reaction is carried out neat or in a suitable solvent (e.g., xylene, toluene, benzene, any appropriate mixture of suitable solvents, etc., preferably xylene) at 80° to 150° C., typically at 80° to 130° C. and preferably at reflux, and requires 4 to 24 hours (for further details see Example 39, infra.).

Compounds of Formula I in which $R^5$ or both $R^4$ and $R^5$ are 1H-tetrazol-5-ylaminocarbamoyl, 2-(dimethylamino)ethylcarbamoyl, 4-methylpiperazin-1-ylcarbonyl, methylsulfonylanilinocarbonyl or 2-(dimethylamino)ethylmercaptocarbonyl can be prepared by reacting a compound of Formula I in which $R^5$ or both $R^4$ and $R^5$ are carboxy, or an acid derivative thereof, with an appropriate amine or thiol (i.e., 5-amino-1H-tetrazole, 2-(dimethylamino)ethylamine, 4-methylpiperizine, 4-methylsulfonylaminoaniline or 2-dimethylaminoethanethiol hydrochloride). For example, compounds of Formula I in which $R^5$ is 1H-tetrazol-5-ylcarbamoyl can be prepared by converting the corresponding carboxylic acid to an acid halide and then reacting the acid halide with 5-amino-1H-tetrazole. The reaction with the 5-amino-1H-tetrazole is carried out in a suitable solvent (e.g., pyridine, DMF, any appropriate mixture of suitable solvents, etc.) at 0° to 40° C., typically at 20° to 30° C. and preferably at approximately 25° C., and requires 1 to 24 hours (for further details see Example 41, infra.).

Compounds of Formula I in which $R^5$ is 2-(dimethylamino)ethylcarbamoyl, 4-methylpiperazin-1-ylcarbonyl or 2-(dimethylamino)ethylmercaptocarbonyl can be prepared by treating a corresponding carboxylic acid with a coupling agent (e.g., 1,1'-carbonyldiimidazole, dicyclohexylcarbodiimide, benzotriazol-1-yloxytripyrrolidinophosphonium hexafluorophosphate (PyBOP), etc.) in a suitable solvent (e.g., THF, methylene chloride, DMF, any appropriate mixture of suitable solvent, etc.) and then reacting with the appropriate amine or thiol. The reaction with the amine or thiol is carried out at 0° to 80° C., typically at 20° to 30° C. and preferably at approximately 25° C., and requires 1 to 24 hours (for further details see Example 42, infra.).

Compounds of Formula I in which $R^3$, $R^6$ or $R^8$ is 2-($C_{1-4}$)alkyloxycarbonylethyl can be prepared by reacting a compound of Formula I in which $R^3$, $R^6$ or $R^8$, respectively, is hydro with ($C_{1-4}$)alkyl acrylate (e.g., methyl acrylate, ethyl acrylate, etc.). The reaction is carried out in the presence of base (e.g., sodium ethoxide, benzyltrimethylammoniumhydroxide, sodium hydride, etc.) and in a suitable solvent (e.g., ethanol, N,N-dimethylformamide, N,N-dimethylacetamide, acetonitrile, etc.) at 50° to 100° C., preferably approximately at 80° C., and requires 1 to 6 hours (for further details see Example 34, infra.).

Compounds of Formula I in which a $R^3$, $R^4$, $R^5$, $R^6$, $R^7$ or $R^8$ substituent is carboxy or a group which is further substituted by a carboxy substituent can be prepared by hydrolysis of a corresponding compound of Formula I in which a $R^3$, $R^4$, $R^5$, $R^6$, $R^7$ or $R^8$ substituent is ($C_{1-4}$)alkyloxycarbonyl or a group which is further substituted by a ($C_{1-4}$)alkyloxycarbonyl substituent. The hydrolysis can be carried out with an aqueous base (e.g., potassium hydroxide, sodium hydroxide, lithium hydroxide, etc.) in a suitable solvent, typically an alcohol (e.g., ethanol, methanol, isopropanol, any appropriate mixture of alcohols, etc.) and preferably ethanol, or an aqueous acid (e.g., hydrochloric acid, trifluoroacetic acid, sulfuric acid, hydrochloric acid, hydrobromic acid, etc.) in a suitable solvent (e.g., methylene chloride, ethyl acetate, dioxane, DMF, THF, etc.) at 20° to 120° C., typically at 90° to 110° C. and preferably at approximately 100° C., and requires 4 to 24 hours (for further details see Example 37, infra.).

Compounds of Formula I in which a $R^3$, $R^4$, $R^5$, $R^6$, $R^7$ or $R^8$ is carbamoyl or a group which is further substituted by a carbamoyl substituent can be prepared by amination of a corresponding compound of Formula I in which a $R^3$, $R^4$, $R^5$, $R^6$, $R^7$ or $R^8$ is carboxy or a group which is further substituent by a carboxy substituent. The amination can be carried out by converting the carboxylic acid to the corresponding acid chloride and then reacting the acid chloride with aqueous ammonium hydroxide. Converting the acid to the acid chloride is carried out with an appropriate chlorinating agent (e.g., thionyl chloride, oxalyl chloride, phosphorus pentachloride, etc.) and in a suitable solvent (e.g., DMF, methylene chloride, dichloroethane, any appropriate mixture of suitable solvents, etc., preferably DMF) at 10° to 40° C., typically at 15° to 30° C. and preferably at approximately 20° C., and requires 2 to 18 hours. The reaction between the acid chloride and the aqueous ammonium hydroxide is carried out at 0° to 50° C., typically at 20° to 30° C. and preferably at approximately 25° C., and requires 0.5 to 24 hours. Further details of the reaction steps set forth in this paragraph are provided in Example 38, infra.

Compounds of Formula I in which $R^3$, $R^4$, $R^5$, $R^6$, $R^7$ or $R^8$ is ($C_{1-4}$)alkyloxycarbonyl or a group that is further substituted by a ($C_{1-4}$)alkyloxycarbonyl group can be prepared by reacting a compound of Formula I in which $R^3$, $R^4$, $R^5$, $R^6$, $R^7$ or $R^8$ is carboxy or a group which is further substituted by a carboxy group with a ($C_{1-4}$)alcohol. The reaction is carried out at 20° to 110° C., preferably approximately 85° C., and requires 8 to 72 hours.

Compounds of Formula I in which $R^{10}$ is ($C_{1-4}$)alkanoyl, trifluoro($C_{1-4}$)alkanoyl, carbamoyl, ($C_{1-4}$)alkyloxycarbonyl, ($C_{1-4}$)alkylcarbamoyl, di($C_{1-4}$)alkylcarbamoyl, amino($C_{1-4}$)alkanoyl, ($C_{1-4}$)alkylamino($C_{1-4}$)alkanoyl, di($C_{1-4}$)alkylamino($C_{1-4}$)alkanoyl, aroyl or heteroaroyl can be prepared by reacting a corresponding compound of Formula I in which $R^3$, $R^4$, $R^5$, $R^7$ or $R^8$ is amino or aminomethyl with an appropriate acylating agent (e.g., acyl halides such as dimethylcarbamyl chloride, benzoyl chloride, nicotinoyl chloride and the like, anhydrides such as acetic anhydride and the like, activated esters such as methyl chloroformate and the like, etc.) or a protected derivative thereof. The reaction is carried out in a suitable solvent (e.g., methylene chloride, THF, pyridine, water, any appropriate mixture of suitable solvents, etc., preferably pyridine) at −10° to 40° C., typically at 15° to 35° C. and preferably at approximately 25° C., and requires 0.5 to 8 hours (for further details see Example 44, infra.).

Alternatively, compounds of Formula I in which $R^{10}$ is carbamoyl, $(C_{1-4})$alkyloxycarbonyl, $(C_{1-4})$alkylcarbamoyl, di$(C_{1-4})$alkylcarbamoyl, amino$(C_{1-4})$alkanoyl, $(C_{1-4})$ alkylamino$(C_{1-4})$alkanoyl, di$(C_{1-4})$alkylamino$(C_{1-4})$ alkanoyl, aroyl or heteroaroyl can be prepared by reacting a corresponding compound of Formula I in which $R^3$, $R^4$, $R^5$, $R^7$ or $R^8$ is amino or aminomethyl with an appropriate acid (e.g., picolinic acid and the like) or a protected derivative thereof (e.g., N-(tert-butoxycarbonyl)glycine and the like). The reaction is carried out in the presence of a non-nucleophilic base (e.g., N,N-diisopropylethylamine (DIEA), N,N-dicyclohexylmethylamine, etc., preferably DIEA) and a suitable coupling agent (e.g., PyBOP, 1,1'-carbonyldiimidazole, dicyclohexylcarbodiimide, etc., preferably PyBOP) in a suitable solvent (e.g., DMF, DMPU, acetonitrile, THF, methylene chloride, any appropriate mixture of suitable solvents, etc., preferably DMF) at −20° to 80° C., typically at 0° to 30° C. and preferably at approximately 25° C. (for further details see Example 45, infra.).

Alternatively, compounds of Formula I in which $R^3$, $R^5$ or $R^8$ is —$NHR^{10}$ or compounds of Formula I in which $R^4$, $R^5$ or $R^7$ is —$CH_2NHR^{10}$, wherein $R^{10}$ is $(C_{1-4})$ alkylcarbamoyl, can be prepared by reacting a corresponding compound of Formula I in which $R^3$, $R^4$, $R^5$, $R^7$ or $R^8$ is amino or aminomethyl with $(C_{1-4})$alkyl isocyanate. The reaction is carried out optionally in the presence of a base (e.g., triethylamine, pyridine, etc.) in a suitable solvent (e.g., THF, benzene, methylene chloride, any appropriate mixture of suitable solvents, etc., preferably THF) at 0° C. to reflux, typically at 25° to 80° C. and preferably at approximately 50° C. (for further details see Example 46, infra.).

Compounds of Formula I in which $R^1$ is hydroxy and/or $R^3$, $R^4$, $R^5$, $R^6$, $R^7$ or $R^8$ is a group selected from aroyl, heteroaroyl, aryl$(C_{1-4})$alkyl and heteroaryl$(C_{1-4})$alkyl (which aroyl, heteroaroyl, aryl and heteroaryl are further substituted with one to two hydroxy substituents) can be prepared by de-methylating a compound of Formula I in which $R^1$ is methoxy and/or in which $R^3$, $R^4$, $R^5$, $R^6$, $R^7$ or $R^8$ is a group selected from aroyl, heteroaroyl, aryl$(C_{1-4})$ alkyl and heteroaryl$(C_{1-4})$alkyl (which aroyl, heteroaroyl, aryl and heteroaryl are further substituted with one to two methoxy substituents). The de-methylation can be carried out with boron tribromide in suitable solvent (e.g., methylene chloride, 1,2-dichloroethane, nitromethane, any appropriate mixture of suitable solvents, etc., preferably methylene chloride) at −10° to 20° C., typically at −5° to 5° C. and preferably at approximately 0° C., requiring 0.5 to 4 hours. For further details of the reactions step set forth in this paragraph see Example 43, infra.

Compounds of Formula I can be prepared as their individual stereoisomers by reacting a racemic mixture thereof with an optically active resolving agent to form a pair of diastereomeric compounds, separating the diastereomers and recovering the optically pure enantiomer. While resolution of enantiomers can be carried out using covalent diastereomeric derivatives of compounds of Formula I, dissociable complexes are preferred (e.g., crystalline diastereoisomeric salts). In that compounds of Formula I contain a basic amine group, such crystalline diastereoisomeric salts can be prepared by using a suitable optically active acid as the resolving agent (e.g., tartaric acid, mandelic acid, malic acid, the 2-arylpropionic acids in general, camphorsulfonic acid, etc.).

Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixtures can be found in Jean Jacques, Andre Collet, Samuel H. Wilen, Enantiomers, Racemates and Resolutions, John Wiley & Sons, Inc. (1981).

In summary, an aspect of this invention is a process for the preparation of a compound of Formula I:

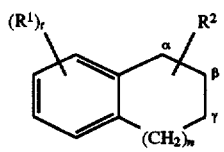

in which:

n is 0, 1 or 2;

t is 0, 1, 2 or 3;

$R^1$ is independently halo, hydroxy or $(C_{1-4})$alkyloxy; and $R^2$ is attached at the α-, β- or γ-position and is a group selected from Formulae (a), (b) and (c):

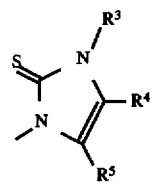

(a)

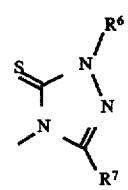

(b)

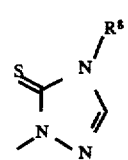

(c)

in which:

$R^4$ is hydro, $R^3$ is hydro or —$(CH_2)_qR^9$ {in which q is 0, 1, 2, 3 or 4 and $R^9$ is carboxy, $(C_{1-4})$alkyloxycarbonyl, carbamoyl or a group selected from aryl and heteroaryl (which group is optionally further substituted with one to two substituents independently selected from hydroxy, $(C_{1-4})$alkyloxy, cyano, 1H-tetrazo-5-yl, carboxy and $(C_{1-4})$alkyloxycarbonyl)} and $R^5$ is hydro or —$NHR^{10}$ {in which $R^{10}$ is hydro, $(C_{1-4})$alkanoyl, trifluoro$(C_{1-4})$alkanoyl, carbamoyl, $(C_{1-4})$ alkyloxycarbonyl, $(C_{1-4})$alkylcarbamoyl, di$(C_{1-4})$ alkylcarbamoyl, amino$(C_{1-4})$alkanoyl, $(C_{1-4})$ alkylamino $(C_{1-4})$alkanoyl, di$(C_{1-4})$alkylamino $(C_{1-4})$ alkanoyl, a group selected from aroyl and heteroaroyl (which aroyl and heteroaroyl are optionally further substituted with one to two substituents independently selected from hydroxy, $(C_{1-4})$alkyloxy, cyano, 1H-tetrazol-5-yl, carboxy and $(C_{1-4})$alkyloxycarbonyl) or —$C(NR^{11})NHR^{12}$ (in which $R^{11}$ and $R^{12}$ are independently hydro, acetyl or tert-butoxycarbonyl)}; or $R^4$ and $R^5$ are each hydro and $R^3$ is —$NHR^{10}$ (in which $R^{10}$ is as defined above); or $R^5$ is hydro, $R^3$ is hydro or
—$(CH_2)_qR^9$ (in which q and $R^9$ are as defined above)
and $R^4$ is $(C_{1-4})$alkyl, di$(C_{1-4})$alkylaminomethyl,
piperidin-1-ylmethyl, morpholin-4-ylmethyl, formyl,
1-hydroxy$(C_{1-4})$alkyl or —$CH_2NHR^{13}$ {in which $R^{13}$
is hydro, $(C_{1-4})$alkyl, $(C_{1-4})$alkanoyl, trifluoro$(C_{1-4})$
alkanoyl, carbamoyl, $(C_{1-4})$alkyloxycarbonyl, $(C_{1-4})$
alkylcarbamoyl, di$(C_{1-4})$alkylcarbamoyl, amino$(C_{1-4})$
alkanoyl, $(C_{1-4})$alkylamino$(C_{1-4})$alkanoyl, di$(C_{1-4})$
alkylamino$(C_{1-4})$alkanoyl, carboxy$(C_{1-4})$alkyl, $(C_{1-4})$
alkyloxycarbonyl$(C_{1-4})$alkyl, carbamoyl$(C_{1-4})$alkyl, a
group selected from aroyl, heteroaroyl, aryl$(C_{1-4})$alkyl
and heteroaryl$(C_{1-4})$alkyl (which aroyl, heteroaroyl,
aryl and heteroaryl are optionally further substituted
with one to two substituents independently selected
from hydroxy, $(C_{1-4})$alkyloxy, cyano, 1H-tetrazol-5-yl,
carboxy and $(C_{1-4})$alkyloxycarbonyl) or —$C(NR^{11})$
$NHR^{12}$ (in which $R^{11}$ and $R^{12}$ are as defined above)};
or $R^3$ is hydro or —$(CH_2)_qR^9$ (in which q and $R^9$ are
as defined above), $R^4$ is hydro, $(C_{1-4})$alkyl or —$C(O)$
$R^{14}$ (in which $R^{14}$ is amino, hydroxy $(C_{1-4})$alkyloxy,
2-(dimethylamino)ethylamino, 4-methylpiperazin-1-
yl, 2-(dimethylamino)ethylmercapto,
4-(methylsulfonylamino)anilino or 1H-tetrazol-5-
ylamino) and $R^5$ is cyano, hydroxymethyl, 1H-tetrazol-
5-yl, 4,5- dihydroimidazol-2-yl, pyrrolidin-1-ylmethyl,
piperidin -1-ylmethyl, morpholin-4-ylmethyl,
piperazin-1-ylmethyl, 4-$(C_{1-4})$alkylpiperazin-1-
ylmethyl, —$C(O)R^{14}$ (in which $R^{14}$ are as defined
above), —$C(NH)NR^{15}R^{16}$ (in which $R^{15}$ and $R^{16}$ inde-
pendently hydro, $(C_{1-4})$alkyl or trifluoro$(C_{1-4})$alkyl) or
—$CH_2NR^{10}R^{17}$ (in which $R^{10}$ is as defined above and
$R^{17}$ is hydro or $C_{1-4}$)alkyl); or $R^3$ is hydro or —$(CH_2)_q$
$R^9$ (in which q and $R^9$ are as defined above) and $R^4$ and
$R^5$ are dependently di$(C_{1-4})$alkylaminomethyl,
piperidin-1-ylmethyl, morpholin-4-ylmethyl or
hydroxymethyl;

$R^6$ is hydro, 2-carboxyethyl, 2-carbamoylethyl or 2-$(C_{1-4})$
alkyloxycarbonylethyl;

$R^7$ is hydro, pyrrolidin-1-ylmethyl, piperidin-1-ylmethyl,
morpholin-4-ylmethyl, piperazin-1-ylmethyl, 4-$(C_{1-4})$
alkylpiperazin-1-ylmethyl or —$CH_2NR^{10}R^{17}$ (in
which $R^{10}$ and $R^{17}$ are as defined above); and $R^8$ is hydro, 2-carboxyethyl, 2-carbamoylethyl, 2-$(C_{1-4})$
alkyloxycarbonylethyl or —$NHR^{10}$ (in which $R^{10}$ are
as defined above); and the pharmaceutically acceptable
salts, individual isomers, and mixtures of isomers
thereof; which process comprises:

(a) reacting a compound of Formula 3:

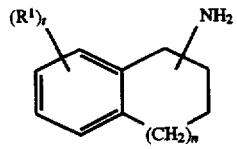

in which each n, t and $R^1$ are as defined above with
respect to Formula I with a dialkyloxyacetaldehyde
in the presence of a chemical reducing agent or
catalytic hydrogenation and then treating with thio-
cyanic acid to give a compound of Formula I in
which $R^2$ is a group of Formula (a) wherein $R^3$, $R^4$
and $R^5$ are each hydro; or (b) reacting a compound of Formula 5:

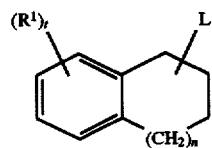

in which each n, t and $R^1$ are as defined above with
respect to Formula I with 1,2,4-triazol-4-ylamino
and then sulfurizing to give a compound of Formula
I in which $R^2$ is a group of Formula (c) wherein $R^8$
is amino; or (c) reacting a compound of Formula 7:

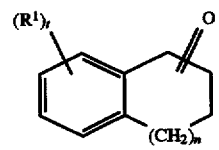

in which each n, t and $R^1$ are as defined above with
respect to Formula I with with a 2,2-
dialkyloxyethylamine in the presence of a chemical
reducing agent or catalytic hydrogenation and then
treating with thiocyanic acid to give a compound of
Formula I in which $R^2$ is a group of Formula (a)
wherein $R^3$, $R^4$ and $R^5$ are each hydro;

(d) reacting a compound of Formula 9:

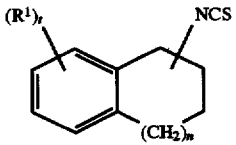

in which each n, t and $R^1$ are as defined above with
respect to Formula I with a 2,2-
dialkyloxyethylamine and then treating with acid to
give a compound of Formula I in which $R^2$ is a group
of Formula (a) wherein $R^3$, $R^4$ and $R^5$ are each
hydro; or (e) reacting a compound of Formula 9 with aminoac-
etonitrile hydrochloride and then treating with base
to give a compound of Formula I in which $R^2$ is a
group of Formula (a) wherein $R^3$ and $R^4$ are each
hydro and $R^5$ is amino; or (f) reacting a compound of Formula 9 with D-(+)-
glucosamine and then oxidizing to give a compound
of Formula I in which $R^2$ is a group of Formula (a)
wherein $R^3$ and $R^5$ are each hydro and $R^4$ is formyl;
or (g) reacting a compound of Formula 9 with a hydrazide
of the formula $H_2NHNC(O)R^{34}$ (in which $R^{34}$ is
hydro, aminomethyl, $(C_{1-4})$alkylaminomethyl,
di$(C_{1-4})$alkylaminomethyl, pyrrolidin-1-ylmethyl,
piperidin-1-ylmethyl, morpholin-4-ylmethyl,
piperazin-1-ylmethyl or 4-$(C_{1-4})$alkylpiperazin-1-
ylmethyl) or a protected derivative thereof, then
treating with base and when necessary deprotecting
to give a compound of Formula I in which $R^2$ is a
group of Formula (b) wherein $R^6$ is hydro and $R^7$ is
hydro, aminomethyl, $(C_{1-4})$alkylaminomethyl,
di$(C_{1-4})$alkylaminomethyl, pyrrolidin-1-ylmethyl,
piperidin-1-ylmethyl, morpholin -4-ylmethyl,
piperazin-1-ylmethyl or 4-$(C_{1-4})$alkylpiperazin-1-
ylmethyl; or

37

(h) reacting a compound of Formula 11:

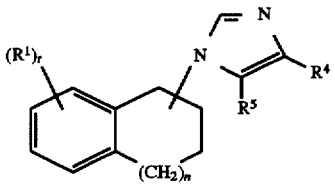

in which each n, t, $R^1$, $R^4$ and $R^5$ are as defined above with respect to Formula I with a strong base and then sulfurizing to give a compound of Formula I in which $R^3$ is hydro; or (i) reacting a compound of Formula 11 in which each n, t, $R^1$, $R^4$ and $R^5$ are as defined above with respect to Formula I with a compound of the formula L—$(CH_2)_q R^9$ in which L is a leaving group and each q and $R^9$ are as defined above with respect to Formula I and then sulfurizing to give a compound of Formula I in which $R^2$ is a group of Formula (a) wherein $R^3$ is —$(CH_2)_q R^9$; or (j) reacting a compound of Formula 11 in which $R^4$ and $R^5$ are each hydro and each n, t, and $R^1$ are as defined above with respect to Formula I, with an amino aryl- or alkylsulfonate to give a compound of Formula I in which $R^2$ is a group of Formula (a) wherein $R^3$ is amino; or (k) alkylating a compound of Formula 11 in which $R^4$ and $R^5$ are each hydro and each n, t, and $R^1$ are as defined above with respect to Formula I, with an appropriately N,N-disubstituted methyleneammonium salt and then sulfurizing to give a compound of Formula I in which $R^2$ is a group of Formula (a) wherein $R^5$ is di($C_{1-4}$)alkylaminomethyl, piperidin-1-ylmethyl or morpholin-4-ylmethyl; or (l) reacting a compound of Formula 16:

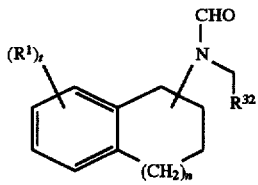

in which $R^{32}$ is cyano or ($C_{1-4}$)alkyloxycarbonyl and each n, t and $R^1$ are as defined above with respect to Formula I with a compound of the formula $R^{33}$C(O)L and then treating with thiocyanic acid to give a compound of Formula I in which $R^2$ is a group of Formula (a) wherein $R^3$ is hydro, $R^5$ is cyano or ($C_{1-4}$)alkyloxycarbonyl and $R^4$ is hydro, ($C_{1-4}$) alkyloxycarbonyl or ($C_{1-4}$)alkyl; or (m) reacting a compound of Formula 24:

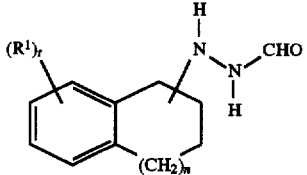

in which n, t and $R^1$ are as defined above with respect to Formula I with isothiocyanate and then treating with base to give a compound of Formula I in which $R^2$ is a group of Formula (c) wherein $R^8$ is hydro; and (n) optionally further reacting a compound of Formula I in which $R^5$ is cyano with a hydrazoic acid deriva-

38 tive to give the compound of Formula I in which $R^5$ is 1H-tetrazol-5-yl;

(o) optionally further reducing a compound of Formula I in which $R^5$ is cyano to give a compound of Formula I in which $R^5$ is aminoethyl;

(p) optionally further hydrolyzing a compound of Formula I in which $R^5$ is cyano to give the compound of Formula I in which $R^5$ is carbamoyl;

(q) optionally further reacting a compound of Formula I in which $R^5$ is cyano with ethylenediamine to give the compound of Formula I in which $R^5$ is 4,5-dihydroimidazol-2-yl;

(r) optionally further reacting a compound of Formula I in which $R^5$ is cyano with a compound of the formula $(CH_3)_2AlNR^{15}R^{16}$ to give the compound of Formula I in which $R^5$ is —C(NH)$NR^{15}R^{16}$, wherein $R^{15}$ and $R^{16}$ are as defined above with respect to Formula I;

(s) optionally further reducing a compound of Formula I in which $R^5$ or both $R^4$ and $R^5$ are ethoxycarbonyl to give a compound of Formula I in which $R^5$ or both $R^4$ and $R^5$ are hydroxymethyl;

(t) optionally further converting a compound of Formula I in which $R^5$ is hydroxymethyl to a compound of Formula 28:

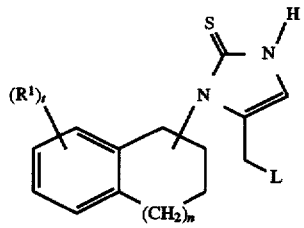

in which L is a leaving group and n, t and $R^1$ are as defined in the Summary of the Invention with respect to Formula I and reacting the compound of Formula 28 with an amine of the formula $HNR^{36}R^{37}$ in which $R^{36}$ and $R^{37}$ are independently ($C_{1-4}$)alkyl or together are —$(CH_2)_4$—, —$(CH_2)_5$—, —$(CH_2)_2O(CH_2)_2$— or —$(C_2)_2NR^{38}(CH_2)_2$—, wherein $R^{38}$ is hydro or ($C_{1-4}$)alkyl, to give a compound of Formula I in which $R^5$ is aminomethyl, ($C_{1-4}$)alkylaminomethyl, di($C_{1-4}$)alkylaminomethyl, pyrrolidin-1-ylmethyl, piperidin-1-ylmethyl, morpholin-4-ylmethyl, piperazin-1-ylmethyl or 4-($C_{1-4}$)alkylpiperazin-1-ylmethyl;

(u) optionally further reacting a compound of Formula I in which $R^4$ is formyl with hydroxylamine hydrochloride and then reducing to give a compound of Formula I in which $R^4$ is aminemethyl;

(v) optionally further reacting a compound of Formula I in which $R^4$ is formyl with an amine of the formula $NH_2R^{10}$ in the presence of a chemical reducing agent or catalytic hydrogenation to give a compound of Formula I in which $R^4$ is —$CH_2NHR^{10}$, wherein $R^{10}$ is as defined above with respect to Formula I;

(w) optionally further alkylating a compound of Formula I in which $R^4$ is formyl to give a compound of Formula I in which $R^4$ is 1-hydroxy($C_{1-4}$)alkyl;

(x) optionally further reacting a compound of Formula I in which $R^3$, $R^5$ or $R^6$ is amino or $R^4$, $R^5$ or $R^8$ is aminomethyl with an appropriately substituted amidine to give a corresponding compound of Formula I in which $R^3$, $R^5$ or $R^6$ is —NHC($NR^{11}$)$NHR^{12}$ or $R^4$, $R^5$ or $R^8$ is —$CH_2NHC(NR^{11})NHR^{12}$ wherein $R^{11}$ is hydro, acetyl or tert-butoxycarbonyl and $R^{12}$ is acetyl or tert-butoxycarbonyl;

(y) optionally further treating a compound of Formula I in which $R^3$, $R^5$ or $R^6$ is —NHC(NR$^{11}$)NHR$^{12}$ or $R^4$, $R^5$ or $R^8$ is —CH$_2$NHC(NR$^{11}$)NHR$^{12}$, wherein $R^{11}$ is hydro, acetyl or tert-butoxycarbonyl and $R^{12}$ is acetyl or tert-butoxycarbonyl, with acid to give a compound of Formula I in which $R^3$, $R^5$ or $R^6$ is —NHC(NH)NH$_2$ or $R^4$, $R^5$ or $R^8$ is —CH$_2$NHC(NH)NH$_2$;

(z) optionally further acylating a compound of Formula I in which $R^3$, $R^5$ or $R^6$ is amino or $R^4$, $R^5$ or $R^8$ is aminomethyl with an appropriate acylating agent, or a protected derivative thereof, and then deprotecting when necessary to give a corresponding compound of Formula I in which $R^3$, $R^5$ or $R^6$ is —NHR$^{10}$ or $R^4$, $R^5$ or $R^8$ is —CH$_2$NHR$^{10}$, wherein $R^{10}$ is (C$_{1-4}$)alkanoyl, trifluoro(C$_{1-4}$)alkanoyl, carbamoyl, (C$_{1-4}$)alkyloxycarbonyl, (C$_{1-4}$)alkylcarbamoyl, di(C$_{1-4}$)alkylcarbamoyl, amino(C$_{1-4}$)alkanoyl, (C$_{1-4}$)alkylamino(C$_{1-4}$)alkanoyl, di(C$_{1-4}$)alkylamino(C$_{1-4}$)alkanoyl or a group selected from aroyl and heteroaroyl, (which aroyl and heteroaroyl are optionally further substituted with one to two substituents independently selected from (C$_{1-4}$)alkyloxy, cyano, carboxy and (C$_{1-4}$)alkyloxycarbonyl);

(aa) optionally further reacting a compound of Formula I in which $R^3$, $R^5$ or $R^6$ is amino or $R^4$, $R^5$ or $R^8$ is aminomethyl with (C$_{1-4}$)alkyl isocyanate to give a compound of Formula I in which $R^3$, $R^5$ or $R^6$ is —NHR$^{10}$ or $R^4$, $R^5$ or $R^8$ is —CH$_2$NHR$^{10}$, wherein $R^{10}$ is (C$_{1-4}$)alkylcarbamoyl;

(bb) optionally further alkylating a compound of Formula I in which $R^3$, $R^4$ and $R^5$ are each hydro with an appropriately N,N-disubstituted methyleneammonium salt to give a compound of Formula I in which $R^3$ and $R^5$ are each hydro and $R^4$ is di(C$_{1-4}$)alkylaminomethyl, piperidin-1-ylmethyl or morpholin-4-ylmethyl;

(cc) optionally further alkylating a compound of Formula I in which $R^4$ is hydro and $R^3$ is other than hydro with an appropriately N,N-disubstituted methyleneammonium salt to give a corresponding compound of Formula I in which $R^5$ is di(C$_{1-4}$)alkylaminomethyl, piperidin-1-ylmethyl or morpholin-4-ylmethyl;

(dd) optionally protecting a compound of Formula I in which $R^3$ is hydro with a thiol protective group, alkylating with an appropriately N,N-disubstituted methyleneammonium salt and then deprotecting to give a compound of Formula I in which $R^3$ and $R^4$ are each hydro and $R^5$ is di(C$_{1-4}$)alkylaminomethyl, piperidin-1-ylmethyl or morpholin-4-ylmethyl or in which $R^3$ is hydro and both $R^4$ and $R^5$ are di(C$_{1-4}$)alkylaminomethyl, piperidin-1-ylmethyl or morpholin-4-ylmethyl;

(ee) optionally further reacting a compound of Formula I in which $R^5$ or both $R^4$ and $R^5$ are carboxy, or an acid derivative thereof, with an appropriate amine or thiol to give a compound of Formula I in which $R^5$ or both $R^4$ and $R^5$ are 1H-tetrazol-5-ylcarbamoyl, 2-(dimethylamino)ethylcarbamoyl, 4-methylpiperazin-1-ylcarbonyl or 2-(dimethylamino)ethylmercapto;

(ff) optionally further reacting a compound of Formula I in which $R^3$, $R^6$ or $R^8$ is hydro with (C$_{1-4}$)alkyl acrylate to give a compound of Formula I in which $R^3$, $R^6$ or $R^8$ is 2-(C$_{1-4}$)alkyloxycarbonylethyl;

(gg) optionally further hydrolyzing a compound of Formula I in which $R^3$, $R^4$, $R^5$, $R^6$, $R^7$ or $R^8$ is (C$_{1-4}$)alkyloxycarbonyl or a group which is further substituted by a (C$_{1-4}$)alkyloxycarbonyl substituent to give a compound of Formula I in which $R^3$, $R^4$, $R^5$, $R^6$, $R^7$ or $R^8$ is carboxy or group which is further substituted by a carboxy substituent;

(hh) optionally further aminating a compound of Formula I in which $R^3$, $R^4$, $R^5$, $R^6$, $R^7$ or $R^8$ is carboxy or a group which is further substituted by a carboxy substituent to give a compound of Formula I in which $R^3$, $R^4$, $R^5$, $R^6$, $R^7$ or $R^8$ is carbamoyl or a group which is further substituted by a carbamoyl substituent;

(ii) optionally further reacting a compound of Formula I in which $R^3$, $R^4$, $R^5$, $R^6$, $R^7$ or $R^8$ is carboxy or a group which is further substituted by a carboxy group with a (C$_{1-4}$)alcohol to give a compound of Formula I in which $R^3$, $R^4$, $R^5$, $R^6$, $R^7$ or $R^8$ is (C$_{1-4}$)alkyloxycarbonyl or a group that is further substituted by a (C$_{1-4}$)alkyloxycarbonyl group;

(jj) optionally further de-methylating a compound of Formula I in which $R^1$ is methoxy and/or in which $R^3$, $R^4$, $R^5$, $R^6$, $R^7$ or $R^8$ is a group selected from aroyl, heteraroyl, aryl(C$_{1-4}$)alkyl and heteroaryl(C$_{1-4}$)alkyl (which aroyl, heteroaroyl, aryl and heteroaryl are further substituted with one to two methoxy substituents) to give a compound of Formula I in which $R^1$ is hydroxy and/or $R^3$, $R^4$, $R^5$, $R^6$, $R^7$ or $R^8$ is a group selected from aroyl, heteraroyl, aryl(C$_{1-4}$)alkyl and heteroaryl(C$_{1-4}$)alkyl (which aroyl, heteroaroyl, aryl and heteroaryl are further substituted with one to two hydroxy substituents);

(kk) optionally further reacting a compound of Formula I in which $R^3$, $R^5$, $R^6$ or $R^8$ is —NHR$^{10}$ or in which $R^4$, $R^5$ or $R^7$ is —CH$_2$NHR$^{10}$, wherein $R^{10}$ is a group selected from aroyl, heteroaroyl, aryl(C$_{1-4}$)alkyl and heteroaryl(C$_{1-4}$)alkyl (which aroyl, heteroaroyl, aryl and heteroaryl are further substituted with a cyano substituent) with a hydrazoic acid derivative to give a compound of Formula I in which $R^{10}$ is a group selected from aroyl, heteroaroyl, aryl(C$_{1-4}$)alkyl and heteroaryl(C$_{1-4}$)alkyl (which aroyl, heteroaroyl, aryl and heteroaryl are further substituted with a 1H-tetrazol-5-yl substituent;

(ll) optionally further reacting the corresponding non-salt form of a compound of Formula I with a pharmaceutically acceptable inorganic or organic acid or base to give a pharmaceutically acceptable salt;

(mm) optionally further reacting the corresponding acid addition salt or base addition salt form of a compound of Formula I with a suitable base or acid, respectively, to give the free acid or free base; and (nn) optionally further separating a mixture of stereoisomers of a compound of Formula I to give a single stereoisomer.

Compounds of Formula 3:

A preferred method for making a compound of Formula 3 in which n is 1 and the amine is attached at the β-position as the individual (S)-enantiomer is depicted by the following Reaction Scheme X:

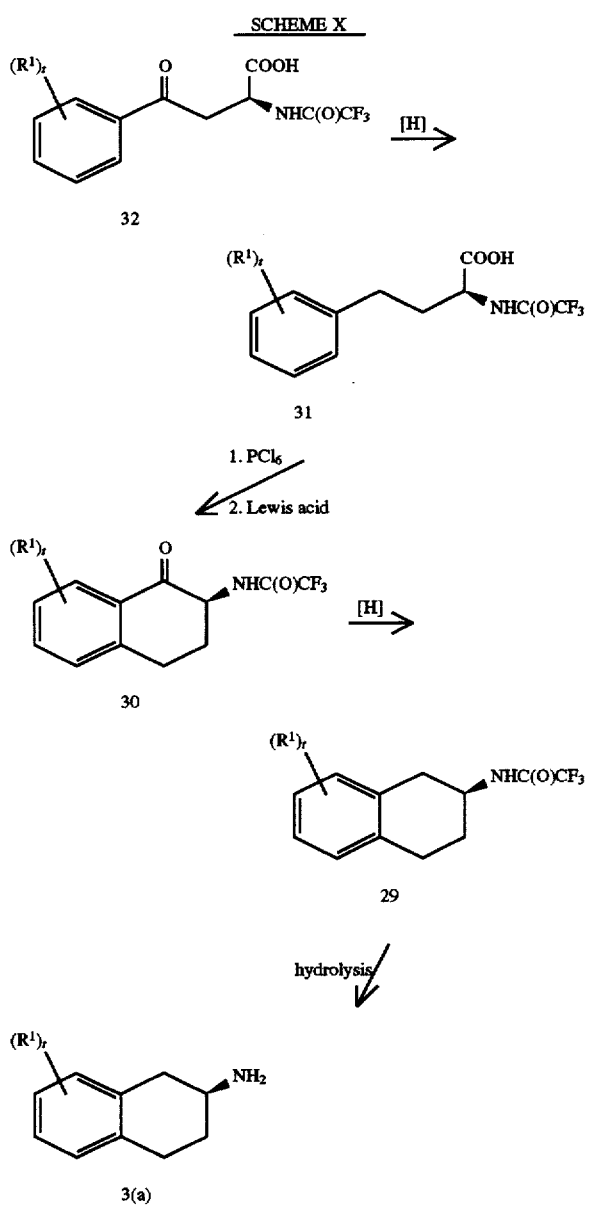

in which each t and $R^1$ are as defined in the Summary of the Invention with respect to Formula I.

Compounds of Formula 3 in which n is 1 and the amine is attached at the β-position can be prepared as the individual (S)-enantiomer (Formula 3(a)) by hydrolyzing a compound of Formula 29. The hydrolysis can be carried out with an aqueous base (e.g., lithium hydroxide monohydrate, sodium hydroxide, potassium hydroxide, potassium carbonate, etc., preferably lithium hydroxide monohydrate) in a suitable solvent, typically an alcohol (e.g., methanol, ethanol, isopropanol) and preferably methanol, at 25° to 100° C., preferably reflux, and requires 0.5 to 5 hours.

Compounds of Formula 29 are prepared by hydrogenolysis of a compound of Formula 30. The hydrogenolysis can be accomplished by a two step process comprising (i) hydrogenating a compound of Formula 30 until conversion to the corresponding 1-naphthol is complete and (ii) adding sulfuric acid and continuing hydrogenation to give the compound of Formula 29. Hydrogenation of the compound of Formula 30 to the 1-naphthol is carried out in the presence of an appropriate catalyst (e.g., Pearlman's catalyst, palladium on carbon, etc., preferably Pearlman's catalyst) in acetic acid or trifluoroacetic acid (TFA), preferably acetic acid, at 1 to 130 psig and 10° to 30° C. and requires 0.5 to 4 hours. Hydrogenation of the 1-naphthol is carried out by adding 1 to 10 equivalents, preferably 4 to 6 equivalents, of sulfuric acid or perchloric acid and continuing the hydrogenation under the same conditions for 3 to 120 hours. Alternatively, the hydrogenolysis is effected by a single step process comprising hydrogenating the compound 30 in the presence of an appropriate catalyst and either sulfuric acid or perchloric acid in acetic acid. The single step hydrogenolysis is carried out at 1 to 130 psig and 10° to 30° C. and requires 3 to 120 hours.

Compounds of Formula 30 are prepared from compounds of Formula 31 by an intramolecular Friedel-Crafts reaction. The reaction is effected by converting a compound of Formula 31 to the corresponding acid chloride and then treating the acid chloride with an appropriate Lewis acid (e.g. aluminum chloride, hydrogen fluoride, etc., preferably aluminum chloride) to give the compound of Formula 30. Conversion to the acid chloride can be carried out with an appropriate chlorinating agent (e.g., phosphorus pentachloride, thionyl chloride, oxalyl chloride, etc., preferably phosphorus pentachloride) in methylene chloride at 0° to 10° C., preferably at 5° to 10° C., and requires 0.5 to 2 hours. The treatment with Lewis acid and the resultant ring closure is carried out at 0° to 10° C., preferably at 5° to 10° C., and requires 1 to 3 hours. Preferably, the crude product is isolated by crystallization from a methanol/water or isopropanol/water mixture; and then, if necessary, recrystallization from a toluene/heptane mixture.

Compounds of Formula 31 are prepared by hydrogenolysis of a compound of Formula 32. The hydrogenolysis is carried out by hydrogenating in the presence of an appropriate catalyst (e.g., 20% palladium hydroxide on carbon (Pearlman's catalyst), palladium on carbon, etc., preferably Pearlman's catalyst) and 1 to 5 equivalents, preferably 1.5 to 2 equivalents, of sulfuric acid, in a glacial acetic acid at 1 to 60 psig and 5° to 30° C. and requires 2 to 48 hours.

Compounds of Formula 32 are prepared via a Friedel-Crafts alkylation of optionally substituted benzene with N-(trifluoroacetyl)-L-aspartic anhydride. The alkylation is carried out in the presence of a Lewis acid (e.g., aluminum chloride, tin chloride, hydrogen fluoride, etc., preferably aluminum chloride) and in a suitable solvent (e.g., methylene chloride, etc., preferably methylene chloride) at 25° to 40° C., preferably at reflux, and requires 2 to 5 hours.

N-(Trifluoroacetyl)-L-aspartic anhydride is prepared by reacting L-aspartic acid with trifluoroacetic anhydride (TFAA). The reaction is highly exothermic and when more than 100 g amounts of reactants are employed, it must be conducted under conditions such that the liberation of heat is controlled. For example, a convenient method for carrying out the reaction is by heating 2 to 4 equivalents, preferably 2.3 to 2.5 equivalents, of TFAA to between 30° and 40° C., preferably to reflux, and then adding 1 equivalent of L-aspartic acid at a rate such that the reaction readily proceeds but the heat generated by the reaction can be dissipated by reflux. Preferably the L-aspartic acid is added to the TFAA as a solution in TFA over 30 to 60 minutes.

Proceeding as described in Reaction Scheme XIII but substituting D-aspartic acid for L-aspartic acid, the (R)-enantiomer of the compound of Formula 3(a) can be prepared. Further details of the reaction steps set forth above for Reaction Scheme XII are provided in Example 6.

Compounds of Formula 6:

Compounds of Formula 6 can be prepared by reducing a corresponding compound of Formula 7. The reduction is carried out with a chemical reducing agent such as sodium borohydride in a suitable solvent, typically an alcohol (e.g., ethanol, methanol, isopropanol, any appropriate mixture of suitable alcohols, etc.) or lithium aluminum hydride (LAH) in a suitable solvent (e.g., diethyl ether, THF, 1,2-dimethoxyethane, any appropriate mixture of suitable solvents, etc.) at 0° to 80° C. and requires 1 to 2 hours (for further details see Example 1, infra.).

An alternative method for making compounds of Formula 6 in which n is 0 or 1 and the hydroxy is attached at the β-position is depicted by the following Reaction Scheme XI:

Scheme XI

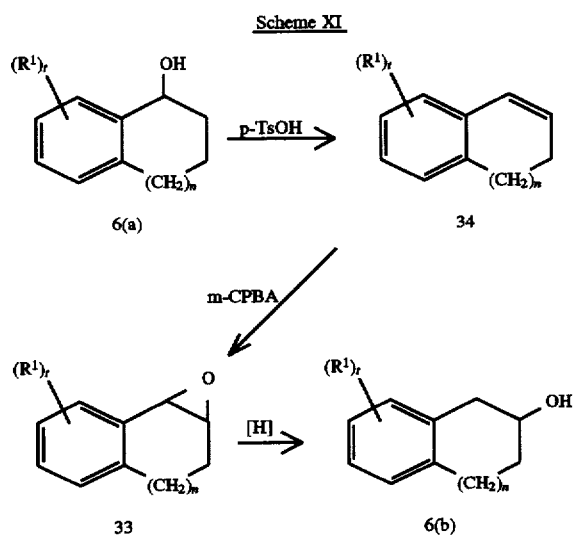

in which each n is 0 or 1 and t and $R^1$ is as defined in the Summary of the Invention with respect to Formula I.

Compounds of Formula 6 in which n is 0 or 1 and the hydroxy is attached at the β-position (Formula 6(b)) can be prepared by reacting a compound of Formula 34 with 3-chloroperoxybenzoic acid (m-CPBA) to give an epoxide of Formula 33 and then reducing the epoxide to give the corresponding β-alcohol. The reaction with m-CPBA is carried out in a suitable solvent (e.g., benzene, methylene chloride, chloroform, any appropriate mixture of suitable solvents, etc.) at 0° to 20° C., preferably approximately 0° C., and requires 0.5 to 5 hours. Reduction of the epoxide can be effected by catalycic hydrogenation (e.g., $H_2$, 10% palladium on carbon; etc.) in a suitable solvent (e.g., ethyl acetate, ethanol, isopropanol, any appropriate mixture of suitable solvents, etc.).

Compounds of Formula 34 can be prepared by reacting an α-alcohol of Formula 6(a) with p-toluenesulfonic acid in a suitable solvent (e.g., benzene, toluene, dichloroethane, methylene chloride, etc.) at 20° to 110° C., typically at 60° to 100° C. and preferably at approximately 80° C., for 1 to 5 hours. Further details of the reaction steps set forth in this and the preceding paragraph are provided in Example 2.

Compounds of Formula I can be prepared as their individual stereoisomers from the individual stereoisomers of starting material. The starting material can be prepared as individual stereoisomers by any of the resolution techniques described above or by any method known to one of ordinary skill in the art. For example, compounds of Formula 6 can be prepared as their individual stereoisomers by kinetic enzymatic resolution with a suitable enzyme (e.g., porcine pancreatic lipase, candida cylindracea, pancreatin, etc.).

Alternatively, certain starting materials in the process for preparing compounds of Formula I can be prepared as their individual stereoisomers by chiral synthesis. For example, compounds of Formula 6 can be prepared as their individual stereoisomers by chiral reduction of the corresponding compound of Formula 7. Compounds of Formula 6, wherein the hydroxy is attached at the α-position, can be prepared as the (R)-enantiomer by reducing the corresponding compound of Formula 7 with borohydride in the presence of (S)-1-aza-2-boro-3-oxa-4,4-diphenyl[3.3.0]bicyclooctane in THF. Similarly, the (S)-enantiomer can be prepared by reducing the compound of Formula 7 in the presence of (R)-1-aza-2-boro-3-oxa-4,4-diphenyl[3.3.0]bicyclooctane.

Compounds of Formula 6, wherein the hydroxy is attached at the β-position, can be prepared as the (R)-enantiomer by reducing the corresponding compound of Formula 7 with lithium aluminum hydride in the presence of (1R,2S)-N-methylephedrine and 2-ethylaminopyridine. The reaction is carried out in diethyl ether at –78° to –65° C., preferably approximately –78° C., and requires 2 to 3 hours (for further details see Example 3, infra.). Similarly, the (S)-enantiomer can be prepared by reducing the compound of Formula 7 in the presence of (1S,2R)-N-methylephedrine and 2-ethylaminopyridine. Compounds of Formula 7:

Compounds of Formula 7 are available commercially or can be readily made by those of ordinary skill in the art. For example, suitable compounds of Formula 7 can be obtained can be prepared by oxidizing an available compound of Formula 6. The oxidation of the compound of Formula 6 can be effected with an appropriate oxidizing agent (e.g., Dess-Martin reagent) in a suitable solvent (e.g., THF, methylene chloride, etc.) at 20° to 50° C.

Compounds of Formula 7 in which n is 0 or 1 and the oxo is attached at the α-position is depicted by the following Reaction Scheme XII:

Scheme XII

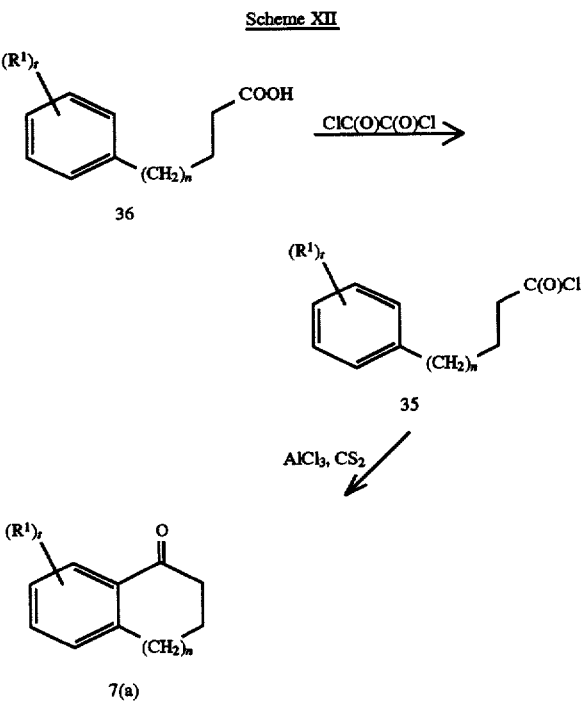

in which n is 0 or 1 and t and $R^1$ are as defined in the Summary of the Invention with respect to Formula I.

Compounds of Formula 7 in which n is 0 or 1 and the oxo is attached at the α-position (Formula 7(a)) can be prepared by reacting a compound of Formula 35 with a Lewis acid (e.g., aluminum chloride, aluminum bromide, boron trifluoride, hydrogen fluoride, etc.) in a suitable solvent (e.g., methylene chloride, carbon disulfide, nitrobenzene, any appropriate mixture of suitable solvents, etc.). The reaction is carried out in the presence of carbon disulfide at 20° to 45° C., typically at 30° to 45° C. and preferably at approximately 45° C., and requires 1 to 8 hours.

Compounds of Formula 35 can be prepared by reacting a compound of Formula 36 with a chlorinating agent (e.g., oxalyl chloride, thionylchloride, phosphorus pentachloride, etc., preferably oxalyl chloride) in a suitable solvent (e.g., methylene chloride, dichloroethane, any appropriate mixture of suitable solvents, etc.) at 20° to 40° C., typically at 10° to 30° C. and preferably at approximately 20° C., for 2 to 18 hours. Further details of the reaction steps set forth in this and the preceding paragraph are provided in Example 1.

Compounds of Formula 36 in which n is 0 can be prepared by reacting optionally substituted bromo- or iodobenzene with ethyl acrylate in a suitable solvent (e.g., DMF, dimethylacetamide, DMPU, any appropriate mixture of suitable solvents, etc.), reducing and then hydrolyzing. The reaction with the ethyl acrylate is carried out in the presence of a suitable palladium catalyst (e.g., bis(triphenylphosphine palladium(II) chloride) at 70° to 110° C., typically at 80° to 100° C. and preferably at approximately 90° C., and requires 4 to 72 hours. The reduction can be effected by catalytic hydrogenation under standard conditions. The hydrolysis can be effected with aqueous base or acid in a suitable solvent (e.g., aqueous sodium hydroxide in ethanol, aqueous sulfuric acid in dioxane, etc.).

Similarly, compounds of Formula 36 in which n is 1 can be prepared by reacting optionally substituted bromo- or iodobenzene with 3-butyl-1-ol in a suitable solvent (e.g., DMF and triethylamine, etc.), reducing and oxidizing. The reaction with the 3-butyn-1-ol is carried out in the presence of a suitable palladium catalyst (e.g., bis(triphenylphosphine palladium(II) chloride) at 80° to 90° C., preferably at approximately 85° C., and requires 4 to 24 hours. The subsequent reduction can be effected by catalytic hydrogenation. The oxidation can be effected with a suitable oxidizing agent (e.g., potassium dichromate(VI), potassium permanganate, etc.).

A method for making compounds of Formula 7 in which n is 1 and the oxo is attached at the β-position is depicted by the following Reaction Scheme XIII:

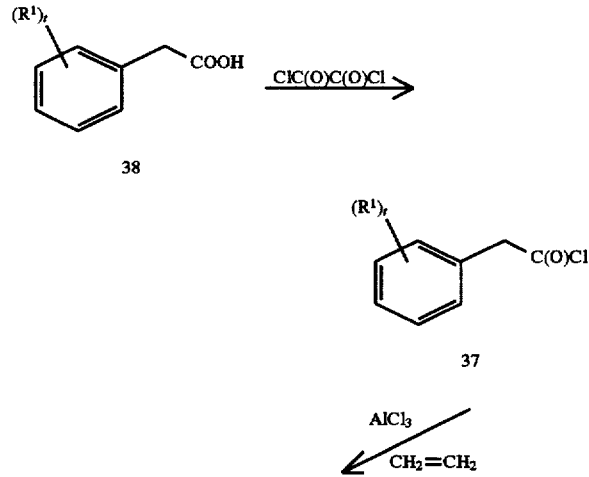

in which each t and $R^1$ is as defined in the Summary of the Invention with respect to Formula I.

Compounds of Formula 7 in which n is 1 and the oxo is attached at the β-position (Formula 7(b)) can be prepared by converting a compound of Formula 38 to the corresponding acid chloride (Formula 37) and then reacting the acid chloride with ethylene in the presence of a Lewis acid (e.g., aluminum chloride, boron trifluoride, aluminum bromide, etc.). The conversion to the acid chloride is carried out with an appropriate chlorinating agent (e.g., thionyl chloride, oxalyl chloride, phosphorus pentachloride, etc.) and in a suitable solvent (e.g., methylene chloride, dichloroethane, any appropriate mixture of suitable solvents, etc.) at 20° to 40° C., typically at 20° to 30° C. and preferably at approximately 20° C., and requires 2 to 18 hours. The reaction with ethylene is carried out in a suitable solvent (e.g., methylene chloride, carbon disulfide, any appropriate mixture of suitable solvents, etc.) and by adding the acid chloride to the Lewis acid at a rate such that the reaction mixture remains below –40° C., preferably below –60° C., and then bubbling the mixture with ethylene gas for 0.1 to 0.5 hours at –78° to –40° C., typically at –60° to –78° C. and preferably at approximately –78° C. Further details of the reaction steps set forth in this paragraph are provided in Example 3.

A method for making compounds of Formula 7 in which n is 2 and the oxo is attached at the β-position is depicted by the following Reaction Scheme XIV:

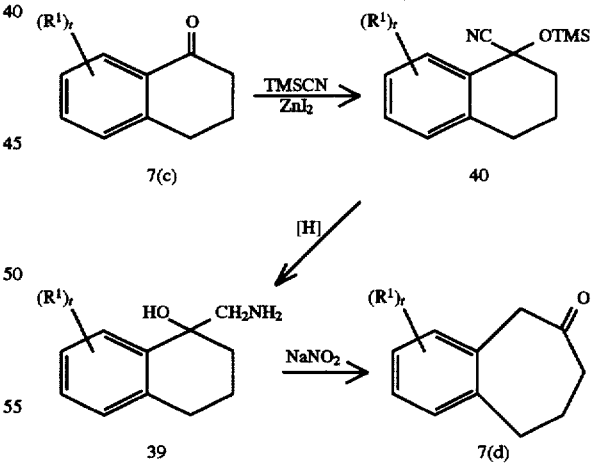

in which each t and $R^1$ is as defined in the Summary of the Invention with respect to Formula I.

Compounds of Formula 7 in which n is 2 and the oxo is attached at the β-position (Formula 7(d)) can be prepared by reacting a compound of Formula 39 with sodium nitrite in a suitable solvent (e.g., acetic acid-water, trifluoroacetic acid-water, acetic acid-ethanol, etc.). The reaction is carried out at –15° to 20° C., typically at –10° to 0° C. and preferably at approximately –0° C., and requires 1 to 18 hours. Compounds of Formula 39 are prepared by reacting a compound of Formula 7(c) with trimethylsilyl cyanide (TMSCN) and zinc chloride neat or in a suitable solvent (e.g., methylene chloride, any appropriate mixture of suitable solvents, etc.) to give a compound of Formula 40 and then reducing. The reaction with TMSCN is carried out at 0° to 20° C., typically at 10° to 20° C. and preferably at approximately 20° C., and requires 1 to 18 hours. The reduction can be effected with a chemical reducing agent in a suitable solvent. Further details of the reaction steps set forth in this and the preceding paragraph is provided in Example 4.

A method for making compounds of Formula 7 in which n is 2 and the oxo attached at the γ-position is described by the following Reaction Scheme XV:

Scheme XV

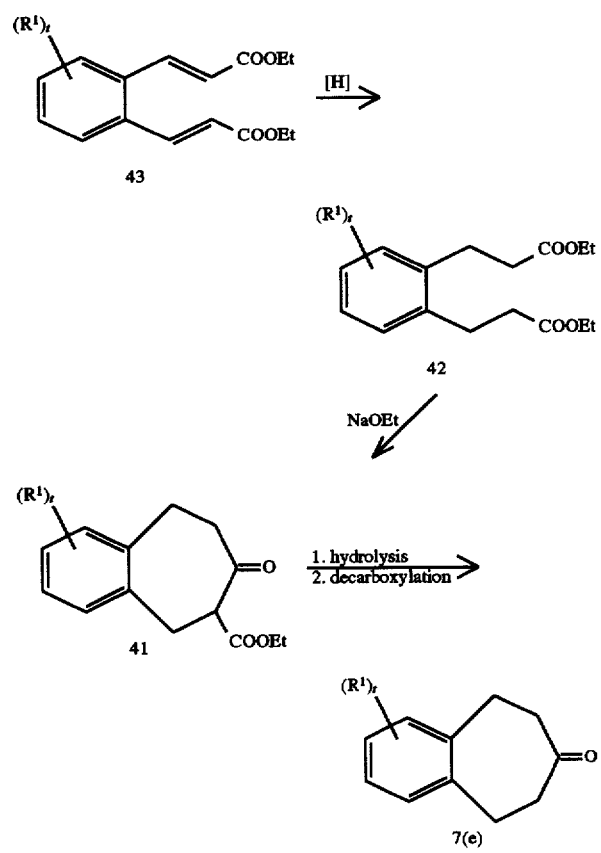

7(e)

in which each t and $R^1$ is as defined in the Summary of the Invention with respect to Formula I.

Compounds of Formula 7 in which n is 2 and the oxo is attached at the γ-position (Formula 7(e)) can be prepared by treating a compound of Formula 42 with sodium ethoxide to effect ring closure and give a compound of Formula 41, hydrolyzing the compound of Formula 41 to give the corresponding acid and then decarboxylating the acid. The reaction with sodium ethoxide and the resultant ring closure is carried in a suitable solvent (e.g., toluene, ethanol, any appropriate mixture of suitable solvents, etc.) at 80° to 110° C., typically at 90° to 110° C. and preferably at approximately 100° C., and requires 3 to 18 hours. The hydrolysis can be effected by heating in an aqueous base or acid. The decarboxylation can be effected by heating to 80° to 125° C., typically at 90° to 110° C. and preferably at approximately 100° C., and requires 4 to 8 hours. Compounds of Formula 42 can be prepared by reducing a compound of Formula 43.

The reduction can be effected by catalytic hydrogenation (e.g., $H_2$, 10% palladium on carbon, etc.).

Compounds of Formula 43 can be prepared by reacting optionally substituted dibromo or diiodo benzene with ethyl acrylate. The reaction with the ethyl acrylate is carried out in the presence of a suitable palladium catalyst (e.g., bis (triphenylphosphine palladium(II) chloride, etc.) and in a suitable solvent (e.g., DMF, any appropriate mixture of suitable solvents, etc.) at 5° to 130° C., typically at 85° to 105° C. and preferably at approximately 95° C., and requires 72 to 168 hours. Further details of the reaction steps set forth in this and the preceding paragraph are provide in Example 5.

Preparation of Compounds of Formula II:

A method for making compounds of Formula II in which $R^{18}$ is a group of Formula (d) wherein $R^{21}$ is —$CH_2NR^{25}R^{26}$ is depicted by the following Reaction Scheme XVI:

Scheme XVI

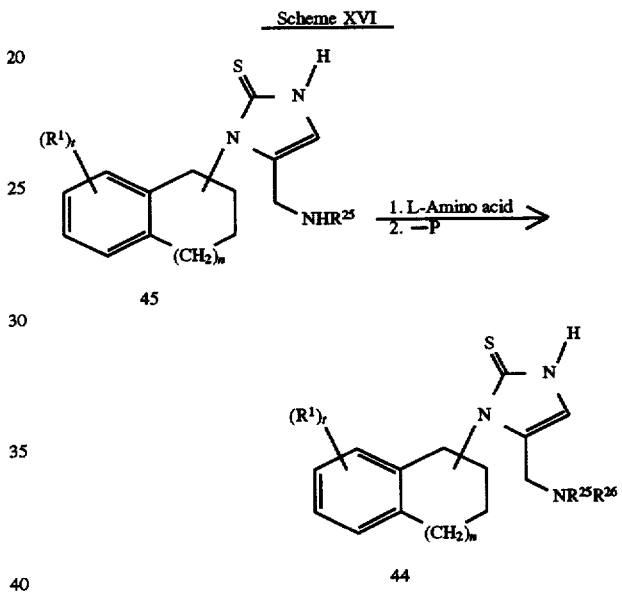

in which each n, t, $R^1$, $R^{25}$ and $R^{26}$ are as defined in the Summary of the Invention with respect to Formula II.

Compounds of Formula II in which $R^{18}$ is a group of Formula (d) wherein $R^{21}$ is —$CH_2NR^{25}R^{26}$ (Formula 44) can be prepared by reacting a compound of Formula I(a) in which $R^5$ is —$CH_2NHR^{25}$ (Formula 45) with a protected derivative of an L-amino acid in a suitable solvent (e.g., DMF, methylene chloride, THF, any appropriate mixture of suitable solvents, etc.) and then removing all protective groups present. The reaction with the L-amino acid is carried out in the presence of a non-nucleophilic base (e.g., DIEA, N,N-dicyclohexylmethylamine, etc.) and a peptide coupling agent (e.g., PyBOP, benzotriazol-1-yloxytris (dimethylamino)-phosphonium hexafluorophosphate, N,N-dicyclohexylcarbodiimide, bromotris(pyrrolidin-1-yl) phosphonium hexafluorophosphate, etc.) at 20° to 80° C., preferably approximately 20° C., and requires 8 to 24 hours (for further details see Example 51, infra.).

Protected L-amino acids are prepared by reacting an appropriate L-amino acid with a suitable protecting agent (e.g., di-tert-butyldicarbonate, 9-fluorenylmethylsuscinimidylcarbonate, etc.). For example, the protected derivative of L-lysine is prepared by reacting L-lysine with di-tert-butyldicarbonate in a suitable solvent (e.g., THF, DMF, any appropriate mixture of suitable solvents, etc.). The reaction is carried out at 0° to 20° C., preferably at approximately 20° C., and requires 8 to 48 hours. Removal of the protective groups can be effected by acid hydrolysis (e.g., 15% hydrogen chloride) in a suitable solvent (e.g., ethyl acetate, 1,2-dimethoxyethane, any appropriate mixture of suitable solvents, etc.). 9-Fluorenylmethoxycarbonyl protective groups can be removed with piperidine in DMF. Carbobenzyloxy protective groups can be removed by hydrogenating with palladium on carbon.

Proceeding similarly, compounds of Formula II in which $R^{18}$ is a group of Formula (d) wherein $R^{20}$ is —$CH_2NR^{25}R^{26}$ are prepared from compounds of Formula I(a) in which $R^4$ is —$CH_2NHR^{25}$. Compounds of Formula II in which $R^{18}$ is a group of Formula (d) wherein $R^{21}$ is —$NR^{25}R^{26}$ are prepared from compounds of Formula I(a) in which $R^5$ is —$NHR^{25}$. Compounds of Formula II in which $R^{18}$ is a group of Formula (e) wherein $R^{23}$ is —$CH_2NR^{25}R^{26}$ are prepared from compounds of Formula I(b) in which $R^7$ is —$CH_2NHR^{25}$. Compounds of Formula II in which $R^{18}$ is a group of Formula (d) wherein $R^{19}$ is —$NR^{25}R^{26}$ can be prepared from a compound of Formula I(a), wherein $R^3$ is —$NHR^{25}$. Compounds of Formula II in which $R^{18}$ is a group of Formula (f) wherein $R^{15}$ is —$NR^{25}R^{26}$ can be prepared from a compound of Formula I(c), wherein $R^8$ is —$NHR^{25}$.

Preparation of Compounds of Formula III:

A method for making compounds of Formula III in which $R^{27}$ is a group of Formula (g) is depicted by the following Reaction Scheme XVII:

N-(tert-butoxycarbonyl)cystine with bromine in a suitable solvent (e.g., dichloroethane, etc.). The reaction is carried out at –40° to 20° C., preferably at approximately –23° C., and requires 1 to 3 hours. Further details of the reaction steps set forth by Reaction Scheme XVII is provided in Example 52, infra.

Proceeding similarly, compounds of Formula III in which $R^{27}$ is a group of Formula (h) are prepared from compounds of Formula I(b). Compounds of Formula III in which $R^{27}$ is a group of Formula (i) are prepared from compounds of Formula I(c) in which $R^8$ is hydro.

EXAMPLE 1

5,6-Difluoro-1-hydroxyindane

The following is the preparation of a compound of Formula 6 in which n is 0, t is 2 and $R^1$ is fluoro and at the 5- and 6-position.

3-(3,4-Difluorophenyl)propionic acid (80.0 g, 0.43 mol) was dissolved in 3 drops of DMF and 350 mL of methylene chloride. Oxalyl chloride (75 mL, 0.860 mol) was added and the mixture was stirred under nitrogen at room temperature for approximately 3 hours. Excess oxalyl chloride was removed by evaporation and the residue was co-evaporated twice with 200 mL of carbon tetrachloride giving 95.0 g of residue as an oil.

Aluminum chloride (200 g) was suspended in 800 mL of carbon disulfide and the suspension was cooled to 0° C. A

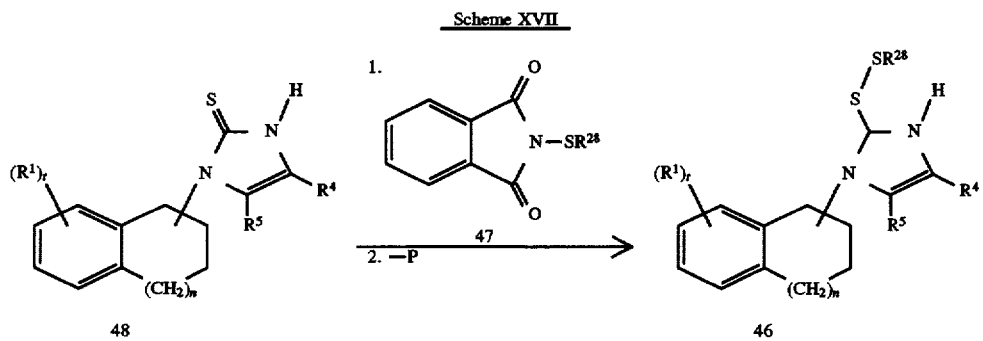

Scheme XVII in which each n, t, $R^1$ and $R^{28}$ are as defined in the Summary of the Invention with respect to Formula III.

Compounds of Formula III in which $R^{27}$ is a group of Formula (g) (Formula 46) can be prepared by reacting a compound of Formula I(a) wherein $R^3$ is hydro (Formula 48) with a compound of Formula 47, or a protected derivative thereof, in a suitable solvent (e.g., ethyl acetate, ethylenedichloride, THF, any appropriate mixture of suitable solvents, etc.) and then removing all protective groups present. The reaction with the compound of Formula 47 is carried out at 20° to 110° C., preferably approximately 80° C., for 1 to 4 hours.

Compounds of Formula 47 can be prepared by reacting a compound of the formula X—$SR^{28}$, in which X is halo, or the protected derivatives thereof, with potassium phthalimide in a suitable solvent (e.g., ethylenedichloride, carbon tetrachloride, 1,1,1,2-tetrachloroethane, etc.). The reaction is carried out at –30° to 20° C., preferably approximately –20° C., and requires 1 to 3 hours. Compounds of the formula X—$SR^{28}$ can be readily prepared by those of skill in the art. For example, a compound of the formula X—$SR^{28}$ in which X is bromo and $R^{28}$ is 2-tert-butoxycarbonyl-2-(tert-butyloxycarbonylamino)ethyl can be prepared by reacting solution of the residue in 300 mL of carbon disulfide was added to the suspension over 20 minutes and the mixture was stirred at reflux for 4 hours. The mixture was poured onto 2 kg of crushed ice and the aqueous layer was extracted with ethyl acetate (3×300 mL). The carbon disulfide layer and ethyl acetate extract were both dried over magnesium sulfate, filtered and then combined. The solvents were removed by evaporation and the residue was crystallized from isopropyl ether giving 54.3 g of 5,6-difluoroindan-1-one as a solid. The mother liquor was purified by column chromatography on silica gel (elution: 10% ethyl acetate/hexane) giving an additional 5.2 g of 5,6-difluoroindan-1-one.

5,6-Difluoroindan-1-one (59.3 g, 0.353 mol) was dissolved in 1 L of ethanol and sodium borohydride (6.68 g, 0.176 mol) was added. The mixture was stirred for 48 hours and the ethanol was removed by evaporation under reduced pressure. The residue was partitioned between diethyl ether and water and the mixture was acidified with 1N hydrochloric acid. The mixture was dried over magnesium sulfate and filtered. The solvents were evaporated giving 5,6-difluoro-1-hydroxyindane (59.8 g) as an oil.

Proceeding as in Example 1 but substituting a different starting material for 3-(3,4-difluorophenyl)propionic acid, the following compounds of Formula 6 were made:

substituting 3-(3,5-difluorophenyl)propionic acid gave 5,7-difluoro-1-hydroxyindane, m.p. 102°–103° C.;
substituting 4-(2,4-difluorophenyl)butyric acid gave 5,7-difluoro-1,2,3,4-tetrahydro-1-hydroxynaphthalene as an oil;
substituting 4-(3,4-difluorophenyl)butyric acid gave 6,7-difluoro-1,2,3,4-tetrahydro-1-hydroxynaphthalene as an oil;
substituting 4-(4-fluorophenyl)butyric acid gave 7-fluoro-1,2,3,4-tetrahydro-1-hydroxynaphthalene as an oil;
substituting 4-(3-fluorophenyl)butyric acid gave 6-fluoro-1,2,3,4-tetrahydro-1-hydroxynaphthalene as an oil; and
substituting 4-(3,5-difluorophenyl)butyric acid gave 6,8-difluoro-1,2,3,4-tetrahydro-1-hydroxynaphthalene, m.p. 102°–103° C.

EXAMPLE 2

5,6-difluoro-2-hydroxyindane

The following is the preparation of a compound of Formula 6 in which n is 0, t is 2 and $R^1$ is fluoro at the 5- and 6-position.

5,6-Difluoro-1-hydroxyindane (59.8 g, 356 mmol), prepared as in Example 1, was dissolved in 600 mL of benzene and p-toluenesulfonic acid monohydrate (3.36 g, 17.66 mol) was added. The mixture was heated to 120° C., distilled for approximately 2 hours and then allowed to cool. Saturated sodium bicarbonate solution was added and the benzene layer was dried over magnesium sulfate. The benzene layer was then filtered and the filter residue was washed with diethyl ether.

The benzene/diethyl ether mixture was cooled to 0° C. and m-CPBA (75.5 g, 0.35 mol) was added over 15 minutes. The mixture was stirred at room temperature for 5 hours. The diethyl ether was removed by rotary evaporation, 400 mL of methylene chloride was added and the mixture was stirred for 2 hours. Additional m-CPBA (30.0 g, 0.14 mol) was added and the mixture was stirred for 2 hours. The mixture was cooled to 0° C. and potassium iodide (45 g) in 150 mL of water was added. The mixture was stirred for approximately 15 minutes and then sodium thiosulfate (40 g) in 150 mL of water was added. Kugelrohr distillation (bp 60°–90° C. [0.1 mm])) gave 30 g of impure 1,2-epoxy-5,6-difluoroindane as an oil.

Impure 1,2-epoxy-5,6-difluoroindane (4.5 g) was dissolved in 100 mL of ethanol and hydrogenated over 10% palladium on carbon (450 mg) for 15 hours. The mixture was filtered and evaporation gave 5,6-difluoro-2-hydroxyindane (2.72 g, 15.9 mmol), m.p. 57°–58° C.

Proceeding as in Example 2 but substituting a different starting material for 5,6-difluoro-1-hydroxyindane, the following compounds of Formula 6 were made:

substituting 5,7-difluoro-1,2,3,4-tetrahydro-1-hydroxynaphthalene gave 5,7-difluoro-1,2,3,4-tetrahydro-2-hydroxynaphthalene, m.p. 93°–94° C.;
substituting 4,6-difluoro-1-hydroxyindane gave 4,6-difluoro-2-hydroxyindane, m.p. 52°–56° C.;
substituting 6,7-difluoro-1,2,3,4-tetrahydro-1-hydroxynaphthalene gave 6,7-difluoro-1,2,3,4-tetrahydro-2-hydroxynaphthalene as an oil; and
substituting 6,8-difluoro-1,2,3,4-tetrahydro-1-hydroxynaphthalene gave 6,8-difluoro-1,2,3,4-tetrahydro-2-hydroxynaphthalene.

EXAMPLE 3

(R)-5,7-Difluoro-1,2,3,4-tetrahydro-2-hydroxynaphthalene

The following is the preparation of a compound of Formula 6 in which t is 2 and $R^1$ is fluoro at the 5- and 7-position.

A mixture 3,5-difluorophenylacetic acid (100 g, 0.58 mmol) and thionyl chloride (13.7M, 100 mL, 1.37 mol) was stirred for 15 hours at room temperature. Evaporation gave 3,5-difluorophenylacetyl chloride as an oily residue. A stirred suspension of aluminum chloride (154 g, 1.16 mmol) in 1 L of methylene chloride was cooled to −65° C. and the acid chloride in 200 mL of methylene chloride was added dropwise such that the reaction temperature did not exceed −60° C. Ethylene gas was bubbled through the suspension at a rapid rate for 10 minutes at −65° C. The reaction mixture was allowed to warm to 0° C. over 2 hours, then cooled to −10° C. and treated with 500 mL of water. The organic layer was separated, washed with 100 mL of aqueous sodium chloride, and then dried over magnesium sulfate. The mixture was filtered and the filtrate was concentrated under reduced pressure. Distillation of the residue in vacuo (bp 90°–110° C. [1.0 to 0.7 mm]) gave a clear distillate. Redistillation (bp 100°–105° C. [0.3 mm]) gave 5,7-difluoro-1,2,3,4-tetrahydronaphthalen-2-one (73.56 g, 0.342 mol) as a white solid, m.p. 46° C.

A solution of (1R,2S)-N-methylephedrine (81.3 g, 0.454 mol) in 1.2 L of anhydrous diethyl ether was added to lithium aluminum hydride (1.0M in diethyl ether, 416 mL, 0.416 mol) over 45 minutes. The mixture was heated under reflux for 1 hour and then allowed to cool to room temperature. A solution of 2-ethylaminopyridine (110.7 g, 0.907 mol) in 100 mL of anhydrous diethyl ether was added over 45 minutes. The mixture was heated under reflux for 1 hour and then cooled to −65° C. A solution of 5,7-difluoro-1,2,3,4-tetrahydro naphthalen-2-one (23.0 g, 0.107 mol) in 100 mL of diethyl ether was added dropwise such that the reaction temperature did not exceed −60° C. The mixture was stirred at −65° C. to −68° C. for 3 hours and then 100 mL of methanol was added such that the reaction temperature did not exceed −60° C. The mixture was stirred at −65° C. to −68° C. for 10 minutes, then allowed to warm to −20° C., and 3.0 L of 3N hydrochloric acid was added such that the reaction temperature did not exceed 35° C. The diethyl ether layer was separated, washed with 200 mL of saturated sodium chloride, and dried over magnesium sulfate. The mixture was filtered and the filtrate concentrated under reduced pressure. Crystallization from 20 mL of diethyl ether and 200 mL of hexane and drying in vacuo gave (R)-5,7-difluoro-1,2,3,4-tetrahydro-2-hydroxynaphthalene (10.87 g, 0.05 mol), m.p. 85° C. $[\alpha]_D^{25}=+36.03°$ (c=1.59, CHCl$_3$).

Proceeding as in Example 3 but substituting a different starting material for 3,5-difluorophenylacetic acid, the following compounds of Formula 6 were made:

substituting 3-fluorophenylacetic acid gave (R)-7-fluoro-1,2,3,4-tetrahydro-2-hydroxynaphthalene, m.p. 59°–61° C., $[\alpha]_D^{25}=+48.8°$ (c=2.0, CHCl$_3$);
substituting 4-fluorophenylacetic acid gave (R)-6-fluoro-1,2,3,4-tetrahydro-2-hydroxynaphthalene, $[\alpha]_D^{25}=+49.2°$ (c=1.84, CHCl$_3$);
substituting phenylacetic acid gave (R)-1,2,3,4-tetrahydro-2-hydroxynaphthalene, as an oil, $[\alpha]_D^{25}=+62.2°$ (c=1.6, CHCl$_3$); and substituting 3,4-difluorophenylacetic acid gave (R)-6,7-difluoro-1,2,3,4-tetrahydro-2-hydroxynaphthalene, m.p. 88°–92° C., $[\alpha]_D^{25}$=+39.0° (c=2.2, CHCl$_3$).

Proceeding as in Example 3 but substituting (1S, 2R)-N-methylephedrine for (1R, 2S) -N-methylephedrine, gave (S)-5,7-difluoro-1,2,3,4-tetrahydro-2-hydroxynaphthalene, m.p. 84°–85° C., $[\alpha]D^{25}$=–37.4° (c=2.6, CHCl$_3$).

Proceeding as in Example 3 but substituting a different starting material for 3,5-difluorophenylacetic acid and reducing without (1R,2S)-N-methylephedrine or 2-ethylaminopyridine present, the following compounds of Formula 6 were made:

substituting 4-bromophenylacetic acid gave 6-bromo-1,2,3,4-tetrahydro-2-hydroxynaphthalene as an oil;
substituting 4-chlorophenylacetic acid gave 6-chloro-1,2,3,4-tetrahydro-2-hydroxy-naphthalene as an oil;
substituting 3-chlorophenylacetic acid gave 7-chloro-1,2,3,4-tetrahydro-2-hydroxynaphthalene, m.p. 79°–81° C.;
substituting 3,5-dichlorophenylacetic acid gave 5,7-dichloro-1,2,3,4-tetrahydro-2-hydroxynaphthalene, m.p. 84°–86° C.;
substituting 3,5-difluorophenylacetic acid gave 5,7-difluoro-1,2,3,4-tetrahydro-2-hydroxynaphthalene;
substituting 3,4-difluorophenylacetic acid gave 6,7-difluoro-1,2,3,4-tetrahydro-2-hydroxynaphthalene,;
substituting 3,4-dichlorophenylacetic acid gave 6,7-dichloro-1,2,3,4-tetrahydro-2-hydroxynaphthalene, m.p. 103°–105° C.; and
substituting 4-fluorophenylacetic acid gave 6-fluoro-1,2,3,4-tetrahydro-2-hydroxynaphthalene.

EXAMPLE 4

1,3-Difluoro-6,7,8,9-tetrahydro-6-hydroxy-5H-banzocycloheptene

The following is the preparation of a compound of Formula 6 in which t is 2 and R$^1$ is fluoro at the 1- and 3-position.

A mixture of 5,7-difluoro-1,2,3,4-tetrahydronaphthalen-1-one (4.0 g, 22.0 mmol), zinc iodide (22.0 mg, 68.9 mmol) and trimethylsilyl cyanide (3.23 mL, 24.2 mmol) was stirred under argon at room temperature for 18 hours. The TMSCN was evaporated under vacuum and the residue (6.13 g) was dissolved in 45 mL of anhydrous diethyl ether. Lithium aluminum hydride (1.0M, 24.2 mL, 24.2 mmol) in diethyl ether was added to the solution at such a rate that gentle reflux was maintained. The mixture was stirred at room temperature for 1 hour and then 0.84 mL of water, 0.84 mL of 15% sodium hydroxide and 1.63 mL of additional water were added sequentially. The aqueous layer was stirred for 10 minutes, filtered and extracted with diethyl ether. The combined extracts were dried over magnesium sulfate and concentrated giving 4.21 g of residue. Purification of the residue by flash chromatography (elution: 10% methanol/methylene chloride) gave 1-aminomethyl-5,7-difluoro-1-hydroxy-1,2,3,4-tetrahydronaphthalene (3.67 g, 17.2 nmol).

A mixture of 1-aminomethyl-5,7-difluoro-1-hydroxy-1,2,3,4-tetrahydro naphthalene (3.58 g, 16.8 mmol) and sodium nitrite (2.32 g, 33.6 mmol) in 8 mL of acetic acid and 20 mL of water was heated at –5° C. and then allowed to warm to room temperature and stirred for 18 hours. The solvents were removed by evaporation and 3.14 g of the residue was purified by flash chromatography (elution: 50% hexane/methylene chloride) giving 1.8 g of residue. A mixture of the purified residue and LAH (9.2 mL, 9.2 mmol) in THF was stirred at 0° C. for 18 hours and then 0.64 mL of water, 0.64 mL of 15% sodium hydroxide and 1.3 mL of additional water were added sequentially. The THF layer was dried over magnesium sulfate and concentrated to 1.8 g of residue. Purification by flash chromatography (elution: methylene chloride) gave 1,3-difluoro-6,7,8,9-tetrahydro-6-hydroxy-5H-benzocycloheptene (1.4 g, 7.06 mmol).

EXAMPLE 5

1,3-Difluoro-6,7,8,9-tetrahydro-7-hydroxy-5H-benzocycloheptene

The following is the preparation of a compound of Formula 6 in which t is 2 and R$^1$ is fluoro and the 1- and 3-position.

A mixture of 1,2-dibromo-3,5-difluorobenzene (24.7 g, 91.6 mmol), bis(triphenylphosphine)palladium(II) chloride (2.57 g, 3.66 mmol) and triethylamine (51.0 mL, 366 mmol) in 300 mL of DMF was stirred under argon at approximately 85° C. for 15 minutes. Hydrazine hydrate (366 μL, 7.54 mmol) was added and the mixture was stirred for an additional 10 minutes. Ethyl acrylate (39.7 mL, 366 mmol) was added and the mixture was stirred under argon at approximately 85° C. for approximately 144 hours. The solvents were removed by evaporation under reduced pressure and the residue was dissolved in 1.0 L of ethyl acetate. The ethyl acetate solution was washed 3 times with water and dried over magnesium sulfate. Evaporation of the solvent gave crude ethyl 3-{3,5-difluoro-2-[2-(ethoxycarbonyl)vinyl]phenyl}acrylate (36 g).

Ethyl 3-{3,5-difluoro-2-[2-(ethoxycarbonyl)vinyl]phenyl}acrylate (5.7 g, 18.4 mmol) in 250 mL of ethyl acetate was hydrogenated at 60 psi over 10% palladium on carbon (0.57 g) for 4 hours and then the mixture was filtered through Celite. Evaporation of the solvent gave ethyl 3-{3,5-difluoro-2-[2-(ethoxycarbonyl)ethyl]phenyl}propionate (5.73 g, 22.4 mmol) as a colorless oil.

Potassium tert-butoxide (167 mL, 0.167 mol) in DMF was added to 400 mL of toluene and the DMF was removed by evaporation. Ethyl 3-{3,5-difluoro-2-[2-(ethoxycarbonyl)ethyl]phenyl}propionate (5.65 g, 18.0 nmol) was added and the mixture was stirred under argon at 100° C. for 8 hours. The mixture was cooled to 0° C., acidified with 11.5 mL of acetic acid, washed 3 times with water and dried over magnesium sulfate. Evaporation of the solvent gave a mixture of ethyl 1,3-difluoro-6,7,8,9-tetrahydro-7-oxo-5H-benzo-cycloheptene-6-carboxylate and ethyl 1,3-difluoro-6,7,8,9-tetrahydro-7-oxo-5H-benzocycloheptene-8-carboxylate (4.3 g).

The carboxylate isomers (4.2 g) were dissolved in 20 mL of acetic acid and 10 mL of 9N hydrochloric acid and the solution was refluxed for 10 hours. The mixture was cooled to room temperature and extracted with diethyl ether (1×200 mL and then 1×50 mL). The extracts were combined and mixed with 120 mL of 10% aqueous sodium carbonate. The organic layer was dried over magnesium sulfate and then the solvent was removed by evaporation. Purification of the residue by flash chromatography (elution: 50% methylene chloride/hexane) gave 1,3-difluoro-6,7,8,9-tetrahydro-5H-benzocyclohepten-7-one (1.5 g, 7.6 mmol).

1,3-Difluoro-6,7,8,9-tetrahydro-5H-benzocyclohepten-7-one (1.5 g, 7.6 mmol) was dissolved in 30 mL of dry THF, the solution was cooled to 0° C. under argon and 1M LAH (7.5 mL, 7.5 mmol) in THF was added over 2 minutes. The mixture was stirred at 0° C. for 1 hour and then 0.28 mL of water, 0.28 mL of 15% aqueous sodium hydroxide and 0.9 mL of water were added sequentially. The mixture was stirred for 5 minutes, filtered, washed with ethyl acetate and dried over magnesium sulfate. Evaporation of the solvents gave 1,3-difluoro-6,7,8,9-tetrahydro-7-hydroxy-5H-benzocycloheptene (1.55 g, 7.8 mmol) as an oil.

EXAMPLE 6

(S)-5,7-Difluoro-1,2,3,4-tetrahydronaphthalen-2-ylamine hydrochloride

The following is the preparation of a compound of Formula 3 in which n is 1, t is 2 and $R^1$ is fluoro at the 5- and 7-position.

(a) Trifluoroacetic anhydride (7.7 kg, 5.3 L, 37.5 mol) was heated to reflux and a solution of L-aspartic acid (2.0 kg, 15.0 mol) in 9 L of trifluoroacetic acid (prepared by gradually heating to 65° C. and stirring for 3 hours) was added to the refluxing TFAA over 30 minutes. The mixture then was distilled and 9 L of TFA was removed. The remaining mixture was added to 8 L of cold hexane under nitrogen. The hexane mixture was stirred for 3 hours in an ice bath giving a crystalline material. The material was isolated by filtration and the filtered residue was washed with approximately 25 L of hexane. Drying to constant weight in a vacuum oven at 50° C. under a nitrogen gas bleed gave N-(trifluoroacetyl)-L-aspartic anhydride (2.9 kg, 13.7 mol), m.p. 140°–141° C. $[\alpha]_D$ −27.4° (c=3.28, THF).

(b) A solution of 1,3-difluorobenzene (2.3 kg, 20.0 mol) in 5 L of methylene chloride was added to a mixture of N-(trifluoroacetyl)-L-aspartic anhydride (4.2 kg, 20.0 mol) and aluminum chloride (7.4 kg, 55.5 mol) in 25 L of methylene chloride. The temperature of the reaction mixture was increased gradually over 1.5 hours and held at reflux for an additional 3 hours. The mixture then was cooled and 10 L of water and 20 L of 6N hydrochloric acid were added with good agitation. The methylene chloride layer was separated, washed with water and then brine, and the volatiles were removed by distilling at atmospheric pressure.

The residue was dissolved in 40 L of toluene and 8 L of volatiles was removed by distilling the mixture in vacuo. The solution was heated to 50° C. and 8 L of hexane was added. The mixture was cooled to 30° C. and 90 L of hexane was added. The mixture then was stirred at 25° C. for 3 hours giving a crystalline material. The material was isolated by filtration and the filtered residue was washed with hexane (3×10 L). Drying to a constant weight in a vacuum oven at room temperature under a nitrogen bleed gave (S)-2-[(trifluoroacetyl)amino]-4-(2,4-difluorophenyl)-4-oxobutanoic acid (5.2 kg, 16.0 mol), m.p. 82.4°–84.0° C. $[\alpha]_D$ +15.2° (c=0.956, $CH_3OH$).

(c) A mixture of (S)-2-[(trifluoroacetyl)amino]-4-(2,4-difluorophenyl)-4-oxobutanoic acid (4.8 kg, 14.7 mol) and activated carbon, Darco®, (0.4 kg) in 5 L of acetic acid was stirred at room temperature for 1 hour. The mixture was filtered on to Pearlman's catalyst (0.5 kg, 50% wet) and washed in with 15 L of glacial acetic acid. Sulfuric acid (1.2 L, 21.8 mol) in 1 L of glacial acetic acid was filtered into the mixture and washed in with 2.8 L of glacial acetic acid. The reaction vessel was vacuum/pressure purged 3 times with nitrogen and then 6 times with hydrogen to 10 psig. The mixture was stirred vigorously under hydrogen at atmospheric pressure at room temperature, for 24 hours. The reaction vessel then was purged with nitrogen and the mixture was filtered onto 4.6 kg of sodium acetate trihydrate. The filter was washed with 10 L of glacial acetic acid. The glacial acetic acid was removed by distilling the mixture in vacuo.

The residue was partitioned between 20 L of methylene chloride and 40 L of water. The aqueous layer was extracted with 10 L of methylene chloride and the combined methylene chloride was washed with 10 L of water. The methylene chloride mixture then was dried over sodium sulfate (10 kg) and filtered. The solvent was removed in vacuo and the residue was dissolved in 5 L of methylene chloride. The solution was added under nitrogen to 15 L of hexane at a rate such that the temperature of the hexane mixture remained between 0° and 5° C. The mixture was allowed to stand for 1 hour giving a crystalline material. The material was isolated by filtration and the filter residue was washed with 10 L of hexane. Drying to constant weight in vacuo at 25° C. with a nitrogen bleed gave (S)-2-[(trifluoroacetyl)amino]-4-(2,4-difluorophenyl)butanoic acid (3.3 kg, 10.4 mol), m.p. 62°–83.5° C. An analytically pure sample had a melting point of 86°–89° C. $[\alpha]_D$ +6.8° (c=0.995, $CH_3OH$).

(d) A suspension of phosphorus pentachloride (2.2 kg, 10.6 mol) in 12 L of methylene chloride was cooled to 5° C. and (S)-4-(2,4-difluorophenyl)-2-[(trifluoroacetyl)amino]butanoic acid (3.1 kg, 9.9 mol) in 12 L of methylene chloride was added over 20 minutes. Thin layer chromatography of a methanol-quenched aliquot confirmed that the butanoic acid had converted to the corresponding acid chloride.

The mixture was stirred for 30 minutes and then was added to a slurry of aluminum chloride (4.3 kg) in 38.8 L of methylene chloride at a rate such that the temperature of the slurry remained between 1° and 5° C. The reaction mixture was stirred for 1 hour and then added to 28 kg of ice and 5.3 kg of concentrated hydrochloric acid. The mixture was stirred for 1 hour and the temperature allowed to rise to 20° C.

The aqueous layer was separated and extracted with methylene chloride (2×15 L). The methylene chloride layer was washed once with water and combined with the methylene chloride extracts. The combined methylene chloride then was washed with water. The pH of the aqueous phase was adjusted to 6 by addition of aqueous sodium bicarbonate solution. The methylene chloride layer was washed with water and then brine. The methylene chloride was dried over sodium sulfate and filtered. The mixture was concentrated by evaporation at atmospheric pressure and the residue was dissolved in 15 L of methanol. The methanol solution was distilled to 9.9 L of methylene chloride and then 9.9 L of water was added. The mixture was warmed to 56° C., allowed to cool to room temperature and then stirred for approximately 12 hours. A crystalline material was obtained and isolated by filtration. The filter residue was washed with 15 L of water. The isolated material was dried to constant weight in vacuo at roan temperature with a nitrogen bleed.

The material was dissolved in 5 L of toluene at a temperature of 90° C. and combined with 10 L of heptane at a temperature of 80° C. The temperature of the mixture gradually was decreased over 1.5 hours. The mixture then was stirred at 5° C. for approximately 12 hours giving a crystalline material. The material was isolated by filtration and the filter residue was washed with 15 L of heptane. Drying to constant weight in vacuo at roan temperature with a nitrogen bleed gave (S)-5,7-difluoro-2-[(trifluoroacetyl) amino]-3,4-dihydro-(2H)-naphthalen-1-one (2.0 kg, 6.8 mol), m.p. 142.4°–144.6° C. $[\alpha]_D$ −59.4° (c=0.994, $CH_3OH$).

(e) A reaction vessel containing a mixture of (S)-5,7-difluoro-2-[(trifluoroacetyl)amino]-3,4-dihydro-(2H)-naphthalen-1-one (1.1 kg, 3.8 mol) and Pearlman's catalyst (0.55 kg, 50% wet) in 11 L of TFA was vacuum/ pressure purged 8 times with nitrogen and then 8 times with hydrogen to 11 psig. The mixture was stirred vigorously under hydrogen (125 psig) at room temperature for 24 hours. Thin layer chromatography confirmed that the naphthalen-1-one had converted to (S)-1-hydroxy-5,7-difluoro-2-[(trifluoroacetyl)amino]-3,4-dihydro-(2H)-naphthalene.

(f) Sulfuric acid (1.1 L, 19.4 mol) in i n of TFA then was added and the mixture stirred under hydrogen (125 psig) at room temperature for an additional 24 hours. The reaction vessel then was purged with nitrogen and the mixture was filtered over Celite and washed through with 11 L of TFA. The filtrate was combined with 2.8 kg sodium acetate trihydrate and 80 L of water. The mixture was cooled to 10° C. giving a crystalline material. The material was isolated by filtration and the filter residue was washed with 10 L of ice water. Drying gave (S)-5,7-difluoro-2-[(trifluoroacetyl)amino]-1,2,3,4-tetrahydronaphthalene (0.8 kg, 2.9 mol), m.p. 159.9°–160.9° C. $[\alpha]_D$ –56.0° (c=1.01, $CH_3OH$).

(g) Lithium hydroxide monohydrate (7.8 g, 0.2 mol) was added to a solution of (S)-5,7-difluoro-2-[(trifluoroacetyl)amino]-1,2,3,4-tetrahydronaphthalene (20.8 g, 74.5 mmol) in 187 mL of methanol and 21 mL of water. The mixture was stirred at reflux for 30 minutes and diluted with 200 mL of methanol. The diluted mixture then was combined with 60 mL of water, 24.8 mL of concentrated hydrochloric acid and 4.2 g of activated carbon, Darco®. The mixture was stirred for 30 minutes and then filtered through Celite. The filtrate was distilled until the head temperature reached 75° C. The remaining mixture was allowed to cool and let stand for approximately 60 hours. The mixture then was cooled in an ice bath giving a crystalline material. The material was isolated by filtration and the filter residue was washed with water. Drying to constant weight in vacuo at room temperature under a nitrogen stream gave (S)-5,7-difluoro-1,2,3,4-tetrahydronaphthalen-2-ylamine hydrochloride (14.8 g, 67.6 mol), m.p.>280° C. $[\alpha]_D$ –66.2° (c=0.162, $CH_3OH$).

EXAMPLE 7

(R)-5,7-Difluoro-1,2,3,4-tetrahydronaphthalan-2-yl methanesulfonate

The following is the preparation of a compound of Formula 5 in which n is 1, t is 2, $R^1$ is fluoro at the 5- and 7-position and L is mesyloxy.

A mixture of (R)-5,7-difluoro-1,2,3,4-tetrahydro-2-hydroxynaphthalene (59.0 g, 0.32 mol), prepared as in Example 3, and triethylamine (13.8M, 74.2 mL, 0.53 mol) in 1.78 L of diethyl ether was cooled using a methanol/ice bath. Methanesulfonyl chloride (12.9M, 37.2 mL, 0.48 mol) was added under argon over 5–10 minutes and the mixture was stirred at room temperature for 18 hours. The mixture was partitioned between water and ether and the ether layer was separated and the aqueous layer was extracted with ether. The combined ether layers were washed once with each of 1N hydrochloric acid, saturated sodium bicarbonate solution and brine and then dried over magnesium sulfate. Evaporation gave crude (R)-5,7-difluoro-1,2,3,4-tetrahydronaphthalen-2-yl methanesulfonate as an off-white solid (87.12 g), m.p. 79°–80° C. $[\alpha]_D^{25}$=+16.77° (c=2.0, $CHCl_3$).

Proceeding as in Example 7 but substituting different starting materials for (R)-5,7-difluoro-1,2,3,4-tetrahydro-2-hydroxynaphthalene, the following compounds of Formula 5 were made:

substituting 1,2,3,4-tetrahydro-2-hydroxynaphthalene gave 1,2,3,4-tetrahydronaphthalen-2-yl methanesulfonate;

substituting (R)-1,2,3,4-tetrahydro-2-hydroxynaphthalene gave (R)-1,2,3,4-tetrahydronaphthalen-2-yl methanesulfonate;

substituting (R)-5-fluoro-1,2,3,4-tetrahydro-2-hydroxynaphthalene gave (S)-5-fluoro-1,2,3,4-tetrahydronaphthalen-2-yl methanesulfonate;

substituting (R)-6-fluoro-1,2,3,4-tetrahydro-2-hydroxynaphthalene gave (S)-6-fluoro-1,2,3,4-tetrahydronaphthalen-2-yl methanesulfonate;

substituting (R)-7-fluoro-1,2,3,4-tetrahydro-2-hydroxynaphthalene gave (S)-7-fluoro-1,2,3,4-tetrahydronaphthalen-2-yl methanesulfonate;

substituting 6,7-dichloro-1,2,3,4-tetrahydro-2-hydroxynaphthalene gave 2-6,7-dichloro-1,2,3,4-tetrahydronaphthalen-2-yl methanesulfonate;

substituting (–)-6,7-difluoro-1,2,3,4-tetrahydro-2-hydroxynaphthalene gave (–)-6,7-difluoro-1,2,3,4-tetrahydronaphthalen-2-yl methanesulfonate;

substituting 6,7-difluoro-1,2,3,4-tetrahydro-2-hydroxynaphthalene gave 6,7-difluoro-1,2,3,4-tetrahydronaphthalen-2-yl methanesulfonate;

substituting (S)-5,7-difluoro-1,2,3,4-tetrahydro-2-hydroxynaphthalene gave (R)-5,7-difluoro-1,2,3,4-tetrahydronaphthalen-2-yl methanesulfonate;

substituting 5,7-difluoro-1,2,3,4-tetrahydro-2-hydroxynaphthalene gave 5,7-difluoro-1,2,3,4-tetrahydronaphthalen-2-yl methanesulfonate;

substituting 6,8-difluoro-1,2,3,4-tetrahydro-2-hydroxynaphthalene gave 6,8-difluoro-1,2,3,4-tetrahydronaphthalen-2-yl methanesulfonate;

substituting (R)-6,8-difluoro-1,2,3,4-tetrahydro-2-hydroxynaphthalene gave (S)-6,8-difluoro-1,2,3,4-tetrahydronaphthalen-2-yl methanesulfonate;

substituting 6,8-difluoro-1,2,3,4-tetrahydro-2-hydroxy-7-methoxynaphthalene gave 6,8-difluoro-1,2,3,4-tetrahydro-7-methoxynaphthalen-2-yl methanesulfonate;

substituting 2-hydroxyindane gave indan-2-yl methanesulfonate;

substituting 4,6-difluoro-2-hydroxyindane gave 4,6-difluoroindan-2-yl methanesulfonate;

substituting 5,6-difluoro-2-hydroxyindane gave 5,6-difluoroindan -2-yl methanesulfonate;

substituting 5,6-difluoro-1-hydroxyindane gave 5,6-difluoroindan-1-yl methanesulfonate; and substituting 5,7-difluoro-1-hydroxyindane gave 5,7-difluoroindan-1-yl methanesulfonate.

EXAMPLE 8

(S)-5,7-Difluoro-1,2,3,4-tetrahydronaphthalen-2-ylamine hydrochloride

The following is the preparation of a compound of Formula 3 in which n is 1, t is 2 and $R^1$ is fluoro at the 5- and 7-position.

A mixture of (R)-5,7-difluoro-1,2,3,4-tetrahydronaphthalen-2-yl methanesulfonate (54.0 g), prepared as in Example 7, and lithium azide (15.8 g, 0.322 mol) in 400 mL of DMF was stirred under argon at 50° C. for 16 hours. The reaction was quenched with 200 mL of water and the mixture extracted with 1 L of pentane. The extract was washed with 50 mL of water and dried over magnesium sulfate. Evaporation under reduced pressure at 35° C. gave crude (S)-2-azido-5,7-difluoro-1,2,3,4-tetrahydronaphthalene as a yellow oil residue (59.8 g).

The azide residue was dissolved in 1.2 L of ethyl acetate and hydrogenated over 10% palladium on carbon (6 g) for 6 hours, recharging with hydrogen every hour to remove evolved nitrogen gas. The mixture was then filtered through Celite and stirred with ethereal hydrogen chloride (1N, 250 mL) giving a crystalline material. The material was isolated by filtering, over 4 hours and the filter residue was washed with ethyl acetate. Removing the remaining solvents in vacuo gave (S)-5,7-difluoro-1,2,3,4-tetrahydronaphthalen-2-ylamine hydrochloride (48.2 g, 0.22 mol) as a white solid, m.p.>280° C. $[=]_D^{25}=-60.15°$ (c=2.7, CH$_3$OH).

Proceeding as in Example 8 but substituting a different starting material for (R)-5,7-difluoro-1,2,3,4-tetrahydronaphthalen-2-yl methanesulfonate, the following compounds of Formula 3 were made:

substituting 1,2,3,4-tetrahydronaphthalen-2-yl methanesulfonate gave 1,2,3,4-tetrahydronaphthalen-2-ylamine hydrochloride, m.p. 239°–242° C.;

substituting (R)-1,2,3,4-tetrahydronaphthalen-2-yl methanesulfonate gave (S)-1,2,3,4-tetrahydronaphthalen-2-ylamine hydrochloride, m.p. 241°–244° C.;

substituting (R)-5-fluoro-1,2,3,4-tetrahydronaphthalen-2-yl methanesulfonate gave (S)-5-fluoro-1,2,3,4-tetrahydronaphthalen-2-ylamine hydrochloride, m.p.>280° C.;

substituting (R)-6-fluoro-1,2,3,4-tetrahydronaphthalen-2-yl methanesulfonate gave (S)-6-fluoro-1,2,3,4-tetrahydronaphthalen-2-ylamine hydrochloride, m.p. 264°–265° C.;

substituting (R)-7-fluoro-1,2,3,4-tetrahydronaphthalen-2-yl methanesulfonate gave (S)-7-fluoro-1,2,3,4-tetrahydronaphthalen-2-ylamine hydrochloride, m.p.>280° C.;

substituting 6,7-dichloro-1,2,3,4-tetrahydronaphthalen-2-yl methanesulfonate gave 6,7-difluoro-1,2,3,4-tetrahydronaphthalen-2-ylamine hydrochloride, m.p.>280° C.;

substituting (−)-6,7-difluoro-1,2,3,4-tetrahydronaphthalen-2-yl methanesulfonate gave (−)-6,7-difluoro-1,2,3,4-tetrahydronaphthalen-2-ylamine hydrochloride;

substituting 6,7-difluoro-1,2,3,4-tetrahydronaphthalen-2-yl methanesulfonate gave 6,7-difluoro-1,2,3,4-tetrahydronaphthalen-2-ylamine hydrochloride;

substituting (S)-5,7-difluoro-1,2,3,4-tetrahydronaphthalen-2-yl methanesulfonate gave (R)-5,7-difluoro-1,2,3,4-tetrahydronaphthalen-2-ylamine hydrochloride, m.p.>280° C.;

substituting 5,7-difluoro-1,2,3,4-tetrahydronaphthalen-2-yl methanesulfonate gave 5,7-difluoro-1,2,3,4-tetrahydronaphthalen-2-ylamine hydrochloride;

substituting 6,8-difluoro-1,2,3,4-tetrahydronaphthalen-2-yl methanesulfonate gave 6,8-difluoro-1,2,3,4-tetrahydronaphthalen-2-ylamine hydrochloride;

substituting (R)-6,8-difluoro-1,2,3,4-tetrahydronaphthalen-2-yl methanesulfonate gave (S)-6,8-difluoro-1,2,3,4-tetrahydronaphthalen-2-ylamine hydrochloride;

substituting 6,8-difluoro-1,2,3,4-tetrahydro-7-methoxynaphthalen-2-yl methanesulfonate gave 6,8-difluoro-7-methoxy-1,2,3,4-tetrahydronaphthalen-2-ylamine hydrochloride;

substituting 2-indan-2-yl methanesulfonate gave indan-2-ylamine hydrochloride;

substituting 4,6-difluoroindan-2-yl methanesulfonate gave 4,6-difluoroindan-2-ylamine;

substituting 5,6-difluoroindan-2-yl methanesulfonate gave 5,6-difluoroindan-2-ylamine hydrochloride, m.p.>280° C.;

substituting 5,6-difluoroindan-1-yl methanesulfonate gave 5,6-difluoroindan-1-ylamine hydrochloride; and substituting 5,7-difluoroindan-1-yl methanesulfonate gave 5,7-difluoroindan-1-ylamine hydrochloride.

EXAMPLE 9

5,7-difluoro-1-(1,2,3,4-tetrahydronaphthalen-2-yl)-1,3-dihydroimidazole-2-thione The following is the preparation of a compound of Formula I(a) in which n is 1, t is 2 and $R^3$, $R^4$ and $R^5$ are each hydro and $R^1$ fluoro at the 5- and 7-position.

A mixture of (S)-5,7-difluoro-1,2,3,4-tetrahydronaphthalen-2-ylamine (2.05 g, 11.2 mmol), prepared as in Example 8, and dimethoxyacetaldehyde (1.73 g, 13.1 mmol) in 50 mL of ethanol was hydrogenated over 10% palladium on carbon (500 mg) for 18 hours. The mixture was filtered and concentrated by evaporation. The residue was combined with potassium thiocyanate (1.57 g, 16.2 mmol) in 30 mL of 1N hydrochloric acid and 20 mL of ethanol and the mixture was heated at 70°–80° C. for 18 hours. The mixture was cooled in an ice bath giving a crystalline material which was isolated by filtration. Recrystallization from ethyl acetate/hexane gave 1-(5,7-difluoro-1,2,3,4-tetrahydronaphthalen-2-yl)-1,3-dihydroimidazole-2-thione (1.27 g, 4.76 mmol), m.p. 250°–251° C.

Proceeding as in Example 9 but substituting a different starting material for (S)-5,7-difluoro-1,2,3,4-tetrahydronaphthalen-2-ylamine, the following compounds of Formula I were made:

substituting 7-fluoro-1,2,3,4-tetrahydronaphthalen-2-ylamine gave 1-(7-fluoro-1,2,3,4-tetrahydronaphthalen-2-yl)-1,3-dihydroimidazole-2-thione, m.p. 215°–217° C.;

substituting 6,7-difluoro-1,2,3,4-tetrahydronaphthalen-2-ylamine gave 1-(6,7-difluoro-1,2,3,4-tetrahydronaphthalen-2-yl)-1,3-dihydroimidazole-2-thione, m.p. 242°–243° C.;

substituting 6,8-difluoro-1,2,3,4-tetrahydronaphthalen-2-ylamine gave 1-(6,8-difluoro-1,2,3,4-tetrahydronaphthalen-2-yl)-1,3-dihydroimidazole-2-thione, m.p. 260°–261° C.;

substituting 5-methoxy-1,2,3,4-tetrahydronaphthalen-2-ylamine gave 1-(1,2,3,4-tetrahydro-5-methoxynaphthalen-2-yl)-1,3-dihydroimidazole-2-thione, m.p. 233°–235° C.;

substituting 6-methoxy-1,2,3,4-tetrahydronaphthalen-2-ylamine gave 1-(1,2,3,4-tetrahydro-6-methoxynaphthalen-2-yl)-1,3-dihydroimidazole-2-thione, m.p. 226°–227° C.;

substituting 7-methoxy-1,2,3,4-tetrahydronaphthalen-2-ylamine gave 1-(1,2,3,4-tetrahydro-7-methoxynaphthalen-2-yl)-1,3-dihydroimidazole-2-thione, m.p. 271°–273° C.;

substituting 8-methoxy-1,2,3,4-tetrahydronaphthalen-2-ylamine gave 1-(1,2,3,4-tetrahydro-8-methoxynaphthalen-2-yl)-1,3-dihydroimidazole-2-thione, m.p. 249°–251° C.;

substituting 6,8-difluoro-7-methoxy-1,2,3,4-tetrahydronaphthalen-2-ylamine gave 1-(6,8-difluoro-1,2,3,4-tetrahydro-7-methoxynaphthalen-2-yl)-1,3-dihydroimidazole-2-thione, m.p. 228°–230° C.;

substituting 5-methoxy-1,2,3,4-tetrahydronaphthalen-1-ylamine gave 1-(1,2,3,4-tetrahydro-5-methoxynaphthalen-1-yl)-1,3-dihydroimidazole-2-thione, m.p. 176°–177° C.;

substituting 6-methoxy-1,2,3,4-tetrahydronaphthalen-1-ylamine gave 1-(1,2,3,4-tetrahydro-6- methoxynaphthalen-1-yl)-1,3-dihydroimidazole-2-thione, m.p. 190°–192° C.;

substituting 7-methoxy-1,2,3,4-tetrahydronaphthalen-1-ylamine gave 1-(1,2,3,4-tetrahydro-7-methoxynaphthalen-1-yl)-1,3-dihydroimidazole-2-thione, m.p. 142°–143° C.;

substituting 4,6-difluoroindan-2-ylamine gave 1-(4,6-difluoroindan-2-yl)-1,3-dihydroimidazole-2-thione, m.p. 185°–186° C.;

substituting 5,6-difluoroindan-2-ylamine gave 1-(5,6-difluoroindan-2-yl)-1,3-dihydroimidazole-2-thione, m.p. 255°–257° C.;

substituting 5-methoxyindan-1-ylamine gave 1-(5-methoxyindan-1-yl)-1,3-dihydroimidazole-2-thione, m.p. 195°–196° C.;

substituting (−)-4,6-difluoroindan-1-ylamine gave (+)-1-(4,6-difluoroindan-1-yl)-1,3-dihydroimidazole-2-thione, m.p. 191°–193° C.;

substituting (+)-4,6-difluoroindan-1-ylamine gave (−)-1-(4,6-difluoroindan-1-yl)-1,3-dihydroimidazole-2-thione, m.p. 181°–191° C.;

substituting 5,6-difluoroindan-1-ylamine gave 1-(5,6-difluoroindan-1-yl)-1,3-dihydroimidazole-2-thione, m.p. 183°–187° C.; and substituting 5,7-difluoroindan-1-ylamine gave 1-(5,7-difluoroindan-1-yl)-1,3-dihydroimidazole-2-thione, m.p. 212°–215° C.

EXAMPLE 10

(−)-6,7-Difluoro-2-isothiocyano-1,2,3,4-tetrahydronaphthalene

The following is the preparation of a compound of Formula 9 in which n is 1, t is 2 and $R^1$ is fluoro at the 6- and 7-position.

A mixture of (−)-6,7-difluoro-1,2,3,4-tetrahydronaphthalen-2-ylamine (0.56 g, 3.06 mmol), prepared as in Example 8, and 1,1'-thiocarbonyldiimidazole (0.82 g, 4.59 mmol) in 15 mL of ethyl acetate was stirred until the reaction was complete. The solvent was removed by evaporation. Purification of the residue by column chromatography on silica gel (solution: 5% acetone/methylene chloride) gave (−)-6,7-difluoro-2-isothiocyano-1,2,3,4-tetrahydronaphthalene (0.55 g, 2.42 mmol). $[\alpha]_D^{25}$ −15.5° (c=1.0, $CH_3OH$)

Proceeding as in Example 10ut substituting a different starting material for (−)-6,7-difluoro-1,2,3,4-tetrahydronaphthalen-2-ylamine, the following compounds of Formula 9 were made:

substituting 1,2,3,4-tetrahydronaphthalen-2-ylamine gave 2-isothiocyano-1,2,3,4-tetrahydronaphthalene as an oil; and substituting (+)-6,7-difluoro-1,2,3,4-tetrahydronaphthalen-2-ylamine gave (+)-6,7-difluoro-2-isothiocyano-1,2,3,4-tetrahydronaphthalene, m.p. 206–207.

EXAMPLE 11

(−)-6,7-Difluoro-1-(1,2,3,4-tetrahydronaphthalen-2-yl)-1,3-dihydroimidazole-2-thione The following is the preparation of a compound of Formula I(a) in which n is 1, t is 2 and $R^3$, $R^4$ and $R^5$ are each hydro and $R^1$ is fluoro at the 6- and 7-position.

A mixture of (−)-6,7-difluoro-2-isothiocyano-1,2,3,4-tetrahydronaphthalene (0.49 g, 2.2 mmol), prepared as in Example 10, and 2,2-dimethoxyethylamine (0.23 g, 2.2 mmol) in DMF was heated at 85° C. under argon for 2.5 hours. The solvent was removed under reduced pressure and the residue was dissolved in 2 to 3 mL of ethanol and 20 mL of 4N hydrochloric acid. The solution was heated at 85° C. for approximately 48 hours and cooled giving a crystalline material. The material was isolated by filtration and dried. Purification by column chromatography on silica gel (elution: 3% methanol/methylene chloride) gave (−)-6,7-difluoro-1-(1,2,3,4-tetrahydronaphthalen-2-yl)-1,3-dihydroimidazole-2-thione (0.225 g, 0.84 mmol), m.p. 200°–205° C. $[\alpha]_D^{25}$ −77.9°, (c=0.6, 2:1 $CHCl_3/CH_3OH$).

Proceeding as in Example 11 but substituting (+)-6,7-difluoro-2-isothiocyano-1,2,3,4-tetrahydronaphthalene for (+)-6,7-difluoro-2-isothiocyano-1,2,3,4-tetrahydronaphthalene gave (+)-6,7-difluoro-1-(1,2,3,4-tetrahydronaphthalen-2-yl)-1,3-dihydroimidazole-2-thione (0.225 g, 0.84 mmol), m.p. 206°–207° C. $[\alpha]_D^{25}$ 86.98°, (c=1.06, 2:1 $CHCl_3/CH_3OH$).

EXAMPLE 12

1-(4,6-Difluoroindan-1-yl)-1,3-dihydroimidazole-2-thione

The following is the preparation of a compound of Formula I(a) in which n is 0, t is 2, $R^1$ is fluoro at the 4- and 6-position and $R^3$, $R^4$ and $R^5$ are each hydro.

A mixture of 4,6-difluoroindan-1-one (11.3 g, 67.26 mmol), 2,2-dimethoxyethylamine (7.07 g, 67.26 mmol) and sodium cyanoborohydride (4.23 g) in 75 mL of methanol was heated at gentle reflux and stirred under nitrogen for approximately 18 hours. Additional sodium cyanoborohydride (2.12 g) was added and the mixture was heated at 65° C. for 20 hours. The solvents were removed by evaporation. Purification of the residue by column chromatography on silica gel (elution: 2.5% methanol/methylene chloride) gave (4,6-difluoroindan-1-yl)-(2,2-dimethoxyethyl)amine.

A mixture of (4,6-difluoroindan-1-yl)-(2,2-dimethoxyethyl)amine (11.68 g, 45.9 mmol), potassium thiocyanate (4.46 g, 45.9 mmol) in 21.6 mL of 12N hydrochloric acid, 86 mL of ethanol and 86 mL of water was heated at 80° to 85° C. for 15 hours. The mixture was cooled in an ice bath and diluted with water giving a crystalline material. The material was isolated by filtration and the filter residue was rinsed with cold ethanol (2×25 mL) and 50 mL of diethyl ether. Drying gave 1-(4,6-difluoroindan-1-yl)-1,3-dihydroimidazole-2-thione (5.65 g, 22.2 mmol), m.p. 205°–207° C.

Proceeding as in Example 12 but substituting a different starting material for 4,6-difluoroindan-1-one, the following compounds of Formula I were made:

substituting 1,2,3,4-tetrahydronaphthalen-1-one gave 1-(1,2,3,4-tetrahydronaphthalen-1-yl)-1,3-dihydroimidazole-2-thione, m.p. 188°–189° C.;

substituting 6-methoxy-1,2,3,4-tetrahydronaphthalen-1-one gave 1-(6-methoxy-1,2,3,4-tetrahydronaphthalen-1-yl)-1,3-dihydroimidazole-2-thione, m.p. 190°–192° C.;

substituting 5-methoxy-1,2,3,4-tetrahydronaphthalen-1-one gave 1-(5-methoxy-1,2,3,4-tetrahydronaphthalen-1-yl)-1,3-dihydroimidazole-2-thione, m.p. 176°–177° C.;

substituting 7-methoxy-1,2,3,4-tetrahydronaphthalen-1-one gave 1-(7-methoxy-1,2,3,4-tetrahydronaphthalen-1-yl)-1,3-dihydroimidazole-2-thione, m.p. 142°–143° C.;

substituting indan-2-one gave 1-(indan-2-yl)-1,3-dihydroimidazole-2-thione, m.p. 210°–211° C.; and substituting indan-1-one gave 1-(indan-1-yl)-1,3-dihydroimidazole-2-thione, m.p. 136°–137° C.

EXAMPLE 13

1-(1,2,3,4-Tetrahydronaphthalen-2-yl)imidazole

The following is the preparation of a compound of Formula 11 in which n is 1 and t is 0.

A mixture of 1,2,3,4-tetrahydronaphthalen-2-yl methanesulfonate (15.74 g, 69.6 mmol), prepared as in Example 7, and imidazole (23.68 g, 349 mmol) in 100 mL of DMF was heated at 80° to 90° C. under argon for 24 hours. The solvent was removed under vacuum by rotary evaporation. The residue was dissolved in 500 mL of ethyl acetate and the solution was washed with water (5×250 mL). The combined aqueous layer was extracted with 500 mL of ethyl acetate and the extract was then washed with water (5×250 mL). The combined ethyl acetate extract was washed with saturated sodium chloride solution, dried over magnesium sulfate and concentrated by rotary evaporation. Purification of the residue by column chromatography on silica gel (elution: 5% methanol/methylene chloride) gave 1-(1,2,3,4-tetrahydronaphthalen-2-yl)imidazole (5.18 g, 26.1 mol), m.p. 93°–95° C.

Proceeding as in Example 13, but substituting 4-methylimidazole for imidazole and 2-bromo-1,2,3,4-tetranaphthalen-1-one for 1,2,3,4-tetrahydronaphthalen-2-yl methanesulfonate and then reducing gave 1-(1,2,3,4-tetrahydronaphthalen-2-yl)-4-methylimidazole.

EXAMPLE 14

(S)-N-[3-(5,7-Difluoro-1,2,3,4-tetrahydronaphthalen-2-yl)-2,3-dihydro-1H-imidazol-4-ylmethyl]formamide The following is the preparation of a compound of Formula 11 in which n is 1, t is 2, $R^1$ is fluoro at the 5- and 7-positions and $R^4$ is hydro.

A mixture of formamide, prepared as in Example 29, (S)-N-[3-(5,7-difluoro-1,2,3,4-tetrahydronaphthalen-2-yl)-2-thioxo-2,3-dihydro-1H-imidazol-4-ylmethyl]formamide (1.38 g, 4.27 mmol) and activated Raney® nickel (11 g) in 50 mL of ethanol was stirred rapidly at 80° C. for 1 hour. The mixture was filtered through Celite and the filtrate evaporated to give a white solid (0.98 g). The solid was recrystallized from ethyl acetate/methanol to give (S)-N-[3-(5,7-difluoro-1,2,3,4-tetrahydronaphthalen-2-yl)-2,3-dihydro-1H-imidazol-4-ylmethyl]formamide, m.p. 194°–195° C.

Proceeding as in Example 14, but substituting a different starting material for (S)-N-[3-(5,7-difluoro-1,2,3,4-tetrahydronaphthalen-2-yl)-2-thioxo-2,3-dihydro-1H-imidazol-4-ylmethyl]formamide gave the following compounds of Formula 11:

substituting (S)-5-aminomethyl-1-(5,7-difluoro-1,2,3,4-tetrahydronaphthalen-2-yl)-1,3-dihydroimidazole-2-thione hydrochloride gave (S)-[3-(5,7-difluoro-1,2,3,4-tetrahydronaphthalen-2-yl)-2,3-dihydro-1H-imidazol-4-ylmethyl]amine, m.p. 273°–274° C.; and substituting 1-(5,7-difluoro-1,2,3,4-tetrahydronaphthalen-2-yl)-1,3-dihydroimidazole-2-thione gave 1-(5,7-difluoro-1,2,3,4-tetrahydronaphthalen-2-yl)-1,3-dihydroimidazole.

EXAMPLE 15

3-Amino-1-(1,2,3,4-tetrahydronaphthalen-2-yl)-1,3-dihydroimidazole-2-thione

The following is the preparation of a compound of Formula I(a) in which n is 1, t is 0, $R^3$ is amino and $R^4$ and $R^5$ are each hydro.

A mixture of 1-(1,2,3,4-tetrahydronaphthalen-2-yl) imidazole (198 mg, 1 mmol), prepared as in Example 13, and O-mesitylenesulfonylhydroxylamine (215 mg, 1 mmol) in acetonitrile was stirred under argon for 18 hours. The reaction mixture was diluted with diethyl ether giving a precipitate as an oil. The solvents were decanted away and the residue was washed with diethyl ether (2×10 mL). Residual solvent was evaporated under vacuum. A mixture of the residue and lac sulfur (32 mg, 1.0 mmol) in 1 mL of pyridine and 0.5 mL of triethylamine were heated at approximately 90° C. under argon for 4 hours. The solvent was removed by evaporation and the residue was co-evaporated with toluene. The residue was purified by column chromatography on silica gel eluting with methylene chloride to give 3-amino-1-(1,2,3,4-tetrahydronaphthalen-2-yl)-1,3-dihydroimidazole-2-thione (5.18 g, 26.1 mmol), m.p. 187°–189° C.

Proceeding as in Example 15, but substituting different starting materials for O-mesitylenesulfonatehydroxylamine and/or 1-(1,2,3,4-tetrahydronaphthalen-2-yl)imidazole gave the following compounds of Formula I:

substituting tert-butyl bromoacetate gave tert-butyl-(1,2,3,4-tetrahydronaphthalen-2-yl)-2-thioxo-2,3-dihydro-1H-imidazol-1-ylacetate, m.p. 167°–169° C.;

substituting methyl 4-bromobutyrate and 1-(1,2,3,4-tetrahydronaphthalen-2-yl)imidazole gave methyl 4-[3-(1,2,3,4-tetrahydro-naphthalen-2-yl)-2-thioxo-2,3-dihydro-1H-imidazol-1-yl]butyrate;

substituting methyl 5-bromomethylpicolinate and 1-(1,2,3,4-tetrahydronaphthalen-2-yl)imidazole gave methyl 5-[3-(1,2,3,4-tetrahydro-naphthalen-2-yl)-2-thioxo-2,3-dihydro-1H-imidazol-1-ylmethyl]picolinate as an oil;

substituting methyl 4-bromomethylbenzoate and 1-(1,2,3,4-tetrahydronaphthalen-2-yl)imidazole gave methyl 4-[3-(1,2,3,4-tetrahydronaphthalen-2-yl)-2-thioxo-2,3-dihydro-1H-imidazol-1-ylmethyl]benzoate, m.p. 133°–135° C.;

substituting methyl 3-bromomethylbenzoate and 1-(1,2,3,4-tetrahydronaphthalen-2-yl)imidazole gave methyl 3-[3-(1,2,3,4-tetrahyfromaphthalen-2-yl)-2-thioxo-2,3-dihydro-1H-imidazol-1-ylmethyl]benzoate, m.p. 130°–132° C.;

substituting 3,4-dimethoxybenzyl chloride and 1-(1,2,3,4-tetrahydronaphthalen-2-yl)imidazole gave 3-(3,4-dimethoxybenzyl)-1-(1,2,3,4-tetrahydronaphthalen-2-yl)-1,3-dihydroimidazole-2-thione, m.p. 129°–131° C.;

substituting methyl 4-bromomethylbenzoate and 1-(1,2,3,4-tetrahydronaphthalen-2-yl)-4-methylimidazole gave methyl 4-[3-(1,2,3,4-tetrahydronaphthalen-2-yl)-5-methyl-2-thioxo-2,3-dihydro-1H-imidazol-1-ylmethyl]benzoate, m.p. 140°–141° C.;

substituting 6-dimethylamino-3-bromopyridazine and 1-(1,2,3,4-tetrahydronaphthalen-2-yl)imidazole gave 3-(6-dimethylaminopyridazin-3-yl)-1-(1,2,3,4-tetrahydronaphthalen-2-yl)-1,3-dihydroimidazole-2-thione, m.p. 198°–199° C.;

substituting 2-bromoethylbenzene and 1-(1,2,3,4-tetrahydronaphthalen-2-yl)-imidazole gave 3-(2-phenylethyl)-1-(1,2,3,4-tetrahydronaphthalen-2-yl)-1,3-dihydroimidazole-2-thione, m.p. 140°–142° C.;

substituting methyl 4-(2-bromoethyl)benzoate and 1-(1,2,3,4-tetrahydronaphthalen-2-yl)imidazole gave methyl 4-{2-[3-(1,2,3,4-tetrahydronaphthalen-2-yl)-2-thioxo-2,3-dihydro-1H-imidazol-1-yl]ethyl}benzoate, m.p. 159°–161° C.;

substituting 4-(2-bromoethyl)benzoic acid and 1-(1,2,3,4-tetrahydronaphthalen-2-yl)imidazole gave 4-[3-(1,2,3,4- tetrahydronaphthalen-2-yl)-2-thioxo-2,3-dihydro-1H-imidazol-1-ylethyl]benzoic acid, m.p. 227–230;

substituting 3,4-dimethoxy-1-(2-bromoethyl)benzene and 1-(1,2,3,4-tetrahydronaphthalen-2-yl) imidazole gave 3-[2-(3,4-dimethoxyphenyl)ethyl]-1-(1,2,3,4-tetrahydronaphthalen-2-yl)-1,3-dihydroimidazole-2-thione, m.p. 97°–101° C.;

substituting 4-(2-bromoethyl)benzoic acid and (S)-1-(5,7-difluoro-1,2,3,4-tetrahydronaphthalen-2-yl)imidazole gave (S)-4-{2-[3-(5,7-difluoro-1,2,3,4-tetrahydronaphthalen-2-yl)-2-thioxo-2,3-dihydro-1H-imidazol-1-yl]ethyl}benzoic acid, m.p. 222°–224° C., and treating with potassium hydroxide in methanol evaporating to dryness and recrystallizing from methanol/isopropanol gave potassium (S)-4-{2-[3-(5,7-difluoro-1,2,3,4-tetrahydronaphthalen-2-yl)-2-thioxo-2,3-dihydro-1H-imidazol-1-yl]ethyl}benzoate, m.p.>280° C.;

substituting 4-(2-bromoethyl)-1-cyanobenzene and (S)-1-(5,7-difluoro-1,2,3,4-tetrahydronaphthalen-2-yl)imidazole gave (S)-3-[2-(4-cyanophenyl)ethyl]-1-(5,7-difluoro-1,2,3,4-tetrahydronaphthalen-2-yl)-1,3-dihydroimidazole-2-thione, m.p. 130°–133° C.;

substituting 4-(2-bromoethyl)benzene and (S)-1-(5,7-difluoro-1,2,3,4-tetrahydronaphthalen-2-yl)imidazole gave (S)-3-(2-phenylethyl)-1-(5,7-difluoro-1,2,3,4-tetrahydronaphthalen-2-yl)-1,3-dihydroimidazole-2-thione, m.p. 131°–133° C.;

substituting 4-(2-bromoethyl)-1-cyanobenzene and 1-(1,2,3,4-tetrahydronaphthalen-2-yl) imidazole gave 3-[2-(4-cyanophenyl)ethyl]-1-(1,2,3,4-tetrahydronaphthalen-2-yl)-1,3-dihydroimidazole-2-thione, m.p. 169°–170° C.;

substituting 4-(2-bromoethyl)benzoic acid and (S)-N-[3-(5,7-difluoro-1,2,3,4-tetrahydronaphthalen-2-yl)-2,3-dihydro-1H-imidazol-4-ylmethyl]formamide gave (S)-4-{2-[4-formylaminomethyl-3-(5,7-difluoro-1,2,3,4-tetrahydronaphthalen-2-yl)-2-thioxo-2,3-dihydro-1H-imidazol-1-yl]ethyl}benzoic acid; and substituting ethyl 3-bromopropionate and (S)-N-[3-(5,7-difluoro-1,2,3,4-tetrahydronaphthalen-2-yl)-2,3-dihydro-1H-imidazol-4-ylmethyl]formamide gave ethyl (S)-3-[4-formylaminomethyl-3-(5,7-difluoro-1,2,3,4-tetrahydronaphthalen-2-yl)-2-thioxo-2,3-dihydro-1H-imidazol-1-yl]propionate.

EXAMPLE 16

1-(1,2,3,4-tetrahydronaphthalen-2-yl)-1,3-dihydroimidazole-2-thione

The following is the preparation of a compound of Formula I(a) in which n is 1, t is 0 and $R^3$, $R^4$ and $R^5$ are each hydro.

A solution of 1-(1,2,3,4-tetrahydronaphthalen-2-yl) imidazole (1.6 g, 8.1 mmol), prepared as in Example 13, in 30 mL of THF was cooled to −78° C. and n-butyllithium (6 mL, 9.7 mmol) was added over 15 minutes. The mixture was stirred at −78° C. for 1 hour and lac sulfur (0.34 g, 10.5 mmol) was added. The mixture was stirred at −78° C. for an additional 2 hours and then allowed to warm to room temperature. The mixture was poured into 100 mL of water giving a crystalline material. The material was isolated by filtration, washed with ethyl ether and dried. The filtrate was extracted with methylene chloride (2×100 mL) and the extracts were washed with brine, dried over sodium sulfate and concentrated by evaporation. The residue was purified by column chromatography on silica gel [elution: 1.5% methanol (containing 2% concentrated ammonium hydroxide)]. Combining the crystalline material gave 1-(1,2,3,4-tetrahydronaphthalen-2-yl)-1,3-dihydroimidazole-2-thione (0.81 g, 3.5 mmol), m.p. 233°–234° C.

EXAMPLE 17

5-Amino-1-(1,2,3,4-tetrahydronaphthalen-2-yl)-1,3-dihydroimidazole-2-thione

The following is the preparation of a compound of Formula I(a) in which n is 1, t is 0, $R^3$ and $R^4$ are hydro and $R^5$ is amino.

A mixture of 2-isothiocyano-1,2,3,4-tetrahydronaphthalene (1.92 g, 10.1 mol), prepared as in Example 10, and aminoacetonitrile hydrochloride (0.94 g, 10.1 mmol) in 1.41 mL of triethylamine was heated at 60° C. for 1 hour. The solvent was evaporated and the residue was purified by flash chromatography (elution: methylene chloride followed by 3% methanol in methylene chloride). The purified residue was recrystallized from ethyl acetate/hexane. The residue (1.06 g) and 44 mL of 0.1N potassium hydroxide was stirred under nitrogen for 15 minutes. The residue was isolated by filtration, washed with water, air dried and then stirred with methylene chloride. Filtration and drying gave 5-amino-1-(1,2,3,4-tetrahydronaphthalen-2-yl)-1,3-dihydroimidazole-2-thione, m.p. 169°–171° C.

EXAMPLE 18

(S)-5-Hydroxymethyl-1-(5,7-difluoro-1,2,3,4-tetrahydronaphthalen-2-yl)-1,3-dihydroimidazole-2-thione The following is the preparation of a compound of Formula I(a) in which n is 1, t is 2, $R^1$ is fluoro at the 5- and 7-position and $R^5$ is hydroxymethyl.

Potassium thiocyanate (15.9 g, 162.6 mmol) was dried by heating to 175° C. under nitrogen and then cooled to 35° C. under vacuum with several nitrogen purges. A mixture of dihydroxyacetone (15.9 g, 176.7 mmol) and (S)-5,7-difluoro-1,2,3,4-tetrahydronaphthalen-2-ylamine hydrochloride (30.0 g, 137.0 mmol), prepared as in Example 6, in 540 mL of ethyl acetate was added to the dry potassium thiocyanate. The reaction vessel was purged with nitrogen and 40.83 g of glacial acetic acid was added. The reaction mixture was stirred at 35° C. for 2 hours and 100 mL of 1.0M sulfuric acid was added. The mixture was stirred for 15 minutes, then cooled in an ice bath and 2.5M sodium hydroxide was added until the mixture was pH 7. The organic layer was washed with 50 mL of saturated aqueous sodium bicarbonate and then 50 mL of brine. The organic layer was concentrated to 480 mL by distillation and the mixture was cooled to 6° C. and allowed to stand for 12 hours giving a crystalline material. The material was isolated by filtration, the filter residue was washed with cold ethyl acetate and the isolated material dried.

The material was dissolved in 650 mL of ethyl acetate and 25 mL of water. The mixture was distilled until 500 mL of volatile were removed. The mixture was cooled to room temperature and stirred for 45 minutes giving a crystalline material. The material was isolated by filtration and the filter residue was washed with cold ethyl acetate. Drying in vacuo with a nitrogen bleed gave (S)-5-hydroxymethyl-1-(5,7-difluoro-1,2,3,4-tetrahydronaphthalen-2-yl)-1,3-dihydroimidazole-2-thione (30.4 g, 107.4 mol), m.p. 206°–207° C. $[\alpha]_D$ −40° (c=0.682, $CH_3OH$).

Proceeding similarly as in Example 18, but substituting (S)-6,7-dichloro-1,2,3,4-tetrahydronaphthalen-2-ylamine hydrochloride for (S)-5,7-difluoro-1,2,3,4- tetrahydronaphthalen-2-ylamine hydrochloride gave (S)-5-hydroxymethyl-1-(6,7-dichloro-1,2,3,4-tetrahydronaphthalen-2-yl)-1,3-dihydroimidazole-2-thione, m.p. 247°–248° C.

EXAMPLE 19

(S)-5-Cyano-1-(5,7-difluoro-1,2,3,4-tetrahydronaphthalen-2-yl)-1,3-dihydroimidazole-2-thione The following is the preparation of a compound of Formula I(a) in which n is 1, t is 2, $R^1$ is fluoro at the 5- and 7-position, $R^3$ and $R^4$ are each hydro and $R^5$ is cyano.

A solution of (S)-5,7-difluoro-1,2,3,4-tetrahydronaphthalen-2-ylamine hydrochloride (50.3 g, 0.23 mol), prepared as in Example 8, and sodium hydroxide (10.0 g, 0.25 mol) in 450 mL of water was heated to 50° C. and then formaldehyde sodium bisulfite complex (30.8 g, 0.23 mol) was added. The mixture was stirred for 30 minutes and potassium cyanide (15.0 g, 0.23 mol) was added. The mixture was heated to 80° C., stirred for 1 hour, cooled to room temperature, and then extracted with ethyl acetate. Evaporation gave an oily residue (51.3 g). Purification by column chromatography on silica gel (elution: 5% methanol/methylene chloride) gave (S)-(5,7-difluoro-1,2,3,4-tetrahydronaphthalen-2-ylamino)acetonitrile (39.4 g) and (S)-5,7-difluoro-1,2,3,4-tetrahydronaphthalen-2-ylamine (7.12 g). Proceeding similarly as above, recycling the recovered starting material and combining yields gave (S)-(5,7-difluoro-1,2,3,4-tetrahydronaphthalen-2-yl-amino) acetonitrile (44.8 g, 0.20 mol), m.p. 73°–76° C. $[\alpha]_D^{25}$=–58.04° (c=1.6, $CHCl_3$).

A solution of the (S)-(5,7-difluoro-1,2,3,4-tetrahydronaphthalen-2-ylamino)acetonitrile in butyl formate (8.7M, 240 mL, 2.10 mol) was heated to reflux and stirred under nitrogen for 19 hours. The solvents were removed under reduced pressure, toluene was added and then evaporated. Drying gave (S)-N-(cyanomethyl)-N-(5,7-difluoro-1,2,3,4-tetrahydronaphthalen-2-yl)formamide as an oily residue (53.2 g). A stirring mixture of the formamide (53.2 g) and ethyl formate (12.4M, 48.7 mL, 0.604 mol) in 0.925 L of anhydrous THF was cooled to –15° C. A solution of potassium tert-butoxide in THF (1.0M, 302 mL, 0.302 mol) was added over 20 minutes and the mixture was stirred for 18 hours. Evaporation of the solvent gave potassium (S)-N-(1-cyano-2-oxyvinyl)-N-(5,7-difluoro-1,2,3,4-tetrahydronaphthalen-2-yl)formamide as a residue.

A mixture of the potassium (S)-N-(1-cyano-2-oxyvinyl)-N-(5,7-difluoro-1,2,3,4-tetrahydronaphthalen-2-yl) formamide and potassium thiocyanate (78.1 g, 0.80 mol) in 0.99 L of 1N hydrochloric acid and 0.497 L of ethanol was heated to 85° C. and stirred for 135 minutes. The mixture was then cooled in an ice bath to form a precipitate which was collected as a slurry. Purification by column chromatography on silica gel packed in hexane (elution: 10% acetone/methylene chloride) gave (S)-5-cyano-1-(5,7-difluoro-1,2,3,4-tetrahydronaphthalen-2-yl)-1,3-dihydroimidazole-2-thione (18.1 g, 0.06 mol), m.p. 241°–249° C. $[\alpha]_D^{25}$=–69.1° (c=1.20, DMSO).

Proceeding as in Example 19, but substituting a different starting material for (S)-5,7-difluoro-1,2,3,4-tetrahydronaphthalen-2-ylamine hydrochloride gave the following compounds of Formula I:

substituting 5,7-difluoro-1,2,3,4-tetrahydronaphthalen-2-ylamine gave 5-cyano-1-(5,7-difluoro-1,2,3,4-tetrahydronaphthalen-2-yl)-1,3-dihydroimidazole-2-thione, m.p. 255° C. (dec);

substituting (R)-5,7-difluoro-1,2,3,4-tetrahydronaphthalen-2-ylamine gave (R)-5-cyano-1-(5,7-difluoro-1,2,3,4-tetrahydronaphthalen-2-yl)-1,3-dihydroimidazole-2-thione;

substituting (S)-7-fluoro-1,2,3,4-tetrahydronaphthalen-2-ylamine gave (S)-5-cyano-1-(7-fluoro-1,2,3,4-tetrahydronaphthalen-2-yl)-1,3-dihydroimidazole-2-thione;

substituting (S)-6-fluoro-1,2,3,4-tetrahydronaphthalen-2-ylamine gave (S)-5-cyano-1-(6-fluoro-1,2,3,4-tetrahydronaphthalen-2-yl)-1,3-dihydroimidazole-2-thione;

substituting (S)-5-fluoro-1,2,3,4-tetrahydronaphthalen-2-ylamine gave (S)-5-cyano-1-(5-fluoro-1,2,3,4-tetrahydronaphthalen-2-yl)-1,3-dihydroimidazole-2-thione;

substituting (S)-1,2,3,4-tetrahydronaphthalen-2-ylamine gave (S)-5-cyano-1-(1,2,3,4-tetrahydronaphthalen-2-yl)-1,3-dihydroimidazole-2-thione;

substituting 6,7-difluoro-1,2,3,4-tetrahydronaphthalen-2-ylamine gave 5-cyano-1-(6,7-difluoro-1,2,3,4-tetrahydronaphthalen-2-yl)-1,3-dihydroimidazole-2-thione;

substituting (S)-6,7-difluoro-1,2,3,4-tetrahydronaphthalen-2-ylamine gave (S)-5-cyano-1-(6,7-difluoro-1,2,3,4-tetrahydronaphthalen-2-yl)-1,3-dihydroimidazole-2-thione; and substituting 5,6-difluoroindan-2-ylamine gave 5-cyano-1-(5,6-difluoroindan-2-yl)-1,3-dihydroimidazole-2-thione.

EXAMPLE 20

(S)-5-Aminomethyl-1-(5,7-difluoro-1,2,3,4-tetrahydronaphthalen-2-yl)-1,3-dihydroimidazole-2-thioxo Hydrochloride The following is the preparation of a compound of Formula I(a) in which n is 1, t is 2, $R^1$ is fluoro at the 5- and 7-position, $R^3$ and $R^4$ are hydro and $R^5$ is aminomethyl.

A solution of (S)-5-cyano-1-(5,7-difluoro-1,2,3,4-tetrahydronaphthalen-2-yl)-1,3-dihydroimidazole-2-thione (5.0 g, 0.017 mol), prepared as in Example 19, in 75 mL of THF was stirred under argon in an ice bath and a solution of LAH in THF (1.0M, 34.3 mL, 34.3 mmol) was added dropwise over 10 minutes. The mixture was cooled to 0° C., stirred for 30 minutes, allowed to warm to room temperature, and let stand for 1.5 hours. The mixture was cooled to 0° C. and then a sufficient amount of saturated sodium potassium tartrate solution was added such that the mixture could by freely stirred. An additional 30 mL of saturated sodium potassium tartrate solution and 200 mL of 10% methanol in methylene chloride were added, the mixture was stirred for 15 minutes, and then 100–150 mL of water was added. The organic layer was separated and the aqueous phase was extracted twice with 10% methanol in methylene chloride (2×125 mL). The combined extracts were washed with 75 mL of water, dried over magnesium sulfate, and concentrated by evaporation to a residue (5.2 g). Purification by column chromatography on silica gel (elution: 5% methanol/methylene chloride) gave (S)-5-aminomethyl-1-(5,7-difluoro-1,2,3,4-tetrahydronaphthalen-2-yl)-1,3-dihydroimidazole-2-thione (2.92 g, 10.0 mmol).

The (S)-5-aminomethyl-1-(5,7-difluoro-1,2,3,4-tetrahydronaphthalen-2-yl)-1,3-dihydroimidazole-2-thione was dissolved in methanol and treated with 1.5 equivalents of anhydrous hydrogen chloride in ethyl ether. Removal of the solvents by co-evaporation with ethyl acetate gave (S)-5-aminomethyl-1-(5,7-difluoro-1,2,3,4-tetrahydronaphthalen-2-yl)-1,3-dihydroimidazole-2-thione hydrochloride, m.p. 245° C., $[a\alpha]_D^{25}=11.30°$ (c=0.5, DMSO).

Proceeding as in Example 20, but substituting a different starting material for (S)-5-cyano-1-(5,7-difluoro-1,2,3,4-tetrahydronaphthalen-2-yl)-1,3-dihydroimidazole-2-thione gave the following compounds of Formula I:

substituting 5-cyano-1-(5,7-difluoro-1,2,3,4-tetrahydronaphthalen-2-yl)-1,3-dihydroimidazole-2-thione gave 5-aminomethyl-1-(5,7-difluoro-1,2,3,4-tetrahydronaphthalen-2-yl)-1,3-dihydroimidazole-2-thione, m.p. 172°–178° C. and 5-aminomethyl-1-(5,7-difluoro-1,2,3,4-tetrahydronaphthalen-2-yl)-1,3-dihydroimidazole-2-thione hydrochloride, m.p. 265°–270° C.;

substituting (R)-5-cyano-1-(5,7-difluoro-1,2,3,4-tetrahydronaphthalen-2-yl)-1,3-dihydroimidazole-2-thione gave (R)-5-aminomethyl-1-(5,7-difluoro-1,2,3,4-tetrahydronaphthalen-2-yl)-1,3-dihydroimidazole-2-thione hydrochloride;

substituting (S)-5-cyano-1-(7-fluoro-1,2,3,4-tetrahydronaphthalen-2-yl)-1,3-dihydroimidazole-2-thione gave (S)-5-aminomethyl-1-(7-fluoro-1,2,3,4-tetrahydronaphthalen-2-yl)-1,3-dihydroimidazole-2-thione hydrochloride, m.p. 237°–247° C.;

substituting (S)-5-cyano-1-(6-fluoro-1,2,3,4-tetrahydronaphthalen-2-yl)-1,3-dihydroimidazole-2-thione gave (S)-5-aminomethyl-1-(6-fluoro-1,2,3,4-tetrahydronaphthalen-2-yl)-1,3-dihydroimidazole-2-thione hydrochloride, m.p. 240°–249° C.;

substituting (S)-5-cyano-1-(5-fluoro-1,2,3,4-tetrahydronaphthalen-2-yl)-1,3-dihydroimidazole-2-thione gave (S)-5-aminomethyl-1-(5-fluoro-1,2,3,4-tetrahydronaphthalen-2-yl)-1,3-dihydroimidazole-2-thione hydrochloride, m.p. 273°–276° C.;

substituting (S)-5-cyano-1-(1,2,3,4-tetrahydronaphthalen-2-yl)-1,3-dihydroimidazole-2-thione gave (S)-5-aminomethyl-1-(1,2,3,4-tetrahydronaphthalen-2-yl)-1,3-dihydroimidazole-2-thione hydrochloride, m.p. 255°–258° C.;

substituting 5-cyano-1-(6,7-difluoro-1,2,3,4-tetrahydronaphthalen-2-yl)-1,3-dihydroimidazole-2-thione gave 5-aminomethyl-1-(6,7-difluoro-1,2,3,4-tetrahydronaphthalen-2-yl)-1,3-dihydroimidazole-2-thione hydrochloride, m.p. 260°–263° C. (dec);

substituting (S)-5-cyano-1-(6,7-difluoro-1,2,3,4-tetrahydronaphthalen-2-yl)-1,3-dihydroimidazole-2-thione gave (S)-5-aminomethyl-1-(6,7-difluoro-1,2,3,4-tetrahydronaphthalen-2-yl)-1,3-dihydroimidazole-2-thione hydrochloride, m.p. 253°–270° C.; and substituting 5-cyano-1-(5,6-difluoroindan-2-yl)-1,3-dihydroimidazole-2-thione gave 5-aminomethyl-1-(5,6-difluoroindan-2-yl)-1,3-dihydroimidazole-2-thione hydrochloride, m.p. >280° C. (dec).

EXAMPLE 21

1-(5,7-Difluoro-1,2,3,4-tetrahydronaphthalen-2-yl)-5 (1H)-tetrazol-5-yl-1,3-dihydroimidazole-2-thione The following is the preparation of a compound of Formula I(a) in which n is 1, t is 2, $R^1$ is fluoro at the 5- and 7-position and $R^5$ is 1H-tetrazol-5-yl.

A mixture of 5-cyano-1-(5,7-difluoro-1,2,3,4-tetrahydronaphthalen-2-yl)-1,3-dihydroimidazole-2-thione (0.554 g, 1.9 mmol), prepared as in Example 19, in 1.6 mL of tributyltin azide was heated at 130° C. under a nitrogen atmosphere for 2.5 hours and then 10 mL of toluene was added. The mixture was allowed to cool to room temperature and approximately 5 mL of diethyl ether was added. The mixture was cooled to 0° C. and then treated with 10 mL of 1N hydrogen chloride in diethyl ether for approximately 15 minutes. The mixture was poured into a solution of potassium fluoride monohydrate (15.0 g) in 15 to 20 mL of water and 75 mL of ethyl acetate. The ethyl acetate layer was extracted with 2N sodium hydroxide and the aqueous layer was washed 6 times with methylene chloride. The aqueous layer was acidified with concentrated hydrochloric acid and then extracted with ethyl acetate. Evaporation of the solvents gave 1-(5,7-difluoro-1,2,3,4-tetrahydronaphthalen-2-yl)-5(1H)-tetrazol-5-yl-1,3-dihydroimidazole-2-thione (0.57 g, 1.7 mmol), m.p. 214°–215° C.

Proceeding as in Example 21, but substituting a different starting material for 5-cyano-1-(5,7-difluoro-1,2,3,4-tetrahydronaphthalen-2-yl)-1,3-dihydroimidazole-2-thione gave the following compounds of Formula I:

substituting 5-cyano-1-(5,6-difluoroindan-2-yl)-1,3-dihydroimidazole-2-thione gave 1-(5,6-difluoroindan-2-yl)-5(1H)-tetrazol-5-yl-1,3-dihydroimidazole-2-thione, m.p. 142°–147° C.; and substituting 5-cyano-1-(6,7-difluoro-1,2,3,4-tetrahydronaphthalen-2-yl)-1,3-dihydroimidazole-2-thione gave 1-(6,7-difluoro-1,2,3,4-tetrahydronaphthalen-2-yl)-5(1H)-tetrazol-5-yl-1,3-dihydroimidazole-2-thione, m.p. 195°–212° C.

EXAMPLE 22

3-(1,2,3,4-Tetrahydronaphthalen-2-yl)-2-thioxo-2,3-dihydro-1H-imidazole-5-carbaldehyde The following is the preparation of a compound of Formula I(a) in which n is 1, t is 0, $R^3$ and $R^5$ are each hydro and $R^4$ is formyl.

A mixture of 2-isothiocyano-1,2,3,4-tetrahydronaphthalene (1.89 g, 10 mmol), prepared as in Example 10, and D-(+)-glucosamine (1.78 g, 10 mmol) was stirred at 90° C. until homogenous and then 0.8 mL of acetic acid was added. The mixture was stirred at 90° C. for 30 minutes and then cooled. The solvents were removed by rotary evaporation and the residue was co-evaporated with toluene (2×25 mL). The residue was dissolved in acetic acid and heated at 90° to 100° C. for 30 minutes. The mixture was cooled and triturated with acetone giving a crystalline material. The material was isolated by filtration and the filter residue washed with acetone. Drying gave 4-(1R,2R,3S,4)-tetrahydroxybut-1-yl)-1-(1,2,3,4-tetrahydronaphthalen-2-yl)-1,3-dihydroimidazole-2-thione (1.48 g, 4.23 mmol).

A suspension of 4-(1R,2R,3S,4)-tetrahydroxybut-1-yl)-1-(1,2,3,4-tetrahydronaphthalen-2-yl)-1,3-dihydroimidazole-2-thione (0.252 g, 0.72 mmol) and lead tetraacetate (0.851 g, 1.92 mmol) in 15 mL of 33% acetic acid/benzene was stirred until the mixture was homogenous and 30 minutes. The reaction mixture was poured into 125 mL of saturated sodium carbonate solution and the mixture was filtered. The organic layer was separated, dried over magnesium sulfate and concentrated. The residue was dissolved in 40 mL of THF and 2 mL of sulfurous acid (6% $SO_2$). Evaporation of the solvent gave 3-(1,2,3,4-tetrahydronaphthalen-2-yl)-2-thioxo-2,3-dihydro-1H-imidazole-5-carbaldehyde (0.15 g, 0.59 mmol), m.p. 206°–210° C.

Proceeding as in Example 22, but substituting (S)-2-isothiocyano-5,7-difluoro-1,2,3,4-tetrahydronaphthalene for 2-isothiocyano-1,2,3,4-tetrahydronaphthalene gave (S)-3-(5,7-difluoro-1,2,3,4-tetrahydronaphthalen-2-yl)-2-thioxo-2,3-dihydro-1H-imidazole-5-carbaldehyde, m.p. >285° C.

EXAMPLE 23

Ethyl[(5,7-Difluoro-1,2,3,4-tetrahydronaphthalen-2-yl)(formyl)amino]acetate

The following is the preparation of a compound of Formula 17 in which n is 1, t is 2, $R^1$ is fluoro at the 5- and 7-position and $R^{32}$ is ethoxycarbonyl.

A mixture of 5,7-difluoro-1,2,3,4-tetrahydronaphthalen-2-ylamine (6.0 g, 32.8 mmol), prepared as in Example 8, and ethyl glyoxylate (4.6 g, 36.0 mmol) in 300 mL of ethanol was hydrogenated over 10% palladium on carbon (0.75 g) for 10 hours. The mixture was filtered and concentrated by evaporation. Purification of the residue by column chromatography on silica gel (elution: 30% ethyl acetate/hexane) gave ethyl[(5,7-difluoro-1,2,3,4-tetrahydronaphthalen-2-yl)amino]acetate (7.5 g, 27.9 mmol) as an oil.

A solution of ethyl[(5,7-difluoro-1,2,3,4-tetrahydronaphthalen-2-yl)-amino]acetate (7.15 g, 25.6 mmol) in 20 mL of methylene chloride under argon was cooled to approximately 0° C. Acetic formic anhydride (9.7 mL, 67.3 mmol) was cooled to 0° C. and added over 5 to 10 minutes. The mixture was stirred 0° C. for 2 hours and then allowed to warm to room temperature. The solvent was removed by co-evaporation with toluene (3×50 mL). Crystallization of the residue under high vacuum gave ethyl[(5,7-difluoro-1,2,3,4-tetrahydronaphthalen-2-yl)(formyl)amino]acetate (7.68 g, 25.0 mmol).

Proceeding as in Example 23, but substituting a different starting material for 5,7-difluoro-1,2,3,4-tetrahydronaphthalen-2-ylamine gave the following compounds of Formula 17:

substituting 6,8-difluoro-1,2,3,4-tetrahydronaphthalen-2-ylamine gave ethyl[(6,8-difluoro-1,2,3,4-tetrahydronaphthalen-2-yl)(formyl)amino]acetate;
substituting 4,6-difluoroindan-2-ylamine gave ethyl[(4,6-difluoroindan-2-yl)(formyl)amino]acetate;
substituting 5,7-difluoroindan-2-ylamine gave ethyl[(5,7-difluoroindan-2-yl)(formyl)amino]acetate; and
substituting 5,6-difluoroindan-2-ylamine gave ethyl[(5,6-difluoroindan-2-yl)(formyl)amino]acetate.

EXAMPLE 24

Ethyl 3-(5,7-difluoro-1,2,3,4-tetrahydronaphthalen-2-yl)-2-thioxo-2,3-dihydro-1H-imidazole-4-carboxylate The following is the preparation of a compound of Formula I(a) in which n is 1, t is 0, $R^1$ is fluoro at the 5- and 7-position, $R^3$ and $R^4$ are hydro and $R^5$ is ethoxycarbonyl.

A mixture of ethyl[(5,7-difluoro-1,2,3,4-tetrahydronaphthalen-2-yl)(formyl)amino]acetate (7.58 g, 24.7 mmol), prepared as in Example 23, and ethyl formate (5.91 mL, 72.7 mmol) in 60 mL of THF was cooled to −10° C. under argon. Potassium tert-butoxide (4.08 g, 36.4 mmol) in 45 mL of THF was added and the mixture was stirred at −10° C. for 2 hours. The mixture then was allowed to warm to room temperature and stirred for an additional 4 hours. The solvent was removed by evaporation and the residue was dissolved in 75 mL of 1N hydrochloric acid and 50 mL of ethanol. Potassium thiocyanate (2.65 g, 75 mmol) was added and the mixture was stirred at 85° C. for 15 hours. The mixture was cooled, diluted with 125 mL of water and extracted with ethyl acetate. The extract was dried over magnesium sulfate and the ethyl acetate was removed by rotary evaporation. Purification of the residue by column chromatography on silica gel (elution: 2.5% methanol/methylene chloride) gave ethyl 3-(5,7-difluoro-1,2,3,4-tetrahydronaphthalen-2-yl)-2-thioxo-2,3-dihydro-1H-imidazole-4-carboxylate (8.07 g, 24.6 mmol), m.p. 159°–161° C.

Proceeding as in Example 24, but substituting a different starting material for ethyl[(5,7-difluoro-1,1,3,4-tetrahydronaphthalen-2-yl)(formyl)amino]acetate gave the following compounds of Formula I:

substituting ethyl[(6,8-difluoro-1,2,3,4-tetrahydronaphthalen-2-yl)(formyl)amino]acetate gave ethyl 3-(6,8-difluoro-1,2,3,4-tetrahydronaphthalen-2-yl)-2-thioxo-2,3-dihydro-1H-imidazole-4-carboxylate, m.p. 187°–189° C.;
substituting ethyl(1,2,3,4-tetrahydronaphthalen-2-yl)(formyl)aminoacetate gave ethyl 3-(1,2,3,4-tetrahydronaphthalen-2-yl)-2-thioxo-2,3-dihydro-1H-imidazole-4-carboxylate, m.p. 70–72;
substituting ethyl(7-fluoro-1,2,3,4-tetrahydronaphthalen-2-yl)(formyl)aminoacetate gave ethyl 3-(7-fluoro-1,2,3,4-tetrahydronaphthalen-2-yl)-2-thioxo-2,3-dihydro-1H-imidazole-4-carboxylate;
substituting ethyl[(4,6-difluoroindan-2-yl)(formyl)amino]acetate gave ethyl 3-(4,6-difluoroindan-2-yl)-2-thioxo-2,3-dihydro-1H-imidazole-4-carboxylate gave;
substituting ethyl[(5,7-difluoroindan-2-yl)(formyl)amino]acetate gave ethyl 3-(5,7-difluoroindan-2-yl)-2-thioxo-2,3-dihydro-1H-imidazole-4-carboxylate; and
substituting ethyl[(5,6-difluoroindan-2-yl)(formyl)amino]acetate gave ethyl 3-(5,6-difluoroindan-2-yl)-2-thioxo-2,3-dihydro-1H-imidazole-4-carboxylate.

EXAMPLE 25

Ethyl 3-(1,2,3,4-tetrahydronaphthalen-2-yl)-5-methyl-2-thioxo-2,3-dihydro-1H-imidazole-4-carboxylate The following is the preparation of a compound of Formula I(a) in which n is 1, t is 0, $R^3$ is hydro, $R^4$ is methyl and $R^5$ is ethoxycarbonyl.

A solution of diisopropylamine (1.54 mL, 11 mmol) in 30 mL of dry THF under argon was cooled to 0° C. and n-butyllithium (6.25) mL, 10 mmol) was added. The mixture was cooled to −78° C. and ethyl[(1,2,3,4-tetrahydronaphthalen-2-yl)(formyl)amino]acetate (1.33 g, 5.0 mmol), prepared as in Example 23, in 20 mL of THF was added over 15 minutes. The mixture was stirred at −78° C. for 1 hour and acetyl chloride (0.427 mL, 6.0 mmol) was added over 5 minutes. The mixture was stirred for 3 hours at −78° C. and then warmed to room temperature over 1 hour. The solvent was removed by evaporation and the residue was dissolved in 25 mL of 1N hydrochloric acid and 25 mL of ethanol. Potassium thiocyanate (1.94 g, 20 mmol) was added and the mixture was stirred at 75°–80° C. for 18 hours. The mixture was cooled, diluted with water and extracted twice with ethyl acetate. The ethyl acetate was concentrated to a dark oil. Purification of the residue by, column chromatography on silica gel (elution: 2% methanol/methylene chloride) and trituration with ethyl acetate/isopropyl ether gave ethyl 3-(1,2,3,4-tetrahydronaphthalen- 2-yl)-5-methyl-2-thioxo-1,3-dihydro-1H-imidazole-4-carboxylate, m.p. 225°–227° C., as a light yellow solid.

Proceeding as in Example 25, but substituting a different material for ethyl[(1,2,3,4-tetrahydronaphthalen-2-yl)(formyl)amino]acetate and/or acetyl chloride gave the following compounds of Formula I:

substituting isobutyryl chloride gave ethyl 3-(1,2,3,4-tetrahydronaphthalen-2-yl)-5-prop-2-yl-2-thioxo-1,3-dihydro-1H-imidazole-4-carboxylate, m.p. 195°–197° C.;

substituting trimethylacetyl chloride gave ethyl 3-(1,2,3,4-tetrahydronaphthalen-2-yl)-5-(1,1-dimethylethyl)-2-thioxo-1,3-dihydro-1H-imidazole-4-carboxylate as a foam;

substituting ethyl(5,7-difluoro-1,2,3,4-tetrahydronaphthalen-2-yl)(formyl)-aminoacetate gave ethyl 3-(5,7-difluoro-1,2,3,4-tetrahydronaphthalen-2-yl)-5-methyl-2-thioxo-1,3-dihydro-1H-imidazole-4-carboxylate, m.p. 207°–209° C.; and substituting ethyl oxalyl chloride gave ethyl 3-(5,7-difluoro-1,2,3,4-tetrahydronaphthalen-2-yl)-5-ethoxycarbonyl-2-thioxo-1,3-dihydro-1H-imidazole-4-carboxylate, m.p. 160°–161° C.

EXAMPLE 26

5-Aminomethyl-4-(1,2,3,4-tetrahydronaphthalen-2-yl)-2,4-dihydro[1,2,4]triazole-3-thione The following is the preparation of a compound of Formula I(b) in which n is 1, t is 0 and $R^7$ is aminoethyl.

A mixture of 2-isothiocyano-1,2,3,4-tetrahydronaphthalene (0.19 g, 1.0 mmol), prepared as in Example 10, and (tert-butyloxycarbonyl)aminoacetylhydrazide (0.19 g, 1.1 mmol) in 5 mL of DMF under nitrogen was heated at 80° C. for 2.5 hours. The solvent was removed by rotary evaporation. The residue was stirred under nitrogen at room temperature and a 4.5 mL of a mixture of sodium ethoxide (prepared from 0.46 g of sodium and 45 mL of ethanol) was added. The reaction mixture was refluxed under nitrogen for approximately 24 hours, allowed to cool and then filtered. The solvent was removed by rotary evaporation and the residue was dissolved in water. The solution was acidified to pH 3 with 10% hydrochloric acid and then filtered. Evaporation of the water under reduced pressure gave 5-(tert-butyloxycarbonyl)aminomethyl-4-(1,2,3,4-tetrahydronaphthalen-2-yl)-2,4-dihydro[1,2,4]triazole-3-thione (0.203 g, 0.56 mmol).

Anhydrous hydrogen chloride (4.22 g) was bubbled into 15 mL of ethyl acetate in an ice-methanol bath. 5-(tert-Butyloxycarbonyl)aminomethyl-4-(1,2,3,4-tetrahydronaphthalen-2-yl)-2,4-dihydro[1,2,4]triazole-3-thione (0.178 g, 0.49 mmol) was added and the mixture was stirred at room temperature. Ether was added and the mixture was filtered under nitrogen. Evaporation of the solvents under reduced pressure gave 5-aminomethyl-4-(1,2,3,4-tetrahydronaphthalen-2-yl)-2,4-dihydro[1,2,4]]triazole-3-thione hydrochloride (0.125 g, 0.41 mmol) m.p. 279°–281° C.

Proceeding as in Example 26, but substituting a different starting material for 2-isothiocyano-1,2,3,4-tetrahydronaphthalene and/or (tert-butyloxycarbonyl)aminoacetylhydrazide gave the following compounds of Formula I:

substituting 2-isothiocyano-1,2,3,4-tetrahydronaphthalene and 4-methylpiperazin-1-ylacetylhydrazide gave 5-(4-methylpiperazin-1-yl)-4-(1,2,3,4-tetrahydronaphthalen-2-yl)-2,4-dihydro[1,2,4]triazole-3-thione, m.p. 217°–218° C. and substituting (S)-5,7-difluoro-2-isothiocyano-1,2,3,4-tetrahydronaphthalene and (tert-butyloxycarbonyl)aminoacetylhydrazide gave (S)-5-aminomethyl-4-(5,7-difluoro-1,2,3,4-tetrahydronaphthalen-2-yl)-2,4-dihydro[1,2,4]triazole-3-thione and (S)-5-aminomethyl-4-(5,7-difluoro-1,2,3,4-tetrahydronaphthalen-2-yl)-2,4-dihydro[1,2,4]triazole-3-thione hydrochloride, m.p. >280° C.

EXAMPLE 27

2-(1,2,3,4-tetrahydronaphthalen-2-yl)-2,4-dihydro[1,2,4]triazole-3-thione

The following is the preparation of a compound of Formula I(c) in which n is 1, t is 0 and $R^8$ is hydro.

A mixture of 1,2,3,4-tetrahydronaphthalen-2-one (3.5 g, 24.0 mmol) and formic hydrazide (1.56 g, 26.0 mmol) in 25 mL of ethanol and 1 drop of concentrated hydrochloric acid was heated at 70° C. for 1 hour. The mixture was cooled to room temperature giving a crystalline material. The material was isolated by filtration and washed with ethanol. Drying gave 2-formylhydrazono-1,2,3,4-tetrahydronaphthalene (3.5 g, 8.7 mmol).

A mixture of 2-formylhydrazono-1,2,3,4-tetrahydronaphthalene (3.0 g, 16.0 mmol) and sodium borohydride (1.2 g, 31.6 mmol) in 25 mL of ethanol was stirred at room temperature for 20 hours. The mixture was quenched with water and then extracted with ethyl acetate (2×50 mL). The combined ethyl acetate extract was washed with brine, dried over sodium sulfate and concentrated. Purification of the residue by flash chromatography (elution: 2% methanol/methylene chloride) gave 2-formylhydrazo-1,2,3,4-tetrahydronaphthalene (2 g, 10.7 mmol).

A mixture of 2-formylhydrazo-1,2,3,4-tetrahydronaphthalene (2.0 g, 10.7 mmol) and trimethylsilyl isothiocyanate (2.8 g, 21.0 mmol) in 20 mL of toluene was stirred at 60° to 65° C. for 20 hours giving a crystalline material. Filtration and drying gave N-[(1,2,3,4-tetrahydronaphthalen-2-yl)(aminothiocarbonyl)amino]formamide (0.6 g, 2.4 mmol).

A solution of N-[(1,2,3,4-tetrahydronaphthalen-2-yl)(aminothiocarbonyl)amino]formamide (0.6 g, 2.4 mmol) in 10 mL of 10% sodium hydroxide was heated at 70° C. for 30 minutes. The solution was cooled, acidified with dilute hydrochloric acid and extracted with ethyl acetate. The ethyl acetate extract was washed with brine, dried over sodium sulfate and concentrated. The residue was recrystallized from ethyl acetate/hexane and filtration gave 2-(1,2,3,4-tetrahydronaphthalen-2-yl)-2,4-dihydro[1,2,4]triazole-3-thione (0.25 g. 1.06 mmol), m.p. 200.5° C.

EXAMPLE 28

4-Amino-2-(1,2,3,4-tetrahydronaphthalen-2-yl)-2,4-dihydro[1,2,4 ]triazole-3-thione The following is the preparation of a compound of Formula I(c) in which n is 1, t is 0 and $R^8$ is amino.

A mixture of 2-bromo-1,2,3,4-tetrahydronaphthalene (1.06 g, 5 mmol) and 4-amino[1,2,4]triazole (2.1 g, 25 mmol) in 8 mL of DMF was heated at 90° C. and stirred for 2 hours. The solvents were removed by evaporation and the residue was dissolved in 5 mL of pyridine. Lac sulfur (0.16 g, 5 mmol) and 2.5 mL of triethylamine were added and the mixture was heated at approximately 90° C. and stirred under argon for 4 hours. The solvents were removed by evaporation and the residue was co-evaporated with toluene (×2). Purification by flash chromatography (elution: 3–5% methanol/methylene chloride) gave 4-amino-2-(1,2,3,4-tetrahydronaphthalen-2-yl)-2,4-dihydro[1,2,4]triazole-3-thione (0.35 g, 1.42 mmol), m.p. 147°–150° C.

EXAMPLE 29

(S)-N-[3-(5,7-Difluoro-1,2,3,4-tetrahydronaphthalen-2-yl)-2-thioxo-2,3-dihydro-1H-imidazol-4-ylmethyl]formamide The following is the preparation of a compound of Formula I(a) in which n is 1, t is 2, $R^1$ is fluoro at the 5- and 7-position and $R^5$ is formylaminomethyl.

Formamide (250 mL, 6.3 mol) was heated to 1750° C. and (S)-5-hydroxymethyl-1-(5,7-difluoro-1,2,3,4-tetrahydronaphthalen-2-yl)-1,3-dihydroimidazole-2-thione (25.0 g, 88.3 mmol), prepared as in Example 18, was added in portions over 30 minutes and the reaction mixture was stirred for 1 hour under a nitrogen sweep. The mixture was cooled to 500° C. and 2.5 g of activated carbon, Darco®, was added. The mixture was cooled to 30° C., filtered through Celite and washed in with 25 mL of formamide. The filtrate was heated to 95° C. and then 1 L of water was added dropwise. The mixture was allowed to cool and then stirred at room temperature for 12 hours. The mixture was cooled to 0° C. giving a crystalline material. The material was isolated by filtration and dried.

The material was stirred with approximately 5 times by weight of 70% THF/30% hexanes for five minutes. The material was isolated by filtration and the filter residue was washed with 50% THF/50% hexanes. Drying to constant weight gave (S)-N-[3-(5,7-difluoro-1,2,3,4-tetrahydronaphthalen-2-yl)-2-thioxo-2,3-dihydro-1H-imidazol-4-ylmethyl]formamide (19.5 g, 62.7 mmol), m.p. 245°–246° C. $[\alpha]_D$ +48.9° (c=0.613, DMSO).

Proceeding as in Example 29, but substituting different starting materials for (S)-5-hydroxymethyl-1-(5,7-difluoro-1,2,3,4-tetrahydro-naphthalen-2-yl)-1,3-dihydroimidazole-2-thione or formamide gave the following compounds of Formula I(a):

substituting (S)-5-hydroxymethyl-1-(6,7-dichloro-1,2,3,4-tetrahydronaphthalen-2-yl)-1,3-dihydroimidazole-2-thione gave (S)-N-[3-(6,7-difluoro-1,2,3,4-tetrahydronaphthalen-2-yl)-2-thioxo-2,3-dihydro-1H-imidazol-4-ylmethyl]formamide; and substituting urea gave (S)-5-ureidomethyl-1-(5,7-difluoro-1,2,3,4-tetrahydronaphthalen-2-yl)-1,3-dihydroimidazole-2-thione, m.p. 258°–260° C., $[\alpha]_D$ +34.3° (C=0.574, DMSO).

EXAMPLE 30

(S)-N-[3-(5,7-Difluoro-1,2,3,4-tetrahydronaphthalen-2-yl)-2-thioxo-2,3-dihydro-1H-imidazol-4-ylmethyl]formamide The following is the preparation of a compound of Formula I(a) in which n is 1, t is 2, $R^1$ is fluoro at the 5- and 7-position and $R^5$ is formylaminomethyl.

A mixture of (S)-5-hydroxymethyl-1-(5,7-difluoro-1,2,3,4-tetrahydronaphthalen-2-yl)-1,3-dihydroimidazole-2-thione (1.0 g, 3.5 mmol), prepared as in Example 18, and ammonium formate (10 g, 158.6 mmol) was stirred at approximately 125° C. for 1 hour. The mixture was then heated to approximately 138° C. and stirred for an additional 35 minutes. The mixture was diluted with 25 mL of water and allowed to cool to room temperature. The mixture was aged for approximately 18 hours giving a crystalline material. The material was isolated by filtration and the filter residue was washed with water. Drying to constant weight gave (S)-N-[3-(5,7-difluoro-1,2,3,4-tetrahydronaphthalen-2-yl)-2-thioxo-2,3-dihydro-1H-imidazol-4-ylmethyl] formamide (0.92 g, 2.96 mmol).

Proceeding as in Example 30, but substituting ammonium acetate for ammonium formate gave (S)-N-[3-(5,7-difluoro-1,2,3,4-tetrahydronaphthalen-2-yl)-2-thioxo-2,3-dihydro-1H-imidazol-4-ylmethyl]acetamide, m.p. 275.5°–276° C. dec. $[\alpha]_D$ +41.3° (c=1.00, DMSO).

EXAMPLE 31

(S)-5-Aminomethyl-1-(5,7-difluoro-1,2,3,4-tetrahydronaphthalen-2-yl)-1,3-dihydroimidazole-2-thione hydrochloride The following is the preparation of a compound of Formula I(a) in which n is 1, t is 2, $R^1$ is fluoro at the 5- and 7-position and $R^5$ is aminomethyl.

A mixture of (S)-N-[3-(5,7-difluoro-1,2,3,4-tetrahydronaphthalen-2-yl)-2-thioxo-2,3-dihydro-1H-imidazol-4-ylmethyl]formamide (19.1 g, 59.0 mmol), prepared as in Example 30, and 25 mL of concentrated hydrochloric acid (12.0M, 25 mL, 300 mmol) in 400 mL of isopropanol was heated to reflux over 12 minutes and stirred for 1 hour 40 minutes. The mixture was distilled removing 150 mL of isopropanol. The mixture was gradually cooled to room temperature and stirred for 3 hours 45 minutes. The material was isolated by filtration and the filter residue was washed with 75 mL of isopropanol. Drying in vacuo at 110° to 125° C. with a nitrogen bleed gave (S)-5-aminomethyl-1-(5,7-difluoro-1,2,3,4-tetrahydronaphthalen-2-yl)-1,3-dihydroimidazole-2-thione hydrochloride (15.6 g, 47.1 mmol), m.p. 251.9° C. $[\alpha]_D$ +10.2° C. (c=0.500, DMSO).

Proceeding as in Example 31, but substituting different starting materials for (S)-N-[3-(5,7-difluoro-1,2,3,4-tetrahydronaphthalen-2-yl)-2-thioxo-2,3-dihydro-1H-imidazol-4-ylmethyl]formamide gave the following compounds of Formula I:

substituting (S)-N-[3-(6,7-dichloro-1,2,3,4-tetrahydronaphthalen-2-yl)-2-thioxo-2,3-dihydro-1H-imidazol-4-yl-methyl]formamide gave (S)-5-aminomethyl-1-(6,7-dichloro-1,2,3,4-tetrahydronaphthalen-2-yl)-1,3-dihydroimidazole-2-thione hydrochloride, m.p. 190° C. dec;

substituting (S)-4-{2-[4-formylaminomethyl-3-(5,7-difluoro-1,2,3,4-tetrahydronaphthalen-2-yl)-2-thioxo-2,3-dihydro-1H-imidazol-1-yl]ethyl}benzoic acid gave (S)-4-{2-[4-aminomethyl-3-(5,7-difluoro-1,2,3,4-tetrahydronaphthalen-2-yl)-2-thioxo-2,3-dihydro-1H-imidazol-1-yl]ethyl}benzoic acid hydrochloride, m.p. 246°–248° C.; and substituting (S)-3-[4-formylaminomethyl-3-(5,7-difluoro-1,2,3,4-tetrahydronaphthalen-2-yl)-2-thioxo-2,3-dihydro-1H-imidazol-1-yl]propionic acid gave (S)-3-[4-aminomethyl-3-(5,7-difluoro-1,2,3,4-tetrahydronaphthalen-2-yl)-2-thioxo-2,3-dihydro-1H-imidazol-1-yl]propionic acid, m.p. 191° C. (eff.).

EXAMPLE 32

(S)-1-(5,7-Difluoro-1,2,3,4-tetrahydronaphthalen-2-yl)-5-pyrrolidin-1-ylmethyl-1,3-dihydroimidazole-2-thione The following is the preparation of a compound of Formula I(a) in which n is 1, t is 2, $R^1$ is fluoro at the 5- and 7-position, $R^3$ and $R^4$ are hydro and $R^5$ is pyrrolidin-1-ylmethyl.

A solution of (S)-1-(5,7-difluoro-1,2,3,4-tetrahydronaphthalen-2-yl)-5-hydroxymethyl-1,3-dihydroimidazole-2-thione (140 mg, 0.47 mmol), prepared as in Example 18, in 20 mL of THP and 1 drop of DMF was cooled to between 0° and 5° C. and thionyl chloride (13.7M, 109 µL, 1.49 mmol) was added drop-wise under a nitrogen atmosphere. The mixture was stirred at room temperature for 0.5 hours, under reflux for 0.5 hours and again at room temperature for 0.5 hours. The mixture then was cooled to between 0° and 5° C. and pyrrolidine (12.0M, 818 µL, 9.8 mmol) was added drop-wise. The mixture was stirred under reflux for 1.5 hours. The solvents were removed by evaporation and the residue was diluted with water. Ethyl acetate was added to the dilution and the mixture was adjusted to pH 7. The ethyl acetate layer was dried and concentrated by evaporation. Purification of the residue by column chromatography gave (S)-1-(5,7-difluoro-1,2,3,4-tetrahydronaphthalen-2-yl)-1,3-dihydro-5-(pyrrolidin-1-ylmethyl)-imidazole-2-thione (100 mg, 0.29 mmol). $[\alpha]_D^{25}$=-10.96° (c=1.3, DMSO).

Treatment with 2 molar equivalents of 1M anhydrous hydrogen chloride in diethyl ether gave (S)-1-(5,7-difluoro-1,2,3,4-tetrahydronaphthalen-2-yl)-1,3-dihydro-5-(pyrrolidin-1-ylmethyl)imidazole-2-thione hydrochloride (100 mg, 0.26 mmol), m.p. 187°–189° C.

Proceeding as in Example 32, but substituting a different starting material for (S)-5-hydroxymethyl-1-(5,7-difluoro-1,2,3,4-tetrahydronaphthalen-2-yl)-1,3-dihydroimidazole-2-thione gave the following compounds of Formula I:

substituting methylamine gave (S)-1-(5,7-difluoro-1,2,3,4-tetrahydronaphthalen-2-yl)-5-(methylaminomethyl)-1,3-dihydroimidazole-2-thione, m.p. 250°–260° C., and (S)-1-(5,7-difluoro-1,2,3,4-tetrahydronaphthalen-2-yl)-5-(methylaminomethyl)-1,3-dihydroimidazole-2-thione hydrochloride, m.p. 250° C., $[\alpha]_D^{25}$=+7.7° (c=2.4, DMSO);

substituting dimethylamine gave (S)-1-(5,7-difluoro-1,2,3,4-tetrahydronaphthalen-2-yl)-5-(dimethylaminomethyl)-1,3-dihydroimidazole-2-thione and (S)-1-(5,7-difluoro-1,2,3,4-tetrahydronaphthalen-2-yl)-5-(dimethylaminomethyl)-1,3-dihydroimidazole-2-thione hydrochloride, m.p. 207°–208° C.;

substituting piperidine gave (S)-1-(5,7-difluoro-1,2,3,4-tetrahydronaphthalen-2-yl)-5-(piperidin-1-ylmethyl)-1,3-dihydroimidazole-2-thione and (S)-1-(5,7-difluoro-1,2,3,4-tetrahydronaphthalen-2-yl)-5-(piperidin-1-ylmethyl)-1,3-dihydroimidazole-2-thione hydrochloride, m.p. 169°–170° C.;

substituting morpholine gave (S)-1-(5,7-difluoro-1,2,3,4-tetrahydronaphthalen-2-yl)-5-(morpholin-4-ylmethyl)-1,3-dihydroimidazole-2-thione, m.p. 198–201, $[\alpha]_D^{25}$=-7.56° (c=2.38, DMSO) and (S)-1-(5,7-difluoro-1,2,3,4-tetrahydronaphthalen-2-yl)-5-(morpholin-4-ylmethyl)-1,3-dihydroimidazole-2-thione hydrochloride, m.p. 182°–184° C.; and substituting 1-methylpiperazine gave (S)-1-(5,7-difluoro-1,2,3,4-tetrahydronaphthalen-2-yl)-5-(4-methylpiperazin-1-ylmethyl)-1,3-dihydroimidazole-2-thione and (S)-1-(5,7-difluoro-1,2,3,4-tetrahydronaphthalen-2-yl)-5-(4-methylpiperazin-1-ylmethyl)-1,3-dihydroimidazole-2-thione hydrochloride, m.p. 237°–245° C.

EXAMPLE 33

1-(1,2,3,4- Tetrahydronaphthalen-2yl)-4,5-dihydromethyl)-1,3-dihydroimidazole-2-thione The following is the preparation of a compound of Formula I(a) in which n is 1, t is 0, $R^3$ is hydro and $R^4$ and $R^5$ are each hydroxymethyl.

A mixture of sodium borohydride (0.22 g, 5.8 mmol) and anhydrous calcium chloride 0.34 g, 3.1 mmol) in 10 mL of dry THF was stirred at approximately 25° C. for 1 hour and then ethyl 3-(1,2,3,4-tetrahydronaphthalen-2-yl)-5-ethoxycarbonyl-2-thioxo-1,3-dihydro-1H-imidazole-4-carboxylate (0.37 g, 1 mmol), prepared as in Example 25, in 10 mL of dry THF was added. The mixture was stirred at 50° C. for approximately 72 hours and then concentrated. The residue was treated with 20 mL of 10% sodium hydroxide and 50 mL of ethyl acetate and filtered and the aqueous phase was extracted again with ethyl acetate (3×50 mL). The combined extracts were dried (MgSO₄) and concentrated. The residue was stirred with methylene chloride/methanol (93:7) and the mixture was filtered. The above aqueous phase was evaporated to dryness and the residue was stirred with methanol. The methanol mixture was filtered and then combined with the methylene chloride/methanol filtrate. The combined mixture was concentrated and the residue was purified by flash chromatography on silica gel eluting with methylene chloride/methanol (93:7 to 96:4) to give 1-(1,2,3,4-tetrahydronaphthalen-2-yl)-4,5-di(hydroxymethyl)-1,3-dihydroimidazole-2-thione (35 mg, 0.12 mmol), m.p. 199°–200° C.

EXAMPLE 34

Ethyl 3-[3-(1,2,3,4-tetrahydronaphthalen-2-yl)-2-thioxo-2,3-dihydro-1H-imidazol-1-yl]propionate The following is the preparation of a compound of Formula I(a) in which n is 1, t is 0, $R^3$ is 2-ethoxycarbonylethyl and $R^4$ and $R^5$ are each hydro.

A mixture of 1-(1,2,3,4-tetrahydronaphthalen-2-yl)-1,3-dihydroimidazole-2-thione (1.3 g, 5.6 mmol), prepared as in Example 9, and ethyl acrylate (3.1 mL, 28.2 mmol) in 14 mL of ethanol and 1.28 mL of N-benzyltrimethylammonium hydroxide (2.8 mmol) in methanol was heated at 80° C. under nitrogen for 2 hours. The mixture was allowed to cool and concentrated by rotoevaporation. The residue was purified by chromatography on silica gel eluting with hexanes/ethyl acetate (3:1) to give ethyl 3-[3-(1,2,3,4-tetrahydronaphthalen-2-yl)-2-thioxo-2,3-dihydro-1H-imidazol-1-yl]propionate (1.2 g, 3.7 mmol), m.p. 71°–73° C.

Proceeding as in Example 34, but substituting different starting materials for 1-(1,2,3,4-tetrahydronaphthalen-2-yl)-1,3-dihydroimidazole-2-thione gave the following compounds of Formula I:

substituting tert-butyl 4-(1,2,3,4-tetrahydronaphthalen-2-yl)-5-thioxo-1,5-dihydro[1,2,4]triazol-3-ylmethylaminoformate gave ethyl 3-[4-(1,2,3,4-tetrahydronaphthalen-2-yl)-3-(tert-butoxycarbonylaminomethyl)-5-thioxo-1,5-dihydro[1,2,4]triazol-1-yl]propionate; and substituting (S)-(1-(5,7-difluoro-1,2,3,4-tetrahydronaphthalen-2-yl)-1,3-dihydroimidazole-2-thione gave ethyl(S)-3-[3-(5,7-difluoro-1,2,3,4-tetrahydronaphthalen-2-yl)-2-thioxo-2,3-dihydro-1H-imidazol-1-yl]propionate, m.p. 105°–1070° C.

EXAMPLE 35

Ethyl 3-[3-(1,2,3,4-tetrahydronaphthalen-2-yl)-4-dimethylaminomethyl 2-thioxo-2,3-dihydro-1H-imidazol-1-yl]propionate The following is the preparation of a compound of Formula I(a) in which n is 1, t is 0, $R^3$ is 2-(ethoxycarbonyl)ethyl, $R^4$ is hydro and $R^5$ is dimethylaminomethyl.

A mixture of ethyl 3-[3-(1,2,3,4-tetrahydronaphthalen-2-yl)-2-thioxo-2,3-dihydro-1H-imidazol-1-yl]propionate (0.5 g, 1.5 mmol), prepared as in Example 34, and N,N-dimethylmethyleneammonium chloride (0.17 g, 1.8 mmol) in 7 mL of DMF was heated at 80° C. under nitrogen for 16 hours. The mixture then was partitioned between saturated sodium bicarbonate solution and ethyl acetate. The organic layer was separated, washed with brine, dried (NaSO$_4$), filtered and concentrated. The residue was purified by column chromatography on silica gel eluting with ethyl acetate/hexane to give ethyl 3-[3-(1,2,3,4-tetrahydronaphthalen-2-yl)-4-dimethylaminomethyl-2-thioxo-2,3-dihydro-1H-imidazol-1-yl]propionate (277 mg, 0.7 mmol), m.p. 128°–130° C.

Proceeding as in Example 35 but substituting methyl 4-[3-(1,2,3,4-tetrahydronaphthalen-2-yl)-5-methyl-2-thioxo-2,3-dihydro-1H-imidazol-1-ylmethyl]benzoate for ethyl 3-[3-(1,2,3,4-tetrahydronaphthalen-2-yl)-2-thioxo-2,3-dihydro-1H-imidazol-1-yl]propionate gave methyl 4-[3-(1,2,3,4-tetrahydronaphthalen-2-yl)-4-dimethylamino-5-methyl-2-thioxo-2,3-dihydro-1H-imidazol-1-ylmethyl] benzoate, as a foam.

EXAMPLE 36

1-(1,2,3,4-tetrahydronaphthalen-2-yl)-4,5-di(dimethylamino)-1,3-dihydroimidazole-2-thione The following is the preparation of a compound of Formula I(a) in which n is 1, t is 0, $R^3$ is hydro and $R^4$ and $R^5$ are each dimethylaminomethyl.

A mixture of 1-(1,2,3,4-tetrahydronaphthalen-2-yl)-1,3-dihydro-imidazole-2-thione (1 g, 4.3 mmol), prepared as in Example 9, ethyl acrylate (4.7 mL, 43 mmol) and hydrochloric acid (1N in ether, 8.7 mL, 8.7 mmol) in 20 mL of ethanol was heated at 80° C. under nitrogen for approximately 5 hours. The mixture was allowed to cool, concentrated and partitioned between saturated sodium bicarbonate solution and methylene chloride. The organic layer was separated and dried (K$_2$CO$_3$), filtered and concentrated. The residue was purified by column chromatography on silica gel eluting with methylene chloride/methanol (99:1) to give ethyl 3-[1-(1,2,3,4-tetrahydronaphthalen-2-yl)imidazol-2-yl-thio]propionate (1.36 g, 4.1 mmol).

A mixture of ethyl 3-[1-(1,2,3,4-tetrahydronaphthalen-2-yl)-imidazol-2-ylthio]propionate (1.36 g, 4.1 mmol) and N,N-dimethylmethylene ammonium chloride (1.66 g, 17.7 mmol) in 25 mL of DMF was heated at 100° C. under nitrogen for approximately 22 hours. The reaction mixture was allowed to cool to approximately 90° C. and then additional N,N-dimethylmethyleneammonium chloride (0.83 g, 8.8 mmol) was added. The mixture was heated for 31.5 hours and then partitioned between sodium bicarbonate and ethyl acetate. The organic layer was separated, washed with brine, dried (K$_2$CO$_3$), filtered and concentrated. The residue was purified by column chromatography on silica gel eluting with 5–10% methanol in methylene chloride to give ethyl 3-[1-(1,2,3,4-tetrahydronaphthalen-2-yl)-4,5-di(dimethylaminomethyl)imidazol-2-ylthio]propionate (0.55 g, 1.2 mmol).

A mixture of ethyl 3-[1-(1,2,3,4-tetrahydronaphthalen-2-yl)-4,5-di(dimethylaminomethyl)imidazol-2-ylthio] propionate (0.55 g, 1.2 mmol) and sodium ethoxide (3.5 mL of a solution prepared free 450 mg sodium in 45 mL of ethanol, 1.4 mmol) in 5 mL of ethanol was stirred at approximately 25° C. for 1.75 hours. The mixture was concentrated and partitioned between water and ethyl acetate. The organic layer was separated, washed with brine, dried (K$_2$CO$_3$), filtered and concentrated. The residue was purified by column chromatography on silica gel eluting with methylene chloride/methanol (97:3) to give 1-(1,2,3,4-tetrahydronaphthalen-2-yl)-4,5-di(dimethylamino)-1,3-dihydroimidazole-2-thione (0.24 g, 0.7 mmol), m.p. 182°–184° C.

EXAMPLE 37

3-(5-7-Difluoro-1,2,3,4-tetrahydronaphthalen-2-yl)-2-thioxo-2,3-dihydro-1H-imidazole-4-carboxylic acid The following is the preparation of a compound of Formula I(a) in which n is 1, t is 2, $R^1$ is fluoro at the 5- and 7-position, $R^3$ and $R^4$ are hydro and $R^5$ is carboxy.

A mixture of ethyl 3-(5,7-difluoro-1,2,3,4-tetrahydronaphthalen-2-yl)-2-thioxo-2,3-dihydro-1H-imidazole-4-carboxylate (4.6 g, 13.6 mmol), prepared as in Example 24, and potassium hydroxide (3.14 g, 47.6 mmol) in 130 mL of ethanol/water (10:3) was stirred at 85°–90° C. for 5 hours. The solvent was removed by evaporation and the residue was dissolved in water. The solution was acidified with 1N hydrochloric acid to a pH of 1 giving a crystalline material. Isolation of the material by filtration gave 3-(5,7-difluoro-1,2,3,4-tetrahydronaphthalen-2-yl)-2-thioxo-2,3-dihydro-1H-imidazole-4-carboxylic acid (3.86 g, 12.5 mmol), m.p. 250°–252° C.

Proceeding as in Example 37, but substituting a different starting material for ethyl 3-(5,7-difluoro-1,2,3,4-tetrahydronaphthalen-2-yl)-2-thioxo-2,3-dihydro-1H-imidazole-4-carboxylate gave the following compounds of Formula I(a):

substituting ethyl 3-(1,2,3,4-tetrahydronaphthalen-2-yl)-2-thioxo-2,3-dihydro-1H-imidazole-4-carboxylate gave ethyl 3-(1,2,3,4-tetrahydronaphthalen-2-yl)-2-thioxo-2,3-dihydro-1H-imidazole-4-carboxylic acid, m.p. 231°–332° C. (dec);

substituting ethyl 3-(7-fluoro-1,2,3,4-tetrahydronaphthalen-2-yl)-2-thioxo-2,3-dihydro-1H-imidazole-4-carboxylate gave ethyl 3-(7-fluoro-1,2,3,4-tetrahydronaphthalen-2-yl)-2-thioxo-2,3-dihydro-1H-imidazole-4-carboxylic acid, m.p. 207°–209° C.;

substituting ethyl 3-(6,8-difluoro-1,2,3,4-tetrahydronaphthalen-2-yl)-2-thioxo-2,3-dihydro-1H-imidazole-4-carboxylate gave 3-(6,8-difluoro-1,2,3,4-tetrahydronaphthalen-2-yl)-2-thioxo-2,3-dihydro-1H-imidazole-4-carboxylic acid, m.p. 207°–208° C., and treating with potassium hydroxide in methanol, evaporating to dryness and recrystallizing from methanol/isopropanol gave potassium 3-(6,8-difluoro-1,2,3,4-tetrahydronaphthalen-2-yl)-2-thioxo-2,3-dihydro-1H-imidazole-4-carboxylate, m.p. 160°–163° C.;

substituting ethyl 3-(4,6-difluoroindan-1-yl)-2-thioxo-2,3-dihydro-1H-imidazole-4-carboxylate gave 3-(4,6-difluoroindan-1-yl)-2-thioxo-2,3-dihydro-1H-imidazole-4-carboxylic acid and treating with potassium hydroxide in methanol, evaporating to dryness and recrystallizing from methanol/isopropanol gave potassium gave potassium 3-(4,6-difluoroindan-1-yl)-2-thioxo-2,3-dihydro-1H-imidazole-4-carboxylate, m.p. 163°–173° C.;

substituting ethyl 3-(5,7-difluoroindan-2-yl)-2-thioxo-2,3-dihydro-1H-imidazole-4-carboxylate gave 3-(5,7-difluoroindan-2-yl)-2-thioxo-2,3-dihydro-1H-imidazole-4-carboxylic acid, m.p. 230°–232° C., and treating with potassium hydroxide in methanol, evaporating to dryness and recrystallizing from methanol/isopropanol gave potassium 3-(5,7-difluoroindan-2-yl)-2-thioxo-2,3-dihydro-1H-imidazole-4-carboxylate, m.p. 170°–174° C.;

substituting ethyl 3-(5,6-difluoroindan-2-yl)-2-thioxo-2,3-dihydro-1H-imidazole-4-carboxylate gave 3-(5,6-difluoroindan-2-yl)-2-thioxo-2,3-dihydro-1H-imidazole-4-carboxylic acid, m.p. 233°–234° C.;

substituting methyl 3-[3-(1,2,3,4-tetrahydronaphthalen-2-yl)-2-thioxo-2,3-dihydro-1H-imidazol-1-ylmethyl]benzoate and sodium hydroxide gave 3-[3-(1,2,3,4-tetrahydronaphthalen-2-yl)-2-thioxo-2,3-dihydro-1H-imidazol-1-ylmethyl]benzoic acid, m.p. 252°–254° C.;

substituting methyl 4-[3-(1,2,3,4-tetrahydronaphthalen-2-yl)-2-thioxo-2,3-dihydro-1H-imidazol-1-ylmethyl]benzoate and sodium hydroxide gave 4-[3-(1,2,3,4-tetrahydronaphthalen-2-yl)-2-thioxo-2,3-dihydro-1H-imidazol-1-ylmethyl]benzoic acid, m.p. 211°–212° C.;

substituting methyl 4-[3-(1,2,3,4-tetrahydronaphthalen-2-yl)-2-thioxo-2,3-dihydro-1H-imidazol-1-yl]butyrate gave 4-[3-(1,2,3,4-tetrahydronaphthalen-2-yl)-2-thioxo-2,3-dihydro-1H-imidazol-1-yl]butyric acid, m.p. 156°–158° C.;

substituting methyl 5-[3-(1,2,3,4-tetrahydronaphthalen-2-yl)-2-thioxo-2,3-dihydro-1H-imidazol-1-ylmethyl]picolinate and recrystallizing from a solution of hydrochloric acid in ethanol gave 5-[3-(1,2,3,4-tetrahydronaphthalen-2-yl)-2-thioxo-2,3-dihydro-1H-imidazol-1-ylmethyl]picolinic acid hydrochloride, m.p. 204°–205° C.;

substituting methyl 3-[3-(1,2,3,4-tetrahydronaphthalen-2-yl)-2-thioxo-2,3-dihydro-1H-imidazol-1-yl]propionate gave 3-[3-(1,2,3,4-tetrahydronaphthalen-2-yl)-2-thioxo-2,3-dihydro-1H-imidazol-1-yl]propionic acid, m.p. 167°–168° C.;

substituting methyl 4-[3-(1,2,3,4-tetrahydronaphthalen-2-yl)-5-methyl-2-thioxo-2,3-dihydro-1H-imidazol-1-ylmethyl]benzoate gave 4-[3-(1,2,3,4-tetrahydronaphthalen-2-yl)-5-methyl-2-thioxo-2,3-dihydro-1H-imidazol-1-ylmethyl]benzoic acid, m.p. 181°–182° C.;

substituting ethyl 3-[4-(1,2,3,4-tetrahydronaphthalen-2-yl)-3-(tert-butoxycarbonylaminomethyl)-5-thioxo-1,5-dihydro[1,2,4]triazol-1-yl]propionate gave 3-[4-(1,2,3,4-tetrahydronaphthalen-2-yl)-3-(tert-butoxycarbonylaminomethyl)-5-thioxo-1,5-dihydro[1,2,4]triazol-1-yl]propionic acid, m.p. 76–78;

substituting ethyl(S)-3-[3-(5,7-difluoro-1,2,3,4-tetrahydronaphthalen-2-yl)-2-thioxo-2,3-dihydro-1H-imidazol-1-yl]propionate gave (S)-3-[3-(5,7-difluoro-1,2,3,4-tetrahydronaphthalen-2-yl)-2-thioxo-2,3-dihydro-1H-imidazol-1-yl]propionic acid, m.p. 182°–184° C.;

substituting ethyl 3-[3-(1,2,3,4-tetrahydronaphthalen-2-yl)-4-dimethylaminomethyl-2-thioxo-2,3-dihydro-1H-imidazol-1-yl]propionate gave 3-[3-(1,2,3,4-tetrahydronaphthalen-2-yl)-4-dimethylaminomethyl-2-thioxo-2,3-dihydro-1H-imidazol-1-yl]propionic acid, m.p. 171°–174° C.;

substituting methyl(S)-4-{2-[3-(1,2,3,4-tetrahydronaphthalen-2-yl)-2-thioxo-2,3-dihydro-1H-imidazol-4-yl-methylamino]ethyl}benzoate gave (S)-4-{2-[3-(1,2,3,4-tetrahydronaphthalen-2-yl)-2-thioxo-2,3-dihydro-1H-imidazol-4-ylmethylamino]ethyl}benzoic acid hydrochloride, m.p. 240°–241° C.; and substituting ethyl(S)-3-[4-formylaminomethyl-3-(5,7-difluoro-1,2,3,4-tetrahydronaphthalen-2-yl)-2-thioxo-2,3-dihydro-1H-imidazol-1-yl]propionate gave (S)-3-[4-formylaminomethyl-3-(5,7-difluoro-1,2,3,4-tetrahydronaphthalen-2-yl)-2-thioxo-2,3-dihydro-1H-imidazol-1-yl]propionic acid.

Proceeding as in Example 37, but substituting a different starting material for ethyl 3-(5,7-difluoro-1,2,3,4-tetrahydronaphthalen-2-yl)-2-thioxo-2,3-dihydro-1H-imidazole-4-carboxylate and performing an acid catalyzed hydrolysis gave the following compounds of Formula I(a):

substituting tert-butyl 3-(1,2,3,4-tetrahydronaphthalen-2-yl)-2-thioxo-2,3-dihydro-1H-imidazol-1-ylacetate and trifluoroacetic acid gave 3-(1,2,3,4-tetrahydronaphthalen-2-yl)-2-thioxo-2,3-dihydro-1H-imidazol-1-yl-acetic acid, m.p. 228°–230° C.;

substituting tert-butyl 1-(5,7-difluoro-1,2,3,4-tetrahydronaphthalen-2-yl)-2-thioxo-2,3-dihydro-1H-imidazol-4-ylmethylaminoacetate and hydrochloric acid gave 1-(5,7-difluoro-1,2,3,4-tetrahydronaphthalen-2-yl)-2-thioxo-2,3-dihydro-1H-imidazol-4-ylmethylaminoacetic acid hydrochloride, m.p. 214°–216° C.;

substituting tert-butyl(S)-1-(5,7-difluoro-1,2,3,4-tetrahydronaphthalen-2-yl)-2-thioxo-2,3-dihydro-1H-imidazol-4-ylmethylaminoacetate and hydrochloric acid gave (S)-1-(5,7-difluoro-1,2,3,4-tetrahydronaphthalen-2-yl)-2-thioxo-2,3-dihydro-1H-imidazol-4-ylmethylaminoacetic acid hydrochloride, m.p. 214° C. (eff.); and substituting tert-butyl 1-(1,2,3,4-tetrahydronaphthalen-2-yl)-2-thioxo-2,3-dihydro-1H-imidazol-4-ylmethylaminoacetate and hydrochloric acid gave 1-(1,2,3,4-tetrahydronaphthalen-2-yl)-2-thioxo-2,3-dihydro-1H-imidazol-4-ylmethylaminoacetic acid hydrochloride, m.p. 208°–211.

EXAMPLE 38

4-[3-(1,2,3,4-Tetrahydronaphthalen-2-yl)-2-thioxo-2,3-dihydro-1H-imidazol-1-yl]butyramide The following is the preparation of a compound of Formula I(a) in which n is 1, t is 0, $R^3$ is 4-(carbamoyl)propyl and $R^4$ and $R^5$ are each hydro.

A mixture 4-[3-(1,2,3,4-tetrahydronaphthalen-2-yl)-2-thioxo-2,3-dihydro-1H-imidazol-1-yl]butyric acid (100 mg, 0.32 mol), prepared as in Example 37, oxalyl chloride (2M, 0.32 mL, 0.64 mol) and 5 drops of DMF in 10 mL of methylene chloride was stirred for 2 hours. Solvents and excess oxalyl chloride were removed by evaporation and the residue was treated with 5 mL of 30% aqueous ammonium hydroxide and stirred for 16 hours. The mixture was poured into aqueous sodium bicarbonate and extracted with methylene chloride. The extract was dried ($Na_2SO_4$) and concentrated. The residue was purified by flash chromatography on silica gel eluting with methylene chloride/methanol (99:1 to 96:4) to give 4-[3-(1,2,3,4-tetrahydronaphthalen-2-yl)-2-thioxo-2,3-dihydro-1H-imidazol-1-yl]butyramide (70 mg, 0.22 nmol), as a foam.

Proceeding as in Example 38, but substituting different starting materials for 4-[3-(1,2,3,4-tetrahydronaphthalen-2-yl)-2-thioxo-2,3-dihydro-1H-imidazol-1-yl]butyric acid gave the following compounds of Formula I:

substituting 4-[3-(1,2,3,4-tetrahydronaphthalen-2-yl)-2-thioxo-2,3-dihydro-1H-imidazol-1-ylethyl]benzoic acid gave 4-[3-(1,2,3,4-tetrahydronaphthalen-2-yl)-2-thioxo-2,3-dihydro-1H-imidazol-1-ylethyl]benzamide, m.p. 158°–160° C.; and substituting 3-[3-(1,2,3,4-tetrahydronaphthalen-2-yl)-2-thioxo-2,3-dihydro-1H-imidazol-1-yl]propionic acid gave 3-[3-(1,2,3,4-tetrahydronaphthalen-2-yl)-2-thioxo-2,3-dihydro-1H-imidazol-1-yl]propionamide, m.p. 180°–181° C.

EXAMPLE 39

3-[2-(4(1H-Tetrazol-5-ylphenyl)ethyl]-1-(1,2,3,4-tetrahydronaphthalen-2-yl)-1,3-dihydroimidazole-2-thione The following is the preparation of a compound of Formula I(a) in which n is 1, t is 0, $R^1$ is 2-(4(1H)-tetrazol-5-ylphenyl)ethyl and $R^4$ and $R^5$ are hydro.

A mixture 3-[2-(4-cyanophenyl)ethyl]-1-(1,2,3,4-tetrahydronaphthalen-2-yl)-1,3-dihydroimidazole-2-thione (0.5 g, 1.4 mmol), prepared as in Example 15, and tributyltin azide (1.39 g, 4.2 mmol) in 3 mL of xylene was heated at 120° C. under nitrogen for approximately 16 hours. The mixture was purified by chromatography on silica gel eluting with methylene chloride/methanol and the purified product was recrystallized from ethyl acetate/methanol to give 3-[2-(4(1H)-tetrazol-5-ylphenyl)ethyl]-1-(1,2,3,4-tetrahydronaphthalen-2-yl)-1,3-dihydroimidazole-2-thione (0.5 g, 1.4 nmol), m.p. 218°–220° C.

EXAMPLE 40

(S)-4-(1-hydroxy)ethyl-1-(5,7-difluoro-1,2,3,4-tetrahydronaphthalen-2-yl)-1,3-dihydroimidazole-2-thione The following is the preparation of a compound of Formula I(a) in which n is 1, t is 0, $R^3$ and $R^5$ are each hydro and $R^4$ is 1-hydroxyethyl.

A mixture of (S)-3-(5,7-difluoro-1,2,3,4-tetrahydronaphthalen-2-yl)-2-thioxo-2,3-dihydro-1H-imidazole-5-carbaldehyde (178 mg, 0.6 mmol), prepared as in Example 22, and methylmagnesium chloride (3M, 0.4 mL, 1.2 mmol) was stirred at approximately 0° C. for 1 hour and at approximately 25° for an additional 1 hour. The mixture was treated with 5 mL of dilute sulfuric acid and extracted with ethyl acetate (2×). The combined extracts were dried (MgSO₄) and concentrated and the residue was purified by flash chromatography on silica gel eluting with methylene chloride/methanol (98:2). The purified residue was further purified by preparative thin layer chromatography on silica gel eluting with methylene chloride/methanol (95:5) to give (S)-4-(1-hydroxy)ethyl-1-(5,7-difluoro-1,2,3,4-tetrahydronaphthalen-2-yl)-1,3-dihydroimidazole-2-thione (22 mg, 0.1 mmol), m.p. 210°–211° C.

Proceeding as in Example 40, but substituting n-propylmagnesium chloride for methylmagnesium chloride gave (S)-4-(1-hydroxy)but-1-yl-1-(5,7-difluoro-1,2,3,4-tetrahydronaphthalen-2-yl)-1,3-dihydroimidazole-2-thione, m.p. 154°–156° C.

EXAMPLE 41

N-1H-Tetrazol-5-yl-3-(5,7-difluoro-1,2,3,4-tetrahydronaphthalen-2-yl)-2-thioxo-2,3-dihydro-1H-imidazole-4-carboxamide The following is the preparation of a compound of Formula I(a) in which n is 1, t is 2, $R^1$ is fluoro at the 5- and 7-position and $R^5$ is 1H-tetrazol-5-yl-carbamoyl.

3-(5,7-Difluoro-1,2,3,4-tetrahydronaphthalen-2-yl)-2-thioxo-2,3-dihydro-1H-imidazole-4-carboxylic acid (1 g, 3.33 mmol), prepared as in Example 37, was dissolved in 15 mL of oxalyl chloride and 1 drop of DMF and the solution was stirred under nitrogen for 3 hours. The excess oxalyl chloride was removed by rotary evaporation and the residue was co-evaporated with carbon tetrachloride (2×25 mL). The residue was cooled at 0° C. and dry 5-amino-1H-tetrazole (0.85 g, 10 mmol) and 25 mL of pyridine were added. The mixture was allowed to warm to room temperature and then stirred for 16 hours. The solvent was removed by evaporation and the residue was co-evaporated with toluene. Purification of the residue by column chromatography on silica gel packed in 5% methanol/methylene chloride containing 1% acetic acid gave 0.9 g of impure product. The impure product was dissolved in aqueous potassium carbonate and the solution was extracted with ethyl acetate. The aqueous layer was acidified giving a solid material. Isolation of the material by filtration gave N-1H-tetrazol-5-yl-3-(5,7-difluoro-1,2,3,4-tetrahydronaphthalen-2-yl)-2-thioxo-2,3-dihydro-1H-imidazole-4-carboxamide (0.54 g, 1.56 mmol) as a light orange solid, m.p. 228°–230° C.

EXAMPLE 42

(4- Methylpiperazin-1-yl)[3-(5,7-difluoro-1,2,3,4-tetrahydronaphthalen-2-yl)-2-thioxo-2,3-dihydro-1H-imidazol-4-yl]methanone The following is the preparation of a compound of Formula I(a) in which n is 1, t is 2, $R^1$ is fluoro at the 5- and 7-position and $R^5$ is 4-methylpiperazin-1-ylcarbonyl.

A mixture of 3-(5,7-difluoro-1,2,3,4-tetrahydronaphthalen-2-yl)-2-thioxo-1,3-dihydro-1H-imidazole-4-carboxylic acid, prepared as in Example 37, (0.75 g, 2.42 mmol) and 1,1'-carbonyldiimidazole (0.43 g, 2.65 mmol) in 6 mL of THF was stirred under argon at room temperature for approximately 18 hours. N-Methylpiperazine (0.29 mL, 2.65 mmol) was added and the mixture was stirred under argon at rote temperature for approximately 18 hours. The mixture was partitioned between methylene chloride and water. The methylene chloride layer was washed 4 times with water, dried over magnesium sulfate and concentrated by evaporation. Recrystallization of the residue from ethyl acetate/methanol gave (4-methylpiperazin-1-yl)[3-(5,7-difluoro-1,2,3,4-tetrahydronaphthalen-2-yl)-2-thioxo-2,3-dihydro-1H-imidazol-4-yl]methanone (0.69 g, 1.76 mmol), 248°–250° C.

Proceeding as in Example 42, but substituting a different starting material for 3-(5,7-difluoro-1,2,3,4-tetrahydronaphthalen-2-yl)-2-thioxo-1,3-dihydro-1H-imidazole-4-carboxylic acid and/or N-methylpiperazine gave the following compounds of Formula I:

substituting 3-(6,8-difluoro-1,2,3,4-tetrahydronaphthalen-2-yl)-2-thioxo-1,3-dihydro-1H-imidazole-4-carboxylic acid gave (4-methylpiperazin-1-yl)[3-(6,8-difluoro-1,2,3,4-tetrahydronaphthalen-2-yl)-2-thioxo-2,3-dihydro-1H-imidazol-4-yl]methanone as an oil;

substituting 3-(5,7-difluoro-1,2,3,4-tetrahydronaphthalen-2-yl)-2-thioxo-1,3-dihydro-1H-imidazole-4-carboxylic acid and N,N-dimethylethylenediamine gave N-(2-dimethylaminoethyl)-3-(5,7-difluoro-1,2,3,4-tetrahydronaphthalen-2-yl)-2-thioxo-2,3-dihydro-1H-imidazole-4-carboxamide, m.p. 125° C.;

substituting 3-(5,7-difluoro-1,2,3,4-tetrahydronaphthalen-2-yl)-2-thioxo-1,3-dihydro-1H-imidazole-4-carboxylic acid and p-methylsulfonylaminoaniline gave N-[4-(methylsulfonylamino)phenyl]-3-(5,7-difluoro-1,2,3,4-tetrahydronaphthalen-2-yl)-2-thioxo-2,3-dihydro-1H-imidazole-4-carboxamide, m.p. 225°–230° C.;

substituting 3-(5,7-difluoro-1,2,3,4-tetrahydronaphthalen-2-yl)-2-thioxo-1,3-dihydro-1H-imidazole-4-carboxylic acid and dimethylaminoethanethiol hydrochloride in the presence of dichlorohexylcarbodiimide gave 3-(5,7-difluoro-1,2,3,4-tetrahydronaphthalen-2-yl)-2-thioxo-2,3-dihydro-1H-imidazole-4-carbothioic acid S-(2-dimethylaminoethyl) ester, m.p. 204°–206° C.; and substituting 3-(6,8-difluoro-1,2,3,4-tetrahydronaphthalen-2-yl)-2-thioxo-1,3-dihydro-1H-imidazole-4-carboxylic acid and dimethylaminoethanethiol hydrochloride in the presence of dichlorohexylcarbodiimide gave 3-(6,8-difluoro-1,2,3,4-tetrahydronaphthalen-2-yl)-2-thioxo-2,3-dihydro-1H-imidazole-4-carbothioic acid S-(2-dimethylaminoethyl)ester, m.p. 275°–277° C.

EXAMPLE 43

3-(3,4-Dihydroxybenzyl)-1-(1,2,3,4-tetrahydronaphthalen-2-yl)-1,3-dihydroimidazole-2-thione The following is the preparation of a compound of Formula I(a) in which n is 1, t is 0, $R^3$ is 3,4-dihydroxybenzyl and $R^4$ and $R^5$ are each hydro.

A solution of 3-(3,4-dimethoxybenzyl)-1-(1,2,3,4-tetrahydronaphthalen-2-yl)-1,3-dihydroimidazole-2-thione (900 mg, 2.37 mol), prepared as in Example 15, in methylene chloride was cooled to 0° C. under nitrogen and then boron tribromide (1M, 7.1 mL, 7.1 mmol) in an additional 10 mL of methylene chloride was added dropwise. The mixture was allowed to cool to room temperature, stirred for 16 hours and then slowly added to water. The organic layer was separated, washed with brine, dried ($Na_2SO_4$) and concentrated. The residue was purified by flash chromatography on silica gel eluting with methylene chloride/methanol (96:4) and then crystallized from methanol/ethanol/hexane to give 3-(3,4-dihydroxybenzyl)-1-(1,2,3,4-tetrahydronaphthalen-2-yl)-1,3-dihydroimidazole-2-thione (520 mg), m.p. 173°–174° C.

Proceeding as in Example 43, but substituting different starting materials for 3-(3,4-dimethoxybenzyl)-1-(1,2,3,4-tetrahydronaphthalen-2-yl)-1,3-dihydroimidazole-2-thione gave the following compounds of Formula I:

substituting 3-[2-(3,4-dimethoxyphenyl)ethyl]-1-(1,2,3,4-tetrahydronaphthalen-2-yl)-1,3-dihydroimidazole-2-thione gave 3-[2-(3,4-dihydroxyphenyl)ethyl]-1-(1,2,3,4-tetrahydronaphthalen-2-yl)-1,3-dihydroimidazole-2-thione, m.p. 165°–167° C.;

substituting 1-(5-methoxyindan-1-yl)-1,3-dihydroimidazole-2-thione gave 1-(5-hydroxyindan-1-yl)-1,3-dihydroimidazole-2-thione, m.p. 208°–209° C.;

substituting 1-(1,2,3,4-tetrahydro-6-methoxynaphthalen-1-yl)-1,3-dihydroimidazole-2-thione gave 1-(1,2,3,4-tetrahydro-6-hydroxynaphthalen-1-yl)-1,3-dihydroimidazole-2-thione, m.p. 213°–215° C.;

substituting 1-(1,2,3,4-tetrahydro-5-methoxynaphthalen-1-yl)-1,3-dihydroimidazole-2-thione gave 1-(1,2,3,4-tetrahydro-5-hydroxynaphthalen-1-yl)-1,3-dihydroimidazole-2-thione, m.p. 188°–190° C.;

substituting 1-(1,2,3,4-tetrahydro-7-methoxynaphthalen-1-yl)-1,3-dihydroimidazole-2-thione gave 1-(1,2,3,4-tetrahydro-7-hydroxynaphthalen-1-yl)-1,3-dihydroimidazole-2-thione, m.p. 195°–196° C.;

substituting 1-(1,2,3,4-tetrahydro-5-methoxynaphthalen-2-yl)-1,3-dihydroimidazole-2-thione gave 1-(1,2,3,4-tetrahydro-5-hydroxynaphthalen-2-yl)-1,3-dihydroimidazole-2-thione, m.p. 263°–265° C.;

substituting 1-(1,2,3,4-tetrahydro-6-methoxynaphthalen-2-yl)-1,3-dihydroimidazole-2-thione gave 1-(1,2,3,4-tetrahydro-6-hydroxynaphthalen-2-yl)-1,3-dihydroimidazole-2-thione, m.p. 240°–241° C.;

substituting 1-(1,2,3,4-tetrahydro-7-methoxynaphthalen-2-yl)-1,3-dihydroimidazole-2-thione gave 1-(1,2,3,4-tetrahydro-7-hydroxynaphthalen-2-yl)-1,3-dihydroimidazole-2-thione, m.p. 248°–250° C.;

substituting 1-(1,2,3,4-tetrahydro-8-methoxynaphthalen-2-yl)-1,3-dihydroimidazole-2-thione gave 1-(1,2,3,4-tetrahydro-8-hydroxynaphthalen-2-yl)-1,3-dihydroimidazole-2-thione, m.p. 274°–276° C.; and substituting 1-(6,8-difluoro-1,2,3,4-tetrahydro-7-methoxynaphthalen-2-yl)-1,3-dihydroimidazole-2-thione gave 1-(6,8-difluoro-1,2,3,4-tetrahydro-7-hydroxynaphthalen-2-yl)-1,3-dihydroimidazole-2-thione, m.p. 258°–260° C.

EXAMPLE 44

(S)-N-[3-(5,7-Difluoro-1,2,3,4-tetrahydronaphthalen-2-yl)-2-thioxo-2,3-dihydro-1H-imidazol-4-ylmethyl]-4-butylbenzamide The following is the preparation of a compound of Formula I(a) in which n is 1, t is 2, $R^1$ is fluoro at the 5- and 7-position and $R^5$ is 4-butylbenzoylaminomethyl.

A mixture of (S)-5-aminomethyl-1-(5,7-difluoro-1,2,3,4-tetrahydronaphthalen-2-yl)-1,3-dihydroimidazole-2-thione (0.30 g, 1 mmol), prepared as in Example 31, and 4-butylbenzoyl chloride (0.21 mL, 1.1 mmol) in 10 mL of dry pyridine was stirred under argon at approximately 0° C. for 1 hour and then at approximately 25° C. for an additional 2 hours. The mixture was concentrated and the residue was treated with water. The mixture was extracted with ethyl acetate (3×) and the combined extracts were dried ($MgSO_4$) and concentrated. The residue was recrystallized from ethyl acetate to give (S)-N-[3-(5,7-difluoro-1,2,3,4-tetrahydronaphthalen-2-yl)-2-thioxo-2,3-dihydro-1H-imidazol-4-ylmethyl]-4-butylbenzamide (0.25 g, 0.55 mmol), m.p. 242°–243° C.

Proceeding as in Example 44, but substituting different starting materials for (S)-5-aminomethyl-1-(5,7-difluoro-1,2,3,4-tetrahydronaphthalen-2-yl)-1,3-dihydroimidazole-2-thione and/or 4-butylbenzoyl chloride gave the following compounds of Formula I:

substituting nicotinoyl chloride hydrochloride gave (S)-N-[3-(5,7-difluoro-1,2,3,4-tetrahydronaphthalen-2-yl)-2-thioxo-2,3-dihydro-1H-imidazol-4-ylmethyl]-nicotinamide, m.p. 218°–221° C.;

substituting benzoyl chloride gave (S)-N-[3-(5,7-difluoro-1,2,3,4-tetrahydronaphthalen-2-yl)-2-thioxo-2,3-dihydro-1H-imidazol-4-ylmethyl]benzamide, m.p. 260°–261° C.;

substituting dimethylcarbamyl chloride gave (S)-N-[3-(5,7-difluoro-1,2,3,4-tetrahydronaphthalen-2-yl)-2-thioxo-2,3-dihydro-1H-imidazol-4-ylmethyl]dimethylcarbamide, m.p. 218°–220° C.;

substituting methyl chloroformate gave methyl(S)-3-(5,7-difluoro-1,2,3,4-tetrahydronaphthalen-2-yl)-2-thioxo-2,3-dihydro-1H-imidazol-4-ylmethylcarbamate, m.p. 220°–222° C.;

substituting (S)-3-amino-1-(1,2,3,4-tetrahydronaphthalen-2-yl)-1,3-dihydroimidazole-2-thione and acetic anhydride gave N-[3-(1,2,3,4-tetrahydronaphthalen-2-yl)-2-thioxo-2,3-dihydro-1H-imidazol-4-yl]acetamide, m.p. 196°–200° C.;

substituting 2-furancarboxylic acid chloride gave (S)-N-[3-(5,7-difluoro-1,2,3,4-tetrahydronaphthalen-2-yl)-2- thioxo-2,3-dihydro-1H-imidazol-4-ylmethyl]-2-furancarboxamide, m.p. 227°–231° C.; and substituting 4-amino-2-(1,2,3,4-tetrahydronaphthalen-2-yl)-2,4-dihydro[1,2,4]triazole-3-thione and acetic anhydride gave N-[1-(1,2,3,4-tetrahydronaphthalen-2-yl)-5-thioxo-4,5-dihydro-1H-[1,2,4]triazol-4-yl]acetamide, m.p. 199°–201° C.

EXAMPLE 45

(S)-N-[3-(5,7-Difluoro-1,2,3,4-tetrahydronaphthalen-2-yl)-2-thioxo-2,3-dihydro-1H-imidazol-4-ylmethyl]picolinamide The following is the preparation of a compound of Formula I(a) in which n is 1, t is 2, $R^1$ is fluoro at the 5- and 7-position and $R^5$ is picolinoylaminomethyl.

A mixture of (S)-5-aminomethyl-1-(5,7-difluoro-1,2,3,4-tetrahydronaphthalen-2-yl)-1,3-dihydroimidazole-2-thione (295 mg, 1 mmol), prepared as in Example 31, picolinic acid (123 mg, 1 mmol) and PyBOP (620 mg, 1.2 mmol) in 10 mL of dry DMF was stirred under argon at approximately 25° C. for 5 minutes and then N,N-diisopropylethylamine (0.58 mL, 3.3 mmol) was added. The mixture was stirred for approximately 12 hours and then 10 mL of water was added. The aqueous layer was extracted with ethyl acetate (3×10 mL) and the combined extracts were washed with water, dried (MgSO$_4$) and concentrated. The residue was purified by flash chromatography on silica gel eluting with hexane/THF (1:1 to 8:2) to give (S)-N-[3-(5,7-difluoro-1,2,3,4-tetrahydronaphthalen-2-yl)-2-thioxo-2,3-dihydro-1H-imidazol-4-ylmethyl]picolinamide (80 mg, 0.2 mmol), m.p. 216°–217° C.

Proceeding as in Example 45, but substituting a different starting material for picolinic acid gave the following compounds of Formula I:

substituting N-(tert-butoxycarbonyl)glycine and deprotecting gave (S)-N-[3-(5,7-difluoro-1,2,3,4-tetrahydronaphthalen-2-yl)-2-thioxo-2,3-dihydro-1H-imidazol-4-ylmethyl]aminoacetamide, m.p. 144°–153° C.;
substituting N-(tert-butoxycarbonyl)-2-methylalanine and deprotecting gave (S)-N-[3-(5,7-difluoro-1,2,3,4-tetrahydronaphthalen-2-yl)-2-thioxo-2,3-dihydro-1H-imidazol-4-ylmethyl]-2-amino-2-methylpropionamide trifluoroacetate, m.p. 158° C.; and substituting 5-butylpicolinic acid gave (S)-N-[3-(5,7-difluoro-1,2,3,4-tetrahydronaphthalen-2-yl)-2-thioxo-2,3-dihydro-1H-imidazol-4-ylmethyl]-5-butylpicolinamide, m.p. 99°–104° C.

EXAMPLE 46

(S)-N-[3-(5,7-Difluoro-1,2,3,4-tetrahydronaphthalen-2-yl)-2-thioxo-2,3-dihydro-1H-imidazol-1-4-ylmethyl]ethylcarbamide The following is the preparation of a compound of Formula I(a) in which n is 1, t is 2, $R^1$ is fluoro at the 5- and 7-position and $R^5$ is ethyluriedomethyl.

A mixture of (S)-5-aminomethyl-1-(5,7-difluoro-1,2,3,4-tetrahydronaphthalen-2-yl)-1,3-dihydroimidazole-2-thione (294 mg, 1 mmol), prepared as in Example 31, and ethyl isocyanate (0.16 mL, 2 mmol) in 10 mL of THF was stirred at approximately 50° C. under argon for approximately 60 hours. The mixture was filtered and the filtered solid was recrystallized from ethyl acetate/methanol to give (S)-N-[3-(5,7-difluoro-1,2,3,4-tetrahydronaphthalen-2-yl)-2-thioxo-2,3-dihydro-1H-imidazol-4-ylmethyl]ethylcarbamide (110 mg, 0.3 mmol), m.p. 219°–220° C.

EXAMPLE 47

4-Aminoethyl-1-(1,2,3,4-tetrahydronaphthalen-2-yl)-1,3-dihydroimidazole-2-thione The following is the preparation of a compound of Formula I(a) in which n is 1, t is 0, $R^3$ and $R^5$ are each hydro and $R^4$ is aminomethyl.

A mixture of 3-(1,2,3,4-tetrahydronaphthalen-2-yl)-2-thioxo-2,3-dihydro-1H-imidazole-4-carbaldehyde (0.25 g, 1.0 mmol), hydroxylamine hydrochloride (0.09 g, 1.3 mmol) and sodium hydroxide (0.064 g, 1.6 mmol) in 2 mL of ethanol and 2 mL of water was stirred at 60° C. for 1 hour. The mixture was cooled giving a crystalline material. The material was isolated by filtration and dried. The filtrate was stirred with ethyl acetate giving more crystalline material. The material was isolated by filtration and dried. Combining the crystalline material gave 1-(1,2,3,4-tetrahydronaphthalen-2-yl)-2-thioxo-2,3-dihydro-1H-imidazole-5-carbaldehyde oxime (0.186 g, 0.68 mmol).

A suspension of 3-(1,2,3,4-tetrahydronaphthalen-2-yl)-2-thioxo-2,3-dihydro-1H-imidazole-5-carbaldehyde oxime (0.158 g, 0.58 mmol), prepared as in Example 22, in 20 mL of THF was cooled to 0° C. and LAH (1.0M, 1.16 mL, 1.16 mmol) in THF was added slowly. The mixture was stirred at 0° C. for 1 hour and then saturated ammonium chloride, water and ethyl acetate were added. The aqueous layer was separated and extracted with ethyl acetate. The combined ethyl acetate was dried over magnesium sulfate and concentrated by evaporation. Purification of the residue by flash chromatography (elution: 3–10% methanol/methylene chloride) gave 4-aminomethyl-1-(1,2,3,4-tetrahydronaphthalen-2-yl)-1,3-dihydroimidazole-2-thione, m.p. 197°–200° C.

EXAMPLE 48

(S)-1-(5,7-difluoro-1,2,3,4-tetrahydronaphthalen-2-yl)-4-(2-phenylethyl)aminomethyl-1,3-dihydroimidazole-2-thione The following is the preparation of a compound of Formula I(a) in which n is 1, t is 2, $R^1$ is fluoro at the 5- and 7-position and $R^4$ is 2-(phenyl)ethylaminomethyl.

A mixture of (S)-3-(5,7-difluoro-1,2,3,4-tetrahydronaphthalen-2-yl)-2-thioxo-2,3-dihydro-1H-imidazole-5-carbaldehyde (147 mg, 0.5 mmol), prepared as in Example 22, phenethylamine (75 μL, 0.6 mmol) and sodium cyanoborohydride (47 mg, 0.75 mmol) in 10 mL of methanol was stirred at approximately 60° C. for 2 hours. The mixture was concentrated and the residue was purified by flash chromatography on silica gel eluting with methylene chloride/methanol (97:3). The purified product was concentrated, converted to the hydrochloride salt and recrystallized from ethyl acetate/methanol to give (S)-1-(5,7-difluoro-1,2,3,4-tetrahydronaphthalen-2-yl)-4-(2-phenylethyl)aminomethyl-1,3-dihydroimidazole-2-thione hydrochloride (68 mg, 0.2 mmol), m.p. 227°–229° C.

Proceeding as in Example 48, but substituting a different starting material for (S)-3-(5,7-difluoro-1,2,3,4-tetrahydronaphthalen-2-yl)-2-thioxo-2,3-dihydro-1H-imidazole-5-carbaldehyde and/or phenethylamine gave the following compounds of Formula I:

substituting 3-(5,7-difluoro-1,2,3,4-tetrahydronaphthalen-2-yl)-2-thioxo-2,3-dihydro-1H-imidazole-5-carbaldehyde and glycine tert-butyl ester hydrochloride gave tert-butyl 3-(5,7-difluoro-1,2,3,4-tetrahydronaphthalen-2-yl)-2-thioxo-2,3-dihydro-1H-imidazol-5-ylmethylaminoacetate;

substituting (S)-3-(5,7-difluoro-1,2,3,4-tetrahydronaphthalen-2-yl)-2-thioxo-2,3-dihydro-1H-imidazole-5-carbaldehyde and glycine tert-butyl ester hydrochloride gave tert-butyl(S)-3-(5,7-difluoro-1,2,3,4-tetrahydronaphthalen-2-yl)-2-thioxo-2,3-dihydro-1H-imidazol-5-ylmethylaminoacetate;

substituting 3-(1,2,3,4-tetrahydronaphthalen-2-yl)-2-thioxo-2,3-dihydro-1H-imidazole-5-carbaldehyde and glycine tert-butyl ester hydrochloride gave tert-butyl 3-(1,2,3,4-tetrahydronaphthalen-2-yl)-2-thioxo-2,3-dihydro-1H-imidazol-5-ylmethylaminoacetate;

substituting glycinamide hydrochloride gave (S)-3-(5,7-difluoro-1,2,3,4-tetrahydronaphthalen-2-yl)-2-thioxo-2,3-dihydro-1H-imidazol-5-yl-methylaminoacetamide, m.p. 212°–213° C.; and substituting methyl 4-(2-aminoethyl)benzoate hydrochloride gave methyl(S)-4-{2-[3-(5,7-difluoro-1,2,3,4-tetrahydronaphthalen-2-yl)-2-thioxo-2,3-dihydro-1H-imidazol-5-yl-methylamino]ethyl}benzoate, m.p. 159°–160° C.

EXAMPLE 49

(S)-N$^3$-[3-(5,7-Difluoro-1,2,3,4-tetrahydronaphthalen-2-yl)-2-thioxo-2,3-dihydro-1H-imidazol-4-ylmethyl]-N$^1$,N$^2$-di(tert-butoxycarbonyl)formamidine The following is the preparation of a compound of Formula I(a) in which n is 1, t is 2, R$^1$ is fluoro at the 5- and 7-position and R$^5$ is N$^1$,N$^2$-di(tert-butoxycarbonyl)amidinoaminomethyl.

A mixture of (S)-1-(5,7-difluoro-1,2,3,4-tetrahydronaphthalen-2-yl)-5-aminomethyl-1,3-dihydroimidazole-2-thione (0.6 g, 2 mmol), prepared as in Example 31, and N$^1$,N$^2$-di(tert-butoxycarbonyl)methylthioamidine (0.65 g, 2.2 mmol) in 15 mL of THF and 0.3 mL of water was stirred at approximately 50° C. under argon for 4 hours. The mixture was concentrated and the residue was combined with 5% aqueous sodium bicarbonate. The mixture was extracted with ethyl acetate and the extract was dried (MgSO$_4$) and concentrated. The residue was purified by flash chromatography on silica gel eluting with methylene chloride/methanol (99:1) to give (S)-N$^3$-[3-(5,7-difluoro-1,2,3,4-tetrahydronaphthalen-2-yl)-2-thioxo-2,3-dihydro-1H-imidazol-4-ylmethyl]-N$^1$,N$^2$-di(tert-butoxycarbonyl)formamidine (0.54 g, 1 mmol), m.p. 155° C. (eff.).

Proceeding as in Example 49, but subsituting a different starting material for N$^1$,N$^2$-di(tert-butoxycarbonyl)methylthioamidine gave the following compounds of Formula I:

substituting N$^1$,N$^2$-di(acetyl)methylthioamidine gave (S)-N$^3$-[3-(5,7-difluoro-1,2,3,4-tetrahydronaphthalen-2-yl)-2-thioxo-2,3-dihydro-1H-imidazol-4-ylmethyl]N$^1$,N$^2$-di(acetyl)formamidine, m.p. 213°–214° C.; and substituting N$^1$-(tert-butoxycarbonyl)methylthioamidine gave (S)-N$^3$-[3-(5,7-difluoro-1,2,3,4-tetrahydronaphthalen-2-yl)-2-thioxo-2,3-dihydro-1H-imidazol-4-yl-methyl]-N$^1$-(tert-butoxycarbonyl)formamidine, m.p.>280° C.

EXAMPLE 50

(S)-N$^3$-[3-(5,7-Difluoro-1,2,3,4-tetrahydronaphthalen-2-yl)-2-thioxo-2,3-dihydro-1H-imidazol-4-ylmethyl]formamidine The following is the preparation of a compound of Formula I(a) in which n is 1, t is 2, R$^1$ is fluoro at the 5- and 7-position and R$^5$ is amidinoaminomethyl.

A solution of (S)-N$^3$-[3-(5,7-difluoro-1,2,3,4-tetrahydronaphthalen-2-yl)-2-thioxo-2,3-dihydro-1H-imidazol-4-ylmethyl]-N$^1$,N$^2$-di(tert-butoxycarbonyl)formamidine (0.34 g, 0.6 mmol), prepared as in Example 50, in 20 mL of trifluoroacetic acid was stirred at approximately 25° C. for 1.5 hours. The solution was concentrated and the residue was combined with 100 mL of diethyl ether. The diethyl ether was decanted away and the residue was combined with 100 mL of diethyl ether. The mixture was filtered and the filtered residue was dissolved in ethyl acetate. The solution was concentrated, evacuated and the resulting foam was treated with diethyl ether. The mixture was filtered to give (S)-N$^3$-[3-(5,7-difluoro-1,2,3,4-tetrahydronaphthalen-2-yl)-2-thioxo-2,3-dihydro-1H-imidazol-4-ylmethyl]formamidine trifluoroacetate (0.28 g, 0.6 mmol), m.p. 103° (eff).

EXAMPLE 51

2S-Amino-3-(3H-imidazol-4-yl)-N-[3-(5,7-difluoro-1,2,3,4-tetrahydronaphthalen-2R-yl)-2-thioxo-2,3-dihydro-1H-imidazol-4-ylmethyl]propionamide hydrochloride The following is the preparation of a compound of Formula II in which n is 1, t is 2, R$^1$ is fluoro at the 5- and 7-position and R$^{18}$ is a group of Formula (d) wherein R$^{21}$ is L-histidylaminomethyl.

A mixture of (R)-5-aminomethyl-1-(5,7-difluoro-1,2,3,4-tetrahydronaphthalen-2-yl)-1,3-dihydroimidazole-2-thione (0.55 g, 1.86 mmol), prepared as in Example 31, (S)-2-(tert-butoxycarbonyl)amino-3-(3-tert-butoxycarbonyl-3H-imidazol-4-yl)propionic acid (0.76 g, 1.86 mol) and PyBOP (1.07 g, 2.05 mmol) in 6.2 mL of DMF was stirred under argon until homogeneous. Diethylisopropylethylamine (1.07 mL, 6.15 mmol) was added and the mixture was stirred for approximately 18 hours. The mixture partitioned between water and ethyl acetate and the organic layer was washed twice with water, dried over magnesium sulfate and concentrated by evaporation. Purification of the residue by column chromatography (elution: 5% methanol/methylene chloride) gave 2S-(tert-butoxy-carbonyl)amino-3-(3-tert-butoxycarbonyl-3H-imidazol-4-yl)-N-[3-(5,7-difluoro-1,2,3,4-tetrahydronaphthalen-2R-yl)-2-thioxo-2,3-dihydro-1H-imidazol-4-yl-methyl]propionamide (1.003 g) as a foam.

2S-(tert-Butoxycarbonyl)amino-3-(3-tert-butoxycarbonyl-3H-imidazol-4-yl)-N-[3-(5,7-difluoro-1,2,3,4-tetrahydronaphthalen-2R-yl)-2-thioxo-2,3-dihydro-1H-imidazol-4-ylmethyl]propionamide (0.935 g) was dissolved in 45 mL of 30% anhydrous hydrogen chloride/ethyl acetate and the mixture was stirred for 18 hours giving a crystalline material. Isolation of the material by filtration and drying at 60° C. under vacuum gave 2S-amino-3-(3H-imidazol-4-yl)-N-[3-(5,7-difluoro-1,2,3,4-tetrahydronaphthalen-2R-yl)-2-thioxo-2,3-dihydro-1H-imidazol-4-ylmethyl]propionamide hydrochloride (0.655 g, 1.24 mmol), m.p. 228° C.

Proceeding as in Example 51, but substituting a starting material for (R)-5-aminomethyl-1-(5,7-difluoro-1,2,3,4-tetrahydronaphthalen-2-yl)-1,3-dihydroimidazole-2-thione and/or (S)-2-(tert-butoxycarbonyl)amino-3-(3-tert-butoxycarbonyl-3H-imidazol-4-yl)propionic acid gave the following compounds of Formula II:

substituting 5-aminomethyl-1-(5,7-difluoro-1,2,3,4-tetrahydronaphthalen-2-yl)-1,3-dihydroimidazole-2-thione and (S)-3-tert-butoxycarbonyl-2-tert-butoxycarbonylaminopropionic acid gave 3S-amino-N-

[3-(5,7-difluoro-1,2,3, 4-tetrahydronaphthalen-2-yl)-2-thioxo-2,3-dihydro-1H-imidazol-4-ylmethyl]succinamic acid hydrochloride, m.p. 220° C.;

substituting 5-aminomethyl-1-(5,7-difluoro-1,2,3,4-tetrahydronaphthalen-2-yl)-1,3-dihydroimidazole-2-thione and (S)-3-(tert-butoxycarbonyl)-3-(tert-butoxycarbonylamino)propionic acid gave 2S-amino-N-[3-(5,7-difluoro-1,2,3,4-tetrahydronaphthalen-2-yl)-2-thioxo-2,3-dihydro-1H-imidazol-4-ylmethyl]succinamic acid hydrochloride, m.p. 220° C.;

substituting 5-aminomethyl-1-(5,7-difluoro-1,2,3,4-tetrahydronaphthalen-2-yl)1,3-dihydroimidazole-2-thione and (S)-2,5-di(tert-butoxycarbonylamino)valeric acid gave 2S,5-diamino-N-[3-(5,7-difluoro-1,2,3,4-tetrahydronaphthalen-2-yl)-2-thioxo-2,3-dihydro-1H-imidazol-4-ylmethyl]valeramide hydrochloride, m.p. 212°–216° C.;

substituting 5-aminomethyl-1-(1,2,3,4-tetrahydronaphthalen-2-yl)-1,3-dihydroimidazole-2-thione and (S)-2,5-di(tert-butoxycarbonylamino)valeric acid gave 2S,5-diamino-N-[3-(1,2,3,4-tetrahydronaphthalen-2-yl)-2-thioxo-2,3-dihydro-1H-imidazol-4-ylmethyl]valeramide hydrochloride, m.p. 191°–205° C.;

substituting 5-aminomethyl-1-(1,2,3,4-tetrahydronaphthalen-2-yl)-1,3-dihydroimidazole-2-thione and (S)-2-(tert-butoxycarbonylamino)-5-(tert-butoxycarbonyl)guanidinovaleric acid gave 2S-amino-N-[3-(1,2,3,4-tetrahydronaphthalen-2-yl)-2-thioxo-2,3-dihydro-1H-imidazol-4-ylmethyl]-5-guanidinovaleramide hydrochloride, m.p. 160° C.;

substituting 3-amino-1-(1,2,3,4-tetrahydronaphthalen-2-yl)-1,3-dihydroimidazole-2-thione and (S)-2-(tert-butoxycarbonyl)amino -3-(3-tert-butoxycarbonyl-3H-imidazol-4-yl)propionic acid gave 2S-amino-3-(3H-imidazol-4-yl)-N-[3-(1,2,3,4-tetrahydronaphthalen-2-yl)-2-thioxo-2,3-dihydro-1H-imidazol-1-yl]propionamide hydrochloride, m.p. 197°–205° C.;

substituting 5-aminomethyl-1-(5,7-difluoro-1,2,3,4-tetrahydronaphthalen-2-yl)-1,3-dihydroimidazole-2-thione and (S)-2-(tert-butoxycarbonyl)amino-3-(3-tert-butoxycarbonyl-3H-imidozol-4-yl) propionic acid gave 2S-amino-3-(3H-imidazol-4-yl)-N-[3-(5,7-difluoro-1,2,3,4-tetrahydronaphthalen-2-yl)-2-thioxo-2,3-dihydro-1H-imidazol-4-ylmethyl]propionamide hydrochloride, m.p. 195°–238° C.;

substituting (S)-5-aminomethyl-1-(5,7-difluoro-1,2,3,4-tetrahydronaphthalen-2-yl)-1,3-dihydroimidazole-2-thione and (S)-2-tert-butoxycarbonylamino-3-(3-tert-butoxycarbonyl-3H-imidazol-4-yl)propionic acid gave 2S-amino-3-(3H-imidazol-4-yl)-N-[3-(5,7-difluoro-1,2,3,4-tetrahydronaphthalen-2S-yl)-2-thioxo-2,3-dihydro-1H-imidazol-4-ylmethyl]propionamide hydrochloride, m.p. 225° C.;

substituting (S)-5-aminomethyl-1-(5,7-difluoro-1,2,3,4-tetrahydronaphthalen-2-yl)-1,3-dihydroimidazole-2-thione and (S)-4-acetylamino-4-tert-butoxycarbonylbutyric acid gave 2S-acetylamino-4-[3-(5,7-difluoro-1,2,3,4-tetrahydronaphthalen-2S-yl)-2-thioxo-2,3-dihydro-1H-imidazol-4-ylmethylaminocarbonyl]butyric acid, m.p. 159° C.;

substituting (S)-5-aminomethyl-1-(5,7-difluoro-1,2,3,4-tetrahydronaphthalen-2-yl)-1,3-dihydroimidazole-2-thione and (S)-2,5-di(tert-butoxycarbonylamino) pentanoic acid gave 2S,5-diamino-N-[3-(5,7-difluoro-1, 2,3,4-tetrahydronaphthalen-2S-yl)-2-thioxo-2,3-dihydro-1H-imidazol-4-ylmethyl]valeramide hydrochloride, m.p. 233°–237° C.;

substituting (R)-5-aminomethyl-1-(5,7-difluoro-1,2,3,4-tetrahydronaphthalen-2-yl)-1,3-dihydroimidazole-2-thione and (S)-2,5-di(tert-butoxycarbonylamino) pentanoic acid gave 2S,5-diamino-N-[3-(5,7-difluoro-1, 2,3,4-tetrahydronaphthalen-2R-yl)-2-thioxo-2,3-dihydro-1H-imidazol-4-ylmethyl]valeramide hydrochloride, m.p. 128°–150° C.;

substituting (S)-5-aminomethyl-1-(5,7-difluoro-1,2,3,4-tetrahydronaphthalen-2-yl)-1,3-dihydroimidazole-2-thione and (S)-3-(tert-butoxycarbonyl)-2-(tert-butoxycarbonylamino)propionic acid gave 3S-amino-N-[3-(5,7-difluoro-1,2,3,4-tetrahydronaphthalen-2S-yl)-2-thioxo-2,3-dihydro-1H-imidazol-4-ylmethyl]succinamic acid hydrochloride, m.p. 194° C.;

substituting (R)-5-aminomethyl-1-(5,7-difluoro-1,2,3,4-tetrahydronaphthalen-2-yl)-1,3-dihydroimidazole-2-thione and (S)-3-(tert-butoxycarbonyl)-2-(tert-butoxycarbonylamino)propionic acid gave 3S-amino-N-[3-(5,7-difluoro-1,2,3,4-tetrahydronaphthalen-2R-yl)-2-thioxo-2,3-dihydro-1H-imidazol-4-ylmethyl]succinamic acid hydrochloride, m.p. 193° C.;

substituting 4-amino-2-(5,7-difluoro-1,2,3,4-tetrahydronaphth-2-yl)-2,4-dihydro[1,2,4]triazole-3-thione and (S)-2,5-di(tert-butoxycarbonylamino)valeric acid gave 2S,5-diamino-N-[1-(5,7-difluoro-1,2,3,4-tetrahydronaphthalen-2-yl)-5-thioxo-4,5-dihydro-1H-[1, 2,4]triazol-4-yl]valeramide hydrochloride;

substituting 4-amino-2-(5,7-difluoro-1,2,3,4-tetrahydronaphthalen-2-yl)-2,4-dihydro[1,2,4]triazole-3-thione and (S)-2-(tert-butoxycarbonyl)amino-3-(3-tert-butoxycarbonyl-]H-imidazol-4-yl)propionic acid gave 2S-amino-3-(3H-imidazol-4-yl)-N-[1-(5,7-difluoro-1,2,3, 4-tetrahydronaphthalen-2-yl)-5-thioxo-4,5-dihydro-1H-[1,2,4]triazol-4-yl]propionamide hydrochloride, m.p. 221°–224° C.;

substituting (S)-5-methylaminomethyl-1-(5,7-difluoro-1,2, 3,4-tetrahydronaphthalen-2-yl)-1,3-dihydroimidazole-2-thione and (S)-3-(tert-butoxycarbonyl)-2-(tert-butoxycarbonylamino)propionic acid gave 3S-amino-N-[3-(5,7-difluoro-1,2,3,4-tetrahydronaphthalen-2S-yl)-2-thioxo-2,3-dihydro-1H-imidazol-4-ylmethyl]-N-methylsuccinamic acid hydrochloride; and substituting 4-amino-2-(5,7-difluoro-1,2,3,4-tetrahydronaphthalen-2-yl)-2,4-dihydro[1,2,4]triazole-3-thione and (S)-3-(tert-butoxycarbonyl)-3-(tert-butoxycarbonylamino)propionic acid gave 2S-amino-N-[1-(5,7-difluoro-1,2,3,4-tetrahydronaphthalen-2-yl)-5-thioxo-4,5-dihydro-1H-[1,2,4]triazol-4-yl]succinamic acid hydrochloride, m.p. 193°–196° C.

EXAMPLE 52

2R-Amino-3-[1-(4,6-difluoroindan-1-yl)-1-H-imidazol-2-yldisulfanyl]propionic Acid Hydrochloride The following is the preparation of a compound of Formula III in which n is 0, t is 2, $R^1$ is fluoro at the 5- and 7-position and $R^{27}$ is a group of Formula (g) wherein $R^4$ and $R^5$ are each hydro and $R^{28}$ is 2-amino-2-carboxyethyl.

A solution of (R,R')-3,3'-disulfanylbis[tert-butyl 2-(tert-butoxycarbonyl)aminopropionate (1.06 g, 2.0 mmol) in 5 mL of ethylenedichloride was cooled to −23° C. under argon. Bromine (51.3 μL, 1.0 mmol) was added dropwise and the mixture was stirred for approximately 20 minutes and then diluted with an additional 2 mL of ethylenedichloride. A suspension of potassium phthalimide (370 mg, 2.0 mmol) in 5 mL of ethylenedichloride was cooled to approximately −23° C. and the disulfide mixture was added. The mixture was stirred for 1 hour at −23° C. and then warmed to room temperature over 45 minutes. The mixture was filtered and concentrated in vacuo. The residue was dissolved in benzene. Purification by chromatography gave (R)-N-[2-(tert-butoxycarbonylamino)-2-(tert-butoxycarbonyl)ethylsulfanyl]phthalimide (684 mg) as an oil.

A mixture of (R)-N-[2-(tert-butoxycarbonylamino)-2-(tert-butoxycarbonyl)ethylsulfanyl]phthalimide (660 mg, 1.61 mmol) and 1-(4,6-difluoroindan-1-yl)-1,3-dihydroimidazole-2-thione (400 mg, 1.59 mmol), prepared as in Example 9, in 8 mL of ethyl acetate was heated at reflux under argon for 1 hour. The mixture was allowed to cool to room temperature giving a crystalline precipitate and then the solvents were removed by evaporation under reduced pressure. The remaining semisolid was triturated with benzene and the benzene mixture was filtered. The benzene solution was concentrated by evaporation. Purification of the residue by chromatography gave tert-butyl 2R-(tert-butoxycarbonyl)amino-3-[1-(4,6-difluoroindan-1-yl)-1H-imidazol-2-yldisulfanyl]propionate (672 mg) .

A mixture of tert-butyl 2R-(tert-butoxycarbonyl)amino-3-[1-(4,6-difluoroindan-1-yl)-1H-imidazol-2-yldisulfanyl]propionate (672 mg) in 15 mL of trifluoroacetic acid and 15 mL of methylenechloride was stirred at room temperature under a nitrogen atmosphere for 2 hours. The solvent was removed by evaporation and the residue was co-evaporated with ethyl acetate (2×50 mL).

Treatment with ethereal hydrogen chloride gave 2R-amino-3-[5-aminomethyl-1-(4,6-difluoroindan-1-yl)-1H-imidazol-2-yldisulfanyl]propionic acid hydrochloride (768 mg, 1.74 mmol) as a solid, m.p. 147°–154° C.

Proceeding as in Example 52, but substituting a different starting material for (R,R')-3,3'-disulfanylbis[tert-butyl 2-(tert-butoxycarbonyl)aminopropionate and/or 1-(4,6-difluoroindan-1-yl)-1,3-dihydroimidazole-2-thione gave the following compounds of Formula III:

substituting (R,R')-3,3'-disulfanylbis[methyl 2-(tert-butoxycarbonyl)aminopropionate] gave methyl 2R-amino-3-[5-aminomethyl-1-(4,6-difluoroindan-1-yl) imidazol-2-yl-disulfanyl]propionate hydrochloride, m.p. 155°–157° C.;

substituting 3,3'-disulfanylbis[2-(tert-butoxycarbonyl) aminoethyl] gave 2-(2-aminoethyldisulfanyl)-1-(4,6-difluoroindan-1-yl)imidazole hydrochloride, m.p. 175°–177° C.;

substituting (R,R')-3,3'-disulfanylbis[methyl 2-(trifluoroacetyl)aminopropionate] gave methyl 2-(trifluoroacetyl)amino-3-[1-(4,6-difluoroindan-1-yl) imidazol-2-yl-disulfanyl]aminopropionate as an oil;

substituting (R,R')-3,3'-disulfanylbis[tert-butyl 2-(tert-butoxycarbonyl)aminopropionate gave 2R-amino-3-[1-(4,6-difluoroindan-2-yl)imidazol-2-yldisulfanyl] propionic acid hydrochloride, m.p. 145°–150° C.;

substituting 1-(4,5-difluoroindan-2-yl)-1,3-dihydroimidazole-2-thione gave 2R-amino-3-[1-(4,5-difluoroindan-2-yl)-1H-imidazol-2-yldisulfanyl] propionic acid hydrochloride, m.p. 140° C.;

substituting 1-(5,7-difluoro-1,2,3,4-tetrahydronaphthalen-2-yl)-1,3-dihydroimidazole-2-thione gave 2R-amino-3-[1-(5,7-difluoro-1,2,3,4-tetrahydronaphthalen-2-yl)-1H-imidazol-2-yldisulfanyl]propionic acid hydrochloride, m.p. 130° C.;

substituting 1-(6,8-difluoro-1,2,3,4-tetrahydronaphthalen-2-yl)-1,3-dihydroimidazole-2-thione gave 2R-amino-3-[1-(6,8-difluoro-1,2,3,4-tetrahydronaphthalen-2-yl)-1H-imidazol-2-yldisulfanyl]propionic acid hydrochloride, m.p. 141° C.;

substituting 1-(6,7-difluoro-1,2,3,4-tetrahydronaphthalen-2-yl)-1,3-dihydroimidazole-2-thione gave 2R-amino-3-[1-(6,7-difluoro-1,2,3,4-tetrahydronaphthalen-2-yl)-1H-imidazol-2-yldisulfanyl]propionic acid hydrochloride, m.p. 130° C.;

substituting 1-(5,7-difluoro-1,2,3,4-tetrahydronaphthalen-2-yl)-2-thioxo-1,3-dihydro-imidazole-5-carboxylic acid gave 2R-amino-3-[5-carboxy-1-(5,7-difluoro-1,2,3,4-tetrahydronaphthalen-2-yl)imidazol-2-yl-disulfanyl] propionic acid hydrochloride, m.p. 129°–138° C.;

substituting 1-(4,5-difluoroindan-2-yl)-1,3-dihydroimidazole-2-thione and (S,S')-4,4'-disulfanylbis [tert-butyl 2-(tert-butoxycarbonyl)aminobutyrate] gave 2S-amino-4-[1-(4,5-difluoroindan-2-yl)imidazol-2-yl-disulfanyl]butyric acid hydrochloride, m.p. 146° C.;

substituting 1-(4,5-difluoroindan-2-yl)-1,3-dihydroimidazole-2-thione and 3,3'-disulfanylbis[2-(tert-butoxycarbonyl)aminoethyl] gave 2-(2-aminoethyldisulfanyl)-1-(4,5-difluoroindan-2-yl) imidazole hydrochloride, m.p. 59° C.;

substituting 1-(4,5-difluoroindan-2-yl)-1,3-dihydroimidazole-2-thione and (S,S')-3,3'-disulfanylbis [tert-butyl 2-(tert-butoxycarbonyl)amino-3-methylbutyrate] gave 2S-amino-3-[1-(4,5-difluoroindan-2-yl)-1-H-imidazol-2-yldisulfanyl]-3-methylbutyric acid hydrochloride, m.p. 143°–149° C.;

substituting 1-(5,7-difluoro-1,2,3,4-tetrahydronaphthalen-2-yl)-5(1H)-tetrazol-5-yl-1,3-dihydroimidazole-2-thione and 3,3'-disulfanylbis[2-(tert-butoxycarbonyl) aminoethyl] gave 2-(2-aminoethyldisulfanyl)-1-(5,7-difluoro-1,2,3,4-tetrahydronaphthalen-2-yl)-5(1H)-tetrazol-5-yl-1,3-dihydroimidazole hydrochloride, m.p. 165° C. dec; and substituting (S)-5-(tert-butoxycarbonyl)aminomethyl-1-(5,7-difluoro-1,2,3,4-tetrahydronaphthalen-2-yl)-1,3-dihydroimidazole-2-thione and (R,R')-3,3'-disulfanylbis [tert-butyl 2-(tert-butoxycarbonyl)aminopropionate gave 2R-amino-3-[5-aminomethyl-1-(5,7-difluoro-1,2,3,4-tetrahydronaphthalen-2-yl)-1H-imidazol-2-yldisulfanyl] propionic acid hydrochloride, m.p. 179°–180° C.

EXAMPLE 53

IN VITRO, DOPAMINE β-HYDROXYLASE INHIBITION

The following describes an in vitro assay to identify compounds that inhibit dopamine β-hydroylase (DBH). The assay relies upon the DBH-catalyzed conversion of tyramine to octopamine and the inhibition of DBH activity by test compounds.

A mixture comprising bovine adrenal DBH (13.8 mUnits/mL), $Cu^{2+}$ (2 mM), ascorbic acid (10 mM), catalase (200 μg/mL), and test compound in 0.65 mL of 50 mM sodium acetate buffer (pH 4.5) was incubated at 37° C. for 10 minutes. Tyramine was added and the reaction mixture was incubated at 37° C. for 10 minutes. The reaction was quenched with 0.1 mL of concentrated ammonium hydroxide. The octopamine product was oxidized to p-hydroxybenzaldehyde by adding 0.2 mL of 2% sodium metaperiodate and incubating for an additional 4 minutes. Excess sodium metaperiodate was reduced with 0.2 mL of 10% sodium bisulfite and the p-hydroxybenzaldehyde concentration was measured by spectrophotometry at a wave length of 330 nanometers.

Alternatively, a mixture comprising bovine adrenal DBH (0.02 mUnits/mL), 0.125M sodium acetate, 10 mM fumarate, 0.5 µM CuSO$_4$, 100 µg/mL catalase and 10 mM tyramine Cu$^{2+}$ (2 mM) was incubated at 30° C. for 5 minutes and then dimethyl-1,4-phenylenediamine (DMPD) was added to initiate the reaction. The absorbance was monitored continously by spectrophotometry at a wave length of 515 nanometers.

The test compounds were assayed over a wide range of concentrations and the concentration of test compound necessary to produce 50% inhibition of DBH activity was interpolated.

Proceeding as in Example 53 the compounds of the invention were tested and found to possess DBH inhibitory activity.

EXAMPLE 54

IN VIVO DOPAMINE β-HYDROXYLASE INHIBITION

The following describes an in vivo assay to identify compounds that inhibit dopamine β-hydroylase (DBH). The assay relies upon dopamine and norepinephrine tissue concentrations and the affect of the test compounds thereon.

Male, normotensive or spontaneously hypertensive rats were dosed with vehicle (1 to 10 mL/kg) or test confound (0.3 to 100 mg/kg) by oral or intravenous administration. Some rats were dosed 1 to 2 times daily for up to 24 days. At 2 to 12 hours post final dose, the rats were anesthetized with halothane and decapitated. Selected tissues (e.g., cerebral cortical, medullary, mesenteric arterial and left ventricular) were rapidly harvested, weighed and placed in 0.4 mL of cold perchloric acid. Tissue concentrations of dopamine and norepinephrine were measured by HPLC and electrochemical detection methods.

The test compounds were assayed over a wide range of doses and their effects compared to those of controls. DBH inhibition was defined as a statistically significant ($p \leq 0.05$) decrease in norepinephrine concentration, a concomitant increase in dopamine concentration and an increase in the dopamine to norepinephrine ratio.

Proceeding as in Example 54 the compounds of the invention were tested and found to possess DBH inhibitory activity.

EXAMPLE 55

BLOOD PRESSURE LOWERING EFFECTS

The following describes an assay to identify compounds that lower blood pressure.

Male, spontaneously hypertensive rats were anesthetized and a femoral or carotid artery was cannulated for continuous blood pressure monitoring. The rats were allowed 30 to 60 minutes to recover from the anesthesia and then basal blood pressure levels were obtained. The rats were dosed with vehicle (10 mL/kg) or test compound (0.3 to 30 mg/kg) by oral or intravenous administration and followed for 4 to 6 hours.

The test compounds were assayed over a wide range of doses and blood pressure lowering activity was defined as a statistically significant ($p \leq 0.05$) lowering of blood pressure as compared to the vehicle treated rats.

Proceeding is in Example 55 the compounds of the invention were tested and found to possess blood pressure lowering activity.

EXAMPLE 56

The following are representative pharmaceutical formulations containing a compound of Formula I.

ORAL FORMULATION

A representative solution for oral administration contains:

| | |
|---|---|
| Compound of Formula I | 70–700 mg |
| Citric Acid Monohydrate | 105 mg |
| Sodium Hydroxide | 18 mg |
| Flavoring | |
| Water | q.s. to 100 mL |

INTRAVENOUS FORMULATION

A representative solution for intravenous administration contains:

| | |
|---|---|
| Compound of Formula I | 7–70 mg |
| Dextrose Monohydrate | q.s to make isotonic |
| Citric Acid Monohydrate | 1.05 mg |
| Sodium Hydroxide | 0.18 mg |
| Water for Injection | q.s. to 1.0 mL |

TABLET FORMULATION

A representative tablet form of a compound of Formula I may contain:

| | |
|---|---|
| Compound of Formula I | 25% |
| Microcrystalline cellulose | 54% |
| Stearic Acid | 20% |
| Colloidal Silica | 1% |

Proceeding as in Example 56 representative pharmaceutical formulations containing a compound of Formula II or III can be prepared.

We claim:

1. A process for the preparation of a compound of Formula I:

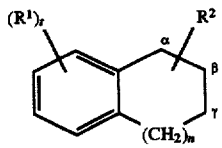

in which:

n is 0, 1 or 2;

t is 0, 1, 2 or 3;

R$^1$ is independently halo, hydroxy or (C$_{1-4}$)alkyloxy; and

R$^2$ is attached at the α-, β- or γ-position and is a group of Formula (a):

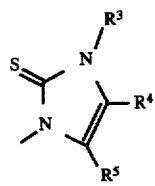

which process comprises reacting a compound selected from the group consisting of Formulas 3, 7, 9, 11, and 16 with an appropriate reactant, wherein Formula 3 is

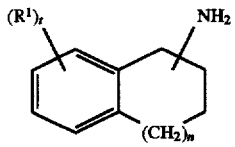

in which each n, t and $R^1$ are as defined above with respect to Formula I, with a dialkyloxyacetaldehyde in the presence of a chemical reducing agent or catalytic hydrogenation and then treating with thiocyanic acid to give a compound of Formula I in which $R^3$, $R^4$ and $R^5$ are each hydro; and wherein Formula 7 is

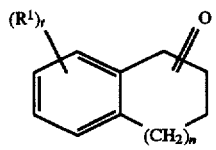

in which each n, t and $R^1$ are as defined above with respect to Formula I, with a a 2,2-dialkyloxyethylamine in the presence of a chemical reducing agent or catalytic hydrogenation and then treating with thiocyanic acid to give a compound of Formula I in which $R^3$, $R^4$ and $R^5$ are each hydro; and wherein Formula 9 is

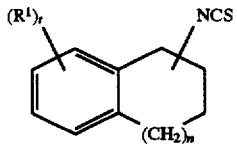

in which each n, t and $R^1$ are as defined above with respect to Formula I with a hydrazide of the formula $H_2NHNC(O)R^{34}$ (in which $R^{34}$ is hydro, aminomethyl, $(C_{1-4})$alkylaminomethyl, di$(C_{1-4})$alkylaminomethyl, pyrrolidin-1-ylmethyl, piperidin-1-ylmethyl, morpholin-4-ylmethyl, piperazin-1-ylmethyl or 4-$(C_{1-4})$alkylpiperazin-1-ylmethyl), or a protected group thereof, then treating with base and when necessary deprotecting to give a compound of Formula I in which $R^4$ is hydro and $R^5$ is hydro, aminomethyl, $(C_{1-4})$alkylaminomethyl, di$(C_{1-4})$alkylaminomethyl, pyrrolidin-1-ylmethyl, piperidin-1-ylmethyl, morpholin-4-ylmethyl, piperazin-1-ylmethyl or 4-$(C_{1-4})$alkylpiperazin-1-ylmethyl; and wherein Formula 11 is

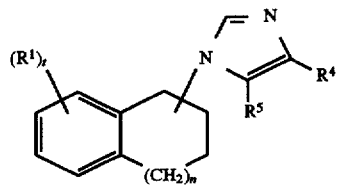

in which each n, t, $R^1$, $R^4$ and $R^5$ are as defined above with respect to Formula I with a strong base and then sulfurizing to give a compound of Formula I in which $R^3$ is hydro; and wherein Formula 16 is

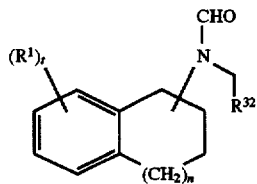

in which $R^{32}$ is cyano or $(C_{1-4})$alkyloxycarbonyl and each n, t and $R^1$ are as defined above with respect to Formula I with a compound of the formula $R^{33}C(O)L$ in which L is a leaving group and $R^{33}$ is hydro, $(C_{1-4})$alkyl or $(C_{1-4})$alkyloxycarbonyl and then treating with thiocyanic acid to give a compound of Formula I in which $R^2$ is a group of Formula (a) wherein $R^3$ is hydro, $R^4$ is hydro, $(C_{1-4})$alkyl or $(C_{1-4})$alkyloxycarbonyl and $R^5$ is cyano or $(C_{1-4})$alkyloxycarbonyl.

2. A process of claim 1 for the preparation of a compound of Formula I:

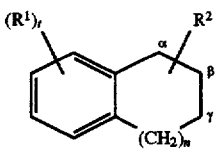

in which:

n is 0, 1 or 2;

t is 0, 1, 2 or 3;

$R^1$ is independently halo, hydroxy or $(C_{1-4})$alkyloxy; and $R^2$ is attached at the α-, β- or γ-position and is a group of Formula (a):

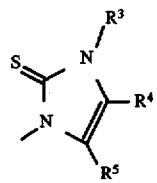

in which:

$R^4$ and $R^5$ are independently hydro, di$(C_{1-4})$alkylaminomethyl, piperidin-1-ylmethyl or morpholin-4-ylmethyl and $R^3$ is hydro, 2-$(C_{1-4})$alkyloxycarbonylethyl, 2-carboxyethyl or 2-carbamoylethyl; and the pharmaceutically acceptable salts, individual isomers, and mixtures of isomers thereof; which process comprises:

(a) reacting a compound of Formula 3:

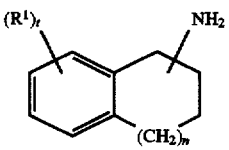

in which each n, t and $R^1$ are as defined above with respect to Formula I, with a dialkyloxyacetaldehyde in the presence of a chemical reducing agent or catalytic hydrogenation and then treating with thiocyanic acid to give a compound of Formula I in which $R^3$, $R^4$ and $R^5$ are each hydro; and (b) optionally further reacting a compound of Formula I in which $R^3$ is hydro with $(C_{1-4})$alkyl acrylate to give a compound of Formula I in which $R^3$ is 2-$(C_{1-4})$alkyloxycarbonylethyl;

(c) optionally further alkylating a compound of Formula I in which $R^3$, $R^4$ and $R^5$ are each hydro with an appropriately N,N-disubstituted methyleneammonium salt to give a compound of Formula I in which $R^3$ and $R^5$ are each hydro and $R^4$ is di($C_{1-4}$) alkylaminomethyl, piperidin-1-ylmethyl or morpholin-4-ylmethyl;

(d) optionally further alkylating a compound of Formula I in which $R^4$ is hydro and $R^3$ is other than hydro with an appropriately N,N-disubstituted methyleneammonium salt to give a corresponding compound of Formula I in which $R^5$ is di($C_{1-4}$) alkylaminomethyl, piperidin-1-ylmethyl or morpholin-4-ylmethyl;

(e) optionally protecting a compound of Formula I in which $R^3$ is hydro with a thiol protective group, alkylating with an appropriately N,N-disubstituted methyleneammonium salt and then deprotecting to give a compound of Formula I in which $R^3$ and $R^4$ are each hydro and $R^5$ is dimethylamino or in which $R^3$ is hydro and both $R^4$ and $R^5$ are di($C_{1-4}$) alkylaminomethyl, piperidin-1-ylmethyl or morpholin-4-ylmethyl;

(f) optionally further hydrolyzing a compound of Formula I in which $R^3$ is 2-($C_{1-4}$)alkyloxycarbonylethyl to give a compound of Formula I in which $R^3$ is 2-carboxyethyl;

(g) optionally further aminating a compound of Formula I in which $R^3$ is 2-carboxyethyl to give a compound of Formula I in which $R^3$ is 2-carbamoylethyl;

(h) optionally further de-methylating a compound of Formula I in which $R^1$ is methoxy to give a compound of Formula I in which $R^1$ is hydroxy;

(i) optionally further reacting the corresponding non-salt form of a compound of Formula I with a pharmaceutically acceptable inorganic or organic acid or base to give a pharmaceutically acceptable salt;

(j) optionally further reacting the corresponding acid addition salt or base addition salt form of a compound of Formula I with a suitable base or acid, respectively, to give the free acid or free base; and (k) optionally further separating a mixture of stereoisomers of a compound of Formula I to give a single stereoisomer.

3. A process of claim 1 for the preparation of a compound of Formula I:

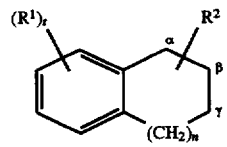

in which:

n is 0, 1 or 2;

t is 0, 1, 2 or 3;

$R^1$ is independently halo, hydroxy or ($C_{1-4}$)alkyloxy; and $R^2$ is attached at the α-, β- or γ-position and is a group of Formula (a):

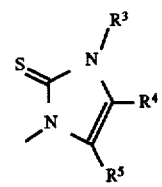

in which:

$R^4$ and $R^5$ are independently hydro, di($C_{1-4}$) alkylaminomethyl, piperidin-1-ylmethyl or morpholin-4-ylmethyl and $R^3$ is hydro, 2-($C_{1-4}$) alkyloxycarbonylethyl, 2-carboxyethyl or 2-carbamoylethyl; and the pharmaceutically acceptable salts, individual isomers, and mixtures of isomers thereof; which process comprises:

(a) reacting a compound of Formula 7:

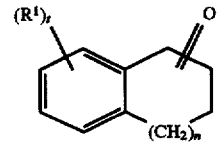

in which each n, t and $R^1$ are as defined above with respect to Formula I, with a a 2,2-dialkyloxyethylamine in the presence of a chemical reducing agent or catalytic hydrogenation and then treating with thiocyanic acid to give a compound of Formula I in which $R^3$, $R^4$ and $R^5$ are each hydro; and (b) optionally further reacting a compound of Formula I in which $R^3$ is hydro with ($C_{1-4}$)alkyl acrylate to give a compound of Formula I in which $R^3$ is 2-($C_{1-4}$)alkyloxycarbonylethyl;

(c) optionally further alkylating a compound of Formula I in which $R^3$, $R^4$ and $R^5$ are each hydro with an appropriately N,N-disubstituted methyleneammonium salt to give a compound of Formula I in which $R^3$ and $R^5$ are each hydro and $R^4$ is di($C_{1-4}$) alkylaminomethyl, piperidin-1-ylmethyl or morpholin-4-ylmethyl;

(d) optionally further alkylating a compound of Formula I in which $R^4$ is hydro and $R^3$ is other than hydro with an appropriately N,N-disubstituted methyleneammonium salt to give a corresponding compound of Formula I in which $R^5$ is di($C_{1-4}$) alkylaminomethyl, piperidin-1-ylmethyl or morpholin-4-ylmethyl;

(e) optionally protecting a compound of Formula I in which $R^3$ is hydro with a thiol protective group, alkylating with an appropriately N,N-disubstituted methyleneammonium salt and then deprotecting to give a compound of Formula I in which $R^3$ and $R^4$ are each hydro and $R^5$ is dimethylamino or in which $R^3$ is hydro and both $R^4$ and $R^5$ are di($C_{1-4}$) alkylaminomethyl, piperidin-1-ylmethyl or morpholin-4-ylmethyl;

(f) optionally further hydrolyzing a compound of Formula I in which $R^3$ is 2-($C_{1-4}$)alkyloxycarbonylethyl to give a compound of Formula I in which $R^3$ is 2-carboxyethyl;

(g) optionally further aminating a compound of Formula I in which $R^3$ is 2-carboxyethyl to give a compound of Formula I in which $R^3$ is 2-carbamoylethyl;

(h) optionally further de-methylating a compound of Formula I in which $R^1$ is methoxy to give a compound of Formula I in which $R^1$ is hydroxy;

(i) optionally further reacting the corresponding non-salt form of a compound of Formula I with a pharmaceutically acceptable inorganic or organic acid or base to give a pharmaceutically acceptable salt;

(j) optionally further reacting the corresponding acid addition salt or base addition salt form of a compound of Formula I with a suitable base or acid, respectively, to give the free acid or free base; and (k) optionally further separating a mixture of stereoisomers of a compound of Formula I to give a single stereoisomer.

4. A process of claim 1 for the preparation of a compound of Formula I:

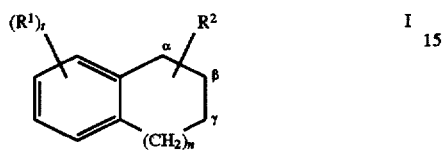

in which:

n is 0, 1 or 2;

t is 0, 1, 2 or 3;

$R^1$ is independently halo, hydroxy or $(C_{1-4})$alkyloxy; and $R^2$ is attached at the α-, β- or γ-position and is a group of Formula (a):

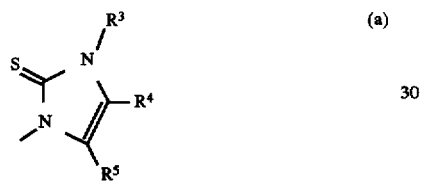

in which:

$R^4$ and $R^5$ independently hydro, di$(C_{1-4})$ alkylaminomethyl, piperidin-1-ylmethyl or morpholin-4-ylmethyl and $R^3$ is hydro, 2-$(C_{1-4})$ alkyloxycarbonylethyl, 2-carboxyethyl or 2-carbamoylethyl; and the pharmaceutically acceptable salts, individual isomers, and mixtures of isomers thereof; which process comprises:

(a) reacting a compound of Formula 9:

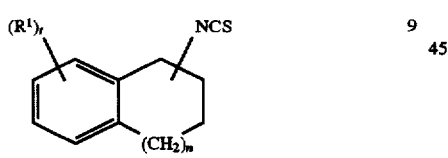

in which each n, t and $R^1$ are as defined above with respect to Formula I with a 2,2-dialkyloxyethylamine and then treating with acid to give a compound of Formula I in which $R^3$, $R^4$ and $R^5$ are each hydro; and (b) optionally further reacting a compound of Formula I in which $R^3$ is hydro with $(C_{1-4})$alkyl acrylate to give a compound of Formula I in which $R^3$ is 2-$(C_{1-4})$alkyloxycarbonylethyl;

(c) optionally further alkylating a compound of Formula I in which $R^3$, $R^4$ and $R^5$ are each hydro with an appropriately N,N-disubstituted methyleneammonium salt to give a compound of Formula I in which $R^3$ and $R^5$ are each hydro and $R^4$ is di$(C_{1-4})$ alkylaminomethyl, piperidin-1-ylmethyl or morpholin-4-ylmethyl;

(d) optionally further alkylating a compound of Formula I in which $R^4$ is hydro and $R^3$ is other than hydro with an appropriately N,N-disubstituted methyleneammonium salt to give a corresponding compound of Formula I in which $R^5$ is di$(C_{1-4})$ alkylaminomethyl, piperidin-1-ylmethyl or morpholin-4-ylmethyl;

(e) optionally protecting a compound of Formula I in which $R^3$ is hydro with a thiol protective group, alkylating with an appropriately N,N-disubstituted methyleneammonium salt and then deprotecting to give a compound of Formula I in which $R^3$ and $R^4$ are each hydro and $R^5$ is di$(C_{1-4})$alkylaminomethyl, piperidin-1-ylmethyl or morpholin-4-ylmethyl or in which $R^3$ is hydro and both $R^4$ and $R^5$ are di$(C_{1-4})$ alkylaminomethyl, piperidin-1-ylmethyl or morpholin-4-ylmethyl;

(f) optionally further hydrolyzing a compound of Formula I in which $R^3$ is 2-$(C_{1-4})$alkyloxycarbonylethyl to give a compound of Formula I in which $R^3$ is 2-carboxyethyl;

(g) optionally further aminating a compound of Formula I in which $R^3$ is 2-carboxyethyl to give a compound of Formula I in which $R^3$ is 2-carbamoylethyl;

(h) optionally further de-methylating a compound of Formula I in which $R^1$ is methoxy to give a compound of Formula I in which $R^1$ is hydroxy;

(i) optionally further reacting the corresponding non-salt form of a compound of Formula I with a pharmaceutically acceptable inorganic or organic acid or base to give a pharmaceutically acceptable salt;

(j) optionally further reacting the corresponding acid addition salt or base addition salt form of a compound of Formula I with a suitable base or acid, respectively, to give the free acid or free base; and (k) optionally further separating a mixture of stereoisomers of a compound of Formula I to give a single stereoisomer.

5. A process of claim 1 for the preparation of a compound of Formula I:

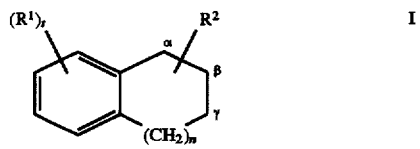

in which:

n is 0, 1 or 2;

t is 0, 1, 2 or 3;

$R^1$ is independently halo, hydroxy or $(C_{1-4})$alkyloxy; and $R^2$ is attached at the α-, β- or γ-position and is a group of Formula (a):

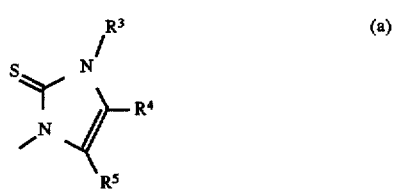

in which $R^4$ is hydro, $R^3$ is —$(CH_2)_qR^9$ {in which q is 0, 1, 2, 3 or 4 and $R^9$ is carboxy, $(C_{1-4})$alkyloxycarbonyl, carbamoyl, a group selected from aryl and heteroaryl (which group is optionally further substituted with one to two substituents independently selected from hydroxy, $(C_{1-4})$alkyloxy, cyano, 1H-tetrazo-5-yl, carboxy and $(C_{1-4})$alkyloxycarbonyl)} and $R^5$ is hydro or —$NHR^{10}$ {in which $R^{10}$ is hydro, $(C_{1-4})$alkanoyl, trifluoro($C_{1-4}$)alkanoyl, carbamoyl, $(C_{1-4})$ alkyloxycarbonyl, $(C_{1-4})$alkylcarbamoyl, di($C_{1-4}$) alkylcarbamoyl, amino($C_{1-4}$)alkanoyl, $(C_{1-4})$ alkylamino($C_{1-4}$)alkanoyl, di($C_{1-4}$)alkylamino($C_{1-4}$) alkanoyl, a group selected from aroyl and heteroaroyl (which aroyl and heteroaroyl are optionally further substituted with one to two substituents independently selected from hydroxy, $(C_{1-4})$alkyloxy, cyano, 1H-tetrazol-5-yl, carboxy and $(C_{1-4})$alkyloxycarbonyl) or —$C(NR^{11})NHR^{12}$ (in which $R^{11}$ and $R^{12}$ are independently hydro, acetyl or tert-butoxycarbonyl)}; or $R^5$ is hydro, $R^3$ is —$(CH_2)_qR^9$ (in which q and $R^9$ are as defined above) and $R^4$ is $(C_{1-4})$alkyl, di($C_{1-4}$) alkylaminomethyl, piperidin-1-ylmethyl, morpholin-4-ylmethyl, formyl, 1-hydroxy($C_{1-4}$)alkyl or —$CH_2NHR^{10}$ (in which $R^{10}$ is as defined above); or $R^3$ is hydro or —$(CH_2)_qR^9$ (in which q and $R^9$ are as defined above), $R^4$ is hydro, $(C_{1-4})$alkyl or —$C(O)R^{14}$ (in which $R^{14}$ is amino, hydroxy($C_{1-4}$)alkyloxy, 2-(dimethylamino)ethylamino, 4-methylpiperazin-1-yl, 2-(dimethylamino)ethylmercapto, 4-(methylsulfonylamino)anilino or 1H-tetrazol-5-ylamino) and $R^5$ is cyano, hydroxymethyl, 1H-tetrazol-5-yl, 4,5-dihydroimidazol-2-yl, pyrrolidin-1-ylmethyl, piperidin-1-ylmethyl, morpholin-4-ylmethyl, piperazin-1-ylmethyl, 4-$(C_{1-4})$alkylpiperazin-1-ylmethyl, —$C(O)R^{14}$ (in which $R^{14}$ are as defined above), —$C(NH)NR^{15}R^{16}$ (in which $R^{15}$ and $R^{16}$ are independently hydro, $(C_{1-4})$alkyl or trifluoro($C_{1-4}$) alkyl) or —$CH_2NR^{10}R^{17}$ (in which $R^{10}$ is as defined above and $R^{17}$ is hydro or $C_{1-4}$)alkyl); or $R^3$ is —$(CH_2)_qR^9$ (in which q and $R^9$ are as defined above) and $R^4$ and $R^5$ are dependently di($C_{1-4}$) alkylaminomethyl, piperidin-1-ylmethyl, morpholin-4-ylmethyl or hydroxymethyl; or hydroxymethyl; and the pharmaceutically acceptable salts, individual isomers, and mixtures of isomers thereof; which process comprises:

(a) reacting a compound of Formula 11:

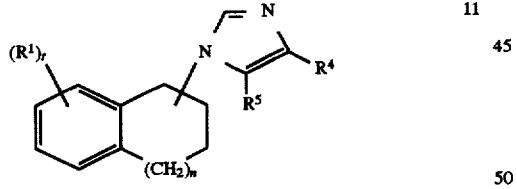

in which each n, t, $R^1$, $R^4$ and $R^5$ are as defined above with respect to Formula I with a compound of the formula L—$(CH_2)_qR^9$, in which L is a leaving group and each q and $R^9$ are as defined above with respect to Formula I, and then sulfurizing to give a compound of Formula I in which $R^3$ is —$(CH_2)_qR^9$; and (b) optionally further hydrolyzing a compound of Formula I in which $R^3$, $R^4$ or $R^5$ is $(C_{1-4})$ alkyloxycarbonyl or a group which is further substituted by a $(C_{1-4})$alkyloxycarbonyl substituent to give a compound of Formula I in which $R^3$, $R^4$ or $R^5$ is carboxy or group which is further substituted by a carboxy substituent;

(c) optionally further aminating a compound of Formula I in which $R^3$, $R^4$ or $R^5$ is carboxy or a group which is further substituted by a carboxy substituent to give a compound of Formula I in which $R^3$, $R^4$ or $R^5$ is carbamoyl or a group which is further substituted by a carbamoyl substituent;

(d) optionally further reacting a compound of Formula I in which $R^3$, $R^4$ or $R^5$ is carboxy or a group which is further substituted by a carboxy group with a $(C_{1-4})$ alcohol to give a compound of Formula I in which $R^3$, $R^4$ or $R^5$ is $(C_{1-4})$alkyloxycarbonyl or a group that is further substituted by a $(C_{1-4})$ alkyloxycarbonyl group;

(e) optionally de-methylating a compound of Formula I in which $R^1$ is methoxy and/or in which $R^3$, $R^4$ or $R^5$ is a group selected from aroyl, heteroaroyl, aryl $(C_{1-4})$alkyl and hetero($C_{1-4}$)alkyl (which aroyl, heteroaroyl, aryl and heteroaryl are further substituted with one to two methoxy substituents) to give a compound of Formula I in which $R^1$ is hydroxy and/or $R^3$, $R^4$ or $R^5$ is a group selected from aroyl, heteroaroyl, aryl($C_{1-4}$)alkyl and hetero($C_{1-4}$)alkyl (which aroyl, heteroaroyl, aryl and heteroaryl are further substituted with one to two hydroxy substituents);

(f) optionally reacting a compound of Formula I in which $R^3$, $R^4$ or $R^5$ is a group selected from aroyl, heteroaroyl, aryl($C_{1-4}$)alkyl and hetero($C_{1-4}$)alkyl (which aroyl, heteroaroyl, aryl and heteroaryl are further substituted with a cyano substituent) with a hydrazoic acid derivative to give a compound of Formula I in which $R^3$, $R^4$ or $R^5$ is a group selected from aroyl, heteroaroyl, aryl($C_{1-4}$)alkyl and hetero $(C_{1-4})$alkyl (which aroyl, heteroaroyl, aryl and heteroaryl are further substituted with a 1H-tetrazol-5-yl substituent);

(g) optionally further reacting the corresponding non-salt form of a compound of Formula I with a pharmaceutically acceptable inorganic or organic acid or base to give a pharmaceutically acceptable salt;

(h) optionally further reacting the corresponding acid addition salt or base addition salt form of a compound of Formula I with a suitable base or acid, respectively, to give the free acid or free base; and (i) optionally further separating a mixture of stereoisomers of a compound of Formula I to give a single stereoisomer.

6. A process of claim 1 for the preparation of a compound of Formula I:

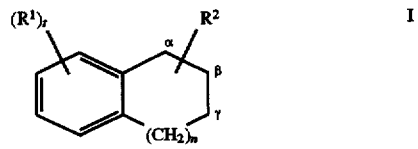

in which:

n is 0, 1 or 2;

t is 0, 1, 2 or 3;

$R^1$ is independently halo, hydroxy or $(C_{1-4})$alkyloxy; and $R^2$ is attached at the α-, β- or γ-position and is a group of Formula (a):

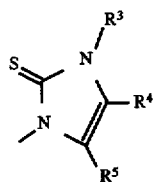

(a)

in which:

R⁴ and R⁵ are each hydro and R³ is —NHR¹⁰ {in which R¹⁰ is hydro, (C₁₋₄)alkanoyl, trifluoro(C₁₋₄)alkanoyl, carbamoyl, (C₁₋₄)alkyloxycarbonyl, (C₁₋₄)alkylcarbamoyl, di(C₁₋₄)alkylcarbamoyl, amino(C₁₋₄)alkanoyl, (C₁₋₄)alkylamino(C₁₋₄)alkanoyl, di(C₁₋₄)alkylamino(C₁₋₄)alkanoyl, a group selected from aroyl and heteroaroyl (which aroyl and heteroaroyl are optionally further substituted with one to two substituents independently selected from hydroxy, (C₁₋₄)alkyloxy, cyano, 1H-tetrazol-5-yl, carboxy and (C₁₋₄)alkyloxycarbonyl) or —C(NR¹¹)NHR¹² (in which R¹¹ and R¹² are independently hydro, acetyl or tert-butoxycarbonyl)}; and the pharmaceutically acceptable salts, individual isomers, and mixtures of isomers thereof; which process comprises:

(a) reacting a compound of Formula 11:

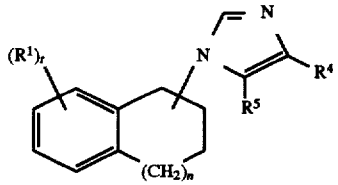

11 in which R⁴ and R⁵ are each hydro and each n, t and R¹ are as defined above with respect to Formula I with an amino aryl- or alkylsulfonate and then sulfurizing to give a compound of Formula I in which R³ is amino; and (b) optionally further reacting a compound of Formula I in which R³ is amino with an appropriately substituted amidine to give a compound of Formula I in which R³ is —NHC(NR¹¹)NHR¹², wherein R¹¹ is hydro, acetyl or tert-butoxycarbonyl and R¹² is acetyl or tert-butoxycarbonyl;

(c) optionally further treating a compound of Formula I in which R³ is —NHC(NR¹¹)NHR¹², wherein R¹¹ is hydro, acetyl or tert-butoxycarbonyl and R¹² is acetyl or tert-butoxycarbonyl, with acid to give a compound of Formula I in which R³ is —NHC(NH)NH₂;

(d) optionally further acylating a compound of Formula I in which R³ is amino with an appropriate acylating agent, or a protected derivative thereof, and then deprotecting when necessary to give a corresponding compound of Formula I in which R³ is —NHR¹⁰, wherein R¹⁰ is (C₁₋₄)alkanonyl, trifluoro(C₁₋₄)alkanoyl, carbamoyl, (C₁₋₄)alkyloxycarbonyl, (C₁₋₄)alkylcarbamoyl, di(C₁₋₄)alkylcarbamoyl, amino(C₁₋₄)alkanoyl, (C₁₋₄)alkylamino(C₁₋₄)alkanoyl, di(C₁₋₄)alkylamino(C₁₋₄)alkanoyl or a group selected from aroyl and heteroaroyl, (which aroyl and heteroaroyl are optionally further substituted with one to two substituents independently selected from (C₁₋₄)alkyloxy, cyano, carboxy and (C₁₋₄)alkyloxycarbonyl);

(e) optionally further reacting a compound of Formula I in which R³ is amino with (C₁₋₄)alkyl isocyanate to give a compound of Formula I in which R³ is —NHR¹⁰, wherein R¹⁰ is (C₁₋₄)alkylcarbamoyl;

(f) optionally further hydrolyzing a compound of Formula I in which R³ is —NHR¹⁰, wherein R¹⁰ is a group which is further substituted by a (C₁₋₄) alkyloxycarbonyl substituent, to give a compound of Formula I in which R³ is —NHR¹⁰, wherein R¹⁰ is a group which is further substituted by a carboxy substituent;

(g) optionally further aminating a compound of Formula I in which R³ is —NHR¹⁰, wherein R¹⁰ is a group which is further substituted by a carboxy substituent, to give a compound of Formula I in which R³ is —NHR¹⁰, wherein R¹⁰ is a group which is further substituted by a carbamoyl substituent;

(h) optionally further reacting a compound of Formula I in which R³ is —NHR¹⁰, wherein R¹⁰ is a group which is further substituted by a carboxy substituent, with a (C₁₋₄)alcohol to give a compound of Formula I in which R³ is —NHR¹⁰, wherein R¹⁰ is a group which is further substituted by a (C₁₋₄) alkyloxycarbonyl substituent;

(i) optionally de-methylating a compound of Formula I in which R¹ is methoxy and/or in which R³ is —NHR¹⁰, wherein R¹⁰ is a group selected from aroyl, heteroaroyl, aryl(C₁₋₄)alkyl and heteroaryl(C₁₋₄)alkyl (which aroyl, heteroaroyl, aryl and heteroaryl are further substituted with one to two methoxy substituents) to give a compound of Formula I in which R¹ is hydroxy and/or R³ is —NHR¹⁰, wherein R¹⁰ is a group selected from aroyl, heteroaroyl, aryl(C₁₋₄)alkyl and heteroaryl(C₁₋₄) alkyl (which aroyl, heteroaroyl, aryl and heteroaryl are further substituted with one to two hydroxy substituents);

(j) optionally reacting a compound of Formula I in which R³ is —NHR¹⁰, wherein R¹⁰ is a group selected from aroyl, heteroaroyl, aryl(C₁₋₄)alkyl and heteroaryl(C₁₋₄)alkyl (which aroyl, heteroaroyl, aryl and heteroaryl are further substituted with a cyano substituent) with a hydrazoic acid derivative to give a compound of Formula I in which R³ is —NHR¹⁰, wherein R¹⁰ is a group selected from aroyl, heteroaroyl, aryl(C₁₋₄)alkyl and heteroaryl(C₁₋₄) alkyl (which aroyl, heteroaroyl, aryl and heteroaryl are further substituted with a 1H-tetrazol-5-yl substituent);

(k) optionally further reacting the corresponding non-salt form of a compound of Formula I with a pharmaceutically acceptable inorganic or organic acid or base to give a pharmaceutically acceptable salt;

(l) optionally further reacting the corresponding acid addition salt or base addition salt form of a compound of Formula I with a suitable base or acid, respectively, to give the free acid or free base; and (m) optionally further separating a mixture of stereoisomers of a compound of Formula I to give a single stereoisomer.

7. A process of claim 1 for the preparation of a compound of Formula I:

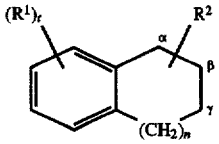

I in which:

n is 0, 1 or 2;

t is 0, 1, 2 or 3;

$R^1$ is independently halo, hydroxy or $(C_{1-4})$alkyloxy; and $R^2$ is attached at the α-, β- or γ-position and is a group of Formula (a):

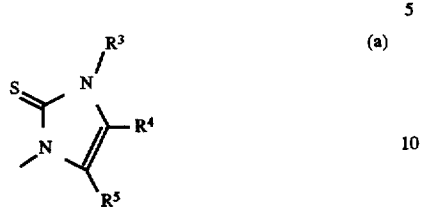

in which:

$R^3$ and $R^4$ are each hydro and $R^5$ is hydro or —NHR$^{10}$ {in which $R^{10}$ is hydro, $(C_{1-4})$alkanoyl, trifluoro$(C_{1-4})$alkanoyl, carbamoyl, $(C_{1-4})$alkyloxycarbonyl, $(C_{1-4})$alkylcarbamoyl, di$(C_{1-4})$alkylcarbamoyl, amino$(C_{1-4})$alkanoyl, $(C_{1-4})$alkylamino$(C_{1-4})$alkanoyl, di$(C_{1-4})$alkylamino$(C_{1-4})$alkanoyl, a group selected from aroyl and heteroaroyl (which aroyl and heteroaroyl are optionally further substituted with one to two substituents independently selected from hydroxy, $(C_{1-4})$alkyloxy, cyano, 1H-tetrazol-5-yl, carboxy and $(C_{1-4})$alkyloxycarbonyl) or —C(NR$^{11}$)NHR$^{12}$ (in which R$^{11}$ and R$^{12}$ are independently hydro, acetyl or tert-butoxycarbonyl)}; or $R^3$ and $R^5$ are each hydro and $R^4$ is $(C_{1-4})$alkyl, di$(C_{1-4})$alkylaminomethyl, piperidin-1-ylmethyl, morpholin-4-ylmethyl, formyl, 1-hydroxy$(C_{1-4})$alkyl or —CH$_2$NHR$^{10}$ (in which R$^{10}$ is as defined above); or $R^3$ is hydro, $R^4$ is hydro, $(C_{1-4})$alkyl or —C(O)R$^{14}$ (in which R$^{14}$ is amino, hydroxy $(C_{1-4})$alkyloxy, 2-(dimethylamino)ethylamino, 4-methylpiperazin-1-yl, 2-(dimethylamino)ethylmercapto, 4-(methylsulfonylamino)anilino or 1H-tetrazol-5-ylamino) and $R^5$ is cyano, hydroxymethyl, 1H-tetrazol-5-yl, 4,5-dihydroimidazol-2-yl, pyrrolidin-1-ylmethyl, piperidin-1-ylmethyl, morpholin-4-ylmethyl, piperazin-1-ylmethyl, 4-$(C_{1-4})$alkylpiperazin-1-ylmethyl, —C(O)R$^{14}$ (in which R$^{14}$ are as defined above), —C(NH)NR$^{15}$R$^{16}$ (in which R$^{15}$ and R$^{16}$ are independently hydro, $(C_{1-4})$alkyl or trifluoro$(C_{1-4})$alkyl) or —CH$_2$NR$^{10}$R$^{17}$ (in which R$^{10}$ is as defined above and R$^{17}$ is hydro or $C_{1-4}$)alkyl); or $R^3$ is hydro and $R^4$ and $R^5$ are dependently di$(C_{1-4})$alkylaminomethyl, piperidin-1-ylmethyl, morpholin-4-ylmethyl or hydroxymethyl; and the pharmaceutically acceptable salts, individual isomers, and mixtures of isomers thereof; which process comprises:

(a) reacting a compound of Formula 11:

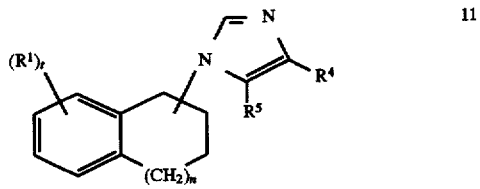

in which each n, t, R$^1$, R$^4$ and R$^5$ are as defined above with respect to Formula I with a strong base and then sulfurizing to give a compound of Formula I in which R$^3$ is hydro; and (b) optionally further reacting a compound of Formula I in which R$^3$ is hydro with $(C_{1-4})$alkyl acrylate to give a compound of Formula I in which R$^3$ is 2-$(C_{1-4})$alkyloxycarbonylethyl;

(c) optionally further hydrolyzing a compound of Formula I in which R$^3$, R$^4$ or R$^5$ is $(C_{1-4})$alkyloxycarbonyl or a group which is further substituted by a $(C_{1-4})$alkyloxycarbonyl substituent to give a compound of Formula I in which R$^3$, R$^4$ or R$^5$ is carboxy or group which is further substituted by a carboxy substituent;

(d) optionally further aminating a compound of Formula I in which R$^3$, R$^4$ or R$^5$ is carboxy or a group which is further substituted by a carboxy substituent to give a compound of Formula I in which R$^3$, R$^4$ or R$^5$ is carbamoyl or a group which is further substituted by a carbamoyl substituent;

(e) optionally further reacting a compound of Formula I in which R$^3$, R$^4$ or R$^5$ is carboxy or a group which is further substituted by a carboxy group with a $(C_{1-4})$alcohol to give a compound of Formula I in which R$^3$, R$^4$ or R$^5$ $(C_{1-4})$alkyloxycarbonyl or a group that is further substituted by a $(C_{1-4})$alkyloxycarbonyl group;

(f) optionally de-methylating a compound of Formula I in which R$^1$ is methoxy and/or in which R$^4$ or R$^5$ is a group selected from aroyl, heteroaroyl, aryl$(C_{1-4})$alkyl and heteroaryl$(C_{1-4}$alkyl (which aroyl, heteroaroyl, aryl and heteroaryl is further substituted with one to two methoxy substituents) to give a compound of Formula I in which R$^1$ is hydroxy and/or R$^4$ or R$^5$ is a group selected from aroyl, heteroaroyl, aryl$(C_{1-4})$alkyl and heteroaryl$(C_{1-4}$alkyl (which aroyl, heteroaroyl, aryl and heteroaryl is further substituted with one to two hydroxy substituents);

(g) optionally reacting a compound of Formula I in which R$^4$ or R$^5$ is a group selected from aroyl, heteroaroyl, aryl$(C_{1-4})$alkyl and heteroaryl$(C_{1-4}$alkyl (which aroyl, heteroaroyl, aryl and heteroaryl is further substituted with a cyano substituent) with a hydrazoic acid derivative to give a compound of Formula I in which R$^4$ or R$^5$ is a group selected from aroyl, heteroaroyl, aryl$(C_{1-4})$alkyl and heteroaryl$(C_{1-4}$alkyl (which aroyl, heteroaroyl, aryl and heteroaryl is further substituted with a 1H-tetrazol-5-yl substituent);

(h) optionally further reacting the corresponding non-salt form of a compound of Formula I with a pharmaceutically acceptable inorganic or organic acid or base to give a pharmaceutically acceptable salt;

(i) optionally further reacting the corresponding acid addition salt or base addition salt form of a compound of Formula I with a suitable base or acid, respectively, to give the free acid or free base; and (j) optionally further separating a mixture of stereoisomers of a compound of Formula I to give a single stereoisomer.

8. A process of claim 1 for the preparation of a compound of Formula I:

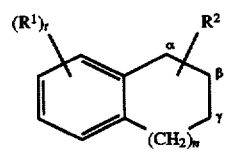

in which:

n is 0, 1 or 2;

t is 0, 1, 2 or 3;

$R^1$ is independently halo, hydroxy or $(C_{1-4})$alkyloxy; and $R^2$ is attached at the α-, β- or γ-position and is a group of Formula (a):

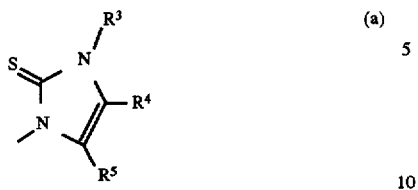

in which:

$R^4$ is hydro, $R^3$ is hydro, 2-($C_{1-4}$)alkyloxycarbonylethyl, 2-carboxyethyl or 2-carbamoylethyl and $R^5$ is —$NHR^{10}$ {in which $R^{10}$ is hydro, ($C_{1-4}$)alkanoyl, trifluoro($C_{1-4}$)alkanoyl, carbamoyl, ($C_{1-4}$) alkyloxycarbonyl, ($C_{1-4}$)alkylcarbamoyl, di($C_{1-4}$) alkylcarbamoyl, amino($C_{1-4}$)alkanoyl, ($C_{1-4}$) alkylamino($C_{1-4}$)alkanoyl, di($C_{1-4}$)alkylamino($C_{1-4}$) alkanoyl, a group selected from aroyl and heteroaroyl (which aroyl and heteroaroyl are optionally further substituted with one to two substituents independently selected from hydroxy, ($C_{1-4}$)alkyloxy, cyano, 1H-tetrazol-5-yl, carboxy and ($C_{1-4}$)alkyloxycarbonyl) or —C($NR^{11}$)$NHR^{12}$ (in which $R^{11}$ and $R^{12}$ are independently hydro, acetyl or tert-butoxycarbonyl)}; and the pharmaceutically acceptable salts, individual isomers, and mixtures of isomers thereof; which process comprises:

(a) reacting a compound of Formula 9:

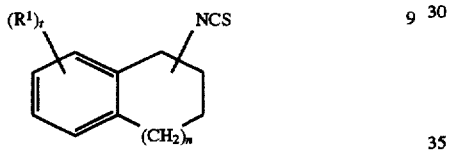

in which each n, t and $R^1$ are as defined above with respect to formula I with aminoacetonitrile hydrochloride and then treating with base to give a compound of Formula I in which $R^3$ and $R^4$ are each hydro and $R^5$ is amino; and (b) optionally further reacting a compound of Formula I in which $R^5$ is amino with an appropriately substituted amidine to give a compound of Formula I in which $R^5$ is —NHC($NR^{11}$)$NHR^{12}$, wherein $R^{11}$ is hydro, acetyl or tert-butoxycarbonyl and $R^{12}$ is acetyl or tert-butoxycarbonyl;

(c) optionally further treating a compound of Formula I in which $R^5$ is —NHC($NR^{11}$)$NHR^{12}$, wherein $R^{11}$ is hydro, acetyl or tert-butoxycarbonyl and $R^{12}$ is acetyl or tert-butoxycarbonyl, with acid to give a compound of Formula I in which $R^5$ is —NHC(NH)$NH_2$;

(d) optionally further acylating a compound of Formula I in which $R^5$ is amino with an appropriate acylating agent, or a protected derivative thereof, and then deprotecting when necessary to give a corresponding compound of Formula I in which $R^5$ is —$NHR^{10}$, wherein $R^{10}$ is ($C_{1-4}$)alkanoyl, trifluoro($C_{1-4}$) alkanoyl, carbamoyl, ($C_{1-4}$)alkyloxycarbonyl, ($C_{1-4}$) alkylcarbamoyl, di($C_{1-4}$)alkylcarbamoyl, amino ($C_{1-4}$)alkanoyl, ($C_{1-4}$)alkylamino($C_{1-4}$)alkanoyl, di($C_{1-4}$)alkylamino($C_{1-4}$)alkanoyl or a group selected from aroyl and heteroaroyl, (which aroyl and heteroaroyl are optionally further substituted with one to two substituents independently selected from ($C_{1-4}$)alkyloxy, cyano, carboxy and ($C_{1-4}$) alkyloxycarbonyl);

(e) optionally further reacting a compound of Formula I in which $R^5$ is amino with ($C_{1-4}$)alkyl isocyanate to give a compound of Formula I in which $R^3$ is —$NHR^{10}$, wherein $R^{10}$ is ($C_{1-4}$)alkylcarbamoyl;

(f) optionally further reacting a compound of Formula I in which $R^3$ is hydro with ($C_{1-4}$)alkyl acrylate to give a compound of Formula I in which $R^3$ is 2-($C_{1-4}$)alkyloxycarbonylethyl;

(g) optionally further hydrolyzing a compound of Formula I in which $R^3$ is 2-($C_{1-4}$)alkyloxycarbonylethyl and/or $R^5$ is —$NHR^{10}$, wherein $R^{10}$ is a group which is further substituted by a ($C_{1-4}$)alkyloxycarbonyl substituent, to give a compound of Formula I in which $R^3$ is 2-carboxyethyl and/or $R^3$ is —$NHR^{10}$, wherein $R^{10}$ is a group which is further substituted by a carboxy substituent;

(h) optionally further aminating a compound of Formula I in which $R^3$ is 2-carboxyethyl and/or $R^5$ is —$NHR^{10}$, wherein $R^{10}$ is a group which is further substituted by a carboxy substituent, to give a compound of Formula I in which $R^3$ is 2-carbamoylethyl and/or $R^5$ is —$NHR^{10}$, wherein $R^{10}$ is a group which is further substituted by a carbamoyl substituent;

(i) optionally further reacting a compound of Formula I in which $R^3$ is 2-carboxyethyl and/or $R^3$ is —$NHR^{10}$, wherein $R^{10}$ is a group which is further substituted by a carboxy substituent, with a ($C_{1-4}$) alcohol to give a compound of Formula I in which $R^3$ is 2-($C_{1-4}$)alkyloxycarbonylethyl and/or $R^5$ is —$NHR^{10}$, wherein $R^{10}$ is a group which is further substituted by a ($C_{1-4}$)alkyloxycarbonyl substituent;

(j) optionally de-methylating a compound of Formula I in which $R^1$ is methoxy and/or in which $R^5$ is —$NHR^{10}$, wherein $R^{10}$ is a group selected from aroyl, heteroaryl, aryl($C_{1-4}$)alkyl and heteroaryl ($C_{1-4}$)alkyl (which aroyl, heteroaroyl, aryl and heteroaryl are further substituted with one to two methoxy substituents) to give a compound of Formula I in which $R^1$ is hydroxy and/or $R^5$ is —$NHR^{10}$, wherein $R^{10}$ is a group selected frown aroyl, heteroaroyl, aryl($C_{1-4}$)alkyl and heteroaryl($C_{1-4}$)alkyl (which aroyl, heteroaroyl, aryl and heteroaryl are further substituted with one to two hydroxy substituents);

(k) optionally reacting a compound of Formula I in which $R^5$ is —$NHR^{10}$, wherein $R^{10}$ is a group selected from aroyl, heteroaroyl, aryl($C_{1-4}$)alkyl and heteroaryl($C_{1-4}$)alkyl (which aroyl, heteroaroyl, aryl and heteroaryl is further substituted with a cyano substituent) with a hydrazoic acid derivative to give a compound of Formula I in which $R^5$ is —$NHR^{10}$, wherein $R^{10}$ is a group selected from aroyl, heteroaroyl, aryl($C_{1-4}$)alkyl and heteroaryl($C_{1-4}$) alkyl (which aroyl, heteroaroyl, aryl and heteroaryl is further substituted with a 1H-tetrazol-5-yl substituent);

(l) optionally further reacting the corresponding non-salt form of a compound of Formula I with a pharmaceutically acceptable inorganic or organic acid or base to give a pharmaceutically acceptable salt;

(m) optionally further reacting the corresponding acid addition salt or base addition salt form of a compound of Formula I with a suitable base or acid, respectively, to give the free acid or free base; and (n) optionally further separating a mixture of stereoisomers of a compound of Formula I to give a single stereoisomer.

9. A process of claim 1 for the preparation of a compound of Formula I:

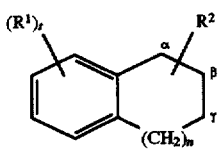

in which:

n is 0, 1 or 2;

t is 0, 1, 2 or 3;

$R^1$ is independently halo, hydroxy or $(C_{1-4})$alkyloxy; and $R^2$ is attached at the α-, β- or γ-position and is a group of Formula (a):

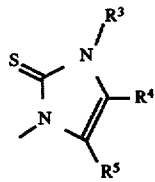

in which:

$R^3$ is hydro, 2-$(C_{1-4})$alkyloxycarbonylethyl, 2-carboxymethyl or 2-carbamoylethyl;

$R^4$ is hydro, $(C_{1-4})$alkyl or —C(O)$R^{14}$ (in which $R^{14}$ is amino, hydroxy$(C_{1-4})$alkyloxy, 2-(dimethylamino)ethylamino, 4-methylpiperazin-1-yl, 2-(dimethylamino)ethylmercapto, 4-(methylsulfonylamino)anilino or 1H-tetrazol-5-ylamino); and $R^5$ is cyano, hydroxymethyl, 1H-tetrazol-5-yl, 4,5-dihydroimidazol-2-yl, pyrrolidin-1-ylmethyl, piperidin-1-ylmethyl, morpholin-4-ylmethyl, piperazin-1-ylmethyl, 4-$(C_{1-4})$alkylpiperazin-1-ylmethyl, —C(O)$R^{14}$ (in which $R^{14}$ are as defined above), —C(NH)NR$^{15}$R$^{16}$ (in which $R^{15}$ and $R^{16}$ are independently hydro, $(C_{1-4})$alkyl or trifluoro$(C_{1-4})$alkyl) or —CH$_2$NHR$^{10}$ {in which $R^{10}$ is hydro, $(C_{1-4})$alkanoyl, trifluoro$(C_{1-4})$alkanoyl, carbamoyl, $(C_{1-4})$alkyloxycarbonyl, $(C_{1-4})$alkylcarbamoyl, di$(C_{1-4})$alkylcarbamoyl, amino$(C_{1-4})$alkanoyl, $(C_{1-4})$alkylamino$(C_{1-4})$alkanoyl, di$(C_{1-4})$alkylamino$(C_{1-4})$alkanoyl, or a group selected from aroyl and heteroaroyl (which aroyl and heteroaroyl are optionally further substituted with one to two substituent independently selected from hydroxy, $(C_{1-4})$alkyloxy, cyano, 1H-tetrazol-5-yl, carboxy and $(C_{1-4})$alkyloxycarbonyl)}; or $R^3$ is hydro, 2-$(C_{1-4})$alkyloxycarbonylethyl, 2-carboxyethyl or 2-carbamoylethyl and $R^4$ and $R^5$ are dependently di$(C_{1-4})$alkylaminomethyl, piperidin-1-ylmethyl, morpholin-4-ylmethyl or hydroxymethyl;

(a) reacting a compound of Formula 16:

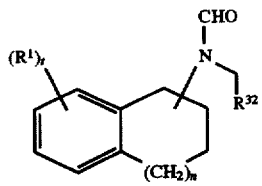

in which $R^{32}$ is cyano or $(C_{1-4})$alkyloxycarbonyl and each n, t and $R^1$ are as defined above with respect to Formula I with a compound of the formula $R^{33}$C(O)L in which L is a leaving group and $R^{33}$ is hydro, $(C_{1-4})$alkyl or $(C_{1-4})$alkyloxycarbonyl and then treating with thiocyanic acid to give a compound of Formula I in which $R^2$ is a group of Formula (a) wherein $R^3$ is hydro, $R^4$ is hydro, $(C_{1-4})$alkyl or $(C_{1-4})$alkyloxycarbonyl and $R^3$ is cyano or $(C_{1-4})$alkyloxycarbonyl; and (b) optionally further reacting a compound of Formula I in which $R^5$ is cyano with a hydrazoic acid derivative to give a compound of Formula I in which $R^5$ is 1H-tetrazol-5-yl;

(c) optionally further hydrolyzing a compound of Formula I in which $R^5$ is cyano to give a compound of Formula I in which $R^5$ is carbamoyl;

(d) optionally further reacting a compound of Formula I in which $R^5$ is cyano with ethylenediamine to give a compound of Formula I in which $R^5$ is 4,5-dihydroimidazol-2-yl;

(e) optionally further reacting a compound of Formula I in which $R^5$ is cyano with a compound of the formula $(CH_3)_2$AlNR$^{15}$R$^{16}$ to give a compound of Formula I in which $R^5$ is —C(NH)NR$^{15}$R$^{16}$, wherein $R^{15}$ and $R^{16}$ are as defined above with respect to Formula I;

(f) optionally further reducing a compound of Formula I in which $R^5$ is cyano to give a compound of Formula I in which $R^5$ is aminomethyl;

(g) optionally further reducing a compound of Formula I in which $R^5$ or both $R^4$ and $R^5$ are ethoxycarbonyl to give a compound of Formula I in which $R^5$ or both $R^4$ and $R^5$ are hydroxymethyl;

(h) optionally further converting a compound of Formula I in which $R^5$ is hydroxymethyl to a compound of Formula 28:

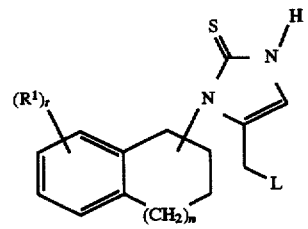

in which L is a leaving group and n, t and $R^1$ are as defined in the Summary of the Invention with respect to Formula I and reacting the compound of Formula 27 with an amine of the formula HNR$^{36}$R$^{37}$ in which $R^{36}$ and $R^{37}$ are independently hydro, $(C_{1-4})$alkyl or together are —(CH$_2$)$_4$—; —(CH$_2$)$_5$—; —(CH$_2$)$_2$O(CH$_2$)$_2$— or —(CH$_2$)$_2$NR$^{38}$(CH$_2$)$_2$—, wherein $R^{38}$ is hydro or $(C_{1-4})$alkyl, to give a compound of Formula I in which $R^5$ is aminomethyl, $(C_{1-4})$alkylaminomethyl, di$(C_{1-4})$alkylaminomethyl, pyrrolidin-1-ylmethyl, piperidin-1-ylmethyl, morpholin-4-ylmethyl, piperazin-1-ylmethyl, 4-$(C_{1-4})$alkylpiperazin-1-ylmethyl;

(i) optionally further reacting a compound of Formula I in which $R^5$ or both $R^4$ and $R^5$ are carboxy, or an acid derivative thereof, with an appropriate amine or thiol to give a compound of Formula I in which $R^5$ or both $R^4$ and $R^5$ are 1H-tetrazol-5-ylcarbamoyl, 2-(dimethylamino)ethylcarbamoyl, 4-methylpiperazin-1-ylcarbonyl or 2-(dimethylamino)ethylmercapto;

(j) optionally further reacting a compound of Formula I in which $R^5$ is aminomethyl with an appropriately substituted amidine to give a compound of Formula I in which $R^5$ is —CH$_2$NHC(NR$^{11}$)NHR$^{12}$, wherein $R^{11}$ is hydro, acetyl or tert-butoxycarbonyl and $R^{12}$ is acetyl or tert-butoxycarbonyl;

(k) optionally further treating a compound of Formula I in which $R^5$ is —$CH_2NHC(NR^{11})NHR^{12}$, wherein $R^{11}$ is hydro, acetyl or tert-butoxycarbonyl and $R^{12}$ is acetyl or tert-butoxycarbonyl, with acid to give a compound of Formula I in which $R^5$ is —$CH_2NHC(NH)NH_2$;

(l) optionally further acylating a compound of Formula I in which $R^5$ is aminomethyl with an appropriate acylating agent, or a protected derivative thereof, and then deprotecting when necessary to give a corresponding compound of Formula I in which $R^5$ is —$CH_2NHR^{10}$, wherein $R^{10}$ is $(C_{1-4})$alkanoyl, trifluoro$(C_{1-4})$alkanoyl, carbamoyl, $(C_{1-4})$ alkyloxycarbonyl, $(C_{1-4})$alkylcarbamoyl, di$(C_{1-4})$ alkylcarbamoyl, amino$(C_{1-4})$alkanoyl, $(C_{1-4})$ alkylamino$(C_{1-4})$alkanoyl, di$(C_{1-4})$alkylamino$(C_{1-4})$ alkanoyl or a group selected from aroyl and heteroaroyl, (which aroyl and heteroaryl are optionally further substituted with one to two substituents independently selected from $(C_{1-4})$alkyloxy, cyano, carboxy and $(C_{1-4})$alkyloxycarbonyl);

(m) optionally further reacting a compound of Formula I in which $R^5$ is aminomethyl with $(C_{1-4})$alkyl isocyanate to give a compound of Formula I in which $R^5$ is —$CH_2NHR^{10}$, wherein $R^{10}$ is $(C_{1-4})$ alkylcarbamoyl;

(n) optionally further reacting a compound of Formula I in which $R^3$ is hydro with $(C_{1-4})$alkyl acrylate to give a compound of Formula I in which $R^3$ is 2-$(C_{1-4})$alkyloxycarbonylethyl;

(o) optionally further hydrolyzing a compound of Formula I in which $R^3$ is 2-$(C_{1-4})$alkyloxycarbonylethyl and/or $R^5$ is $(C_{1-4})$alkyloxycarbonyl or a group which is further substituted by a $(C_{1-4})$ alkyloxycarbonyl substituent, to give a compound of Formula I in which $R^3$ is 2-carboxyethyl and/or $R^5$ is carboxy or a group which is further substituted by a carboxy substituent;

(p) optionally further aminating a compound of Formula I in which $R^3$ is 2-carboxyethyl and/or $R^5$ is carboxy or a group which is further substituted by a carboxy substituent, to give a compound of Formula I in which $R^3$ is 2-carbamoylethyl and/or $R^5$ is carbamoyl or a group which is further substituted by a carbamoyl substituent;

(q) optionally further reacting a compound of Formula I in which $R^3$ is 2-carboxyethyl and/or $R^5$ is carboxy or a group which is further substituted by a carboxy substituent, with a $(C_{1-4})$alcohol to give a compound of Formula I in which $R^3$ is 2-$(C_{1-4})$ alkyloxycarbonylethyl and/or $R^5$ is $(C_{1-4})$ alkyloxycarbonyl or a group which is further substituted by a $(C_{1-4})$alkyloxycarbonyl substituent;

(r) optionally de-methylating a compound of Formula I in which $R^1$ is methoxy and/or in which $R^5$ is —$CH_2NHR^{10}$, wherein $R^{10}$ is a group selected from aroyl, heteroaroyl, aryl$(C_{1-4})$alkyl and heteroaryl $(C_{1-4})$alkyl (which aroyl, heteroaroyl, aryl and heteroaryl are further substituted with one to two methoxy substituents), to give a compound of Formula I in which $R^1$ is hydroxy and/or $R^5$ is —$CH_2NHR^{10}$, wherein $R^{10}$ is a group selected from aroyl, heteroaroyl, aryl$(C_{1-4})$alkyl and heteroaryl$(C_{1-4})$ alkyl (which aroyl, heteroaroyl, aryl and heteroaryl are further substituted with one to two hydroxy substituents);

(s) optionally reacting a compound of Formula I in which $R^5$ is —$CH_2NHR^{10}$, wherein $R^{10}$ is a group selected from aroyl, heteroaroyl, aryl$(C_{1-4})$alkyl and heteroaryl$(C_{1-4})$alkyl (which aroyl, heteroaroyl, aryl and heteroaryl are further substituted with a cyano substituent), with a hydrazoic acid derivative to give a compound of Formula I in which $R^5$ is —$CH_2NHR^{10}$, wherein $R^{10}$ is a group selected from aroyl, heteroaroyl, aryl$(C_{1-4})$alkyl and heteroaryl $(C_{1-4})$alkyl (which aroyl, heteroaroyl, aryl and heteroaryl are further substituted with a 1H-tetrazol-5-yl substituent);

(t) optionally further reacting the corresponding non-salt form of a compound of Formula I with a pharmaceutically acceptable inorganic or organic acid or base to give a pharmaceutically acceptable salt;

(u) optionally further reacting the corresponding acid addition salt or base addition salt form of a compound of Formula I with a suitable base or acid, respectively, to give the free acid or free base; and (v) optionally further separating a mixture of stereoisomers of a compound of Formula I to give a single stereoisomer.

10. A process of claim 1 for the preparation of a compound of Formula I:

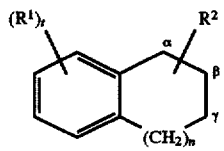

in which:

n is 0, 1 or 2;

t is 0, 1, 2 or 3;

$R^1$ is independently halo, hydroxy or $(C_{1-4})$alkyloxy; and $R^2$ is attached at the α-, β- or γ-position and is a group of Formula (a):

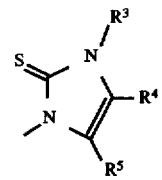

in which:

$R^5$ is hydro, $R^3$ is hydro, 2-$(C_{1-4})$alkyloxycarbonylethyl, 2-carboxyethyl or 2-carbamoylethyl and $R^5$ is formyl, 1-hydroxy$(C_{1-4})$alkyl or —$CH_2NHR^{10}$ {in which $R^{10}$ is hydro, $(C_{1-4})$alkyl, $(C_{1-4})$alkanoyl, trifluoro$(C_{1-4})$ alkanoyl, carbamoyl, $(C_{1-4})$alkyloxycarbonyl, $(C_{1-4})$ alkylcarbamoyl, di$(C_{1-4})$alkylcarbamoyl, amino$(C_{1-4})$ alkanoyl, $(C_{1-4})$alkylamino$(C_{1-4})$alkanoyl, di$(C_{1-4})$ alkylamino$(C_{1-4})$alkanoyl, carboxy$(C_{1-4})$alkyl, $(C_{1-4})$ alkyloxycarbonyl$(C_{1-4})$alkyl, carbamoyl$(C_{1-4})$alkyl, a group selected from aroyl, heteroaroyl, aryl$(C_{1-4})$alkyl and heteroaryl$(C_{1-4})$alkyl (which aroyl, heteroaroyl, aryl and heteroaryl are optionally further substituted with one to two substituents independently selected from hydroxy, $(C_{1-4})$alkyloxy, cyano, 1H-tetrazol-5-yl, carboxy and $(C_{1-4})$alkyloxycarbonyl) or —$C(NR^{11})$ $NHR^{12}$ (in which $R^{11}$ and $R^{12}$ are independently hydro, acetyl or tert-butoxycarbonyl)}; and the pharmaceutically acceptable salts, individual isomers, and mixtures of isomer thereof; which process comprises:

(a) reacting a compound of Formula 9:

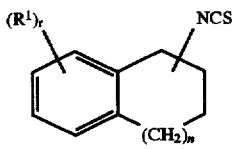

in which each n, t and $R^1$ are as defined above with respect to Formula I, with D-(+)-glucosamine and then oxidizing to give a compound of Formula I in which $R^4$ is formyl;

(b) optionally further reacting a compound of Formula I in which $R^4$ is formyl with hydroxylamine hydrochloride and then reducing to give a compound of Formula I in which $R^4$ is aminomethyl;

(c) optionally further alkylating a compound of Formula I in which $R^5$ is formyl to give a compound of Formula I in which $R^4$ is 1-hydroxy($C_{1-4}$)alkyl;

(d) optionally further reacting a compound of Formula I in which $R^4$ is formyl with an amine of the formula $NH_2R^{10}$, wherein $R^{10}$ is as defined above with respect to Formula I, in the presence of a chemical reducing agent or catalytic hydrogenation to give a corresponding compound of Formula I in which $R^4$ is —$CH_2NHR^{10}$;

(e) optionally further reacting a compound of Formula I in which $R^4$ is aminomethyl with an appropriately substituted amidine to give a compound of Formula I in which $R^4$ is —$CH_2NHC(NR^{11})NHR^{12}$, wherein $R^{11}$ is hydro, acetyl or tert-butoxycarbonyl and $R^{12}$ is acetyl or tert-butoxycarbonyl;

(f) optionally further treating a compound of Formula I in which $R^4$ is —$CH_2NHC(NR^{11})NHR^{12}$, wherein $R^{11}$ is hydro, acetyl or tert-butoxycarbonyl and $R^{12}$ is acetyl or tert-butoxycarbonyl, with acid to give a compound of Formula I in which $R^4$ is —$CH_2NHC(NH)NH_2$;

(g) optionally further acylating a compound of Formula I in which $R^4$ is aminomethyl with an appropriate acylating agent, or a protected derivative thereof, and then deprotecting when necessary to give a corresponding compound of Formula I in which $R^4$ is —$CH_2NHR^{10}$, wherein $R^{10}$ is ($C_{1-4}$)alkanoyl, trifluoro($C_{1-4}$)alkanoyl, carbamoyl, ($C_{1-4}$)alkyloxycarbonyl, ($C_{1-4}$)alkylcarbamoyl, di($C_{1-4}$)alkylcarbamoyl, amino($C_{1-4}$)alkanoyl, ($C_{1-4}$)alkylamino($C_{1-4}$)alkanoyl, di($C_{1-4}$)alkylamino($C_{1-4}$)alkanoyl or a group selected from aroyl and heteroaroyl, (which aroyl and heteroaroyl are optionally further substituted with one to two substituents independently selected from ($C_{1-4}$)alkyloxy, cyano, carboxy and ($C_{1-4}$)alkyloxycarbonyl);

(h) optionally further reacting a compound of Formula I in which $R^4$ is aminomethyl with ($C_{1-4}$)alkyl isocyanate to give a compound of Formula I in which $R^4$ is —$CH_2NHR^{10}$, wherein $R^{10}$ is ($C_{1-4}$)alkylcarbamoyl;

(i) optionally further reacting a compound of Formula I in which $R^3$ is hydro with ($C_{1-4}$)alkyl acrylate to give a compound of Formula I in which $R^3$ is 2-($C_{1-4}$)alkyloxycarbonylethyl;

(j) optionally further hydrolyzing a compound of Formula I in which $R^3$ is 2-($C_{1-4}$)alkyloxycarbonylethyl and/or $R^4$ is —$CH_2NHR^{10}$, wherein $R^{10}$ is a group which is further substituted by a ($C_{1-4}$) alkyloxycarbonyl substituent, to give a compound of Formula I in which $R^3$ is 2-carboxyethyl and/or $R^4$ is —$CH_2NHR^{10}$, wherein $R^{10}$ is a group which is further substituted by a carboxy substituent;

(k) optionally further aminating a compound of Formula I in which $R^3$ is 2-carboxyethyl and/or $R^4$ is —$CH_2NHR^{10}$, wherein $R^{10}$ is a group which is further substituted by a carboxy substituent, to give a compound of Formula I in which $R^3$ is 2-carbamoylethyl and/or $R^4$ is —$CH_2NHR^{10}$, wherein $R^{10}$ is a group which is further substituted by a carbamoyl substituent;

(l) optionally further reacting a compound of Formula I in which $R^3$ is 2-carboxyethyl and/or $R^4$ is —$CH_2NHR^{10}$, wherein $R^{10}$ is a group which is further substituted by a carboxy substituent, with a ($C_{1-4}$)alcohol to give a compound of Formula I in which $R^3$ is 2-($C_{1-4}$)alkyloxycarbonylethyl and/or $R^4$ is —$CH_2NHR^{10}$, wherein $R^{10}$ is a group which is further substituted by a ($C_{1-4}$)alkyloxycarbonyl substituent;

(m) optionally de-methylating a compound of Formula I in which $R^1$ is methoxy and/or in which $R^4$ is —$CH_2NHR^{10}$, wherein $R^{10}$ is a group selected from aroyl, heteroaroyl, aryl($C_{1-4}$)alkyl and heteroaryl ($C_{1-4}$)alkyl (which aroyl, heteroaroyl, aryl and heteroaryl are further substituted with one to two methoxy substituents) to give a compound of Formula I in which $R^1$ is hydroxy and/or $R^4$ is —$CH_2NHR^{10}$, wherein $R^{10}$ is a group selected from aroyl, heteroaroyl, aryl($C_{1-4}$)alkyl and heteroaryl($C_{1-4}$) alkyl (which aroyl, heteroaroyl, aryl and heteroaryl are further substituted with one to two hydroxy substituents);

(n) optionally reacting a compound of Formula I in which $R^4$ is —$CH_2NHR^{10}$, wherein $R^{10}$ is a group selected from aroyl, heteroaroyl, aryl($C_{1-4}$)alkyl and heteroaryl($C_{1-4}$)alkyl (which aroyl, heteroaroyl, aryl and heteroaryl are further substituted with a cyano substituent) with a hydrazoic acid derivative to give a compound of Formula I in which $R^4$ is —$CH_2NHR^{10}$, wherein $R^{10}$ is a group selected from aroyl, heteroaroyl, aryl($C_{1-4}$)alkyl and heteroaryl ($C_{1-4}$)alkyl (which aroyl, heteroaroyl, aryl and heteroaryl are further substituted with a 1H-tetrazol-5-yl substituent);

(o) optionally further reacting the corresponding non-salt form of a compound of Formula I with a pharmaceutically acceptable inorganic or organic acid or base to give a pharmaceutically acceptable salt;

(p) optionally further reacting the corresponding acid addition salt or base addition salt form of a compound of Formula I with a suitable base or acid, respectively, to give the free acid or free base; and (q) optionally further separating a mixture of stereoisomers of a compound of Formula I to give a single stereoisomer.

11. A process for the preparation of a compound of Formula I:

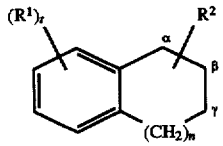

in which:
n is 0, 1 or 2;
t is 0, 1, 2 or 3;

$R^1$ is independently halo, hydroxy or $(C_{1-4})$alkyloxy; and $R^2$ is attached at the α-, β- or γ-position and is a group of Formula (b):

in which:

$R^6$ is hydro, 2-carboxyethyl, 2-carbamoylethyl or 2-$(C_{1-4})$ alkyloxycarbonylethyl and $R^7$ is hydro, pyrrolidin-1-ylmethyl, piperidin-1-ylmethyl, morpholin-4-ylmethyl, piperazin-1-ylmethyl, 4-$(C_{1-4})$ alkylpiperazin-1-ylmethyl or —$CH_2NR^{10}R^{17}$ {in which $R^{10}$ is hydro, $(C_{1-4})$alkanoyl, trifluoro$(C_{1-4})$ alkanoyl, carbamoyl, $(C_{1-4})$alkyloxycarbonyl, $(C_{1-4})$ alkylcarbamoyl, di$(C_{1-4})$alkylcarbamoyl, amino$(C_{1-4})$ alkanoyl, $(C_{1-4})$alkylamino$(C_{1-4})$alkanoyl, di$(C_{1-4})$ alkylamino$(C_{1-4})$alkanoyl, a group selected from aroyl and heteroaroyl (which aroyl and heteroaroyl are optionally substituted with one to two substituents independently selected from hydroxy, $(C_{1-4})$ alkyloxy, cyano, 1H-tetrazol-5-yl, carboxy and $(C_{1-4})$ alkyloxycarbonyl) or —$C(NR^{11})NHR^{12}$ (in which $R^{11}$ and $R^{12}$ are independently hydro, acetyl or tert-butoxycarbonyl) and $R^{17}$ is hydro or $C_{1-4}$alkyl}; and the pharmaceutically acceptable salts, individual isomers, and mixtures of isomers thereof; which process comprises:

(a) reacting a compound of Formula 9:

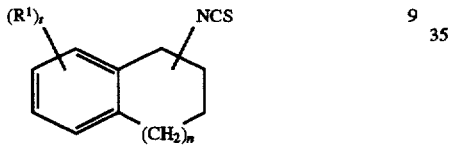

in which each n, t and $R^1$ are as defined above with respect to Formula I with a hydrazide of the formula $H_2C(O)R^{34}$ (in which $R^{34}$ is hydro, aminomethyl, $(C_{1-4})$alkylaminomethyl, di$(C_{1-4})$alkylaminomethyl, pyrrolidin-1-ylmethyl, piperidin-1-ylmethyl, morpholin-4-ylmethyl, piperazin-1-ylmethyl or 4-$(C_{1-4})$alkylpiperazin-1-ylmethyl), or a protected derivative thereof, then treating with base and when necessary deprotecting to give a compound of Formula I in which $R^6$ is hydro and $R^7$ is hydro, aminomethyl, $(C_{1-4})$alkylaminomethyl, di$(C_{1-4})$ alkylaminomethyl, pyrrolidin-1-ylmethyl, piperidin-1-ylmethyl, morpholin-4-ylmethyl, piperazin-1-ylmethyl or 4-$(C_{1-4})$alkylpiperazin-1-ylmethyl;

(b) optionally further reacting a compound of Formula I in which $R^7$ is aminomethyl with an appropriately substituted amidine to give a compound of Formula I in which $R^4$ is —$CH_2NHC(NR^{11})NHR^{12}$, wherein $R^{11}$ is hydro, acetyl or tert-butoxycarbonyl and $R^{12}$ is acetyl or tert-butoxycarbonyl;

(c) optionally further treating a compound of Formula I in which $R^7$ is —$CH_2NHC(NR^{11})NHR^{12}$, wherein $R^{11}$ is hydro, acetyl or tert-butoxycarbonyl and $R^{12}$ is acetyl or tert-butoxycarbonyl, with acid to give a compound of Formula I in which $R^4$ is —$CH_2NHC(NH)NH_2$;

(d) optionally further acylating a compound of Formula I in which $R^7$ is aminomethyl with an appropriate acylating agent, or a protected derivative thereof, and then deprotecting when necessary to give a corresponding compound of Formula I in which $R^7$ is —$CH_2NHR^{10}$, wherein $R^{10}$ is $(C_{1-4})$alkanoyl, trifluoro$(C_{1-4})$alkanoyl, carbamoyl, $(C_{1-4})$ alkyloxycarbonyl, $(C_{1-4})$alkylcarbamoyl, di$(C_{1-4})$ alkylcarbamoyl, amino$(C_{1-4})$alkanoyl, $(C_{1-4})$ alkylamino$(C_{1-4})$alkanoyl, di$(C_{1-4})$alkylamino$(C_{1-4})$ alkanoyl or a group selected from aroyl and heteroaroyl, (which aroyl and heteroaroyl are optionally further substituted with one to two substituents independently selected from $(C_{1-4})$alkyloxy, cyano, carboxy and $(C_{1-4})$alkyloxycarbonyl);

(e) optionally further reacting a compound of Formula I in which $R^7$ is aminomethyl with $(C_{1-4})$alkyl isocyanate to give a compound of Formula I in which $R^7$ is —$CH_2NHR^{10}$, wherein $R^{10}$ is $(C_{1-4})$ alkylcarbamoyl;

(f) optionally further reacting a compound of Formula I in which $R^6$ is hydro with $(C_{1-4})$alkyl acrylate to give a compound of Formula I in which $R^6$ is 2-$(C_{1-4})$alkyloxycarbonylethyl;

(g) optionally further hydrolyzing a compound of Formula I in which $R^6$ is 2-$(C_{1-4})$alkyloxycarbonylethyl and/or $R^7$ is —$CH_2NHR^{10}$, wherein $R^{10}$ is a group which is further substituted by a $(C_{1-4})$ alkyloxycarbonyl substituent, to give a compound of Formula I in which $R^6$ is 2-carboxyethyl and/or $R^7$ is —$CH_2NHR^{10}$, wherein $R^{10}$ is a group which is further substituted by a carboxy substituent;

(h) optionally further aminating a compound of Formula I in which $R^6$ is 2-carboxyethyl and/or $R^7$ is —$CH_2NHR^{10}$, wherein $R^{10}$ is a group which is further substituted by a carboxy substituent, to give a compound of Formula I in which $R^6$ is 2-carbamoylethyl and/or $R^7$ is —$CH_2NHR^{10}$, wherein $R^{10}$ is a group which is further substituted by a carbamoyl substituent;

(i) optionally further reacting a compound of Formula I in which $R^6$ is 2-carboxyethyl and/or $R^7$ is —$CH_2NHR^{10}$, wherein $R^{10}$ is a group which is further substituted by a carboxy substituent, with a $(C_{1-4})$alcohol to give a compound of Formula I in which $R^6$ is 2-$(C_{1-4})$alkyloxycarbonylethyl and/or $R^7$ is —$CH_2NHR^{10}$, wherein $R^{10}$ is a group which is further substituted by a $(C_{1-4})$alkyloxycarbonyl substituent;

(j) optionally de-methylating a compound of Formula I in which $R^1$ is methoxy and/or in which $R^7$ is —$CH_2NHR^{10}$, wherein $R^{10}$ is a group selected from aroyl, heteraroyl, aryl$(C_{1-4})$alkyl and heteroaryl $(C_{1-4})$alkyl (which aroyl, heteroaroyl, aryl and heteroaryl are further substituted with one to two methoxy substituents) to give a compound of Formula I in which $R^1$ is hydroxy and/or $R^7$ is —$CH_2NHR^{10}$, wherein $R^{10}$ is a group selected from aroyl, heteraroyl, aryl$(C_{1-4})$alkyl and heteroaryl$(C_{1-4})$alkyl (which aroyl, heteroaroyl, aryl and heteroaryl are further substituted with one to two hydroxy substituents);

(k) optionally reacting a compound of Formula I in which $R^7$ is —$CH_2NHR^{10}$, wherein $R^{10}$ is a group selected from aroyl, heteraroyl, aryl$(C_{1-4})$alkyl and heteroaryl$(C_{1-4})$alkyl (which aroyl, heteroaroyl, aryl and heteroaryl are further substituted with a cyano substituent) with a hydrazoic acid derivative to give a compound of Formula I in which $R^7$ is —$CH_2NHR^{10}$, wherein $R^{10}$ is a group selected from aroyl, heteraroyl, aryl($C_{1-4}$)alkyl and heteroaryl ($C_{1-4}$)alkyl (which aroyl, heteroaroyl, aryl and heteroaryl are further substituted with a 1H-tetrazol-5-yl substituent);

(l) optionally further reacting the corresponding non-salt form of a compound of Formula I with a pharmaceutically acceptable inorganic or organic acid or base to give a pharmaceutically acceptable salt;

(m) optionally further reacting the corresponding acid addition salt or base addition salt form of a compound of Formula I with a suitable base or acid, respectively, to give the free acid or free base; and (n) optionally further separating a mixture of stereoisomers of a compound of Formula I to give a single stereoisomer.

12. A process for the preparation of a compound of Formula I:

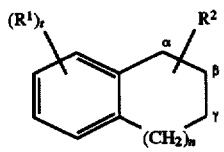

in which:
n is 0, 1 or 2;
t is 0, 1, 2 or 3;
$R^1$ is independently halo, hydroxy or ($C_{1-4}$)alkyloxy; and
$R^2$ is attached at the α-, β- or γ-position and is a group of Formula (c):

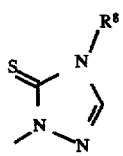

in which:
$R^8$ is hydro, 2-carboxyethyl, 2-carbamoylethyl or 2-($C_{1-4}$)alkyloxycarbonylethyl; and the pharmaceutically acceptable salts, individual isomers and mixtures of isomers thereof; which process comprises:

(a) reacting a compound of Formula 24:

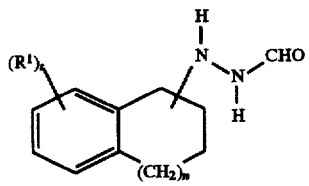

in which n, t and $R^1$ are as defined above with respect to Formula I with an isothiocyanate and then treating with base to give a compound of Formula I in which $R^8$ is hydro; and (b) optionally further reacting a compound of Formula I in which $R^8$ is hydro with ($C_{1-4}$)alkyl acrylate to give a compound of Formula I in which $R^8$ is 2-($C_{1-4}$)alkyloxycarbonylethyl;

(c) optionally further hydrolyzing a compound of Formula I in which $R^8$ is 2-($C_{1-4}$)alkyloxycarbonylethyl to give a compound of Formula I in which $R^8$ is 2-carboxyethyl;

(d) optionally further aminating a compound of Formula I in which $R^8$ is 2-carboxyethyl to give a compound of Formula I in which $R^8$ is 2-carbamoylethyl;

(e) optionally further reacting a compound of Formula I in which $R^8$ is 2-carboxyethyl with a ($C_{1-4}$)alcohol to give a compound of Formula I in which $R^8$ is 2-($C_{1-4}$)alkyloxycarbonylethyl;

(f) optionally de-methylating a compound of Formula I in which $R^1$ is methoxy to give a compound of Formula I in which $R^1$ is hydroxy;

(g) optionally further reacting the corresponding non-salt form of a compound of Formula I with a pharmaceutically acceptable inorganic or organic acid or base to give a pharmaceutically acceptable salt;

(h) optionally further reacting the corresponding acid addition salt or base addition salt form of a compound of Formula I with a suitable base or acid, respectively, to give the free acid or free base; and (i) optionally further separating a mixture of stereoisomers of a compound of Formula I to give a single stereoisomer.

13. A process for the preparation of a compound of Formula I:

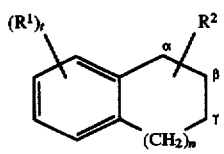

in which:
n is 0, 1 or 2;
t is 0, 1, 2 or 3;
$R^1$ is independently halo, hydroxy or ($C_{1-4}$)alkyloxy; and
$R^2$ is attached at the α-, β- or γ-position and is a group of Formula (c):

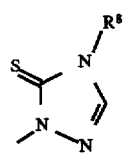

in which:
$R^8$ is —$NHR^{10}$ {in which $R^{10}$ is hydro, ($C_{1-4}$)alkanoyl, trifluoro($C_{1-4}$)alkanoyl, carbamoyl, ($C_{1-4}$)alkyloxycarbonyl, ($C_{1-4}$)alkylcarbamoyl, di($C_{1-4}$)alkylcarbamoyl, amino($C_{1-4}$)alkanoyl, ($C_{1-4}$)alkylamino($C_{1-4}$)alkanoyl, di($C_{1-4}$)alkylamino($C_{1-4}$)alkanoyl, a group selected from aroyl and heteroaroyl (which aroyl and heteroaroyl are optionally further substituted with one to two substituents independently selected from hydroxy, ($C_{1-4}$)alkyloxy, cyano, 1H-tetrazol-5-yl, carboxy and ($C_{1-4}$)alkyloxycarbonyl) or —$C(NR^{11})NHR^{12}$ (in which $R^{11}$ and $R^{12}$ are independently hydro, acetyl or tert-butoxycarbonyl)}; and the pharmaceutically acceptable salts, individual isomers, and mixtures of isomers thereof; which process comprises:

(a) reacting a compound of Formula 5:

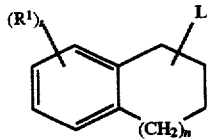

in which n, t and $R^1$ are as defined above with respect to Formula I with 1,2,4-triazol-4-ylamino and then sulfurizing to give a compound of Formula I in which $R^8$ is amino; and (b) optionally further reacting a compound of Formula I in which $R^8$ is amino with an appropriately substituted amidine to give a compound of Formula I in which $R^8$ is —NHC(NR$^{11}$)NHR$^{12}$, wherein $R^{11}$ is hydro, acetyl or tert-butoxycarbonyl and $R^{12}$ is acetyl or tert-butoxycarbonyl;

(c) optionally further treating a compound of Formula I in which $R^8$ is —NHC(NR$^{11}$)NHR$^{12}$, wherein $R^{11}$ is hydro, acetyl or tert-butoxycarbonyl and $R^{12}$ is acetyl or tert-butoxycarbonyl, with acid to give a compound of Formula I in which $R^8$ is —NHC(NH)NH$_2$; (d) optionally further acylating a compound of Formula I in which $R^8$ is amino with an appropriate acylating agent, or a protected derivative thereof, and then deprotecting when necessary to give a corresponding compound of Formula I in which $R^8$ is —NHR$^{10}$, wherein $R^{10}$ is $(C_{1-4})$alkanoyl, trifluoro $(C_{1-4})$alkanoyl, carbamoyl, $(C_{1-4})$alkyloxycarbonyl, $(C_{1-4})$alkylcarbamoyl, di$(C_{1-4})$alkylcarbamoyl, amino$(C_{1-4})$alkanoyl, $(C_{1-4})$alkylamino$(C_{1-4})$ alkanoyl, di$(C_{1-4})$alkylamino$(C_{1-4})$alkanoyl or a group selected from aroyl and heteroaroyl, (which aroyl and heteroaroyl are optionally further substituted with one to two substituents independently selected from $(C_{1-4})$alkyloxy, cyano, carboxy and $(C_{1-4})$alkyloxycarbonyl);

(e) optionally further hydrolyzing a compound of Formula I in which $R^8$ is —NHR$^{10}$, wherein $R^{10}$ is a group which is further substituted by a $(C_{1-4})$ alkyloxycarbonyl substituent, to give a compound of Formula I in which $R^8$ is —NHR$^{10}$, wherein $R^{10}$ is a group which is further substituted by a carboxy substituent;

(f) optionally further aminating a compound of Formula I in which $R^8$ is —NHR$^{10}$, wherein $R^{10}$ is a group which is further substituted by a carboxy substituent, to give a compound of Formula I in which $R^8$ is —NHR$^{10}$, wherein $R^{10}$ is a group which is further substituted by a carbamoyl substituent;

(g) optionally further reacting a compound of Formula I in which $R^8$ is —NHR$^{10}$, wherein $R^{10}$ is a group which is further substituted by a carboxy substituent, with a $(C_{1-4})$alcohol to give a compound of Formula I in which $R^8$ is —NHR$^{10}$, wherein $R^{10}$ is a group which is further substituted by a $(C_{1-4})$ alkyloxycarbonyl substituent;

(h) optionally de-methylating a compound of Formula I in which $R^{10}$ is methoxy and/or in which $R^8$ is —NHR$^{10}$, wherein $R^{10}$ is a group selected from aroyl, heteroaroyl, aryl$(C_{1-4})$alkyl and heteroaryl $(C_{1-4})$alkyl (which aroyl, heteroaroyl, aryl and heteroaryl are further substituted with one to two methoxy substituents) to give a compound of Formula I in which $R^1$ is hydroxy and/or $R^8$ is —NHR$^{10}$, wherein $R^{10}$ is a group selected from aroyl, heteroaroyl, aryl$(C_{1-4})$alkyl and heteroaryl$(C_{1-4})$alkyl (which aroyl, heteroaroyl, aryl and heteroaryl are further substituted with one to two hydroxy substituents);

(i) optionally reacting a compound of Formula I in which $R^8$ is —NHR$^{10}$, wherein $R^{10}$ is a group selected from aroyl, heteroaroyl, aryl$(C_{1-4})$alkyl and heteroaryl$(C_{1-4})$alkyl (which aroyl, heteroaroyl, aryl and heteroaryl are further substituted with a cyano substituent) with a hydrazoic acid derivative to give a compound of Formula I in which $R^8$ is —NHR$^{10}$, wherein $R^{10}$ is a group selected from aroyl, heteroaroyl, aryl$(C_{1-4})$alkyl and heteroaryl$(C_{1-4})$ alkyl (which aroyl, heteroaroyl, aryl and heteroaryl are further substituted with a 1H-tetrazol-5-yl substituent);

(j) optionally further reacting the corresponding non-salt form of a compound of Formula I with a pharmaceutically acceptable inorganic or organic acid or base to give a pharmaceutically acceptable salt;

(k) optionally further reacting the corresponding acid addition salt or base addition salt form of a compound of Formula I with a suitable base or acid, respectively, to give the free acid or free base; and (l) optionally further separating a mixture of stereoisomers of a compound of Formula I to give a single stereoisomer.

14. A process for the preparation of a compound of Formula II:

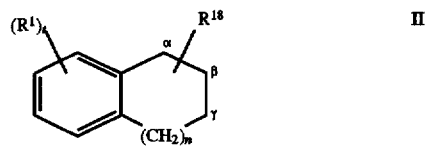

in which:

n is 0, 1 or 2;

t is 0, 1, 2 or 3;

$R^1$ is independently halo, hydroxy or $(C_{1-4})$alkyloxy; and $R^{18}$ is attached at the α-, β- or γ-position and is a group selected from Formula (d), (e) or (f):

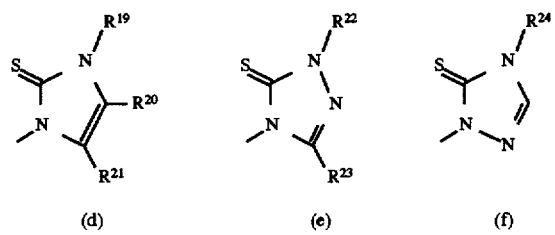

in which:

$R^{20}$ is hydro, $R^{19}$ is hydro or —(CH$_2$)$_q$R$^9$ {in which q is 0, 1, 2, 3 or 4 and $R^9$ is carboxy, $(C_{1-4})$ alkyloxycarbonyl, carbamoyl or a group selected from aryl and heteroaryl (which group is optionally further substituted with one to two substituents independently selected from hydroxy, $(C_{1-4})$alkyloxy, cyano, 1H-tetrazo-5-yl, carboxy and $(C_{1-4})$alkyloxycarbonyl)} and $R^{21}$ is —NR$^{25}$R$^{26}$ (in which $R^{25}$ is hydro or $(C_{1-4})$alkyl and $R^{26}$ is L-alanyl, L-arginyl, L-asparaginyl, L-α-aspartyl, L-β-aspartyl, L-cysteinyl, L-glutaminyl, L-α-glutamyl, L-γ-glutamyl, N-(C$_{1-4}$) alkanoyl-L-α-glutamyl, N-(C$_{1-4}$)alkanoyl-L-γ-glutamyl, glycyl, L-histidyl, L-isoleucyl, L-leucyl, L-lysyl, L-methionyl, L-ornithinyl, L-phenylalanyl, L-prolyl, L-seryl, L-threonyl, L-tryptophyl, L-tyrosyl, L-valyl, 1-amino-cyclopropylcarbonyl, 1-aminocyclobutylcarbonyl, 1-aminocyclopentylcarbonyl or 1-aminocyclohexylcarbonyl); or $R^{20}$ and $R^{21}$ are each hydro and $R^{19}$ is —NR$^{25}$R$^{26}$ (in which $R^{25}$ and $R^{26}$ are as defined above); or $R^{21}$ is hydro, $R^{19}$ is hydro or —(CH$_2$)$_q$R$^9$ (in which q and $R^9$ are as defined above) and $R^{20}$ is —CH$_2$R$^{25}$R$^{26}$ (in which $R^{25}$ and $R^{26}$ are as defined above); or $R^{19}$ is hydro or —(CH$_2$)$_q$R$^9$ (in which q and $R^9$ are as defined above), $R^{20}$ is hydro, $(C_{1-4})$alkyl or —C(O)R$^{14}$ (in which $R^{14}$ is amino, hydroxy($C_{1-4}$)alkyloxy, 2-(dimethylamino)ethylamino, 4-methylpiperazin-1-yl, 2-(dimethylamino) ethylmercapto, 4-(methylsulfonylamino)anilino or 1H-tetrazol-5-ylamino) and $R^{21}$ is —$CH_2NR^{25}R^{26}$ (in which $R^{25}$ and $R^{26}$ is as defined above); and $R^{22}$ is hydro, 2-carboxyethyl, 2-carbamoylethyl or 2-($C_{1-4}$)alkyloxycarbonylethyl;

$R^{23}$ is —$CH_2NR^{25}R^{26}$ (in which $R^{25}$ and $R^{26}$ are as defined above); and $R^{24}$ is —$NR^{25}R^{26}$ (in which $R^{25}$ and $R^{26}$ are as defined above); and the pharmaceutically acceptable salts, individual isomers and mixtures of isomers thereof, which process comprises:

(a) reacting a protected derivative of an L-amino acid with a compound of Formula I:

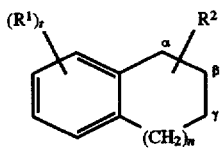

or a pharmaceutically acceptable salt, an individual isomer or a mixture of isomers thereof, in which each n, t and $R^1$ are as defined above with respect to Formula II; and $R^2$ is attached at the α-, β- or γ-position and is a group selected from Formulae (a), (b) and (c):

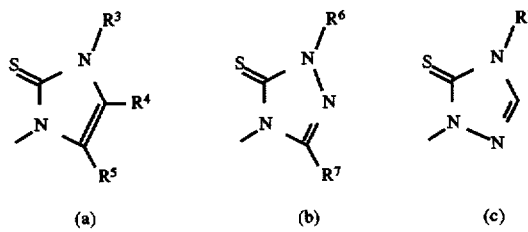

(a)  (b)  (c)

in which:

$R^4$ is hydro, $R^3$ is hydro or —$(CH_2)_qR^9$ (in which q and $R^9$ are as defined above) and $R^5$ is —$NHR^{10}$ (in which $R^{10}$ is hydro or ($C_{1-4}$)alkyl); or $R^4$ and $R^5$ are each hydro and $R^3$ is —$NHR^{10}$ (in which $R^{10}$ is as defined above); or $R^5$ is hydro, $R^3$ is hydro or —$(CH_2)_qR^9$ (in which q and $R^9$ are as defined above) and $R^4$ is —$CH_2NHR^{10}$ (in which $R^{10}$ is as defined above); or $R^3$ is hydro or —$(CH_2)_qR^9$ (in which q and $R^9$ are as defined above), $R^4$ is hydro, ($C_{1-4}$)alkyl or —$C(O)R^{14}$ (in which $R^{14}$ is amino, hydroxy($C_{1-4}$)alkyloxy, 2-(dimethylamino)ethylamino, 4-methylpiperazin-1-yl, 2-(dimethylamino) ethylmercapto, 4-(methylsulfonylamino)anilino or 1H-tetrazol-5-ylamino) and $R^5$ is —$CH_2NHR^{10}$ (in which $R^{10}$ is as defined above); and $R^6$ is hydro, 2-carboxyethyl, 2-carbamoylethyl or 2-($C_{1-4}$) alkyloxycarbonylethyl;

$R^7$ is —$CH_2NHR^{10}$ (in which $R^{10}$ is as defined above); and $R^8$ is —$NHR^{10}$ (in which $R^{10}$ is as defined above); and (b) optionally further reacting the corresponding non-salt form of a compound of Formula II with a pharmaceutically acceptable inorganic or organic acid or base to give a pharmaceutically acceptable salt;

(c) optionally further reacting the corresponding acid addition salt or base addition salt form of a compound of Formula II with a suitable base or acid, respectively, to give the free acid or free base; and (d) optionally further separating a mixture of stereoisomers of a compound of Formula II to give a single stereoisomer.

15. A process for the preparation of a compound of Formula III:

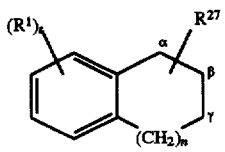

in which:

n is 0, 1 or 2;

t is 0, 1, 2 or 3;

$R^1$ is independently halo, hydroxy or ($C_{1-4}$)alkyloxy; and $R^{27}$ is attached at the α-, β- or γ-position and is a group selected from Formulae (g), (h) and (i):

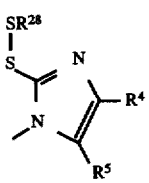 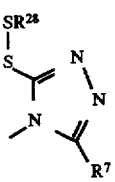 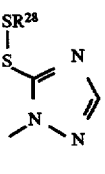

(g)  (h)  (i)

in which:

$R^4$ is hydro and $R^5$ is hydro or —$NHR^{10}$ {in which $R^{10}$ is hydro, ($C_{1-4}$)alkanoyl, trifluoro($C_{1-4}$)alkanoyl, carbamoyl, ($C_{1-4}$)alkyloxycarbonyl, ($C_{1-4}$) alkylcarbamoyl, di($C_{1-4}$)alkylcarbamoyl, amino($C_{1-4}$) alkanoyl, ($C_{1-4}$)alkylamino($C_{1-4}$)alkanoyl, di($C_{1-4}$) alkylamino($C_{1-4}$)alkanoyl, a group selected from aroyl and heteroaroyl (which aroyl and heteroaroyl are optionally further substituted with one to two substituents independently selected from hydroxy, ($C_{1-4}$) alkyloxy, cyano, 1H-tetrazol-5-yl, carboxy and ($C_{1-4}$) alkyloxycarbonyl) or —$C(NR^{11})NHR^{12}$ (in which $R^{11}$ and $R^{12}$ are independently hydro, acetyl or tert-butoxycarbonyl)}; or $R^5$ is hydro and $R^4$ is ($C_{1-4}$)alkyl, di($C_{1-4}$)alkylaminomethyl, piperidin-1-ylmethyl, morpholin-4-ylmethyl, 1-hydroxy($C_{1-4}$)alkyl or —$CH_2NHR^{13}$ {in which $R^{13}$ is hydro, ($C_{1-4}$)alkyl, ($C_{1-4}$)alkanoyl, trifluoro($C_{1-4}$)alkanoyl, carbamoyl, ($C_{1-4}$)alkyloxycarbonyl, ($C_{1-4}$)alkylcarbamoyl, di($C_{1-4}$)alkylcarbamoyl, amino($C_{1-4}$)alkanoyl, ($C_{1-4}$) alkylamino($C_{1-4}$)alkanoyl, di($C_{1-4}$)alkylamino($C_{1-4}$) alkanoyl, carboxy($C_{1-4}$)alkyl, ($C_{1-4}$)alkyloxycarbonyl ($C_{1-4}$)alkyl, carbamoyl ($C_{1-4}$)alkyl, a group selected from aroyl, heteroaroyl, aryl($C_{1-4}$)alkyl and heteroaryl ($C_{1-4}$)alkyl (which aroyl, heteroaroyl, aryl and heteroaryl are optionally further substituted with one to two substituents independently selected from hydroxy, ($C_{1-4}$)alkyloxy, cyano, 1H-tetrazol-5-yl, carboxy and ($C_{1-4}$)alkyloxycarbonyl) or —$C(NR^{11})$ $NHR^{12}$ (in which $R^{11}$ and $R^{12}$ are as defined above)}; or $R^4$ is hydro, ($C_{1-4}$)alkyl or —$C(O)R^{14}$ (in which $R^{14}$ is amino, hydroxy($C_{1-4}$)alkyloxy, 2-(dimethylamino) ethylamino, 4-methylpiperazin-1-yl, 2-(dimethylamino)ethylmercapto, 4-(methylsulfonylamino)anilino or 1H-tetrazol-5-ylamino) and $R^5$ is hydroxymethyl, 1H-tetrazol-5-yl, 4,5-dihydroimidazol-2-yl, pyrrolidin-1-ylmethyl, piperidin-1-ylmethyl, morpholin-4-ylmethyl, piperazin-1-ylmethyl, 4-($C_{1-4}$)alkylpiperazin-1-ylmethyl, —C(O)$R^{14}$ (in which $R^{14}$ are as defined above), —C(NH)NR$^{15}$R$^{16}$ (in which $R^{15}$ and $R^{16}$ are independently hydro, ($C_{1-4}$)alkyl or trifluoro($C_{1-4}$) alkyl) or —CH$_2$NR$^{17}$ (in which $R^{10}$ is as defined above and $R^{17}$ is hydro or ($C_{1-4}$)alkyl); or $R^4$ and $R^5$ are dependently di($C_{1-4}$)alkylaminomethyl, piperidin-1-ylmethyl, morpholin-4-ylmethyl or hydroxymethyl;

$R^6$ is hydro, 2-carboxyethyl, 2-carbamoylethyl or 2-($C_{1-4}$)alkyloxycarbonylethyl;

$R^7$ is hydro, pyrrolidin-1-ylmethyl, piperidin-1-ylmethyl, morpholin-4-ylmethyl, piperazin-1-ylmethyl, 4-($C_{1-4}$)alkylpiperazin-1-ylmethyl or —CH$_2$NR$^{10}$R$^7$ (in which $R^{10}$ and $R^{17}$ are as defined above); and $R^{28}$ is ($C_{1-4}$)alkyl {which alkyl is further substituted by one to two substituents independently selected from —N(R$^{29}$)$_2$, —C(O)OR$^{30}$, —PO(OR$^{30}$)$_2$, —SO$_3$NHR$^{30}$, —SO$_2$NHR$^{30}$ and —OR$^{30}$ (in which each R$^{29}$ is independently hydro, acetyl or trifluoroacetyl and each R$^{30}$ is independently hydro or ($C_{1-4}$) alkyl)}; and the pharmaceutically acceptable salts, individual isomers, and mixtures of isomers thereof, which process comprises:

(a) reacting a compound of Formula 47:

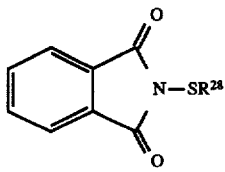

or a protected derivative thereof, in which $R^{28}$ is as defined above with respect to Formula III, with a compound of Formula I:

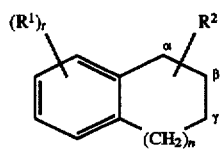

or a pharmaceutically acceptable salt, an individual isomer or a mixture of isomers thereof, in which n, t and $R^1$ are as defined above and $R^2$ is attached at the α-, β- or γ-position and is a group selected from Formulae (a), (b) and (c):

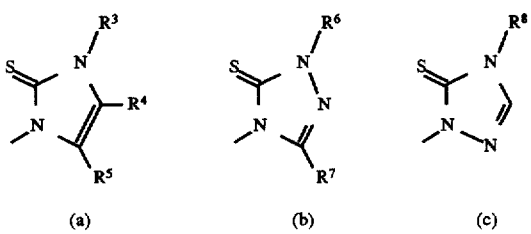

in which $R^3$, $R^7$ and $R^8$ are hydro and $R^4$, $R^5$ and $R^6$ are as defined above with respect to Formula III; and when necessary deprotecting; and (b) optionally reacting the corresponding non-salt form of a compound of Formula III with a pharmaceutically acceptable inorganic or organic acid or base to give a pharmaceutically acceptable salt;

(c) optionally reacting the corresponding acid addition salt or base addition salt form of a compound of Formula III with a suitable base or acid, respectively, to give the free acid or free base; and (d) optionally separating a mixture of stereoisomers of a compound of Formula III to give a single stereoisomer.

16. A compound of the formula:

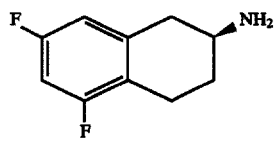

namely (S)-5,7-difluoro-1,2,3,4-tetrahydronaphthalen-2-ylamine.

17. A process for the preparation of a S-enantiomer of Formula 3(a):

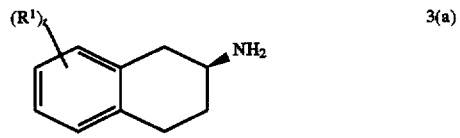

in which:

t is 0, 1, 2 or 3; and $R^1$ is independently halo, hydroxy or ($C_{1-4}$)alkyloxy; which process comprises:

(a) reducing, in the presence of 2S-dimethylamino-1R-phenylpropanol and 2-ethylaminopyridine, a compound of Formula 7(b):

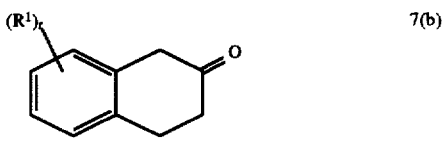

to give an (R)-enantiomer of Formula 6(c):

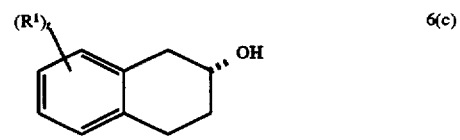

(b) treating the (R)-enantiomer of Formula 6(c) with methanesulfonyl chloride and then reacting with an azide salt to give a (S)-enantiomer of Formula 4(a):

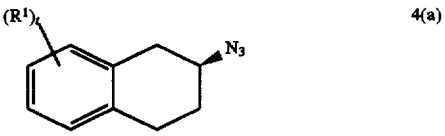

and (c) reducing.

18. The process of claim 17 in which t is 2 and $R^1$ is fluoro at the 5- and 7-position.

* * * * *